US012441782B2

(12) United States Patent
Nussenzweig et al.

(10) Patent No.: US 12,441,782 B2
(45) Date of Patent: Oct. 14, 2025

(54) ANTI-HIV ANTIBODY 10-1074 VARIANTS

(71) Applicant: The Rockefeller University, New York, NY (US)

(72) Inventors: Michel Nussenzweig, New York, NY (US); Randal R. Ketchem, Snohomish, WA (US); Christine C. Siska, Seattle, WA (US); Alison J. Gillespie, Seattle, WA (US); Rutilio H. Clark, Bainbridge Island, WA (US); Bruce A Kerwin, Bainbridge Island, WA (US)

(73) Assignee: The Rockefeller University, New York, NY (US)

( * ) Notice: Subject to any disclaimer, the term of this patent is extended or adjusted under 35 U.S.C. 154(b) by 1119 days.

(21) Appl. No.: 17/275,310

(22) PCT Filed: Sep. 12, 2019

(86) PCT No.: PCT/US2019/050823

§ 371 (c)(1),
(2) Date: Mar. 11, 2021

(87) PCT Pub. No.: WO2020/056145

PCT Pub. Date: Mar. 19, 2020

(65) Prior Publication Data

US 2022/0119504 A1 Apr. 21, 2022

Related U.S. Application Data

(60) Provisional application No. 62/731,356, filed on Sep. 14, 2018.

(51) Int. Cl.

| | |
|---|---|
| ***C07K 16/10*** | (2006.01) |
| ***A61K 39/00*** | (2006.01) |
| ***A61K 45/06*** | (2006.01) |
| ***A61P 31/18*** | (2006.01) |

(52) U.S. Cl.

CPC .......... *C07K 16/1045* (2013.01); *A61K 45/06* (2013.01); *A61P 31/18* (2018.01); *A61K 2039/507* (2013.01)

(58) Field of Classification Search

CPC ..... C07K 16/1045; A61P 31/18; A61K 45/06; A61K 2039/507

See application file for complete search history.

(56) References Cited

U.S. PATENT DOCUMENTS 9,464,131 B2 * 10/2016 Chan-Hui .......... C07K 16/1063
2018/0230203 A1 8/2018 Diskin et al.

FOREIGN PATENT DOCUMENTS

WO 2014/063059 A1 4/2014
WO 2016/014484 A1 1/2016
WO 2018/125813 A1 7/2018
WO 2020/086782 A1 4/2020

OTHER PUBLICATIONS

Rüker F, Ebert V, Kohl J, Steindl F, Riegler H, Katinger H. Expression of a human monoclonal anti-HIV-1 antibody in CHO cells. Ann N Y Acad Sci. Dec. 27, 1991;646:212-9. (Year: 1991).*

Caskey et al. Viraemia suppressed in HIV-1-infected humans by broadly neutralizing antibody 3BNC117. Nature. Jun. 25, 2015;522(7557):487-91. (Year: 2015).*

Clercq E. Anti-HIV drugs: 25 compounds approved within 25 years after the discovery of HIV. Int J Antimicrob Agents. Apr. 2009;33(4):307-20. (Year: 2009).*

Clinical Trial: NCT02825797: "3BNC117 and 10-1074 in HIV-infected Individuals—Full Text View—ClinicalTrials.gov", Aug. 21, 2018 (Aug. 21, 2018), 10 pages.

Bournazos, Stylianos et al. "Bispecific Anti-HIV-1 Antibodies with Enhanced Breadth and Potency", Cell, Elsevier, Amsterdam NL, vol. 165, No. 7, Jun. 16, 2016 (Jun. 16, 2016) , pp. 1609-1620.

Caskey, Marina et al. "Antibody 10-1074 suppresses viremia in HIV-1-infected individuals", Nature Medicine, vol. 23, No. 2, Feb. 1, 2017 (Feb. 1, 2017), pp. 185-191.

Mendoza, Pilar et al. "Combination therapy with anti-HIV-1 antibodies maintains viral suppression", Nature, Nature Publishing Group UK, London, vol. 561, No. 7724, Sep. 26, 2018 (Sep. 26, 2018), pp. 479-484.

Extended European Search Report mailed Jun. 3, 2022 in European Application No. 19859927.6, 14 pages.

Kerwin et al., "Framework Mutations of the 10-1074 bnAb Increase Conformational Stability, Manufacturability, and Stability While Preserving Full Neutralization Activity", Journal of Pharmaceutical Sciences, 2019, pp. 1-14.

Klein et al., "Somatic mutations of the immunoglobulin framework are generally required for broad and potent HIV-1 neutralization", Cell, 2013, vol. 153, No. 1, pp. 126-138.

Mouquet et al., "Complex-type N-glycan recognition by potent broadly neutralizing HIV antibodies", Proc. Natl. Acad. Sci. U.S.A., 2012, vol. 109, iss. 47, pp. 3268-3277.

Caskey et al., "Broadly neutralizing anti-HIV-1 monoclonal antibodies in the clinic", Nature Medicine, vol. 25, 2019, pp. 547-553.

Dashti et al., "Broadly Neutralizing Antibodies against HIV: Back to Blood", Trends in Molecular Medicine, vol. 25, No. 3, 2019.

McCoy, "The expanding array of HIV broadly neutralizing antibodies", Retrovirology, 2018, 15:70.

Parsons et al., "Importance of Fc-mediated functions of anti-HIV-1 broadly neutralizing antibodies", Retrovirology, 2018, 15:58.

Possas et al., "HIV cure: global overview of bNAbs' patents and related scientific publications", Expert Opinion on Therapeutic Patents, 2018, vol. 28, No. 7, pp. 551-560.

(Continued)

*Primary Examiner* — Nicole Kinsey White
*Assistant Examiner* — Ruixue Wang
(74) *Attorney, Agent, or Firm* — Fox Rothschild LLP

(57) ABSTRACT

The present disclosure provides optimized broadly-neutralizing anti-HIV antibodies, having modified light chain variable regions and/or heavy chain variable regions leading to improved biophysical characteristics. The present disclosure also provides methods for producing these anti-HIV antibodies and methods of use thereof.

16 Claims, 15 Drawing Sheets

Specification includes a Sequence Listing.

(56) References Cited

OTHER PUBLICATIONS

Sok et al., “Recent progress in broadly neutralizing antibodies to HIV”, Nature Immunology, 2018, vol. 19, pp. 1179-1188.
Liu et al., “Broadly neutralizing antibodies for HIV-1: effecacies, challenges and opportunities”, Emerging Microbes & Infections, 2020, vol. 9.
Mahomed et al., “Clinical Trials of Broadly Neutralizing Monoclonal Antibodies for Human Immunodeficiency Virus Prevention: A Review”, The Journal of Infectious Diseases, 2021, 13;223(3), pp. 370-380.

* cited by examiner

| Baseline characteristics of participants (*n*=15) | |
|---|---|
| **Male sex** - *n* (%) | 14(93%) |
| **Age** - Median years (range) | 40 (22-55) |
| **Race or ethnicity** - *n* (%) | |
| White non-Hispanic | 6 (40.0%) |
| Black non-Hispanic | 4 (26.7%) |
| Hispanic, regardless of race | 4 (26.7%) |
| Multiple, non-Hispanic | 1 (6.7%) |
| **Years since HIV-1 diagnosis** - Median (range) | 6 (3-23) |
| **HIV-1 RNA level prior to ATI** - *n* (%) | |
| < 20 copies/ml (screen) | 15 (100%) |
| < 20 copies/ml (week-2 and day 0) | 11 (73%) |
| **$CD4^+$ T-cell count** - Median cells/μl (range) | |
| Day 0 | 730 (515-1,360) |
| Reported nadir | 450 (270- 1,000) |
| **Years on ART** - Median (range) | |
| First ART | 5 (2-21) |
| Uninterrupted ART | 5 (2-21) |
| **ART regimen at screening** - *n* (%) | |
| Integrase inhibitor-based | 10 (66.7%) |
| NNRTI*-based | 3 (20.0%) |
| Protease inhibitor-based | 2 (13.3%) |

FIG. 6A

SEQUENCE LISTING

```
<160> NUMBER OF SEQ ID NOS: 753

<210> SEQ ID NO 1
<211> LENGTH: 233
<212> TYPE: PRT
<213> ORGANISM: Homo sapiens

<400> SEQUENCE: 1

Met Gly Trp Ser Cys Ile Ile Leu Phe Leu Val Ala Thr Ala Thr Gly
1               5                   10                  15

Val His Ser Ser Tyr Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 2
<211> LENGTH: 233
<212> TYPE: PRT
<213> ORGANISM: Homo sapiens

<400> SEQUENCE: 2

Met Gly Trp Ser Cys Ile Ile Leu Phe Leu Val Ala Thr Ala Thr Gly
1               5                   10                  15

Val His Ser Ser Tyr Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45
```

```
Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230
```

<210> SEQ ID NO 3
<211> LENGTH: 233
<212> TYPE: PRT
<213> ORGANISM: Homo sapiens

<400> SEQUENCE: 3

```
Met Gly Trp Ser Cys Ile Ile Leu Phe Leu Val Ala Thr Ala Thr Gly
1               5                   10                  15

Val His Ser Ser Pro Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
```

```
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 4
<211> LENGTH: 233
<212> TYPE: PRT
<213> ORGANISM: Homo sapiens

<400> SEQUENCE: 4

Met Gly Trp Ser Cys Ile Ile Leu Phe Leu Val Ala Thr Ala Thr Gly
1               5                   10                  15

Val His Ser Ser Tyr Val Pro Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 5
<211> LENGTH: 233
<212> TYPE: PRT
<213> ORGANISM: Homo sapiens

<400> SEQUENCE: 5

Met Gly Trp Ser Cys Ile Ile Leu Phe Leu Val Ala Thr Ala Thr Gly
1               5                   10                  15

Val His Ser Ser Tyr Val Arg Ser Leu Ser Val Ala Leu Gly Glu Thr
            20                  25                  30

Ala Arg Ile Ser Cys Gly Arg Gln Ala Leu Gly Ser Arg Ala Val Gln
```

```
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 6
<211> LENGTH: 233
<212> TYPE: PRT
<213> ORGANISM: Homo sapiens

<400> SEQUENCE: 6

Met Gly Trp Ser Cys Ile Ile Leu Phe Leu Val Ala Thr Ala Thr Gly
1               5                   10                  15

Val His Ser Ser Tyr Val Arg Pro Leu Ser Val Ala Leu Gly Gln Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175
```

Lys Ala Gly Val Glu Thr Thr Thr Pro Ser Lys Gln Ser Asn Asn Lys
180 185 190

Tyr Ala Ala Ser Ser Tyr Leu Ser Leu Thr Pro Glu Gln Trp Lys Ser
195 200 205

His Arg Ser Tyr Ser Cys Gln Val Thr His Glu Gly Ser Thr Val Glu
210 215 220

Lys Thr Val Ala Pro Thr Glu Cys Ser
225 230

<210> SEQ ID NO 7
<211> LENGTH: 233
<212> TYPE: PRT
<213> ORGANISM: Homo sapiens

<400> SEQUENCE: 7

Met Gly Trp Ser Cys Ile Ile Leu Phe Leu Val Ala Thr Ala Thr Gly
1 5 10 15

Val His Ser Ser Tyr Val Arg Pro Leu Ser Val Ala Leu Gly Glu Thr
20 25 30

Ala Arg Ile Ser Cys Gly Arg Gln Ala Leu Gly Ser Arg Ala Val Gln
35 40 45

Trp Tyr Gln Gln Arg Pro Gly Gln Ala Pro Ile Leu Leu Ile Tyr Asn
50 55 60

Asn Gln Asp Arg Pro Ser Gly Ile Pro Glu Arg Phe Ser Gly Thr Pro
65 70 75 80

Asp Ile Asn Phe Gly Thr Arg Ala Thr Leu Thr Ile Ser Gly Val Glu
85 90 95

Ala Gly Asp Glu Ala Asp Tyr Tyr Cys His Met Trp Asp Ser Arg Ser
100 105 110

Gly Phe Ser Trp Ser Phe Gly Gly Ala Thr Arg Leu Thr Val Leu Gly
115 120 125

Gln Pro Lys Ala Ala Pro Ser Val Thr Leu Phe Pro Pro Ser Ser Glu
130 135 140

Glu Leu Gln Ala Asn Lys Ala Thr Leu Val Cys Leu Ile Ser Asp Phe
145 150 155 160

Tyr Pro Gly Ala Val Thr Val Ala Trp Lys Ala Asp Ser Ser Pro Val
165 170 175

Lys Ala Gly Val Glu Thr Thr Thr Pro Ser Lys Gln Ser Asn Asn Lys
180 185 190

Tyr Ala Ala Ser Ser Tyr Leu Ser Leu Thr Pro Glu Gln Trp Lys Ser
195 200 205

His Arg Ser Tyr Ser Cys Gln Val Thr His Glu Gly Ser Thr Val Glu
210 215 220

Lys Thr Val Ala Pro Thr Glu Cys Ser
225 230

<210> SEQ ID NO 8
<211> LENGTH: 233
<212> TYPE: PRT
<213> ORGANISM: Homo sapiens

<400> SEQUENCE: 8

Met Gly Trp Ser Cys Ile Ile Leu Phe Leu Val Ala Thr Ala Thr Gly
1 5 10 15

Val His Ser Ser Tyr Val Arg Pro Leu Ser Val Ala Leu Gly Glu Thr
20 25 30

```
Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Asn
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 9
<211> LENGTH: 233
<212> TYPE: PRT
<213> ORGANISM: Homo sapiens

<400> SEQUENCE: 9

Met Gly Trp Ser Cys Ile Ile Leu Phe Leu Val Ala Thr Ala Thr Gly
1               5                   10                  15

Val His Ser Ser Tyr Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ser Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175
```

Lys Ala Gly Val Glu Thr Thr Thr Pro Ser Lys Gln Ser Asn Asn Lys
180 185 190

Tyr Ala Ala Ser Ser Tyr Leu Ser Leu Thr Pro Glu Gln Trp Lys Ser
195 200 205

His Arg Ser Tyr Ser Cys Gln Val Thr His Glu Gly Ser Thr Val Glu
210 215 220

Lys Thr Val Ala Pro Thr Glu Cys Ser
225 230

<210> SEQ ID NO 10
<211> LENGTH: 233
<212> TYPE: PRT
<213> ORGANISM: Homo sapiens

<400> SEQUENCE: 10

Met Gly Trp Ser Cys Ile Ile Leu Phe Leu Val Ala Thr Ala Thr Gly
1 5 10 15

Val His Ser Ser Tyr Val Arg Pro Leu Ser Val Ala Leu Gly Glu Thr
20 25 30

Ala Arg Ile Ser Cys Gly Arg Gln Ala Leu Gly Ser Arg Ala Val Gln
35 40 45

Trp Tyr Gln His Arg Pro Gly Gln Ala Pro Ile Leu Leu Ile Tyr Asn
50 55 60

Asn Gln Asp Arg Pro Ser Gly Ile Pro Glu Arg Phe Ser Gly Thr Pro
65 70 75 80

Asp Ile Gly Phe Gly Thr Arg Ala Thr Leu Thr Ile Ser Gly Val Glu
85 90 95

Ala Gly Asp Glu Ala Asp Tyr Tyr Cys His Met Trp Asp Ser Arg Ser
100 105 110

Gly Phe Ser Trp Ser Phe Gly Gly Ala Thr Arg Leu Thr Val Leu Gly
115 120 125

Gln Pro Lys Ala Ala Pro Ser Val Thr Leu Phe Pro Pro Ser Ser Glu
130 135 140

Glu Leu Gln Ala Asn Lys Ala Thr Leu Val Cys Leu Ile Ser Asp Phe
145 150 155 160

Tyr Pro Gly Ala Val Thr Val Ala Trp Lys Ala Asp Ser Ser Pro Val
165 170 175

Lys Ala Gly Val Glu Thr Thr Thr Pro Ser Lys Gln Ser Asn Asn Lys
180 185 190

Tyr Ala Ala Ser Ser Tyr Leu Ser Leu Thr Pro Glu Gln Trp Lys Ser
195 200 205

His Arg Ser Tyr Ser Cys Gln Val Thr His Glu Gly Ser Thr Val Glu
210 215 220

Lys Thr Val Ala Pro Thr Glu Cys Ser
225 230

<210> SEQ ID NO 11
<211> LENGTH: 233
<212> TYPE: PRT
<213> ORGANISM: Homo sapiens

<400> SEQUENCE: 11

Met Gly Trp Ser Cys Ile Ile Leu Phe Leu Val Ala Thr Ala Thr Gly
1 5 10 15

Val His Ser Ser Tyr Val Arg Pro Leu Ser Val Ala Leu Gly Glu Thr
20 25 30

```
Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Thr Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 12
<211> LENGTH: 233
<212> TYPE: PRT
<213> ORGANISM: Homo sapiens

<400> SEQUENCE: 12

Met Gly Trp Ser Cys Ile Ile Leu Phe Leu Val Ala Thr Ala Thr Gly
1               5                   10                  15

Val His Ser Ser Tyr Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Glu Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
```

```
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 13
<211> LENGTH: 233
<212> TYPE: PRT
<213> ORGANISM: Homo sapiens

<400> SEQUENCE: 13

Met Gly Trp Ser Cys Ile Ile Leu Phe Leu Val Ala Thr Ala Thr Gly
1               5                   10                  15

Val His Ser Ser Tyr Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Gly Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 14
<211> LENGTH: 233
<212> TYPE: PRT
<213> ORGANISM: Homo sapiens

<400> SEQUENCE: 14

Met Gly Trp Ser Cys Ile Ile Leu Phe Leu Val Ala Thr Ala Thr Gly
1               5                   10                  15

Val His Ser Ser Tyr Val Arg Pro Leu Ser Val Ala Leu Gly Glu Thr
```

```
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 15
<211> LENGTH: 233
<212> TYPE: PRT
<213> ORGANISM: Homo sapiens

<400> SEQUENCE: 15

Met Gly Trp Ser Cys Ile Ile Leu Phe Leu Val Ala Thr Ala Thr Gly
1               5                   10                  15

Val His Ser Ser Tyr Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160
```

```
Tyr Pro Gly Ala Val Thr Val Ala Trp Lys Ala Asp Ser Ser Pro Val
            165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230
```

<210> SEQ ID NO 16
<211> LENGTH: 233
<212> TYPE: PRT
<213> ORGANISM: Homo sapiens

<400> SEQUENCE: 16

```
Met Gly Trp Ser Cys Ile Ile Leu Phe Leu Val Ala Thr Ala Thr Gly
1               5                   10                  15

Val His Ser Ser Tyr Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
            165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230
```

<210> SEQ ID NO 17
<211> LENGTH: 233
<212> TYPE: PRT
<213> ORGANISM: Homo sapiens

<400> SEQUENCE: 17

```
Met Gly Trp Ser Cys Ile Ile Leu Phe Leu Val Ala Thr Ala Thr Gly
1               5                   10                  15
```

```
Val His Ser Ser Tyr Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 18
<211> LENGTH: 233
<212> TYPE: PRT
<213> ORGANISM: Homo sapiens

<400> SEQUENCE: 18

Met Gly Trp Ser Cys Ile Ile Leu Phe Leu Val Ala Thr Ala Thr Gly
1               5                   10                  15

Val His Ser Ser Tyr Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160
```

```
Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 19
<211> LENGTH: 233
<212> TYPE: PRT
<213> ORGANISM: Homo sapiens

<400> SEQUENCE: 19

Met Gly Trp Ser Cys Ile Ile Leu Phe Leu Val Ala Thr Ala Thr Gly
1               5                   10                  15

Val His Ser Ser Tyr Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 20
<211> LENGTH: 233
<212> TYPE: PRT
<213> ORGANISM: Homo sapiens

<400> SEQUENCE: 20

Met Gly Trp Ser Cys Ile Ile Leu Phe Leu Val Ala Thr Ala Thr Gly
1               5                   10                  15
```

```
Val His Ser Ser Tyr Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230
```

<210> SEQ ID NO 21
<211> LENGTH: 233
<212> TYPE: PRT
<213> ORGANISM: Homo sapiens

<400> SEQUENCE: 21

```
Met Gly Trp Ser Cys Ile Ile Leu Phe Leu Val Ala Thr Ala Thr Gly
1               5                   10                  15

Val His Ser Ser Tyr Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
```

145 150 155 160

Tyr Pro Gly Ala Val Thr Val Ala Trp Lys Ala Asp Ser Ser Pro Val
165 170 175

Lys Ala Gly Val Glu Thr Thr Thr Pro Ser Lys Gln Ser Asn Asn Lys
180 185 190

Tyr Ala Ala Ser Ser Tyr Leu Ser Leu Thr Pro Glu Gln Trp Lys Ser
195 200 205

His Arg Ser Tyr Ser Cys Gln Val Thr His Glu Gly Ser Thr Val Glu
210 215 220

Lys Thr Val Ala Pro Thr Glu Cys Ser
225 230

<210> SEQ ID NO 22
<211> LENGTH: 233
<212> TYPE: PRT
<213> ORGANISM: Homo sapiens

<400> SEQUENCE: 22

Met Gly Trp Ser Cys Ile Ile Leu Phe Leu Val Ala Thr Ala Thr Gly
1 5 10 15

Val His Ser Ser Pro Val Arg Pro Leu Ser Val Ala Leu Gly Glu Thr
20 25 30

Ala Arg Ile Ser Cys Gly Arg Gln Ala Leu Gly Ser Arg Ala Val Gln
35 40 45

Trp Tyr Gln His Arg Pro Gly Gln Ala Pro Ile Leu Leu Ile Tyr Asn
50 55 60

Asn Gln Asp Arg Pro Ser Gly Ile Pro Glu Arg Phe Ser Gly Thr Pro
65 70 75 80

Asp Ile Asn Phe Gly Thr Arg Ala Thr Leu Thr Ile Ser Gly Val Glu
85 90 95

Ala Gly Asp Glu Ala Asp Tyr Tyr Cys His Met Trp Asp Ser Arg Ser
100 105 110

Gly Phe Ser Trp Ser Phe Gly Gly Ala Thr Arg Leu Thr Val Leu Gly
115 120 125

Gln Pro Lys Ala Ala Pro Ser Val Thr Leu Phe Pro Pro Ser Ser Glu
130 135 140

Glu Leu Gln Ala Asn Lys Ala Thr Leu Val Cys Leu Ile Ser Asp Phe
145 150 155 160

Tyr Pro Gly Ala Val Thr Val Ala Trp Lys Ala Asp Ser Ser Pro Val
165 170 175

Lys Ala Gly Val Glu Thr Thr Thr Pro Ser Lys Gln Ser Asn Asn Lys
180 185 190

Tyr Ala Ala Ser Ser Tyr Leu Ser Leu Thr Pro Glu Gln Trp Lys Ser
195 200 205

His Arg Ser Tyr Ser Cys Gln Val Thr His Glu Gly Ser Thr Val Glu
210 215 220

Lys Thr Val Ala Pro Thr Glu Cys Ser
225 230

<210> SEQ ID NO 23
<211> LENGTH: 233
<212> TYPE: PRT
<213> ORGANISM: Homo sapiens

<400> SEQUENCE: 23

Met Gly Trp Ser Cys Ile Ile Leu Phe Leu Val Ala Thr Ala Thr Gly

```
1               5                   10                  15

Val His Ser Ser Tyr Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 24
<211> LENGTH: 233
<212> TYPE: PRT
<213> ORGANISM: Homo sapiens

<400> SEQUENCE: 24

Met Gly Trp Ser Cys Ile Ile Leu Phe Leu Val Ala Thr Ala Thr Gly
1               5                   10                  15

Val His Ser Ser Pro Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140
```

Glu Leu Gln Ala Asn Lys Ala Thr Leu Val Cys Leu Ile Ser Asp Phe
145 150 155 160

Tyr Pro Gly Ala Val Thr Val Ala Trp Lys Ala Asp Ser Ser Pro Val
165 170 175

Lys Ala Gly Val Glu Thr Thr Thr Pro Ser Lys Gln Ser Asn Asn Lys
180 185 190

Tyr Ala Ala Ser Ser Tyr Leu Ser Leu Thr Pro Glu Gln Trp Lys Ser
195 200 205

His Arg Ser Tyr Ser Cys Gln Val Thr His Glu Gly Ser Thr Val Glu
210 215 220

Lys Thr Val Ala Pro Thr Glu Cys Ser
225 230

<210> SEQ ID NO 25
<211> LENGTH: 233
<212> TYPE: PRT
<213> ORGANISM: Homo sapiens

<400> SEQUENCE: 25

Met Gly Trp Ser Cys Ile Ile Leu Phe Leu Val Ala Thr Ala Thr Gly
1 5 10 15

Val His Ser Ser Pro Val Arg Pro Leu Ser Val Ala Leu Gly Glu Thr
20 25 30

Ala Arg Ile Ser Cys Gly Arg Gln Ala Leu Gly Ser Arg Ala Val Gln
35 40 45

Trp Tyr Gln His Arg Pro Gly Gln Ala Pro Ile Leu Leu Ile Tyr Asn
50 55 60

Asn Gln Asp Arg Pro Ser Gly Ile Pro Glu Arg Phe Ser Gly Thr Pro
65 70 75 80

Asp Ile Asn Phe Gly Thr Arg Ala Thr Leu Thr Ile Ser Gly Val Glu
85 90 95

Ala Gly Asp Glu Ala Asp Tyr Tyr Cys His Met Trp Asp Ser Arg Ser
100 105 110

Gly Phe Ser Trp Ser Phe Gly Gly Ala Thr Arg Leu Thr Val Leu Gly
115 120 125

Gln Pro Lys Ala Ala Pro Ser Val Thr Leu Phe Pro Pro Ser Ser Glu
130 135 140

Glu Leu Gln Ala Asn Lys Ala Thr Leu Val Cys Leu Ile Ser Asp Phe
145 150 155 160

Tyr Pro Gly Ala Val Thr Val Ala Trp Lys Ala Asp Ser Ser Pro Val
165 170 175

Lys Ala Gly Val Glu Thr Thr Thr Pro Ser Lys Gln Ser Asn Asn Lys
180 185 190

Tyr Ala Ala Ser Ser Tyr Leu Ser Leu Thr Pro Glu Gln Trp Lys Ser
195 200 205

His Arg Ser Tyr Ser Cys Gln Val Thr His Glu Gly Ser Thr Val Glu
210 215 220

Lys Thr Val Ala Pro Thr Glu Cys Ser
225 230

<210> SEQ ID NO 26
<211> LENGTH: 233
<212> TYPE: PRT
<213> ORGANISM: Homo sapiens

<400> SEQUENCE: 26

```
Met Gly Trp Ser Cys Ile Ile Leu Phe Leu Val Ala Thr Ala Thr Gly
1               5                   10                  15

Val His Ser Ser Pro Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 27
<211> LENGTH: 233
<212> TYPE: PRT
<213> ORGANISM: Homo sapiens

<400> SEQUENCE: 27

Met Gly Trp Ser Cys Ile Ile Leu Phe Leu Val Ala Thr Ala Thr Gly
1               5                   10                  15

Val His Ser Ser Pro Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140
```

Glu Leu Gln Ala Asn Lys Ala Thr Leu Val Cys Leu Ile Ser Asp Phe
145 150 155 160

Tyr Pro Gly Ala Val Thr Val Ala Trp Lys Ala Asp Ser Ser Pro Val
165 170 175

Lys Ala Gly Val Glu Thr Thr Thr Pro Ser Lys Gln Ser Asn Asn Lys
180 185 190

Tyr Ala Ala Ser Ser Tyr Leu Ser Leu Thr Pro Glu Gln Trp Lys Ser
195 200 205

His Arg Ser Tyr Ser Cys Gln Val Thr His Glu Gly Ser Thr Val Glu
210 215 220

Lys Thr Val Ala Pro Thr Glu Cys Ser
225 230

<210> SEQ ID NO 28
<211> LENGTH: 233
<212> TYPE: PRT
<213> ORGANISM: Homo sapiens

<400> SEQUENCE: 28

Met Gly Trp Ser Cys Ile Ile Leu Phe Leu Val Ala Thr Ala Thr Gly
1 5 10 15

Val His Ser Ser Pro Val Arg Pro Leu Ser Val Ala Leu Gly Glu Thr
20 25 30

Ala Arg Ile Ser Cys Gly Arg Gln Ala Leu Gly Ser Arg Ala Val Gln
35 40 45

Trp Tyr Gln His Arg Pro Gly Gln Ala Pro Ile Leu Leu Ile Tyr Asn
50 55 60

Asn Gln Asp Arg Pro Ser Gly Ile Pro Glu Arg Phe Ser Gly Thr Pro
65 70 75 80

Asp Ile Asn Phe Gly Thr Arg Ala Thr Leu Thr Ile Ser Gly Val Glu
85 90 95

Ala Gly Asp Glu Ala Asp Tyr Tyr Cys His Met Trp Asp Ser Arg Ser
100 105 110

Gly Phe Ser Trp Ser Phe Gly Gly Ala Thr Arg Leu Thr Val Leu Gly
115 120 125

Gln Pro Lys Ala Ala Pro Ser Val Thr Leu Phe Pro Pro Ser Ser Glu
130 135 140

Glu Leu Gln Ala Asn Lys Ala Thr Leu Val Cys Leu Ile Ser Asp Phe
145 150 155 160

Tyr Pro Gly Ala Val Thr Val Ala Trp Lys Ala Asp Ser Ser Pro Val
165 170 175

Lys Ala Gly Val Glu Thr Thr Thr Pro Ser Lys Gln Ser Asn Asn Lys
180 185 190

Tyr Ala Ala Ser Ser Tyr Leu Ser Leu Thr Pro Glu Gln Trp Lys Ser
195 200 205

His Arg Ser Tyr Ser Cys Gln Val Thr His Glu Gly Ser Thr Val Glu
210 215 220

Lys Thr Val Ala Pro Thr Glu Cys Ser
225 230

<210> SEQ ID NO 29
<211> LENGTH: 233
<212> TYPE: PRT
<213> ORGANISM: Homo sapiens

<400> SEQUENCE: 29

Met Gly Trp Ser Cys Ile Ile Leu Phe Leu Val Ala Thr Ala Thr Gly
1 5 10 15

Val His Ser Ser Tyr Val Arg Pro Leu Ser Val Ala Leu Gly Glu Thr
20 25 30

Ala Arg Ile Ser Cys Gly Arg Gln Ala Leu Gly Ser Arg Ala Val Gln
35 40 45

Trp Tyr Gln His Arg Pro Gly Gln Ala Pro Ile Leu Leu Ile Tyr Asn
50 55 60

Asn Gln Asp Arg Pro Ser Gly Ile Pro Glu Arg Phe Ser Gly Thr Pro
65 70 75 80

Asp Ile Asn Phe Gly Thr Arg Ala Thr Leu Thr Ile Ser Gly Val Glu
85 90 95

Ala Gly Asp Glu Ala Asp Tyr Tyr Cys His Met Trp Asp Ser Arg Ser
100 105 110

Gly Phe Ser Trp Ser Phe Gly Gly Ala Thr Arg Leu Thr Val Leu Gly
115 120 125

Gln Pro Lys Ala Ala Pro Ser Val Thr Leu Phe Pro Pro Ser Ser Glu
130 135 140

Glu Leu Gln Ala Asn Lys Ala Thr Leu Val Cys Leu Ile Ser Asp Phe
145 150 155 160

Tyr Pro Gly Ala Val Thr Val Ala Trp Lys Ala Asp Ser Ser Pro Val
165 170 175

Lys Ala Gly Val Glu Thr Thr Thr Pro Ser Lys Gln Ser Asn Asn Lys
180 185 190

Tyr Ala Ala Ser Ser Tyr Leu Ser Leu Thr Pro Glu Gln Trp Lys Ser
195 200 205

His Arg Ser Tyr Ser Cys Gln Val Thr His Glu Gly Ser Thr Val Glu
210 215 220

Lys Thr Val Ala Pro Thr Glu Cys Ser
225 230

<210> SEQ ID NO 30
<211> LENGTH: 233
<212> TYPE: PRT
<213> ORGANISM: Homo sapiens

<400> SEQUENCE: 30

Met Gly Trp Ser Cys Ile Ile Leu Phe Leu Val Ala Thr Ala Thr Gly
1 5 10 15

Val His Ser Ser Tyr Val Arg Pro Leu Ser Val Ala Leu Gly Glu Thr
20 25 30

Ala Arg Ile Ser Cys Gly Arg Gln Ala Leu Gly Ser Arg Ala Val Gln
35 40 45

Trp Tyr Gln His Arg Pro Gly Gln Ala Pro Ile Leu Leu Ile Tyr Asn
50 55 60

Asn Gln Asp Arg Pro Ser Gly Ile Pro Glu Arg Phe Ser Gly Thr Pro
65 70 75 80

Asp Ile Asn Phe Gly Thr Arg Ala Thr Leu Thr Ile Ser Gly Val Glu
85 90 95

Ala Gly Asp Glu Ala Asp Tyr Tyr Cys His Met Trp Asp Ser Arg Ser
100 105 110

Gly Phe Ser Trp Ser Phe Gly Gly Ala Thr Arg Leu Thr Val Leu Gly
115 120 125

Gln Pro Lys Ala Ala Pro Ser Val Thr Leu Phe Pro Pro Ser Ser Glu

```
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 31
<211> LENGTH: 233
<212> TYPE: PRT
<213> ORGANISM: Homo sapiens

<400> SEQUENCE: 31

Met Gly Trp Ser Cys Ile Ile Leu Phe Leu Val Ala Thr Ala Thr Gly
1               5                   10                  15

Val His Ser Ser Tyr Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 32
<211> LENGTH: 233
<212> TYPE: PRT
<213> ORGANISM: Homo sapiens
```

<400> SEQUENCE: 32

Met Gly Trp Ser Cys Ile Ile Leu Phe Leu Val Ala Thr Ala Thr Gly
1 5 10 15

Val His Ser Ser Tyr Val Arg Pro Leu Ser Val Ala Leu Gly Glu Thr
20 25 30

Ala Arg Ile Ser Cys Gly Arg Gln Ala Leu Gly Ser Arg Ala Val Gln
35 40 45

Trp Tyr Gln His Arg Pro Gly Gln Ala Pro Ile Leu Leu Ile Tyr Asn
50 55 60

Asn Gln Asp Arg Pro Ser Gly Ile Pro Glu Arg Phe Ser Gly Thr Pro
65 70 75 80

Asp Ile Asn Phe Gly Thr Arg Ala Thr Leu Thr Ile Ser Gly Val Glu
85 90 95

Ala Gly Asp Glu Ala Asp Tyr Tyr Cys His Met Trp Asp Ser Arg Ser
100 105 110

Gly Phe Ser Trp Ser Phe Gly Gly Ala Thr Arg Leu Thr Val Leu Gly
115 120 125

Gln Pro Lys Ala Ala Pro Ser Val Thr Leu Phe Pro Pro Ser Ser Glu
130 135 140

Glu Leu Gln Ala Asn Lys Ala Thr Leu Val Cys Leu Ile Ser Asp Phe
145 150 155 160

Tyr Pro Gly Ala Val Thr Val Ala Trp Lys Ala Asp Ser Ser Pro Val
165 170 175

Lys Ala Gly Val Glu Thr Thr Thr Pro Ser Lys Gln Ser Asn Asn Lys
180 185 190

Tyr Ala Ala Ser Ser Tyr Leu Ser Leu Thr Pro Glu Gln Trp Lys Ser
195 200 205

His Arg Ser Tyr Ser Cys Gln Val Thr His Glu Gly Ser Thr Val Glu
210 215 220

Lys Thr Val Ala Pro Thr Glu Cys Ser
225 230

<210> SEQ ID NO 33
<211> LENGTH: 233
<212> TYPE: PRT
<213> ORGANISM: Homo sapiens

<400> SEQUENCE: 33

Met Gly Trp Ser Cys Ile Ile Leu Phe Leu Val Ala Thr Ala Thr Gly
1 5 10 15

Val His Ser Ser Tyr Val Arg Pro Leu Ser Val Ala Leu Gly Glu Thr
20 25 30

Ala Arg Ile Ser Cys Gly Arg Gln Ala Leu Gly Ser Arg Ala Val Gln
35 40 45

Trp Tyr Gln His Arg Pro Gly Gln Ala Pro Ile Leu Leu Ile Tyr Asn
50 55 60

Asn Gln Asp Arg Pro Ser Gly Ile Pro Glu Arg Phe Ser Gly Thr Pro
65 70 75 80

Asp Ile Asn Phe Gly Thr Arg Ala Thr Leu Thr Ile Ser Gly Val Glu
85 90 95

Ala Gly Asp Glu Ala Asp Tyr Tyr Cys His Met Trp Asp Ser Arg Ser
100 105 110

Gly Phe Ser Trp Ser Phe Gly Gly Ala Thr Arg Leu Thr Val Leu Gly
115 120 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 34
<211> LENGTH: 233
<212> TYPE: PRT
<213> ORGANISM: Homo sapiens

<400> SEQUENCE: 34

Met Gly Trp Ser Cys Ile Ile Leu Phe Leu Val Ala Thr Ala Thr Gly
1               5                   10                  15

Val His Ser Ser Tyr Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 35
<211> LENGTH: 233
<212> TYPE: PRT
<213> ORGANISM: Homo sapiens

<400> SEQUENCE: 35

```
Met Gly Trp Ser Cys Ile Ile Leu Phe Leu Val Ala Thr Ala Thr Gly
1               5                   10                  15

Val His Ser Ser Pro Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230
```

<210> SEQ ID NO 36
<211> LENGTH: 233
<212> TYPE: PRT
<213> ORGANISM: Homo sapiens

<400> SEQUENCE: 36

```
Met Gly Trp Ser Cys Ile Ile Leu Phe Leu Val Ala Thr Ala Thr Gly
1               5                   10                  15

Val His Ser Ser Pro Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125
```

Gln Pro Lys Ala Ala Pro Ser Val Thr Leu Phe Pro Pro Ser Ser Glu
130 135 140

Glu Leu Gln Ala Asn Lys Ala Thr Leu Val Cys Leu Ile Ser Asp Phe
145 150 155 160

Tyr Pro Gly Ala Val Thr Val Ala Trp Lys Ala Asp Ser Ser Pro Val
165 170 175

Lys Ala Gly Val Glu Thr Thr Thr Pro Ser Lys Gln Ser Asn Asn Lys
180 185 190

Tyr Ala Ala Ser Ser Tyr Leu Ser Leu Thr Pro Glu Gln Trp Lys Ser
195 200 205

His Arg Ser Tyr Ser Cys Gln Val Thr His Glu Gly Ser Thr Val Glu
210 215 220

Lys Thr Val Ala Pro Thr Glu Cys Ser
225 230

<210> SEQ ID NO 37
<211> LENGTH: 233
<212> TYPE: PRT
<213> ORGANISM: Homo sapiens

<400> SEQUENCE: 37

Met Gly Trp Ser Cys Ile Ile Leu Phe Leu Val Ala Thr Ala Thr Gly
1 5 10 15

Val His Ser Ser Pro Val Arg Pro Leu Ser Val Ala Leu Gly Glu Thr
20 25 30

Ala Arg Ile Ser Cys Gly Arg Gln Ala Leu Gly Ser Arg Ala Val Gln
35 40 45

Trp Tyr Gln His Arg Pro Gly Gln Ala Pro Ile Leu Leu Ile Tyr Asn
50 55 60

Asn Gln Asp Arg Pro Ser Gly Ile Pro Glu Arg Phe Ser Gly Thr Pro
65 70 75 80

Asp Ile Asn Phe Gly Thr Arg Ala Thr Leu Thr Ile Ser Gly Val Glu
85 90 95

Ala Gly Asp Glu Ala Asp Tyr Tyr Cys His Met Trp Asp Ser Arg Ser
100 105 110

Gly Phe Ser Trp Ser Phe Gly Gly Ala Thr Arg Leu Thr Val Leu Gly
115 120 125

Gln Pro Lys Ala Ala Pro Ser Val Thr Leu Phe Pro Pro Ser Ser Glu
130 135 140

Glu Leu Gln Ala Asn Lys Ala Thr Leu Val Cys Leu Ile Ser Asp Phe
145 150 155 160

Tyr Pro Gly Ala Val Thr Val Ala Trp Lys Ala Asp Ser Ser Pro Val
165 170 175

Lys Ala Gly Val Glu Thr Thr Thr Pro Ser Lys Gln Ser Asn Asn Lys
180 185 190

Tyr Ala Ala Ser Ser Tyr Leu Ser Leu Thr Pro Glu Gln Trp Lys Ser
195 200 205

His Arg Ser Tyr Ser Cys Gln Val Thr His Glu Gly Ser Thr Val Glu
210 215 220

Lys Thr Val Ala Pro Thr Glu Cys Ser
225 230

<210> SEQ ID NO 38
<211> LENGTH: 233
<212> TYPE: PRT

<213> ORGANISM: Homo sapiens

<400> SEQUENCE: 38

Met Gly Trp Ser Cys Ile Ile Leu Phe Leu Val Ala Thr Ala Thr Gly
1 5 10 15

Val His Ser Ser Pro Val Arg Pro Leu Ser Val Ala Leu Gly Glu Thr
20 25 30

Ala Arg Ile Ser Cys Gly Arg Gln Ala Leu Gly Ser Arg Ala Val Gln
35 40 45

Trp Tyr Gln His Arg Pro Gly Gln Ala Pro Ile Leu Leu Ile Tyr Asn
50 55 60

Asn Gln Asp Arg Pro Ser Gly Ile Pro Glu Arg Phe Ser Gly Thr Pro
65 70 75 80

Asp Ile Asn Phe Gly Thr Arg Ala Thr Leu Thr Ile Ser Gly Val Glu
85 90 95

Ala Gly Asp Glu Ala Asp Tyr Tyr Cys His Met Trp Asp Ser Arg Ser
100 105 110

Gly Phe Ser Trp Ser Phe Gly Gly Ala Thr Arg Leu Thr Val Leu Gly
115 120 125

Gln Pro Lys Ala Ala Pro Ser Val Thr Leu Phe Pro Pro Ser Ser Glu
130 135 140

Glu Leu Gln Ala Asn Lys Ala Thr Leu Val Cys Leu Ile Ser Asp Phe
145 150 155 160

Tyr Pro Gly Ala Val Thr Val Ala Trp Lys Ala Asp Ser Ser Pro Val
165 170 175

Lys Ala Gly Val Glu Thr Thr Thr Pro Ser Lys Gln Ser Asn Asn Lys
180 185 190

Tyr Ala Ala Ser Ser Tyr Leu Ser Leu Thr Pro Glu Gln Trp Lys Ser
195 200 205

His Arg Ser Tyr Ser Cys Gln Val Thr His Glu Gly Ser Thr Val Glu
210 215 220

Lys Thr Val Ala Pro Thr Glu Cys Ser
225 230

<210> SEQ ID NO 39
<211> LENGTH: 233
<212> TYPE: PRT
<213> ORGANISM: Homo sapiens

<400> SEQUENCE: 39

Met Gly Trp Ser Cys Ile Ile Leu Phe Leu Val Ala Thr Ala Thr Gly
1 5 10 15

Val His Ser Ser Pro Val Arg Pro Leu Ser Val Ala Leu Gly Glu Thr
20 25 30

Ala Arg Ile Ser Cys Gly Arg Gln Ala Leu Gly Ser Arg Ala Val Gln
35 40 45

Trp Tyr Gln His Arg Pro Gly Gln Ala Pro Ile Leu Leu Ile Tyr Asn
50 55 60

Asn Gln Asp Arg Pro Ser Gly Ile Pro Glu Arg Phe Ser Gly Thr Pro
65 70 75 80

Asp Ile Asn Phe Gly Thr Arg Ala Thr Leu Thr Ile Ser Gly Val Glu
85 90 95

Ala Gly Asp Glu Ala Asp Tyr Tyr Cys His Met Trp Asp Ser Arg Ser
100 105 110

Gly Phe Ser Trp Ser Phe Gly Gly Ala Thr Arg Leu Thr Val Leu Gly

```
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 40
<211> LENGTH: 233
<212> TYPE: PRT
<213> ORGANISM: Homo sapiens

<400> SEQUENCE: 40

Met Gly Trp Ser Cys Ile Ile Leu Phe Leu Val Ala Thr Ala Thr Gly
1               5                   10                  15

Val His Ser Ser Tyr Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 41
<211> LENGTH: 233
```

<212> TYPE: PRT
<213> ORGANISM: Homo sapiens

<400> SEQUENCE: 41

Met Gly Trp Ser Cys Ile Ile Leu Phe Leu Val Ala Thr Ala Thr Gly
1               5                   10                  15

Val His Ser Ser Tyr Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 42
<211> LENGTH: 233
<212> TYPE: PRT
<213> ORGANISM: Homo sapiens

<400> SEQUENCE: 42

Met Gly Trp Ser Cys Ile Ile Leu Phe Leu Val Ala Thr Ala Thr Gly
1               5                   10                  15

Val His Ser Ser Tyr Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

```
Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 43
<211> LENGTH: 233
<212> TYPE: PRT
<213> ORGANISM: Homo sapiens

<400> SEQUENCE: 43

Met Gly Trp Ser Cys Ile Ile Leu Phe Leu Val Ala Thr Ala Thr Gly
1               5                   10                  15

Val His Ser Ser Pro Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 44
```

<211> LENGTH: 233
<212> TYPE: PRT
<213> ORGANISM: Homo sapiens

<400> SEQUENCE: 44

```
Met Gly Trp Ser Cys Ile Ile Leu Phe Leu Val Ala Thr Ala Thr Gly
1               5                   10                  15

Val His Ser Ser Pro Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230
```

<210> SEQ ID NO 45
<211> LENGTH: 233
<212> TYPE: PRT
<213> ORGANISM: Homo sapiens

<400> SEQUENCE: 45

```
Met Gly Trp Ser Cys Ile Ile Leu Phe Leu Val Ala Thr Ala Thr Gly
1               5                   10                  15

Val His Ser Ser Pro Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110
```

Gly Phe Ser Trp Ser Phe Gly Gly Ala Thr Arg Leu Thr Val Leu Gly
115 120 125

Gln Pro Lys Ala Ala Pro Ser Val Thr Leu Phe Pro Pro Ser Ser Glu
130 135 140

Glu Leu Gln Ala Asn Lys Ala Thr Leu Val Cys Leu Ile Ser Asp Phe
145 150 155 160

Tyr Pro Gly Ala Val Thr Val Ala Trp Lys Ala Asp Ser Ser Pro Val
165 170 175

Lys Ala Gly Val Glu Thr Thr Thr Pro Ser Lys Gln Ser Asn Asn Lys
180 185 190

Tyr Ala Ala Ser Ser Tyr Leu Ser Leu Thr Pro Glu Gln Trp Lys Ser
195 200 205

His Arg Ser Tyr Ser Cys Gln Val Thr His Glu Gly Ser Thr Val Glu
210 215 220

Lys Thr Val Ala Pro Thr Glu Cys Ser
225 230

<210> SEQ ID NO 46
<211> LENGTH: 233
<212> TYPE: PRT
<213> ORGANISM: Homo sapiens

<400> SEQUENCE: 46

Met Gly Trp Ser Cys Ile Ile Leu Phe Leu Val Ala Thr Ala Thr Gly
1 5 10 15

Val His Ser Ser Tyr Val Arg Pro Leu Ser Val Ala Leu Gly Glu Thr
20 25 30

Ala Arg Ile Ser Cys Gly Arg Gln Ala Leu Gly Ser Arg Ala Val Gln
35 40 45

Trp Tyr Gln His Arg Pro Gly Gln Ala Pro Ile Leu Leu Ile Tyr Asn
50 55 60

Asn Gln Asp Arg Pro Ser Gly Ile Pro Glu Arg Phe Ser Gly Thr Pro
65 70 75 80

Asp Ile Asn Phe Gly Thr Arg Ala Thr Leu Thr Ile Ser Gly Val Glu
85 90 95

Ala Gly Asp Glu Ala Asp Tyr Tyr Cys His Met Trp Asp Ser Arg Ser
100 105 110

Gly Phe Ser Trp Ser Phe Gly Gly Ala Thr Arg Leu Thr Val Leu Gly
115 120 125

Gln Pro Lys Ala Ala Pro Ser Val Thr Leu Phe Pro Pro Ser Ser Glu
130 135 140

Glu Leu Gln Ala Asn Lys Ala Thr Leu Val Cys Leu Ile Ser Asp Phe
145 150 155 160

Tyr Pro Gly Ala Val Thr Val Ala Trp Lys Ala Asp Ser Ser Pro Val
165 170 175

Lys Ala Gly Val Glu Thr Thr Thr Pro Ser Lys Gln Ser Asn Asn Lys
180 185 190

Tyr Ala Ala Ser Ser Tyr Leu Ser Leu Thr Pro Glu Gln Trp Lys Ser
195 200 205

His Arg Ser Tyr Ser Cys Gln Val Thr His Glu Gly Ser Thr Val Glu
210 215 220

Lys Thr Val Ala Pro Thr Glu Cys Ser
225 230

```
<210> SEQ ID NO 47
<211> LENGTH: 233
<212> TYPE: PRT
<213> ORGANISM: Homo sapiens

<400> SEQUENCE: 47

Met Gly Trp Ser Cys Ile Ile Leu Phe Leu Val Ala Thr Ala Thr Gly
1               5                   10                  15

Val His Ser Ser Pro Val Arg Pro Leu Ser Val Ala Leu Gly Glu Thr
            20                  25                  30

Ala Arg Ile Ser Cys Gly Arg Gln Ala Leu Gly Ser Arg Ala Val Gln
        35                  40                  45

Trp Tyr Gln His Arg Pro Gly Gln Ala Pro Ile Leu Leu Ile Tyr Asn
    50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Gly Ala Thr Arg Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 48
<211> LENGTH: 481
<212> TYPE: PRT
<213> ORGANISM: Homo sapiens

<400> SEQUENCE: 48

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Val Ile Ser Arg Asp Thr Ser Lys Asn Gln
                85                  90                  95

Leu Ser Leu Lys Leu Asn Ser Val Thr Pro Ala Asp Thr Ala Val Tyr
```

```
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys
```

<210> SEQ ID NO 49
<211> LENGTH: 481
<212> TYPE: PRT
<213> ORGANISM: Homo sapiens

<400> SEQUENCE: 49

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Val Ile Ser Arg Asp Thr Ser Lys Asn Gln
                85                  90                  95

Leu Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

```
Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys


<210> SEQ ID NO 50
<211> LENGTH: 481
<212> TYPE: PRT
<213> ORGANISM: Homo sapiens

<400> SEQUENCE: 50

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Val Ile Ser Arg Asp Thr Ser Lys Asn Gln
                85                  90                  95

Leu Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300
```

Pro Glu Val Lys Phe Asn Trp Tyr Val Asp Gly Val Glu Val His Asn
305 310 315 320

Ala Lys Thr Lys Pro Arg Glu Glu Gln Tyr Asn Ser Thr Tyr Arg Val
325 330 335

Val Ser Val Leu Thr Val Leu His Gln Asp Trp Leu Asn Gly Lys Glu
340 345 350

Tyr Lys Cys Lys Val Ser Asn Lys Ala Leu Pro Ala Pro Ile Glu Lys
355 360 365

Thr Ile Ser Lys Ala Lys Gly Gln Pro Arg Glu Pro Gln Val Tyr Thr
370 375 380

Leu Pro Pro Ser Arg Asp Glu Leu Thr Lys Asn Gln Val Ser Leu Thr
385 390 395 400

Cys Leu Val Lys Gly Phe Tyr Pro Ser Asp Ile Ala Val Glu Trp Glu
405 410 415

Ser Asn Gly Gln Pro Glu Asn Asn Tyr Lys Thr Thr Pro Pro Val Leu
420 425 430

Asp Ser Asp Gly Ser Phe Phe Leu Tyr Ser Lys Leu Thr Val Asp Lys
435 440 445

Ser Arg Trp Gln Gln Gly Asn Val Phe Ser Cys Ser Val Leu His Glu
450 455 460

Ala Leu His Ser His Tyr Thr Gln Lys Ser Leu Ser Leu Ser Pro Gly
465 470 475 480

Lys

<210> SEQ ID NO 51
<211> LENGTH: 481
<212> TYPE: PRT
<213> ORGANISM: Homo sapiens

<400> SEQUENCE: 51

Met Gly Trp Ser Cys Ile Ile Leu Phe Leu Val Ala Thr Ala Thr Gly
1 5 10 15

Val His Ser Gln Val Gln Leu Gln Glu Ser Gly Pro Gly Leu Val Lys
20 25 30

Pro Ser Glu Thr Leu Ser Val Thr Cys Ser Val Ser Gly Asp Ser Met
35 40 45

Asn Asn Tyr Tyr Trp Thr Trp Ile Arg Gln Ser Pro Gly Lys Gly Leu
50 55 60

Glu Trp Ile Gly Tyr Ile Ser Asp Arg Glu Ser Ala Thr Tyr Asn Pro
65 70 75 80

Ser Leu Asn Ser Arg Val Val Ile Ser Arg Asp Thr Ser Lys Asn Gln
85 90 95

Leu Ser Leu Lys Leu Asn Ser Val Thr Pro Ala Asp Thr Ala Val Tyr
100 105 110

Tyr Cys Ala Thr Ala Arg Arg Gly Gln Arg Ile Tyr Gly Val Val Ser
115 120 125

Phe Gly Glu Phe Phe Tyr Tyr Tyr Ser Met Asp Val Trp Gly Lys Gly
130 135 140

Thr Thr Val Thr Val Ser Ser Ala Ser Thr Lys Gly Pro Ser Val Phe
145 150 155 160

Pro Leu Ala Pro Ser Ser Lys Ser Thr Ser Gly Gly Thr Ala Ala Leu
165 170 175

Gly Cys Leu Val Lys Asp Tyr Phe Pro Glu Pro Val Thr Val Ser Trp
180 185 190

```
Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys


<210> SEQ ID NO 52
<211> LENGTH: 481
<212> TYPE: PRT
<213> ORGANISM: Homo sapiens

<400> SEQUENCE: 52

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80
```

```
Ser Leu Asn Ser Arg Val Val Ile Ser Arg Asp Thr Ser Lys Asn Gln
                85                  90                  95

Leu Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys
```

<210> SEQ ID NO 53
<211> LENGTH: 481
<212> TYPE: PRT
<213> ORGANISM: Homo sapiens

<400> SEQUENCE: 53

```
Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Val Ile Ser Arg Asp Thr Ser Lys Asn Gln
                85                  90                  95

Leu Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380
```

Leu Pro Pro Ser Arg Asp Glu Leu Thr Lys Asn Gln Val Ser Leu Thr
385 390 395 400

Cys Leu Val Lys Gly Phe Tyr Pro Ser Asp Ile Ala Val Glu Trp Glu
405 410 415

Ser Asn Gly Gln Pro Glu Asn Asn Tyr Lys Thr Thr Pro Pro Val Leu
420 425 430

Asp Ser Asp Gly Ser Phe Phe Leu Tyr Ser Lys Leu Thr Val Asp Lys
435 440 445

Ser Arg Trp Gln Gln Gly Asn Val Phe Ser Cys Ser Val Leu His Glu
450 455 460

Ala Leu His Ser His Tyr Thr Gln Lys Ser Leu Ser Leu Ser Pro Gly
465 470 475 480

Lys

<210> SEQ ID NO 54
<211> LENGTH: 481
<212> TYPE: PRT
<213> ORGANISM: Homo sapiens

<400> SEQUENCE: 54

Met Gly Trp Ser Cys Ile Ile Leu Phe Leu Val Ala Thr Ala Thr Gly
1 5 10 15

Val His Ser Gln Val Gln Leu Gln Glu Ser Gly Pro Gly Leu Val Lys
20 25 30

Pro Ser Glu Thr Leu Ser Val Thr Cys Ser Val Ser Gly Asp Ser Met
35 40 45

Asn Asn Tyr Tyr Trp Thr Trp Ile Arg Gln Ser Pro Gly Lys Gly Leu
50 55 60

Glu Trp Ile Gly Tyr Ile Ser Asp Arg Glu Ser Ala Thr Tyr Asn Pro
65 70 75 80

Ser Leu Asn Ser Arg Val Val Ile Ser Arg Asp Thr Ser Lys Asn Gln
85 90 95

Leu Ser Leu Lys Leu Asn Ser Val Thr Pro Ala Asp Thr Ala Val Tyr
100 105 110

Tyr Cys Ala Thr Ala Arg Arg Gly Gln Arg Ile Tyr Gly Val Val Ser
115 120 125

Phe Gly Glu Phe Phe Tyr Tyr Tyr Ser Met Asp Val Trp Gly Lys Gly
130 135 140

Thr Thr Val Thr Val Ser Ser Ala Ser Thr Lys Gly Pro Ser Val Phe
145 150 155 160

Pro Leu Ala Pro Ser Ser Lys Ser Thr Ser Gly Gly Thr Ala Ala Leu
165 170 175

Gly Cys Leu Val Lys Asp Tyr Phe Pro Glu Pro Val Thr Val Ser Trp
180 185 190

Asn Ser Gly Ala Leu Thr Ser Gly Val His Thr Phe Pro Ala Val Leu
195 200 205

Gln Ser Ser Gly Leu Tyr Ser Leu Ser Ser Val Val Thr Val Pro Ser
210 215 220

Ser Ser Leu Gly Thr Gln Thr Tyr Ile Cys Asn Val Asn His Lys Pro
225 230 235 240

Ser Asn Thr Lys Val Asp Lys Lys Val Glu Pro Lys Ser Cys Asp Lys
245 250 255

Thr His Thr Cys Pro Pro Cys Pro Ala Pro Glu Leu Leu Gly Gly Pro
260 265 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys

<210> SEQ ID NO 55
<211> LENGTH: 481
<212> TYPE: PRT
<213> ORGANISM: Homo sapiens

<400> SEQUENCE: 55

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Val Ile Ser Arg Asp Thr Ser Lys Asn Gln
                85                  90                  95

Leu Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

```
Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys
```

<210> SEQ ID NO 56
<211> LENGTH: 481
<212> TYPE: PRT
<213> ORGANISM: Homo sapiens

<400> SEQUENCE: 56

```
Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45
```

```
Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Val Ile Ser Arg Asp Thr Ser Lys Asn Gln
                85                  90                  95

Leu Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
```

465 470 475 480

Lys

<210> SEQ ID NO 57
<211> LENGTH: 481
<212> TYPE: PRT
<213> ORGANISM: Homo sapiens

<400> SEQUENCE: 57

Met Gly Trp Ser Cys Ile Ile Leu Phe Leu Val Ala Thr Ala Thr Gly
1 5 10 15

Val His Ser Gln Val Gln Leu Gln Glu Ser Gly Pro Gly Leu Val Lys
20 25 30

Pro Ser Glu Thr Leu Ser Val Thr Cys Ser Val Ser Gly Asp Ser Met
35 40 45

Asn Asn Tyr Tyr Trp Thr Trp Ile Arg Gln Ser Pro Gly Lys Gly Leu
50 55 60

Glu Trp Ile Gly Tyr Ile Ser Asp Arg Glu Ser Ala Thr Tyr Asn Pro
65 70 75 80

Ser Leu Asn Ser Arg Val Val Ile Ser Arg Asp Thr Ser Lys Asn Gln
85 90 95

Leu Ser Leu Lys Leu Asn Ser Val Thr Pro Ala Asp Thr Ala Val Tyr
100 105 110

Tyr Cys Ala Thr Ala Arg Arg Gly Gln Arg Ile Tyr Gly Val Val Ser
115 120 125

Phe Gly Glu Phe Phe Tyr Tyr Tyr Ser Met Asp Val Trp Gly Lys Gly
130 135 140

Thr Thr Val Thr Val Ser Ser Ala Ser Thr Lys Gly Pro Ser Val Phe
145 150 155 160

Pro Leu Ala Pro Ser Ser Lys Ser Thr Ser Gly Gly Thr Ala Ala Leu
165 170 175

Gly Cys Leu Val Lys Asp Tyr Phe Pro Glu Pro Val Thr Val Ser Trp
180 185 190

Asn Ser Gly Ala Leu Thr Ser Gly Val His Thr Phe Pro Ala Val Leu
195 200 205

Gln Ser Ser Gly Leu Tyr Ser Leu Ser Ser Val Val Thr Val Pro Ser
210 215 220

Ser Ser Leu Gly Thr Gln Thr Tyr Ile Cys Asn Val Asn His Lys Pro
225 230 235 240

Ser Asn Thr Lys Val Asp Lys Lys Val Glu Pro Lys Ser Cys Asp Lys
245 250 255

Thr His Thr Cys Pro Pro Cys Pro Ala Pro Glu Leu Leu Gly Gly Pro
260 265 270

Ser Val Phe Leu Phe Pro Pro Lys Pro Lys Asp Thr Leu Met Ile Ser
275 280 285

Arg Thr Pro Glu Val Thr Cys Val Val Val Asp Val Ser His Glu Asp
290 295 300

Pro Glu Val Lys Phe Asn Trp Tyr Val Asp Gly Val Glu Val His Asn
305 310 315 320

Ala Lys Thr Lys Pro Arg Glu Glu Gln Tyr Asn Ser Thr Tyr Arg Val
325 330 335

Val Ser Val Leu Thr Val Leu His Gln Asp Trp Leu Asn Gly Lys Glu
340 345 350

Tyr Lys Cys Lys Val Ser Asn Lys Ala Leu Pro Ala Pro Ile Glu Lys

```
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys


<210> SEQ ID NO 58
<211> LENGTH: 481
<212> TYPE: PRT
<213> ORGANISM: Homo sapiens

<400> SEQUENCE: 58

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Val Ile Ser Arg Asp Thr Ser Lys Asn Gln
                85                  90                  95

Leu Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
```

245 250 255

Thr His Thr Cys Pro Pro Cys Pro Ala Pro Glu Leu Leu Gly Gly Pro
260 265 270

Ser Val Phe Leu Phe Pro Pro Lys Pro Lys Asp Thr Leu Met Ile Ser
275 280 285

Arg Thr Pro Glu Val Thr Cys Val Val Val Asp Val Ser His Glu Asp
290 295 300

Pro Glu Val Lys Phe Asn Trp Tyr Val Asp Gly Val Glu Val His Asn
305 310 315 320

Ala Lys Thr Lys Pro Arg Glu Glu Gln Tyr Asn Ser Thr Tyr Arg Val
325 330 335

Val Ser Val Leu Thr Val Leu His Gln Asp Trp Leu Asn Gly Lys Glu
340 345 350

Tyr Lys Cys Lys Val Ser Asn Lys Ala Leu Pro Ala Pro Ile Glu Lys
355 360 365

Thr Ile Ser Lys Ala Lys Gly Gln Pro Arg Glu Pro Gln Val Tyr Thr
370 375 380

Leu Pro Pro Ser Arg Asp Glu Leu Thr Lys Asn Gln Val Ser Leu Thr
385 390 395 400

Cys Leu Val Lys Gly Phe Tyr Pro Ser Asp Ile Ala Val Glu Trp Glu
405 410 415

Ser Asn Gly Gln Pro Glu Asn Asn Tyr Lys Thr Thr Pro Pro Val Leu
420 425 430

Asp Ser Asp Gly Ser Phe Phe Leu Tyr Ser Lys Leu Thr Val Asp Lys
435 440 445

Ser Arg Trp Gln Gln Gly Asn Val Phe Ser Cys Ser Val Leu His Glu
450 455 460

Ala Leu His Ser His Tyr Thr Gln Lys Ser Leu Ser Leu Ser Pro Gly
465 470 475 480

Lys

<210> SEQ ID NO 59
<211> LENGTH: 481
<212> TYPE: PRT
<213> ORGANISM: Homo sapiens

<400> SEQUENCE: 59

Met Gly Trp Ser Cys Ile Ile Leu Phe Leu Val Ala Thr Ala Thr Gly
1 5 10 15

Val His Ser Gln Val Gln Leu Gln Glu Ser Gly Pro Gly Leu Val Lys
20 25 30

Pro Ser Glu Thr Leu Ser Val Thr Cys Ser Val Ser Gly Asp Ser Met
35 40 45

Asn Asn Tyr Tyr Trp Thr Trp Ile Arg Gln Ser Pro Gly Lys Gly Leu
50 55 60

Glu Trp Ile Gly Tyr Ile Ser Asp Arg Glu Ser Ala Thr Tyr Asn Pro
65 70 75 80

Ser Leu Asn Ser Arg Val Val Ile Ser Arg Asp Thr Ser Lys Asn Gln
85 90 95

Leu Ser Leu Lys Leu Asn Ser Val Thr Pro Ala Asp Thr Ala Val Tyr
100 105 110

Tyr Cys Ala Thr Ala Arg Arg Gly Gln Arg Ile Tyr Gly Val Val Ser
115 120 125

Phe Gly Glu Phe Phe Tyr Tyr Tyr Ser Met Asp Val Trp Gly Lys Gly

```
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys


<210> SEQ ID NO 60
<211> LENGTH: 481
<212> TYPE: PRT
<213> ORGANISM: Homo sapiens

<400> SEQUENCE: 60

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
```

```
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Val Ile Ser Arg Asp Thr Ser Lys Asn Gln
                85                  90                  95

Leu Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445
```

Ser Arg Trp Gln Gln Gly Asn Val Phe Ser Cys Ser Val Leu His Glu
450 455 460

Ala Leu His Ser His Tyr Thr Gln Lys Ser Leu Ser Leu Ser Pro Gly
465 470 475 480

Lys

<210> SEQ ID NO 61
<211> LENGTH: 481
<212> TYPE: PRT
<213> ORGANISM: Homo sapiens

<400> SEQUENCE: 61

Met Gly Trp Ser Cys Ile Ile Leu Phe Leu Val Ala Thr Ala Thr Gly
1 5 10 15

Val His Ser Gln Val Gln Leu Gln Glu Ser Gly Pro Gly Leu Val Lys
20 25 30

Pro Ser Glu Thr Leu Ser Val Thr Cys Ser Val Ser Gly Gly Ser Met
35 40 45

Asn Asn Tyr Tyr Trp Thr Trp Ile Arg Gln Ser Pro Gly Lys Gly Leu
50 55 60

Glu Trp Ile Gly Tyr Ile Ser Asp Arg Glu Ser Ala Thr Tyr Asn Pro
65 70 75 80

Ser Leu Asn Ser Arg Val Val Ile Ser Arg Asp Thr Ser Lys Asn Gln
85 90 95

Leu Ser Leu Lys Leu Asn Ser Val Thr Pro Ala Asp Thr Ala Val Tyr
100 105 110

Tyr Cys Ala Thr Ala Arg Arg Gly Gln Arg Ile Tyr Gly Val Val Ser
115 120 125

Phe Gly Glu Phe Phe Tyr Tyr Tyr Ser Met Asp Val Trp Gly Lys Gly
130 135 140

Thr Thr Val Thr Val Ser Ser Ala Ser Thr Lys Gly Pro Ser Val Phe
145 150 155 160

Pro Leu Ala Pro Ser Ser Lys Ser Thr Ser Gly Gly Thr Ala Ala Leu
165 170 175

Gly Cys Leu Val Lys Asp Tyr Phe Pro Glu Pro Val Thr Val Ser Trp
180 185 190

Asn Ser Gly Ala Leu Thr Ser Gly Val His Thr Phe Pro Ala Val Leu
195 200 205

Gln Ser Ser Gly Leu Tyr Ser Leu Ser Ser Val Val Thr Val Pro Ser
210 215 220

Ser Ser Leu Gly Thr Gln Thr Tyr Ile Cys Asn Val Asn His Lys Pro
225 230 235 240

Ser Asn Thr Lys Val Asp Lys Lys Val Glu Pro Lys Ser Cys Asp Lys
245 250 255

Thr His Thr Cys Pro Pro Cys Pro Ala Pro Glu Leu Leu Gly Gly Pro
260 265 270

Ser Val Phe Leu Phe Pro Pro Lys Pro Lys Asp Thr Leu Met Ile Ser
275 280 285

Arg Thr Pro Glu Val Thr Cys Val Val Val Asp Val Ser His Glu Asp
290 295 300

Pro Glu Val Lys Phe Asn Trp Tyr Val Asp Gly Val Glu Val His Asn
305 310 315 320

Ala Lys Thr Lys Pro Arg Glu Glu Gln Tyr Asn Ser Thr Tyr Arg Val
325 330 335

Val Ser Val Leu Thr Val Leu His Gln Asp Trp Leu Asn Gly Lys Glu
340 345 350

Tyr Lys Cys Lys Val Ser Asn Lys Ala Leu Pro Ala Pro Ile Glu Lys
355 360 365

Thr Ile Ser Lys Ala Lys Gly Gln Pro Arg Glu Pro Gln Val Tyr Thr
370 375 380

Leu Pro Pro Ser Arg Asp Glu Leu Thr Lys Asn Gln Val Ser Leu Thr
385 390 395 400

Cys Leu Val Lys Gly Phe Tyr Pro Ser Asp Ile Ala Val Glu Trp Glu
405 410 415

Ser Asn Gly Gln Pro Glu Asn Asn Tyr Lys Thr Thr Pro Pro Val Leu
420 425 430

Asp Ser Asp Gly Ser Phe Phe Leu Tyr Ser Lys Leu Thr Val Asp Lys
435 440 445

Ser Arg Trp Gln Gln Gly Asn Val Phe Ser Cys Ser Val Leu His Glu
450 455 460

Ala Leu His Ser His Tyr Thr Gln Lys Ser Leu Ser Leu Ser Pro Gly
465 470 475 480

Lys

<210> SEQ ID NO 62
<211> LENGTH: 481
<212> TYPE: PRT
<213> ORGANISM: Homo sapiens

<400> SEQUENCE: 62

Met Gly Trp Ser Cys Ile Ile Leu Phe Leu Val Ala Thr Ala Thr Gly
1 5 10 15

Val His Ser Gln Val Gln Leu Gln Glu Ser Gly Pro Gly Leu Val Lys
20 25 30

Pro Ser Glu Thr Leu Ser Val Thr Cys Ser Val Ser Gly Asp Ser Met
35 40 45

Asn Asn Tyr Tyr Trp Thr Trp Ile Arg Gln Pro Pro Gly Lys Gly Leu
50 55 60

Glu Trp Ile Gly Tyr Ile Ser Asp Arg Glu Ser Ala Thr Tyr Asn Pro
65 70 75 80

Ser Leu Asn Ser Arg Val Val Ile Ser Arg Asp Thr Ser Lys Asn Gln
85 90 95

Leu Ser Leu Lys Leu Asn Ser Val Thr Pro Ala Asp Thr Ala Val Tyr
100 105 110

Tyr Cys Ala Thr Ala Arg Arg Gly Gln Arg Ile Tyr Gly Val Val Ser
115 120 125

Phe Gly Glu Phe Phe Tyr Tyr Tyr Ser Met Asp Val Trp Gly Lys Gly
130 135 140

Thr Thr Val Thr Val Ser Ser Ala Ser Thr Lys Gly Pro Ser Val Phe
145 150 155 160

Pro Leu Ala Pro Ser Ser Lys Ser Thr Ser Gly Gly Thr Ala Ala Leu
165 170 175

Gly Cys Leu Val Lys Asp Tyr Phe Pro Glu Pro Val Thr Val Ser Trp
180 185 190

Asn Ser Gly Ala Leu Thr Ser Gly Val His Thr Phe Pro Ala Val Leu
195 200 205

Gln Ser Ser Gly Leu Tyr Ser Leu Ser Ser Val Val Thr Val Pro Ser
210 215 220

```
Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys
```

<210> SEQ ID NO 63
<211> LENGTH: 481
<212> TYPE: PRT
<213> ORGANISM: Homo sapiens

<400> SEQUENCE: 63

```
Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Thr Ile Ser Arg Asp Thr Ser Lys Asn Gln
                85                  90                  95

Leu Ser Leu Lys Leu Asn Ser Val Thr Pro Ala Asp Thr Ala Val Tyr
            100                 105                 110
```

```
Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys
```

<210> SEQ ID NO 64
<211> LENGTH: 481
<212> TYPE: PRT
<213> ORGANISM: Homo sapiens

<400> SEQUENCE: 64

```
Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Val Ile Ser Val Asp Thr Ser Lys Asn Gln
                85                  90                  95

Leu Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415
```

Ser Asn Gly Gln Pro Glu Asn Asn Tyr Lys Thr Thr Pro Pro Val Leu
420 425 430

Asp Ser Asp Gly Ser Phe Phe Leu Tyr Ser Lys Leu Thr Val Asp Lys
435 440 445

Ser Arg Trp Gln Gln Gly Asn Val Phe Ser Cys Ser Val Leu His Glu
450 455 460

Ala Leu His Ser His Tyr Thr Gln Lys Ser Leu Ser Leu Ser Pro Gly
465 470 475 480

Lys

<210> SEQ ID NO 65
<211> LENGTH: 481
<212> TYPE: PRT
<213> ORGANISM: Homo sapiens

<400> SEQUENCE: 65

Met Gly Trp Ser Cys Ile Ile Leu Phe Leu Val Ala Thr Ala Thr Gly
1 5 10 15

Val His Ser Gln Val Gln Leu Gln Glu Ser Gly Pro Gly Leu Val Lys
20 25 30

Pro Ser Glu Thr Leu Ser Val Thr Cys Ser Val Ser Gly Asp Ser Met
35 40 45

Asn Asn Tyr Tyr Trp Thr Trp Ile Arg Gln Ser Pro Gly Lys Gly Leu
50 55 60

Glu Trp Ile Gly Tyr Ile Ser Asp Arg Glu Ser Ala Thr Tyr Asn Pro
65 70 75 80

Ser Leu Asn Ser Arg Val Val Ile Ser Arg Asp Thr Ser Lys Asn Gln
85 90 95

Phe Ser Leu Lys Leu Asn Ser Val Thr Pro Ala Asp Thr Ala Val Tyr
100 105 110

Tyr Cys Ala Thr Ala Arg Arg Gly Gln Arg Ile Tyr Gly Val Val Ser
115 120 125

Phe Gly Glu Phe Phe Tyr Tyr Tyr Ser Met Asp Val Trp Gly Lys Gly
130 135 140

Thr Thr Val Thr Val Ser Ser Ala Ser Thr Lys Gly Pro Ser Val Phe
145 150 155 160

Pro Leu Ala Pro Ser Ser Lys Ser Thr Ser Gly Gly Thr Ala Ala Leu
165 170 175

Gly Cys Leu Val Lys Asp Tyr Phe Pro Glu Pro Val Thr Val Ser Trp
180 185 190

Asn Ser Gly Ala Leu Thr Ser Gly Val His Thr Phe Pro Ala Val Leu
195 200 205

Gln Ser Ser Gly Leu Tyr Ser Leu Ser Ser Val Val Thr Val Pro Ser
210 215 220

Ser Ser Leu Gly Thr Gln Thr Tyr Ile Cys Asn Val Asn His Lys Pro
225 230 235 240

Ser Asn Thr Lys Val Asp Lys Lys Val Glu Pro Lys Ser Cys Asp Lys
245 250 255

Thr His Thr Cys Pro Pro Cys Pro Ala Pro Glu Leu Leu Gly Gly Pro
260 265 270

Ser Val Phe Leu Phe Pro Pro Lys Pro Lys Asp Thr Leu Met Ile Ser
275 280 285

Arg Thr Pro Glu Val Thr Cys Val Val Val Asp Val Ser His Glu Asp
290 295 300

Pro Glu Val Lys Phe Asn Trp Tyr Val Asp Gly Val Glu Val His Asn
305 310 315 320

Ala Lys Thr Lys Pro Arg Glu Glu Gln Tyr Asn Ser Thr Tyr Arg Val
325 330 335

Val Ser Val Leu Thr Val Leu His Gln Asp Trp Leu Asn Gly Lys Glu
340 345 350

Tyr Lys Cys Lys Val Ser Asn Lys Ala Leu Pro Ala Pro Ile Glu Lys
355 360 365

Thr Ile Ser Lys Ala Lys Gly Gln Pro Arg Glu Pro Gln Val Tyr Thr
370 375 380

Leu Pro Pro Ser Arg Asp Glu Leu Thr Lys Asn Gln Val Ser Leu Thr
385 390 395 400

Cys Leu Val Lys Gly Phe Tyr Pro Ser Asp Ile Ala Val Glu Trp Glu
405 410 415

Ser Asn Gly Gln Pro Glu Asn Asn Tyr Lys Thr Thr Pro Pro Val Leu
420 425 430

Asp Ser Asp Gly Ser Phe Phe Leu Tyr Ser Lys Leu Thr Val Asp Lys
435 440 445

Ser Arg Trp Gln Gln Gly Asn Val Phe Ser Cys Ser Val Leu His Glu
450 455 460

Ala Leu His Ser His Tyr Thr Gln Lys Ser Leu Ser Leu Ser Pro Gly
465 470 475 480

Lys

<210> SEQ ID NO 66
<211> LENGTH: 481
<212> TYPE: PRT
<213> ORGANISM: Homo sapiens

<400> SEQUENCE: 66

Met Gly Trp Ser Cys Ile Ile Leu Phe Leu Val Ala Thr Ala Thr Gly
1 5 10 15

Val His Ser Gln Val Gln Leu Gln Glu Ser Gly Pro Gly Leu Val Lys
20 25 30

Pro Ser Glu Thr Leu Ser Val Thr Cys Ser Val Ser Gly Asp Ser Met
35 40 45

Asn Asn Tyr Tyr Trp Thr Trp Ile Arg Gln Ser Pro Gly Lys Gly Leu
50 55 60

Glu Trp Ile Gly Tyr Ile Ser Asp Arg Glu Ser Ala Thr Tyr Asn Pro
65 70 75 80

Ser Leu Asn Ser Arg Val Val Ile Ser Arg Asp Thr Ser Lys Asn Gln
85 90 95

Leu Ser Leu Lys Leu Asn Ser Val Thr Pro Ala Asp Thr Ala Val Tyr
100 105 110

Tyr Cys Ala Arg Ala Arg Arg Gly Gln Arg Ile Tyr Gly Val Val Ser
115 120 125

Phe Gly Glu Phe Phe Tyr Tyr Tyr Ser Met Asp Val Trp Gly Lys Gly
130 135 140

Thr Thr Val Thr Val Ser Ser Ala Ser Thr Lys Gly Pro Ser Val Phe
145 150 155 160

Pro Leu Ala Pro Ser Ser Lys Ser Thr Ser Gly Gly Thr Ala Ala Leu
165 170 175

Gly Cys Leu Val Lys Asp Tyr Phe Pro Glu Pro Val Thr Val Ser Trp
180 185 190

```
Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys
```

<210> SEQ ID NO 67
<211> LENGTH: 481
<212> TYPE: PRT
<213> ORGANISM: Homo sapiens

<400> SEQUENCE: 67

```
Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80
```

```
Ser Leu Asn Ser Arg Val Val Ile Ser Arg Asp Thr Ser Lys Asn Gln
                85                  90                  95

Leu Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Gln Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys
```

<210> SEQ ID NO 68

<211> LENGTH: 481
<212> TYPE: PRT
<213> ORGANISM: Homo sapiens

<400> SEQUENCE: 68

```
Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Gln Ser Arg Val Val Ile Ser Arg Asp Thr Ser Lys Asn Gln
                85                  90                  95

Leu Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
```

385 390 395 400

Cys Leu Val Lys Gly Phe Tyr Pro Ser Asp Ile Ala Val Glu Trp Glu
405 410 415

Ser Asn Gly Gln Pro Glu Asn Asn Tyr Lys Thr Thr Pro Pro Val Leu
420 425 430

Asp Ser Asp Gly Ser Phe Phe Leu Tyr Ser Lys Leu Thr Val Asp Lys
435 440 445

Ser Arg Trp Gln Gln Gly Asn Val Phe Ser Cys Ser Val Leu His Glu
450 455 460

Ala Leu His Ser His Tyr Thr Gln Lys Ser Leu Ser Leu Ser Pro Gly
465 470 475 480

Lys

<210> SEQ ID NO 69
<211> LENGTH: 481
<212> TYPE: PRT
<213> ORGANISM: Homo sapiens

<400> SEQUENCE: 69

Met Gly Trp Ser Cys Ile Ile Leu Phe Leu Val Ala Thr Ala Thr Gly
1 5 10 15

Val His Ser Gln Val Gln Leu Gln Glu Ser Gly Pro Gly Leu Val Lys
20 25 30

Pro Ser Glu Thr Leu Ser Val Thr Cys Ser Val Ser Gly Asp Ser Met
35 40 45

Asn Asn Tyr Tyr Trp Thr Trp Ile Arg Gln Ser Pro Gly Lys Gly Leu
50 55 60

Glu Trp Ile Gly Tyr Ile Ser Asp Arg Glu Ser Ala Thr Tyr Asn Pro
65 70 75 80

Ser Leu Asn Ser Arg Val Val Ile Ser Val Asp Thr Ser Lys Asn Gln
85 90 95

Leu Ser Leu Lys Leu Asn Ser Val Thr Pro Ala Asp Thr Ala Val Tyr
100 105 110

Tyr Cys Ala Arg Ala Arg Arg Gly Gln Arg Ile Tyr Gly Val Val Ser
115 120 125

Phe Gly Glu Phe Phe Tyr Tyr Tyr Ser Met Asp Val Trp Gly Lys Gly
130 135 140

Thr Thr Val Thr Val Ser Ser Ala Ser Thr Lys Gly Pro Ser Val Phe
145 150 155 160

Pro Leu Ala Pro Ser Ser Lys Ser Thr Ser Gly Gly Thr Ala Ala Leu
165 170 175

Gly Cys Leu Val Lys Asp Tyr Phe Pro Glu Pro Val Thr Val Ser Trp
180 185 190

Asn Ser Gly Ala Leu Thr Ser Gly Val His Thr Phe Pro Ala Val Leu
195 200 205

Gln Ser Ser Gly Leu Tyr Ser Leu Ser Ser Val Val Thr Val Pro Ser
210 215 220

Ser Ser Leu Gly Thr Gln Thr Tyr Ile Cys Asn Val Asn His Lys Pro
225 230 235 240

Ser Asn Thr Lys Val Asp Lys Lys Val Glu Pro Lys Ser Cys Asp Lys
245 250 255

Thr His Thr Cys Pro Pro Cys Pro Ala Pro Glu Leu Leu Gly Gly Pro
260 265 270

Ser Val Phe Leu Phe Pro Pro Lys Pro Lys Asp Thr Leu Met Ile Ser

```
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys


<210> SEQ ID NO 70
<211> LENGTH: 481
<212> TYPE: PRT
<213> ORGANISM: Homo sapiens

<400> SEQUENCE: 70

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Thr Ile Ser Arg Asp Thr Ser Lys Asn Gln
                85                  90                  95

Phe Ser Leu Lys Leu Asn Ser Val Thr Pro Ala Asp Thr Ala Val Tyr
            100                 105                 110

Tyr Cys Ala Arg Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
```

```
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys


<210> SEQ ID NO 71
<211> LENGTH: 481
<212> TYPE: PRT
<213> ORGANISM: Homo sapiens

<400> SEQUENCE: 71

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
```

```
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Thr Ile Ser Arg Asp Thr Ser Lys Asn Gln
                85                  90                  95

Phe Ser Leu Lys Leu Asn Ser Val Thr Pro Ala Asp Thr Ala Val Tyr
            100                 105                 110

Tyr Cys Ala Arg Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480
```

Lys

<210> SEQ ID NO 72
<211> LENGTH: 481
<212> TYPE: PRT
<213> ORGANISM: Homo sapiens

<400> SEQUENCE: 72

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Thr Ile Ser Arg Asp Thr Ser Lys Asn Gln
                85                  90                  95

Leu Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

```
Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys


<210> SEQ ID NO 73
<211> LENGTH: 481
<212> TYPE: PRT
<213> ORGANISM: Homo sapiens

<400> SEQUENCE: 73

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Val Ile Ser Val Asp Thr Ser Lys Asn Gln
                85                  90                  95

Leu Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255
```

```
Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys


<210> SEQ ID NO 74
<211> LENGTH: 481
<212> TYPE: PRT
<213> ORGANISM: Homo sapiens

<400> SEQUENCE: 74

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Val Ile Ser Arg Asp Thr Ser Lys Asn Gln
                85                  90                  95

Phe Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140
```

```
Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys


<210> SEQ ID NO 75
<211> LENGTH: 481
<212> TYPE: PRT
<213> ORGANISM: Homo sapiens

<400> SEQUENCE: 75

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30
```

```
Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Val Ile Ser Arg Asp Thr Ser Lys Asn Gln
                85                  90                  95

Leu Ser Leu Lys Leu Asn Ser Val Thr Pro Ala Asp Thr Ala Val Tyr
            100                 105                 110

Tyr Cys Ala Arg Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445
```

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys

<210> SEQ ID NO 76
<211> LENGTH: 481
<212> TYPE: PRT
<213> ORGANISM: Homo sapiens

<400> SEQUENCE: 76

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Thr Ile Ser Val Asp Thr Ser Lys Asn Gln
                85                  90                  95

Leu Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
340 345 350

Tyr Lys Cys Lys Val Ser Asn Lys Ala Leu Pro Ala Pro Ile Glu Lys
355 360 365

Thr Ile Ser Lys Ala Lys Gly Gln Pro Arg Glu Pro Gln Val Tyr Thr
370 375 380

Leu Pro Pro Ser Arg Asp Glu Leu Thr Lys Asn Gln Val Ser Leu Thr
385 390 395 400

Cys Leu Val Lys Gly Phe Tyr Pro Ser Asp Ile Ala Val Glu Trp Glu
405 410 415

Ser Asn Gly Gln Pro Glu Asn Asn Tyr Lys Thr Thr Pro Pro Val Leu
420 425 430

Asp Ser Asp Gly Ser Phe Phe Leu Tyr Ser Lys Leu Thr Val Asp Lys
435 440 445

Ser Arg Trp Gln Gln Gly Asn Val Phe Ser Cys Ser Val Leu His Glu
450 455 460

Ala Leu His Ser His Tyr Thr Gln Lys Ser Leu Ser Leu Ser Pro Gly
465 470 475 480

Lys

<210> SEQ ID NO 77
<211> LENGTH: 481
<212> TYPE: PRT
<213> ORGANISM: Homo sapiens

<400> SEQUENCE: 77

Met Gly Trp Ser Cys Ile Ile Leu Phe Leu Val Ala Thr Ala Thr Gly
1 5 10 15

Val His Ser Gln Val Gln Leu Gln Glu Ser Gly Pro Gly Leu Val Lys
20 25 30

Pro Ser Glu Thr Leu Ser Val Thr Cys Ser Val Ser Gly Asp Ser Met
35 40 45

Asn Asn Tyr Tyr Trp Thr Trp Ile Arg Gln Ser Pro Gly Lys Gly Leu
50 55 60

Glu Trp Ile Gly Tyr Ile Ser Asp Arg Glu Ser Ala Thr Tyr Asn Pro
65 70 75 80

Ser Leu Asn Ser Arg Val Thr Ile Ser Arg Asp Thr Ser Lys Asn Gln
85 90 95

Phe Ser Leu Lys Leu Asn Ser Val Thr Pro Ala Asp Thr Ala Val Tyr
100 105 110

Tyr Cys Ala Thr Ala Arg Arg Gly Gln Arg Ile Tyr Gly Val Val Ser
115 120 125

Phe Gly Glu Phe Phe Tyr Tyr Tyr Ser Met Asp Val Trp Gly Lys Gly
130 135 140

Thr Thr Val Thr Val Ser Ser Ala Ser Thr Lys Gly Pro Ser Val Phe
145 150 155 160

Pro Leu Ala Pro Ser Ser Lys Ser Thr Ser Gly Gly Thr Ala Ala Leu
165 170 175

Gly Cys Leu Val Lys Asp Tyr Phe Pro Glu Pro Val Thr Val Ser Trp
180 185 190

Asn Ser Gly Ala Leu Thr Ser Gly Val His Thr Phe Pro Ala Val Leu
195 200 205

Gln Ser Ser Gly Leu Tyr Ser Leu Ser Ser Val Val Thr Val Pro Ser
210 215 220

```
Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys


<210> SEQ ID NO 78
<211> LENGTH: 481
<212> TYPE: PRT
<213> ORGANISM: Homo sapiens

<400> SEQUENCE: 78

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Thr Ile Ser Arg Asp Thr Ser Lys Asn Gln
                85                  90                  95

Leu Ser Leu Lys Leu Asn Ser Val Thr Pro Ala Asp Thr Ala Val Tyr
            100                 105                 110
```

```
Tyr Cys Ala Arg Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys
```

<210> SEQ ID NO 79
<211> LENGTH: 481
<212> TYPE: PRT
<213> ORGANISM: Homo sapiens

<400> SEQUENCE: 79

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Val Ile Ser Val Asp Thr Ser Lys Asn Gln
                85                  90                  95

Phe Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu

```
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys


<210> SEQ ID NO 80
<211> LENGTH: 481
<212> TYPE: PRT
<213> ORGANISM: Homo sapiens

<400> SEQUENCE: 80

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Val Ile Ser Val Asp Thr Ser Lys Asn Gln
                85                  90                  95

Leu Ser Leu Lys Leu Asn Ser Val Thr Pro Ala Asp Thr Ala Val Tyr
            100                 105                 110

Tyr Cys Ala Arg Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
```

305 310 315 320

Ala Lys Thr Lys Pro Arg Glu Glu Gln Tyr Asn Ser Thr Tyr Arg Val
325 330 335

Val Ser Val Leu Thr Val Leu His Gln Asp Trp Leu Asn Gly Lys Glu
340 345 350

Tyr Lys Cys Lys Val Ser Asn Lys Ala Leu Pro Ala Pro Ile Glu Lys
355 360 365

Thr Ile Ser Lys Ala Lys Gly Gln Pro Arg Glu Pro Gln Val Tyr Thr
370 375 380

Leu Pro Pro Ser Arg Asp Glu Leu Thr Lys Asn Gln Val Ser Leu Thr
385 390 395 400

Cys Leu Val Lys Gly Phe Tyr Pro Ser Asp Ile Ala Val Glu Trp Glu
405 410 415

Ser Asn Gly Gln Pro Glu Asn Asn Tyr Lys Thr Thr Pro Pro Val Leu
420 425 430

Asp Ser Asp Gly Ser Phe Phe Leu Tyr Ser Lys Leu Thr Val Asp Lys
435 440 445

Ser Arg Trp Gln Gln Gly Asn Val Phe Ser Cys Ser Val Leu His Glu
450 455 460

Ala Leu His Ser His Tyr Thr Gln Lys Ser Leu Ser Leu Ser Pro Gly
465 470 475 480

Lys

<210> SEQ ID NO 81
<211> LENGTH: 481
<212> TYPE: PRT
<213> ORGANISM: Homo sapiens

<400> SEQUENCE: 81

Met Gly Trp Ser Cys Ile Ile Leu Phe Leu Val Ala Thr Ala Thr Gly
1 5 10 15

Val His Ser Gln Val Gln Leu Gln Glu Ser Gly Pro Gly Leu Val Lys
20 25 30

Pro Ser Glu Thr Leu Ser Val Thr Cys Ser Val Ser Gly Asp Ser Met
35 40 45

Asn Asn Tyr Tyr Trp Thr Trp Ile Arg Gln Ser Pro Gly Lys Gly Leu
50 55 60

Glu Trp Ile Gly Tyr Ile Ser Asp Arg Glu Ser Ala Thr Tyr Asn Pro
65 70 75 80

Ser Leu Asn Ser Arg Val Val Ile Ser Arg Asp Thr Ser Lys Asn Gln
85 90 95

Phe Ser Leu Lys Leu Asn Ser Val Thr Pro Ala Asp Thr Ala Val Tyr
100 105 110

Tyr Cys Ala Arg Ala Arg Arg Gly Gln Arg Ile Tyr Gly Val Val Ser
115 120 125

Phe Gly Glu Phe Phe Tyr Tyr Tyr Ser Met Asp Val Trp Gly Lys Gly
130 135 140

Thr Thr Val Thr Val Ser Ser Ala Ser Thr Lys Gly Pro Ser Val Phe
145 150 155 160

Pro Leu Ala Pro Ser Ser Lys Ser Thr Ser Gly Gly Thr Ala Ala Leu
165 170 175

Gly Cys Leu Val Lys Asp Tyr Phe Pro Glu Pro Val Thr Val Ser Trp
180 185 190

Asn Ser Gly Ala Leu Thr Ser Gly Val His Thr Phe Pro Ala Val Leu

```
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys


<210> SEQ ID NO 82
<211> LENGTH: 481
<212> TYPE: PRT
<213> ORGANISM: Homo sapiens

<400> SEQUENCE: 82

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Thr Ile Ser Val Asp Thr Ser Lys Asn Gln
```

```
                85                  90                  95

Leu Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys
```

<210> SEQ ID NO 83
<211> LENGTH: 481

<212> TYPE: PRT
<213> ORGANISM: Homo sapiens

<400> SEQUENCE: 83

Met Gly Trp Ser Cys Ile Ile Leu Phe Leu Val Ala Thr Ala Thr Gly
1 5 10 15

Val His Ser Gln Val Gln Leu Gln Glu Ser Gly Pro Gly Leu Val Lys
20 25 30

Pro Ser Glu Thr Leu Ser Val Thr Cys Ser Val Ser Gly Asp Ser Met
35 40 45

Asn Asn Tyr Tyr Trp Thr Trp Ile Arg Gln Ser Pro Gly Lys Gly Leu
50 55 60

Glu Trp Ile Gly Tyr Ile Ser Asp Arg Glu Ser Ala Thr Tyr Asn Pro
65 70 75 80

Ser Leu Asn Ser Arg Val Thr Ile Ser Arg Asp Thr Ser Lys Asn Gln
85 90 95

Phe Ser Leu Lys Leu Asn Ser Val Thr Pro Ala Asp Thr Ala Val Tyr
100 105 110

Tyr Cys Ala Thr Ala Arg Arg Gly Gln Arg Ile Tyr Gly Val Val Ser
115 120 125

Phe Gly Glu Phe Phe Tyr Tyr Tyr Ser Met Asp Val Trp Gly Lys Gly
130 135 140

Thr Thr Val Thr Val Ser Ser Ala Ser Thr Lys Gly Pro Ser Val Phe
145 150 155 160

Pro Leu Ala Pro Ser Ser Lys Ser Thr Ser Gly Gly Thr Ala Ala Leu
165 170 175

Gly Cys Leu Val Lys Asp Tyr Phe Pro Glu Pro Val Thr Val Ser Trp
180 185 190

Asn Ser Gly Ala Leu Thr Ser Gly Val His Thr Phe Pro Ala Val Leu
195 200 205

Gln Ser Ser Gly Leu Tyr Ser Leu Ser Ser Val Val Thr Val Pro Ser
210 215 220

Ser Ser Leu Gly Thr Gln Thr Tyr Ile Cys Asn Val Asn His Lys Pro
225 230 235 240

Ser Asn Thr Lys Val Asp Lys Lys Val Glu Pro Lys Ser Cys Asp Lys
245 250 255

Thr His Thr Cys Pro Pro Cys Pro Ala Pro Glu Leu Leu Gly Gly Pro
260 265 270

Ser Val Phe Leu Phe Pro Pro Lys Pro Lys Asp Thr Leu Met Ile Ser
275 280 285

Arg Thr Pro Glu Val Thr Cys Val Val Val Asp Val Ser His Glu Asp
290 295 300

Pro Glu Val Lys Phe Asn Trp Tyr Val Asp Gly Val Glu Val His Asn
305 310 315 320

Ala Lys Thr Lys Pro Arg Glu Glu Gln Tyr Asn Ser Thr Tyr Arg Val
325 330 335

Val Ser Val Leu Thr Val Leu His Gln Asp Trp Leu Asn Gly Lys Glu
340 345 350

Tyr Lys Cys Lys Val Ser Asn Lys Ala Leu Pro Ala Pro Ile Glu Lys
355 360 365

Thr Ile Ser Lys Ala Lys Gly Gln Pro Arg Glu Pro Gln Val Tyr Thr
370 375 380

Leu Pro Pro Ser Arg Asp Glu Leu Thr Lys Asn Gln Val Ser Leu Thr
385 390 395 400

Cys Leu Val Lys Gly Phe Tyr Pro Ser Asp Ile Ala Val Glu Trp Glu
405 410 415

Ser Asn Gly Gln Pro Glu Asn Asn Tyr Lys Thr Thr Pro Pro Val Leu
420 425 430

Asp Ser Asp Gly Ser Phe Phe Leu Tyr Ser Lys Leu Thr Val Asp Lys
435 440 445

Ser Arg Trp Gln Gln Gly Asn Val Phe Ser Cys Ser Val Leu His Glu
450 455 460

Ala Leu His Ser His Tyr Thr Gln Lys Ser Leu Ser Leu Ser Pro Gly
465 470 475 480

Lys

<210> SEQ ID NO 84
<211> LENGTH: 481
<212> TYPE: PRT
<213> ORGANISM: Homo sapiens

<400> SEQUENCE: 84

Met Gly Trp Ser Cys Ile Ile Leu Phe Leu Val Ala Thr Ala Thr Gly
1 5 10 15

Val His Ser Gln Val Gln Leu Gln Glu Ser Gly Pro Gly Leu Val Lys
20 25 30

Pro Ser Glu Thr Leu Ser Val Thr Cys Ser Val Ser Gly Asp Ser Met
35 40 45

Asn Asn Tyr Tyr Trp Thr Trp Ile Arg Gln Ser Pro Gly Lys Gly Leu
50 55 60

Glu Trp Ile Gly Tyr Ile Ser Asp Arg Glu Ser Ala Thr Tyr Asn Pro
65 70 75 80

Ser Leu Asn Ser Arg Val Thr Ile Ser Arg Asp Thr Ser Lys Asn Gln
85 90 95

Leu Ser Leu Lys Leu Asn Ser Val Thr Pro Ala Asp Thr Ala Val Tyr
100 105 110

Tyr Cys Ala Arg Ala Arg Arg Gly Gln Arg Ile Tyr Gly Val Val Ser
115 120 125

Phe Gly Glu Phe Phe Tyr Tyr Tyr Ser Met Asp Val Trp Gly Lys Gly
130 135 140

Thr Thr Val Thr Val Ser Ser Ala Ser Thr Lys Gly Pro Ser Val Phe
145 150 155 160

Pro Leu Ala Pro Ser Ser Lys Ser Thr Ser Gly Gly Thr Ala Ala Leu
165 170 175

Gly Cys Leu Val Lys Asp Tyr Phe Pro Glu Pro Val Thr Val Ser Trp
180 185 190

Asn Ser Gly Ala Leu Thr Ser Gly Val His Thr Phe Pro Ala Val Leu
195 200 205

Gln Ser Ser Gly Leu Tyr Ser Leu Ser Ser Val Val Thr Val Pro Ser
210 215 220

Ser Ser Leu Gly Thr Gln Thr Tyr Ile Cys Asn Val Asn His Lys Pro
225 230 235 240

Ser Asn Thr Lys Val Asp Lys Lys Val Glu Pro Lys Ser Cys Asp Lys
245 250 255

Thr His Thr Cys Pro Pro Cys Pro Ala Pro Glu Leu Leu Gly Gly Pro
260 265 270

Ser Val Phe Leu Phe Pro Pro Lys Pro Lys Asp Thr Leu Met Ile Ser
275 280 285

```
Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys


<210> SEQ ID NO 85
<211> LENGTH: 481
<212> TYPE: PRT
<213> ORGANISM: Homo sapiens

<400> SEQUENCE: 85

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Val Ile Ser Val Asp Thr Ser Lys Asn Gln
                85                  90                  95

Phe Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175
```

Gly Cys Leu Val Lys Asp Tyr Phe Pro Glu Pro Val Thr Val Ser Trp
180 185 190

Asn Ser Gly Ala Leu Thr Ser Gly Val His Thr Phe Pro Ala Val Leu
195 200 205

Gln Ser Ser Gly Leu Tyr Ser Leu Ser Ser Val Val Thr Val Pro Ser
210 215 220

Ser Ser Leu Gly Thr Gln Thr Tyr Ile Cys Asn Val Asn His Lys Pro
225 230 235 240

Ser Asn Thr Lys Val Asp Lys Lys Val Glu Pro Lys Ser Cys Asp Lys
245 250 255

Thr His Thr Cys Pro Pro Cys Pro Ala Pro Glu Leu Leu Gly Gly Pro
260 265 270

Ser Val Phe Leu Phe Pro Pro Lys Pro Lys Asp Thr Leu Met Ile Ser
275 280 285

Arg Thr Pro Glu Val Thr Cys Val Val Val Asp Val Ser His Glu Asp
290 295 300

Pro Glu Val Lys Phe Asn Trp Tyr Val Asp Gly Val Glu Val His Asn
305 310 315 320

Ala Lys Thr Lys Pro Arg Glu Glu Gln Tyr Asn Ser Thr Tyr Arg Val
325 330 335

Val Ser Val Leu Thr Val Leu His Gln Asp Trp Leu Asn Gly Lys Glu
340 345 350

Tyr Lys Cys Lys Val Ser Asn Lys Ala Leu Pro Ala Pro Ile Glu Lys
355 360 365

Thr Ile Ser Lys Ala Lys Gly Gln Pro Arg Glu Pro Gln Val Tyr Thr
370 375 380

Leu Pro Pro Ser Arg Asp Glu Leu Thr Lys Asn Gln Val Ser Leu Thr
385 390 395 400

Cys Leu Val Lys Gly Phe Tyr Pro Ser Asp Ile Ala Val Glu Trp Glu
405 410 415

Ser Asn Gly Gln Pro Glu Asn Asn Tyr Lys Thr Thr Pro Pro Val Leu
420 425 430

Asp Ser Asp Gly Ser Phe Phe Leu Tyr Ser Lys Leu Thr Val Asp Lys
435 440 445

Ser Arg Trp Gln Gln Gly Asn Val Phe Ser Cys Ser Val Leu His Glu
450 455 460

Ala Leu His Ser His Tyr Thr Gln Lys Ser Leu Ser Leu Ser Pro Gly
465 470 475 480

Lys

<210> SEQ ID NO 86
<211> LENGTH: 481
<212> TYPE: PRT
<213> ORGANISM: Homo sapiens

<400> SEQUENCE: 86

Met Gly Trp Ser Cys Ile Ile Leu Phe Leu Val Ala Thr Ala Thr Gly
1 5 10 15

Val His Ser Gln Val Gln Leu Gln Glu Ser Gly Pro Gly Leu Val Lys
20 25 30

Pro Ser Glu Thr Leu Ser Val Thr Cys Ser Val Ser Gly Asp Ser Met
35 40 45

Asn Asn Tyr Tyr Trp Thr Trp Ile Arg Gln Ser Pro Gly Lys Gly Leu
50 55 60

-continued

```
Glu Trp Ile Gly Tyr Ile Ser Asp Arg Glu Ser Ala Thr Tyr Asn Pro
65                  70                  75                  80

Ser Leu Asn Ser Arg Val Val Ile Ser Arg Asp Thr Ser Lys Asn Gln
                85                  90                  95

Phe Ser Leu Lys Leu Asn Ser Val Thr Pro Ala Asp Thr Ala Val Tyr
            100                 105                 110

Tyr Cys Ala Arg Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480
```

Lys

<210> SEQ ID NO 87
<211> LENGTH: 481
<212> TYPE: PRT
<213> ORGANISM: Homo sapiens

<400> SEQUENCE: 87

```
Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Thr Ile Ser Val Asp Thr Ser Lys Asn Gln
                85                  90                  95

Phe Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365
```

```
Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys


<210> SEQ ID NO 88
<211> LENGTH: 481
<212> TYPE: PRT
<213> ORGANISM: Homo sapiens

<400> SEQUENCE: 88

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Thr Ile Ser Val Asp Thr Ser Lys Asn Gln
                85                  90                  95

Leu Ser Leu Lys Leu Asn Ser Val Thr Pro Ala Asp Thr Ala Val Tyr
            100                 105                 110

Tyr Cys Ala Arg Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255
```

Thr His Thr Cys Pro Pro Cys Pro Ala Pro Glu Leu Leu Gly Gly Pro
260 265 270

Ser Val Phe Leu Phe Pro Pro Lys Pro Lys Asp Thr Leu Met Ile Ser
275 280 285

Arg Thr Pro Glu Val Thr Cys Val Val Val Asp Val Ser His Glu Asp
290 295 300

Pro Glu Val Lys Phe Asn Trp Tyr Val Asp Gly Val Glu Val His Asn
305 310 315 320

Ala Lys Thr Lys Pro Arg Glu Glu Gln Tyr Asn Ser Thr Tyr Arg Val
325 330 335

Val Ser Val Leu Thr Val Leu His Gln Asp Trp Leu Asn Gly Lys Glu
340 345 350

Tyr Lys Cys Lys Val Ser Asn Lys Ala Leu Pro Ala Pro Ile Glu Lys
355 360 365

Thr Ile Ser Lys Ala Lys Gly Gln Pro Arg Glu Pro Gln Val Tyr Thr
370 375 380

Leu Pro Pro Ser Arg Asp Glu Leu Thr Lys Asn Gln Val Ser Leu Thr
385 390 395 400

Cys Leu Val Lys Gly Phe Tyr Pro Ser Asp Ile Ala Val Glu Trp Glu
405 410 415

Ser Asn Gly Gln Pro Glu Asn Asn Tyr Lys Thr Thr Pro Pro Val Leu
420 425 430

Asp Ser Asp Gly Ser Phe Phe Leu Tyr Ser Lys Leu Thr Val Asp Lys
435 440 445

Ser Arg Trp Gln Gln Gly Asn Val Phe Ser Cys Ser Val Leu His Glu
450 455 460

Ala Leu His Ser His Tyr Thr Gln Lys Ser Leu Ser Leu Ser Pro Gly
465 470 475 480

Lys

<210> SEQ ID NO 89
<211> LENGTH: 481
<212> TYPE: PRT
<213> ORGANISM: Homo sapiens

<400> SEQUENCE: 89

Met Gly Trp Ser Cys Ile Ile Leu Phe Leu Val Ala Thr Ala Thr Gly
1 5 10 15

Val His Ser Gln Val Gln Leu Gln Glu Ser Gly Pro Gly Leu Val Lys
20 25 30

Pro Ser Glu Thr Leu Ser Val Thr Cys Ser Val Ser Gly Asp Ser Met
35 40 45

Asn Asn Tyr Tyr Trp Thr Trp Ile Arg Gln Ser Pro Gly Lys Gly Leu
50 55 60

Glu Trp Ile Gly Tyr Ile Ser Asp Arg Glu Ser Ala Thr Tyr Asn Pro
65 70 75 80

Ser Leu Asn Ser Arg Val Val Ile Ser Val Asp Thr Ser Lys Asn Gln
85 90 95

Phe Ser Leu Lys Leu Asn Ser Val Thr Pro Ala Asp Thr Ala Val Tyr
100 105 110

Tyr Cys Ala Arg Ala Arg Arg Gly Gln Arg Ile Tyr Gly Val Val Ser
115 120 125

Phe Gly Glu Phe Phe Tyr Tyr Tyr Ser Met Asp Val Trp Gly Lys Gly
130 135 140

```
Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys


<210> SEQ ID NO 90
<211> LENGTH: 481
<212> TYPE: PRT
<213> ORGANISM: Homo sapiens

<400> SEQUENCE: 90

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30
```

```
Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Thr Ile Ser Val Asp Thr Ser Lys Asn Gln
                85                  90                  95

Phe Ser Leu Lys Leu Asn Ser Val Thr Pro Ala Asp Thr Ala Val Tyr
            100                 105                 110

Tyr Cys Ala Thr Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
```

```
    450                 455                 460

Ala Leu His Ser His Tyr Thr Gln Lys Ser Leu Ser Leu Ser Pro Gly
465                 470                 475                 480

Lys


<210> SEQ ID NO 91
<211> LENGTH: 481
<212> TYPE: PRT
<213> ORGANISM: Homo sapiens

<400> SEQUENCE: 91

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Thr Ile Ser Val Asp Thr Ser Lys Asn Gln
                85                  90                  95

Leu Ser Leu Lys Leu Asn Ser Val Thr Pro Ala Asp Thr Ala Val Tyr
            100                 105                 110

Tyr Cys Ala Arg Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
```

340 345 350

Tyr Lys Cys Lys Val Ser Asn Lys Ala Leu Pro Ala Pro Ile Glu Lys
355 360 365

Thr Ile Ser Lys Ala Lys Gly Gln Pro Arg Glu Pro Gln Val Tyr Thr
370 375 380

Leu Pro Pro Ser Arg Asp Glu Leu Thr Lys Asn Gln Val Ser Leu Thr
385 390 395 400

Cys Leu Val Lys Gly Phe Tyr Pro Ser Asp Ile Ala Val Glu Trp Glu
405 410 415

Ser Asn Gly Gln Pro Glu Asn Asn Tyr Lys Thr Thr Pro Pro Val Leu
420 425 430

Asp Ser Asp Gly Ser Phe Phe Leu Tyr Ser Lys Leu Thr Val Asp Lys
435 440 445

Ser Arg Trp Gln Gln Gly Asn Val Phe Ser Cys Ser Val Leu His Glu
450 455 460

Ala Leu His Ser His Tyr Thr Gln Lys Ser Leu Ser Leu Ser Pro Gly
465 470 475 480

Lys

<210> SEQ ID NO 92
<211> LENGTH: 481
<212> TYPE: PRT
<213> ORGANISM: Homo sapiens

<400> SEQUENCE: 92

Met Gly Trp Ser Cys Ile Ile Leu Phe Leu Val Ala Thr Ala Thr Gly
1 5 10 15

Val His Ser Gln Val Gln Leu Gln Glu Ser Gly Pro Gly Leu Val Lys
20 25 30

Pro Ser Glu Thr Leu Ser Val Thr Cys Ser Val Ser Gly Asp Ser Met
35 40 45

Asn Asn Tyr Tyr Trp Thr Trp Ile Arg Gln Ser Pro Gly Lys Gly Leu
50 55 60

Glu Trp Ile Gly Tyr Ile Ser Asp Arg Glu Ser Ala Thr Tyr Asn Pro
65 70 75 80

Ser Leu Asn Ser Arg Val Val Ile Ser Val Asp Thr Ser Lys Asn Gln
85 90 95

Phe Ser Leu Lys Leu Asn Ser Val Thr Pro Ala Asp Thr Ala Val Tyr
100 105 110

Tyr Cys Ala Arg Ala Arg Arg Gly Gln Arg Ile Tyr Gly Val Val Ser
115 120 125

Phe Gly Glu Phe Phe Tyr Tyr Tyr Ser Met Asp Val Trp Gly Lys Gly
130 135 140

Thr Thr Val Thr Val Ser Ser Ala Ser Thr Lys Gly Pro Ser Val Phe
145 150 155 160

Pro Leu Ala Pro Ser Ser Lys Ser Thr Ser Gly Gly Thr Ala Ala Leu
165 170 175

Gly Cys Leu Val Lys Asp Tyr Phe Pro Glu Pro Val Thr Val Ser Trp
180 185 190

Asn Ser Gly Ala Leu Thr Ser Gly Val His Thr Phe Pro Ala Val Leu
195 200 205

Gln Ser Ser Gly Leu Tyr Ser Leu Ser Ser Val Val Thr Val Pro Ser
210 215 220

Ser Ser Leu Gly Thr Gln Thr Tyr Ile Cys Asn Val Asn His Lys Pro

```
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys


<210> SEQ ID NO 93
<211> LENGTH: 481
<212> TYPE: PRT
<213> ORGANISM: Homo sapiens

<400> SEQUENCE: 93

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Thr Ile Ser Val Asp Thr Ser Lys Asn Gln
                85                  90                  95

Phe Ser Leu Lys Leu Asn Ser Val Thr Pro Ala Asp Thr Ala Val Tyr
            100                 105                 110

Tyr Cys Ala Arg Ala Arg Arg Gly Gln Arg Ile Tyr Gly Val Val Ser
```

```
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys


<210> SEQ ID NO 94
<211> LENGTH: 481
<212> TYPE: PRT
<213> ORGANISM: Homo sapiens

<400> SEQUENCE: 94

Met Gly Trp Ser Cys Ile Ile Leu Phe Leu Val Ala Thr Ala Thr Gly
```

-continued

```
1               5                   10                  15

Val His Ser Gln Val Gln Leu Gln Glu Ser Gly Pro Gly Leu Val Lys
            20                  25                  30

Pro Ser Glu Thr Leu Ser Val Thr Cys Ser Val Ser Gly Asp Ser Met
        35                  40                  45

Asn Asn Tyr Tyr Trp Thr Trp Ile Arg Gln Ser Pro Gly Lys Gly Leu
    50                  55                  60

Glu Trp Ile Gly Tyr Ile Ser Asp Arg Glu Ser Ala Thr Tyr Asn Pro
65                  70                  75                  80

Ser Leu Asn Ser Arg Val Thr Ile Ser Val Asp Thr Ser Lys Asn Gln
                85                  90                  95

Phe Ser Leu Lys Leu Asn Ser Val Thr Pro Ala Asp Thr Ala Val Tyr
            100                 105                 110

Tyr Cys Ala Arg Ala Arg Arg Gly Gln Arg Ile Tyr Gly Val Val Ser
        115                 120                 125

Phe Gly Glu Phe Phe Tyr Tyr Tyr Ser Met Asp Val Trp Gly Lys Gly
    130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430
```

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Leu His Glu
    450                 455                 460

Ala Leu His Ser His Tyr Thr Gln Lys Ser Leu Ser Leu Ser Pro Gly
465                 470                 475                 480

Lys

<210> SEQ ID NO 95
<211> LENGTH: 11
<212> TYPE: PRT
<213> ORGANISM: Homo sapiens

<400> SEQUENCE: 95

Gly Arg Gln Ala Leu Gly Ser Arg Ala Val Gln
1               5                   10

<210> SEQ ID NO 96
<211> LENGTH: 7
<212> TYPE: PRT
<213> ORGANISM: Homo sapiens

<400> SEQUENCE: 96

Asn Asn Gln Asp Arg Pro Ser
1               5

<210> SEQ ID NO 97
<211> LENGTH: 12
<212> TYPE: PRT
<213> ORGANISM: Homo sapiens

<400> SEQUENCE: 97

His Met Trp Asp Ser Arg Ser Gly Phe Ser Trp Ser
1               5                   10

<210> SEQ ID NO 98
<211> LENGTH: 6
<212> TYPE: PRT
<213> ORGANISM: Homo sapiens

<400> SEQUENCE: 98

Asn Asn Tyr Tyr Trp Thr
1               5

<210> SEQ ID NO 99
<211> LENGTH: 16
<212> TYPE: PRT
<213> ORGANISM: Homo sapiens

<400> SEQUENCE: 99

Tyr Ile Ser Asp Arg Glu Ser Ala Thr Tyr Asn Pro Ser Leu Asn Ser
1               5                   10                  15

<210> SEQ ID NO 100
<211> LENGTH: 24
<212> TYPE: PRT
<213> ORGANISM: Homo sapiens

<400> SEQUENCE: 100

Ala Arg Arg Gly Gln Arg Ile Tyr Gly Val Val Ser Phe Gly Glu Phe
1               5                   10                  15

Phe Tyr Tyr Tyr Ser Met Asp Val

20

<210> SEQ ID NO 101
<211> LENGTH: 11
<212> TYPE: PRT
<213> ORGANISM: Homo sapiens

<400> SEQUENCE: 101

Gly Arg Gln Ala Leu Gly Ser Arg Ala Val Gln
1 5 10

<210> SEQ ID NO 102
<211> LENGTH: 7
<212> TYPE: PRT
<213> ORGANISM: Homo sapiens

<400> SEQUENCE: 102

Asn Asn Gln Asp Arg Pro Ser
1 5

<210> SEQ ID NO 103
<211> LENGTH: 12
<212> TYPE: PRT
<213> ORGANISM: Homo sapiens

<400> SEQUENCE: 103

His Met Trp Asp Ser Arg Ser Gly Phe Ser Trp Ser
1 5 10

<210> SEQ ID NO 104
<211> LENGTH: 6
<212> TYPE: PRT
<213> ORGANISM: Homo sapiens

<400> SEQUENCE: 104

Asn Asn Tyr Tyr Trp Thr
1 5

<210> SEQ ID NO 105
<211> LENGTH: 16
<212> TYPE: PRT
<213> ORGANISM: Homo sapiens

<400> SEQUENCE: 105

Tyr Ile Ser Asp Arg Glu Ser Ala Thr Tyr Asn Pro Ser Leu Asn Ser
1 5 10 15

<210> SEQ ID NO 106
<211> LENGTH: 24
<212> TYPE: PRT
<213> ORGANISM: Homo sapiens

<400> SEQUENCE: 106

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 107
<211> LENGTH: 11
<212> TYPE: PRT
<213> ORGANISM: Homo sapiens

<400> SEQUENCE: 107

Gly Arg Gln Ala Leu Gly Ser Arg Ala Val Gln
1 5 10

<210> SEQ ID NO 108
<211> LENGTH: 7
<212> TYPE: PRT
<213> ORGANISM: Homo sapiens

<400> SEQUENCE: 108

Asn Asn Gln Asp Arg Pro Ser
1 5

<210> SEQ ID NO 109
<211> LENGTH: 12
<212> TYPE: PRT
<213> ORGANISM: Homo sapiens

<400> SEQUENCE: 109

His Met Trp Asp Ser Arg Ser Gly Phe Ser Trp Ser
1 5 10

<210> SEQ ID NO 110
<211> LENGTH: 6
<212> TYPE: PRT
<213> ORGANISM: Homo sapiens

<400> SEQUENCE: 110

Asn Asn Tyr Tyr Trp Thr
1 5

<210> SEQ ID NO 111
<211> LENGTH: 16
<212> TYPE: PRT
<213> ORGANISM: Homo sapiens

<400> SEQUENCE: 111

Tyr Ile Ser Asp Arg Glu Ser Ala Thr Tyr Asn Pro Ser Leu Asn Ser
1 5 10 15

<210> SEQ ID NO 112
<211> LENGTH: 24
<212> TYPE: PRT
<213> ORGANISM: Homo sapiens

<400> SEQUENCE: 112

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 113
<211> LENGTH: 11
<212> TYPE: PRT
<213> ORGANISM: Homo sapiens

<400> SEQUENCE: 113

Gly Arg Gln Ala Leu Gly Ser Arg Ala Val Gln
1 5 10

<210> SEQ ID NO 114
<211> LENGTH: 7
<212> TYPE: PRT
<213> ORGANISM: Homo sapiens

<400> SEQUENCE: 114

Asn Asn Gln Asp Arg Pro Ser
1 5

<210> SEQ ID NO 115
<211> LENGTH: 12
<212> TYPE: PRT
<213> ORGANISM: Homo sapiens

<400> SEQUENCE: 115

His Met Trp Asp Ser Arg Ser Gly Phe Ser Trp Ser
1 5 10

<210> SEQ ID NO 116
<211> LENGTH: 6
<212> TYPE: PRT
<213> ORGANISM: Homo sapiens

<400> SEQUENCE: 116

Asn Asn Tyr Tyr Trp Thr
1 5

<210> SEQ ID NO 117
<211> LENGTH: 16
<212> TYPE: PRT
<213> ORGANISM: Homo sapiens

<400> SEQUENCE: 117

Tyr Ile Ser Asp Arg Glu Ser Ala Thr Tyr Asn Pro Ser Leu Asn Ser
1 5 10 15

<210> SEQ ID NO 118
<211> LENGTH: 24
<212> TYPE: PRT
<213> ORGANISM: Homo sapiens

<400> SEQUENCE: 118

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 119
<211> LENGTH: 11
<212> TYPE: PRT
<213> ORGANISM: Homo sapiens

<400> SEQUENCE: 119

Gly Arg Gln Ala Leu Gly Ser Arg Ala Val Gln
1 5 10

<210> SEQ ID NO 120
<211> LENGTH: 7
<212> TYPE: PRT
<213> ORGANISM: Homo sapiens

<400> SEQUENCE: 120

Asn Asn Gln Asp Arg Pro Ser
1 5

<210> SEQ ID NO 121
<211> LENGTH: 12
<212> TYPE: PRT
<213> ORGANISM: Homo sapiens

<400> SEQUENCE: 121

His Met Trp Asp Ser Arg Ser Gly Phe Ser Trp Ser
1 5 10

<210> SEQ ID NO 122
<211> LENGTH: 6
<212> TYPE: PRT
<213> ORGANISM: Homo sapiens

<400> SEQUENCE: 122

Asn Asn Tyr Tyr Trp Thr
1 5

<210> SEQ ID NO 123
<211> LENGTH: 16
<212> TYPE: PRT
<213> ORGANISM: Homo sapiens

<400> SEQUENCE: 123

Tyr Ile Ser Asp Arg Glu Ser Ala Thr Tyr Asn Pro Ser Leu Asn Ser
1 5 10 15

<210> SEQ ID NO 124
<211> LENGTH: 24
<212> TYPE: PRT
<213> ORGANISM: Homo sapiens

<400> SEQUENCE: 124

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 125
<211> LENGTH: 11
<212> TYPE: PRT
<213> ORGANISM: Homo sapiens

<400> SEQUENCE: 125

Gly Arg Gln Ala Leu Gly Ser Arg Ala Val Gln
1 5 10

<210> SEQ ID NO 126
<211> LENGTH: 7
<212> TYPE: PRT
<213> ORGANISM: Homo sapiens

<400> SEQUENCE: 126

Asn Asn Gln Asp Arg Pro Ser
1 5

<210> SEQ ID NO 127
<211> LENGTH: 12
<212> TYPE: PRT
<213> ORGANISM: Homo sapiens

<400> SEQUENCE: 127

His Met Trp Asp Ser Arg Ser Gly Phe Ser Trp Ser
1 5 10

<210> SEQ ID NO 128
<211> LENGTH: 6
<212> TYPE: PRT
<213> ORGANISM: Homo sapiens

<400> SEQUENCE: 128

Asn Asn Tyr Tyr Trp Thr
1 5

<210> SEQ ID NO 129
<211> LENGTH: 16
<212> TYPE: PRT
<213> ORGANISM: Homo sapiens

<400> SEQUENCE: 129

Tyr Ile Ser Asp Arg Glu Ser Ala Thr Tyr Asn Pro Ser Leu Asn Ser
1 5 10 15

<210> SEQ ID NO 130
<211> LENGTH: 24
<212> TYPE: PRT
<213> ORGANISM: Homo sapiens

<400> SEQUENCE: 130

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 131
<211> LENGTH: 11
<212> TYPE: PRT
<213> ORGANISM: Homo sapiens

<400> SEQUENCE: 131

Gly Arg Gln Ala Leu Gly Ser Arg Ala Val Gln
1 5 10

<210> SEQ ID NO 132
<211> LENGTH: 7
<212> TYPE: PRT
<213> ORGANISM: Homo sapiens

<400> SEQUENCE: 132

Asn Asn Gln Asp Arg Pro Ser
1 5

<210> SEQ ID NO 133
<211> LENGTH: 12
<212> TYPE: PRT
<213> ORGANISM: Homo sapiens

<400> SEQUENCE: 133

His Met Trp Asp Ser Arg Ser Gly Phe Ser Trp Ser
1 5 10

<210> SEQ ID NO 134
<211> LENGTH: 6
<212> TYPE: PRT
<213> ORGANISM: Homo sapiens

<400> SEQUENCE: 134

Asn Asn Tyr Tyr Trp Thr
1 5

<210> SEQ ID NO 135
<211> LENGTH: 16
<212> TYPE: PRT

<213> ORGANISM: Homo sapiens

<400> SEQUENCE: 135

Tyr Ile Ser Asp Arg Glu Ser Ala Thr Tyr Asn Pro Ser Leu Asn Ser
1               5                   10                  15

<210> SEQ ID NO 136
<211> LENGTH: 24
<212> TYPE: PRT
<213> ORGANISM: Homo sapiens

<400> SEQUENCE: 136

Ala Arg Arg Gly Gln Arg Ile Tyr Gly Val Val Ser Phe Gly Glu Phe
1               5                   10                  15

Phe Tyr Tyr Tyr Ser Met Asp Val
            20

<210> SEQ ID NO 137
<211> LENGTH: 11
<212> TYPE: PRT
<213> ORGANISM: Homo sapiens

<400> SEQUENCE: 137

Gly Arg Gln Ala Leu Gly Ser Arg Ala Val Gln
1               5                   10

<210> SEQ ID NO 138
<211> LENGTH: 7
<212> TYPE: PRT
<213> ORGANISM: Homo sapiens

<400> SEQUENCE: 138

Asn Asn Gln Asp Arg Pro Ser
1               5

<210> SEQ ID NO 139
<211> LENGTH: 12
<212> TYPE: PRT
<213> ORGANISM: Homo sapiens

<400> SEQUENCE: 139

His Met Trp Asp Ser Arg Ser Gly Phe Ser Trp Ser
1               5                   10

<210> SEQ ID NO 140
<211> LENGTH: 6
<212> TYPE: PRT
<213> ORGANISM: Homo sapiens

<400> SEQUENCE: 140

Asn Asn Tyr Tyr Trp Thr
1               5

<210> SEQ ID NO 141
<211> LENGTH: 16
<212> TYPE: PRT
<213> ORGANISM: Homo sapiens

<400> SEQUENCE: 141

Tyr Ile Ser Asp Arg Glu Ser Ala Thr Tyr Asn Pro Ser Leu Asn Ser
1               5                   10                  15

<210> SEQ ID NO 142
<211> LENGTH: 24

<212> TYPE: PRT
<213> ORGANISM: Homo sapiens

<400> SEQUENCE: 142

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 143
<211> LENGTH: 11
<212> TYPE: PRT
<213> ORGANISM: Homo sapiens

<400> SEQUENCE: 143

Gly Arg Gln Ala Leu Gly Ser Arg Ala Val Gln
1 5 10

<210> SEQ ID NO 144
<211> LENGTH: 7
<212> TYPE: PRT
<213> ORGANISM: Homo sapiens

<400> SEQUENCE: 144

Asn Asn Gln Asp Arg Pro Ser
1 5

<210> SEQ ID NO 145
<211> LENGTH: 12
<212> TYPE: PRT
<213> ORGANISM: Homo sapiens

<400> SEQUENCE: 145

His Met Trp Asp Ser Arg Ser Gly Phe Ser Trp Ser
1 5 10

<210> SEQ ID NO 146
<211> LENGTH: 6
<212> TYPE: PRT
<213> ORGANISM: Homo sapiens

<400> SEQUENCE: 146

Asn Asn Tyr Tyr Trp Thr
1 5

<210> SEQ ID NO 147
<211> LENGTH: 16
<212> TYPE: PRT
<213> ORGANISM: Homo sapiens

<400> SEQUENCE: 147

Tyr Ile Ser Asp Arg Glu Ser Ala Thr Tyr Asn Pro Ser Leu Asn Ser
1 5 10 15

<210> SEQ ID NO 148
<211> LENGTH: 24
<212> TYPE: PRT
<213> ORGANISM: Homo sapiens

<400> SEQUENCE: 148

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 149
<211> LENGTH: 11
<212> TYPE: PRT
<213> ORGANISM: Homo sapiens

<400> SEQUENCE: 149

Gly Arg Gln Ala Leu Gly Ser Arg Ala Val Gln
1 5 10

<210> SEQ ID NO 150
<211> LENGTH: 7
<212> TYPE: PRT
<213> ORGANISM: Homo sapiens

<400> SEQUENCE: 150

Asn Asn Gln Asp Arg Pro Ser
1 5

<210> SEQ ID NO 151
<211> LENGTH: 12
<212> TYPE: PRT
<213> ORGANISM: Homo sapiens

<400> SEQUENCE: 151

His Met Trp Asp Ser Arg Ser Gly Phe Ser Trp Ser
1 5 10

<210> SEQ ID NO 152
<211> LENGTH: 6
<212> TYPE: PRT
<213> ORGANISM: Homo sapiens

<400> SEQUENCE: 152

Asn Asn Tyr Tyr Trp Thr
1 5

<210> SEQ ID NO 153
<211> LENGTH: 16
<212> TYPE: PRT
<213> ORGANISM: Homo sapiens

<400> SEQUENCE: 153

Tyr Ile Ser Asp Arg Glu Ser Ala Thr Tyr Asn Pro Ser Leu Asn Ser
1 5 10 15

<210> SEQ ID NO 154
<211> LENGTH: 24
<212> TYPE: PRT
<213> ORGANISM: Homo sapiens

<400> SEQUENCE: 154

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 155
<211> LENGTH: 11
<212> TYPE: PRT
<213> ORGANISM: Homo sapiens

<400> SEQUENCE: 155

Gly Arg Gln Ala Leu Gly Ser Arg Ala Val Gln 1 5 10

<210> SEQ ID NO 156
<211> LENGTH: 7
<212> TYPE: PRT
<213> ORGANISM: Homo sapiens

<400> SEQUENCE: 156

Asn Asn Gln Asp Arg Pro Ser
1 5

<210> SEQ ID NO 157
<211> LENGTH: 12
<212> TYPE: PRT
<213> ORGANISM: Homo sapiens

<400> SEQUENCE: 157

His Met Trp Asp Ser Arg Ser Gly Phe Ser Trp Ser
1 5 10

<210> SEQ ID NO 158
<211> LENGTH: 6
<212> TYPE: PRT
<213> ORGANISM: Homo sapiens

<400> SEQUENCE: 158

Asn Asn Tyr Tyr Trp Thr
1 5

<210> SEQ ID NO 159
<211> LENGTH: 16
<212> TYPE: PRT
<213> ORGANISM: Homo sapiens

<400> SEQUENCE: 159

Tyr Ile Ser Asp Arg Glu Ser Ala Thr Tyr Asn Pro Ser Leu Asn Ser
1 5 10 15

<210> SEQ ID NO 160
<211> LENGTH: 24
<212> TYPE: PRT
<213> ORGANISM: Homo sapiens

<400> SEQUENCE: 160

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 161
<211> LENGTH: 11
<212> TYPE: PRT
<213> ORGANISM: Homo sapiens

<400> SEQUENCE: 161

Gly Arg Gln Ala Leu Gly Ser Arg Ala Val Gln
1 5 10

<210> SEQ ID NO 162
<211> LENGTH: 7
<212> TYPE: PRT
<213> ORGANISM: Homo sapiens

<400> SEQUENCE: 162

Asn Asn Gln Asp Arg Pro Ser
1               5

<210> SEQ ID NO 163
<211> LENGTH: 12
<212> TYPE: PRT
<213> ORGANISM: Homo sapiens

<400> SEQUENCE: 163

His Met Trp Glu Ser Arg Ser Gly Phe Ser Trp Ser
1               5                   10

<210> SEQ ID NO 164
<211> LENGTH: 6
<212> TYPE: PRT
<213> ORGANISM: Homo sapiens

<400> SEQUENCE: 164

Asn Asn Tyr Tyr Trp Thr
1               5

<210> SEQ ID NO 165
<211> LENGTH: 16
<212> TYPE: PRT
<213> ORGANISM: Homo sapiens

<400> SEQUENCE: 165

Tyr Ile Ser Asp Arg Glu Ser Ala Thr Tyr Asn Pro Ser Leu Asn Ser
1               5                   10                  15

<210> SEQ ID NO 166
<211> LENGTH: 24
<212> TYPE: PRT
<213> ORGANISM: Homo sapiens

<400> SEQUENCE: 166

Ala Arg Arg Gly Gln Arg Ile Tyr Gly Val Val Ser Phe Gly Glu Phe
1               5                   10                  15

Phe Tyr Tyr Tyr Ser Met Asp Val
            20

<210> SEQ ID NO 167
<211> LENGTH: 11
<212> TYPE: PRT
<213> ORGANISM: Homo sapiens

<400> SEQUENCE: 167

Gly Arg Gln Ala Leu Gly Ser Arg Ala Val Gln
1               5                   10

<210> SEQ ID NO 168
<211> LENGTH: 7
<212> TYPE: PRT
<213> ORGANISM: Homo sapiens

<400> SEQUENCE: 168

Asn Asn Gln Asp Arg Pro Ser
1               5

<210> SEQ ID NO 169
<211> LENGTH: 12
<212> TYPE: PRT
<213> ORGANISM: Homo sapiens

<400> SEQUENCE: 169

```
His Met Trp Asp Ser Arg Ser Gly Phe Ser Trp Ser
1               5                   10


<210> SEQ ID NO 170
<211> LENGTH: 6
<212> TYPE: PRT
<213> ORGANISM: Homo sapiens

<400> SEQUENCE: 170

Asn Asn Tyr Tyr Trp Thr
1               5


<210> SEQ ID NO 171
<211> LENGTH: 16
<212> TYPE: PRT
<213> ORGANISM: Homo sapiens

<400> SEQUENCE: 171

Tyr Ile Ser Asp Arg Glu Ser Ala Thr Tyr Asn Pro Ser Leu Asn Ser
1               5                   10                  15


<210> SEQ ID NO 172
<211> LENGTH: 24
<212> TYPE: PRT
<213> ORGANISM: Homo sapiens

<400> SEQUENCE: 172

Ala Arg Arg Gly Gln Arg Ile Tyr Gly Val Val Ser Phe Gly Glu Phe
1               5                   10                  15

Phe Tyr Tyr Tyr Ser Met Asp Val
            20


<210> SEQ ID NO 173
<211> LENGTH: 11
<212> TYPE: PRT
<213> ORGANISM: Homo sapiens

<400> SEQUENCE: 173

Gly Arg Gln Ala Leu Gly Ser Arg Ala Val Gln
1               5                   10


<210> SEQ ID NO 174
<211> LENGTH: 7
<212> TYPE: PRT
<213> ORGANISM: Homo sapiens

<400> SEQUENCE: 174

Asn Asn Gln Asp Arg Pro Ser
1               5


<210> SEQ ID NO 175
<211> LENGTH: 12
<212> TYPE: PRT
<213> ORGANISM: Homo sapiens

<400> SEQUENCE: 175

His Met Trp Asp Ser Arg Ser Gly Phe Ser Trp Ser
1               5                   10


<210> SEQ ID NO 176
<211> LENGTH: 6
<212> TYPE: PRT
<213> ORGANISM: Homo sapiens
```

<400> SEQUENCE: 176

Asn Asn Tyr Tyr Trp Thr
1 5

<210> SEQ ID NO 177
<211> LENGTH: 16
<212> TYPE: PRT
<213> ORGANISM: Homo sapiens

<400> SEQUENCE: 177

Tyr Ile Ser Asp Arg Glu Ser Ala Thr Tyr Asn Pro Ser Leu Asn Ser
1 5 10 15

<210> SEQ ID NO 178
<211> LENGTH: 24
<212> TYPE: PRT
<213> ORGANISM: Homo sapiens

<400> SEQUENCE: 178

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 179
<211> LENGTH: 11
<212> TYPE: PRT
<213> ORGANISM: Homo sapiens

<400> SEQUENCE: 179

Gly Arg Gln Ala Leu Gly Ser Arg Ala Val Gln
1 5 10

<210> SEQ ID NO 180
<211> LENGTH: 7
<212> TYPE: PRT
<213> ORGANISM: Homo sapiens

<400> SEQUENCE: 180

Asn Asn Gln Asp Arg Pro Ser
1 5

<210> SEQ ID NO 181
<211> LENGTH: 12
<212> TYPE: PRT
<213> ORGANISM: Homo sapiens

<400> SEQUENCE: 181

His Met Trp Asp Ser Arg Ser Gly Phe Ser Trp Ser
1 5 10

<210> SEQ ID NO 182
<211> LENGTH: 6
<212> TYPE: PRT
<213> ORGANISM: Homo sapiens

<400> SEQUENCE: 182

Asn Asn Tyr Tyr Trp Thr
1 5

<210> SEQ ID NO 183
<211> LENGTH: 16
<212> TYPE: PRT
<213> ORGANISM: Homo sapiens

<400> SEQUENCE: 183

Tyr Ile Ser Asp Arg Glu Ser Ala Thr Tyr Asn Pro Ser Leu Asn Ser
1 5 10 15

<210> SEQ ID NO 184
<211> LENGTH: 24
<212> TYPE: PRT
<213> ORGANISM: Homo sapiens

<400> SEQUENCE: 184

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 185
<211> LENGTH: 11
<212> TYPE: PRT
<213> ORGANISM: Homo sapiens

<400> SEQUENCE: 185

Gly Arg Gln Ala Leu Gly Ser Arg Ala Val Gln
1 5 10

<210> SEQ ID NO 186
<211> LENGTH: 7
<212> TYPE: PRT
<213> ORGANISM: Homo sapiens

<400> SEQUENCE: 186

Asn Asn Gln Asp Arg Pro Ser
1 5

<210> SEQ ID NO 187
<211> LENGTH: 12
<212> TYPE: PRT
<213> ORGANISM: Homo sapiens

<400> SEQUENCE: 187

His Met Trp Asp Ser Arg Ser Gly Phe Ser Trp Ser
1 5 10

<210> SEQ ID NO 188
<211> LENGTH: 6
<212> TYPE: PRT
<213> ORGANISM: Homo sapiens

<400> SEQUENCE: 188

Asn Asn Tyr Tyr Trp Thr
1 5

<210> SEQ ID NO 189
<211> LENGTH: 16
<212> TYPE: PRT
<213> ORGANISM: Homo sapiens

<400> SEQUENCE: 189

Tyr Ile Ser Asp Arg Glu Ser Ala Thr Tyr Asn Pro Ser Leu Asn Ser
1 5 10 15

<210> SEQ ID NO 190
<211> LENGTH: 24
<212> TYPE: PRT

<213> ORGANISM: Homo sapiens

<400> SEQUENCE: 190

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 191
<211> LENGTH: 11
<212> TYPE: PRT
<213> ORGANISM: Homo sapiens

<400> SEQUENCE: 191

Gly Arg Gln Ala Leu Gly Ser Arg Ala Val Gln
1 5 10

<210> SEQ ID NO 192
<211> LENGTH: 7
<212> TYPE: PRT
<213> ORGANISM: Homo sapiens

<400> SEQUENCE: 192

Asn Asn Gln Asp Arg Pro Ser
1 5

<210> SEQ ID NO 193
<211> LENGTH: 12
<212> TYPE: PRT
<213> ORGANISM: Homo sapiens

<400> SEQUENCE: 193

His Met Trp Asp Ser Arg Ser Gly Phe Ser Trp Ser
1 5 10

<210> SEQ ID NO 194
<211> LENGTH: 6
<212> TYPE: PRT
<213> ORGANISM: Homo sapiens

<400> SEQUENCE: 194

Asn Asn Tyr Tyr Trp Thr
1 5

<210> SEQ ID NO 195
<211> LENGTH: 16
<212> TYPE: PRT
<213> ORGANISM: Homo sapiens

<400> SEQUENCE: 195

Tyr Ile Ser Asp Arg Glu Ser Ala Thr Tyr Asn Pro Ser Leu Asn Ser
1 5 10 15

<210> SEQ ID NO 196
<211> LENGTH: 24
<212> TYPE: PRT
<213> ORGANISM: Homo sapiens

<400> SEQUENCE: 196

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 197
<211> LENGTH: 11
<212> TYPE: PRT
<213> ORGANISM: Homo sapiens

<400> SEQUENCE: 197

Gly Arg Gln Ala Leu Gly Ser Arg Ala Val Gln
1 5 10

<210> SEQ ID NO 198
<211> LENGTH: 7
<212> TYPE: PRT
<213> ORGANISM: Homo sapiens

<400> SEQUENCE: 198

Asn Asn Gln Asp Arg Pro Ser
1 5

<210> SEQ ID NO 199
<211> LENGTH: 12
<212> TYPE: PRT
<213> ORGANISM: Homo sapiens

<400> SEQUENCE: 199

His Met Trp Asp Ser Arg Ser Gly Phe Ser Trp Ser
1 5 10

<210> SEQ ID NO 200
<211> LENGTH: 6
<212> TYPE: PRT
<213> ORGANISM: Homo sapiens

<400> SEQUENCE: 200

Asn Asn Tyr Tyr Trp Thr
1 5

<210> SEQ ID NO 201
<211> LENGTH: 16
<212> TYPE: PRT
<213> ORGANISM: Homo sapiens

<400> SEQUENCE: 201

Tyr Ile Ser Asp Arg Glu Ser Ala Thr Tyr Asn Pro Ser Leu Asn Ser
1 5 10 15

<210> SEQ ID NO 202
<211> LENGTH: 24
<212> TYPE: PRT
<213> ORGANISM: Homo sapiens

<400> SEQUENCE: 202

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 203
<211> LENGTH: 11
<212> TYPE: PRT
<213> ORGANISM: Homo sapiens

<400> SEQUENCE: 203

Gly Arg Gln Ala Leu Gly Ser Arg Ala Val Gln
1 5 10

<210> SEQ ID NO 204
<211> LENGTH: 7
<212> TYPE: PRT
<213> ORGANISM: Homo sapiens

<400> SEQUENCE: 204

Asn Asn Gln Asp Arg Pro Ser
1               5

<210> SEQ ID NO 205
<211> LENGTH: 12
<212> TYPE: PRT
<213> ORGANISM: Homo sapiens

<400> SEQUENCE: 205

His Met Trp Asp Ser Arg Ser Gly Phe Ser Trp Ser
1               5                   10

<210> SEQ ID NO 206
<211> LENGTH: 6
<212> TYPE: PRT
<213> ORGANISM: Homo sapiens

<400> SEQUENCE: 206

Asn Asn Tyr Tyr Trp Thr
1               5

<210> SEQ ID NO 207
<211> LENGTH: 16
<212> TYPE: PRT
<213> ORGANISM: Homo sapiens

<400> SEQUENCE: 207

Tyr Ile Ser Asp Arg Glu Ser Ala Thr Tyr Asn Pro Ser Leu Asn Ser
1               5                   10                  15

<210> SEQ ID NO 208
<211> LENGTH: 24
<212> TYPE: PRT
<213> ORGANISM: Homo sapiens

<400> SEQUENCE: 208

Ala Arg Arg Gly Gln Arg Ile Tyr Gly Val Val Ser Phe Gly Glu Phe
1               5                   10                  15

Phe Tyr Tyr Tyr Ser Met Asp Val
            20

<210> SEQ ID NO 209
<211> LENGTH: 11
<212> TYPE: PRT
<213> ORGANISM: Homo sapiens

<400> SEQUENCE: 209

Gly Arg Gln Ala Leu Gly Ser Arg Ala Val Gln
1               5                   10

<210> SEQ ID NO 210
<211> LENGTH: 7
<212> TYPE: PRT
<213> ORGANISM: Homo sapiens

<400> SEQUENCE: 210

Asn Asn Gln Asp Arg Pro Ser 1 5

<210> SEQ ID NO 211
<211> LENGTH: 12
<212> TYPE: PRT
<213> ORGANISM: Homo sapiens

<400> SEQUENCE: 211

His Met Trp Asp Ser Arg Ser Gly Phe Ser Trp Ser
1 5 10

<210> SEQ ID NO 212
<211> LENGTH: 6
<212> TYPE: PRT
<213> ORGANISM: Homo sapiens

<400> SEQUENCE: 212

Asn Asn Tyr Tyr Trp Thr
1 5

<210> SEQ ID NO 213
<211> LENGTH: 16
<212> TYPE: PRT
<213> ORGANISM: Homo sapiens

<400> SEQUENCE: 213

Tyr Ile Ser Asp Arg Glu Ser Ala Thr Tyr Asn Pro Ser Leu Asn Ser
1 5 10 15

<210> SEQ ID NO 214
<211> LENGTH: 24
<212> TYPE: PRT
<213> ORGANISM: Homo sapiens

<400> SEQUENCE: 214

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 215
<211> LENGTH: 11
<212> TYPE: PRT
<213> ORGANISM: Homo sapiens

<400> SEQUENCE: 215

Gly Arg Gln Ala Leu Gly Ser Arg Ala Val Gln
1 5 10

<210> SEQ ID NO 216
<211> LENGTH: 7
<212> TYPE: PRT
<213> ORGANISM: Homo sapiens

<400> SEQUENCE: 216

Asn Asn Gln Asp Arg Pro Ser
1 5

<210> SEQ ID NO 217
<211> LENGTH: 12
<212> TYPE: PRT
<213> ORGANISM: Homo sapiens

<400> SEQUENCE: 217

His Met Trp Asp Ser Arg Ser Gly Phe Ser Trp Ser
1 5 10

<210> SEQ ID NO 218
<211> LENGTH: 6
<212> TYPE: PRT
<213> ORGANISM: Homo sapiens

<400> SEQUENCE: 218

Asn Asn Tyr Tyr Trp Thr
1 5

<210> SEQ ID NO 219
<211> LENGTH: 16
<212> TYPE: PRT
<213> ORGANISM: Homo sapiens

<400> SEQUENCE: 219

Tyr Ile Ser Asp Arg Glu Ser Ala Thr Tyr Asn Pro Ser Leu Gln Ser
1 5 10 15

<210> SEQ ID NO 220
<211> LENGTH: 24
<212> TYPE: PRT
<213> ORGANISM: Homo sapiens

<400> SEQUENCE: 220

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 221
<211> LENGTH: 11
<212> TYPE: PRT
<213> ORGANISM: Homo sapiens

<400> SEQUENCE: 221

Gly Arg Gln Ala Leu Gly Ser Arg Ala Val Gln
1 5 10

<210> SEQ ID NO 222
<211> LENGTH: 7
<212> TYPE: PRT
<213> ORGANISM: Homo sapiens

<400> SEQUENCE: 222

Asn Asn Gln Asp Arg Pro Ser
1 5

<210> SEQ ID NO 223
<211> LENGTH: 12
<212> TYPE: PRT
<213> ORGANISM: Homo sapiens

<400> SEQUENCE: 223

His Met Trp Asp Ser Arg Ser Gly Phe Ser Trp Ser
1 5 10

<210> SEQ ID NO 224
<211> LENGTH: 6
<212> TYPE: PRT
<213> ORGANISM: Homo sapiens

<400> SEQUENCE: 224

Asn Asn Tyr Tyr Trp Thr
1 5

<210> SEQ ID NO 225
<211> LENGTH: 16
<212> TYPE: PRT
<213> ORGANISM: Homo sapiens

<400> SEQUENCE: 225

Tyr Ile Ser Asp Arg Glu Ser Ala Thr Tyr Asn Pro Ser Leu Asn Ser
1 5 10 15

<210> SEQ ID NO 226
<211> LENGTH: 24
<212> TYPE: PRT
<213> ORGANISM: Homo sapiens

<400> SEQUENCE: 226

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 227
<211> LENGTH: 11
<212> TYPE: PRT
<213> ORGANISM: Homo sapiens

<400> SEQUENCE: 227

Gly Arg Gln Ala Leu Gly Ser Arg Ala Val Gln
1 5 10

<210> SEQ ID NO 228
<211> LENGTH: 7
<212> TYPE: PRT
<213> ORGANISM: Homo sapiens

<400> SEQUENCE: 228

Asn Asn Gln Asp Arg Pro Ser
1 5

<210> SEQ ID NO 229
<211> LENGTH: 12
<212> TYPE: PRT
<213> ORGANISM: Homo sapiens

<400> SEQUENCE: 229

His Met Trp Asp Ser Arg Ser Gly Phe Ser Trp Ser
1 5 10

<210> SEQ ID NO 230
<211> LENGTH: 6
<212> TYPE: PRT
<213> ORGANISM: Homo sapiens

<400> SEQUENCE: 230

Asn Asn Tyr Tyr Trp Thr
1 5

<210> SEQ ID NO 231
<211> LENGTH: 16
<212> TYPE: PRT
<213> ORGANISM: Homo sapiens

<400> SEQUENCE: 231

Tyr Ile Ser Asp Arg Glu Ser Ala Thr Tyr Asn Pro Ser Leu Asn Ser
1 5 10 15

<210> SEQ ID NO 232
<211> LENGTH: 24
<212> TYPE: PRT
<213> ORGANISM: Homo sapiens

<400> SEQUENCE: 232

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 233
<211> LENGTH: 11
<212> TYPE: PRT
<213> ORGANISM: Homo sapiens

<400> SEQUENCE: 233

Gly Arg Gln Ala Leu Gly Ser Arg Ala Val Gln
1 5 10

<210> SEQ ID NO 234
<211> LENGTH: 7
<212> TYPE: PRT
<213> ORGANISM: Homo sapiens

<400> SEQUENCE: 234

Asn Asn Gln Asp Arg Pro Ser
1 5

<210> SEQ ID NO 235
<211> LENGTH: 12
<212> TYPE: PRT
<213> ORGANISM: Homo sapiens

<400> SEQUENCE: 235

His Met Trp Asp Ser Arg Ser Gly Phe Ser Trp Ser
1 5 10

<210> SEQ ID NO 236
<211> LENGTH: 6
<212> TYPE: PRT
<213> ORGANISM: Homo sapiens

<400> SEQUENCE: 236

Asn Asn Tyr Tyr Trp Thr
1 5

<210> SEQ ID NO 237
<211> LENGTH: 16
<212> TYPE: PRT
<213> ORGANISM: Homo sapiens

<400> SEQUENCE: 237

Tyr Ile Ser Asp Arg Glu Ser Ala Thr Tyr Asn Pro Ser Leu Asn Ser
1 5 10 15

<210> SEQ ID NO 238
<211> LENGTH: 24
<212> TYPE: PRT
<213> ORGANISM: Homo sapiens

<400> SEQUENCE: 238

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 239
<211> LENGTH: 11
<212> TYPE: PRT
<213> ORGANISM: Homo sapiens

<400> SEQUENCE: 239

Gly Arg Gln Ala Leu Gly Ser Arg Ala Val Gln
1 5 10

<210> SEQ ID NO 240
<211> LENGTH: 7
<212> TYPE: PRT
<213> ORGANISM: Homo sapiens

<400> SEQUENCE: 240

Asn Asn Gln Asp Arg Pro Ser
1 5

<210> SEQ ID NO 241
<211> LENGTH: 12
<212> TYPE: PRT
<213> ORGANISM: Homo sapiens

<400> SEQUENCE: 241

His Met Trp Asp Ser Arg Ser Gly Phe Ser Trp Ser
1 5 10

<210> SEQ ID NO 242
<211> LENGTH: 6
<212> TYPE: PRT
<213> ORGANISM: Homo sapiens

<400> SEQUENCE: 242

Asn Asn Tyr Tyr Trp Thr
1 5

<210> SEQ ID NO 243
<211> LENGTH: 16
<212> TYPE: PRT
<213> ORGANISM: Homo sapiens

<400> SEQUENCE: 243

Tyr Ile Ser Asp Arg Glu Ser Ala Thr Tyr Asn Pro Ser Leu Asn Ser
1 5 10 15

<210> SEQ ID NO 244
<211> LENGTH: 24
<212> TYPE: PRT
<213> ORGANISM: Homo sapiens

<400> SEQUENCE: 244

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 245
<211> LENGTH: 11
<212> TYPE: PRT
<213> ORGANISM: Homo sapiens

<400> SEQUENCE: 245

Gly Arg Gln Ala Leu Gly Ser Arg Ala Val Gln
1 5 10

<210> SEQ ID NO 246
<211> LENGTH: 7
<212> TYPE: PRT
<213> ORGANISM: Homo sapiens

<400> SEQUENCE: 246

Asn Asn Gln Asp Arg Pro Ser
1 5

<210> SEQ ID NO 247
<211> LENGTH: 12
<212> TYPE: PRT
<213> ORGANISM: Homo sapiens

<400> SEQUENCE: 247

His Met Trp Asp Ser Arg Ser Gly Phe Ser Trp Ser
1 5 10

<210> SEQ ID NO 248
<211> LENGTH: 6
<212> TYPE: PRT
<213> ORGANISM: Homo sapiens

<400> SEQUENCE: 248

Asn Asn Tyr Tyr Trp Thr
1 5

<210> SEQ ID NO 249
<211> LENGTH: 16
<212> TYPE: PRT
<213> ORGANISM: Homo sapiens

<400> SEQUENCE: 249

Tyr Ile Ser Asp Arg Glu Ser Ala Thr Tyr Asn Pro Ser Leu Asn Ser
1 5 10 15

<210> SEQ ID NO 250
<211> LENGTH: 24
<212> TYPE: PRT
<213> ORGANISM: Homo sapiens

<400> SEQUENCE: 250

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 251
<211> LENGTH: 11
<212> TYPE: PRT
<213> ORGANISM: Homo sapiens

<400> SEQUENCE: 251

Gly Arg Gln Ala Leu Gly Ser Arg Ala Val Gln
1 5 10

<210> SEQ ID NO 252
<211> LENGTH: 7
<212> TYPE: PRT
<213> ORGANISM: Homo sapiens

<400> SEQUENCE: 252

Asn Asn Gln Asp Arg Pro Ser
1 5

<210> SEQ ID NO 253
<211> LENGTH: 12
<212> TYPE: PRT
<213> ORGANISM: Homo sapiens

<400> SEQUENCE: 253

His Met Trp Asp Ser Arg Ser Gly Phe Ser Trp Ser
1 5 10

<210> SEQ ID NO 254
<211> LENGTH: 6
<212> TYPE: PRT
<213> ORGANISM: Homo sapiens

<400> SEQUENCE: 254

Asn Asn Tyr Tyr Trp Thr
1 5

<210> SEQ ID NO 255
<211> LENGTH: 16
<212> TYPE: PRT
<213> ORGANISM: Homo sapiens

<400> SEQUENCE: 255

Tyr Ile Ser Asp Arg Glu Ser Ala Thr Tyr Asn Pro Ser Leu Asn Ser
1 5 10 15

<210> SEQ ID NO 256
<211> LENGTH: 24
<212> TYPE: PRT
<213> ORGANISM: Homo sapiens

<400> SEQUENCE: 256

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 257
<211> LENGTH: 11
<212> TYPE: PRT
<213> ORGANISM: Homo sapiens

<400> SEQUENCE: 257

Gly Arg Gln Ala Leu Gly Ser Arg Ala Val Gln
1 5 10

<210> SEQ ID NO 258
<211> LENGTH: 7
<212> TYPE: PRT
<213> ORGANISM: Homo sapiens

<400> SEQUENCE: 258

Asn Asn Gln Asp Arg Pro Ser
1 5

<210> SEQ ID NO 259
<211> LENGTH: 12
<212> TYPE: PRT
<213> ORGANISM: Homo sapiens

<400> SEQUENCE: 259

His Met Trp Asp Ser Arg Ser Gly Phe Ser Trp Ser
1 5 10

<210> SEQ ID NO 260
<211> LENGTH: 6
<212> TYPE: PRT
<213> ORGANISM: Homo sapiens

<400> SEQUENCE: 260

Asn Asn Tyr Tyr Trp Thr
1 5

<210> SEQ ID NO 261
<211> LENGTH: 16
<212> TYPE: PRT
<213> ORGANISM: Homo sapiens

<400> SEQUENCE: 261

Tyr Ile Ser Asp Arg Glu Ser Ala Thr Tyr Asn Pro Ser Leu Asn Ser
1 5 10 15

<210> SEQ ID NO 262
<211> LENGTH: 24
<212> TYPE: PRT
<213> ORGANISM: Homo sapiens

<400> SEQUENCE: 262

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 263
<211> LENGTH: 11
<212> TYPE: PRT
<213> ORGANISM: Homo sapiens

<400> SEQUENCE: 263

Gly Arg Gln Ala Leu Gly Ser Arg Ala Val Gln
1 5 10

<210> SEQ ID NO 264
<211> LENGTH: 7
<212> TYPE: PRT
<213> ORGANISM: Homo sapiens

<400> SEQUENCE: 264

Asn Asn Gln Asp Arg Pro Ser
1 5

<210> SEQ ID NO 265
<211> LENGTH: 12
<212> TYPE: PRT
<213> ORGANISM: Homo sapiens

<400> SEQUENCE: 265

His Met Trp Asp Ser Arg Ser Gly Phe Ser Trp Ser 1 5 10

<210> SEQ ID NO 266
<211> LENGTH: 6
<212> TYPE: PRT
<213> ORGANISM: Homo sapiens

<400> SEQUENCE: 266

Asn Asn Tyr Tyr Trp Thr
1 5

<210> SEQ ID NO 267
<211> LENGTH: 16
<212> TYPE: PRT
<213> ORGANISM: Homo sapiens

<400> SEQUENCE: 267

Tyr Ile Ser Asp Arg Glu Ser Ala Thr Tyr Asn Pro Ser Leu Asn Ser
1 5 10 15

<210> SEQ ID NO 268
<211> LENGTH: 24
<212> TYPE: PRT
<213> ORGANISM: Homo sapiens

<400> SEQUENCE: 268

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 269
<211> LENGTH: 11
<212> TYPE: PRT
<213> ORGANISM: Homo sapiens

<400> SEQUENCE: 269

Gly Arg Gln Ala Leu Gly Ser Arg Ala Val Gln
1 5 10

<210> SEQ ID NO 270
<211> LENGTH: 7
<212> TYPE: PRT
<213> ORGANISM: Homo sapiens

<400> SEQUENCE: 270

Asn Asn Gln Asp Arg Pro Ser
1 5

<210> SEQ ID NO 271
<211> LENGTH: 12
<212> TYPE: PRT
<213> ORGANISM: Homo sapiens

<400> SEQUENCE: 271

His Met Trp Asp Ser Arg Ser Gly Phe Ser Trp Ser
1 5 10

<210> SEQ ID NO 272
<211> LENGTH: 6
<212> TYPE: PRT
<213> ORGANISM: Homo sapiens

<400> SEQUENCE: 272

Asn Asn Tyr Tyr Trp Thr
1               5

<210> SEQ ID NO 273
<211> LENGTH: 16
<212> TYPE: PRT
<213> ORGANISM: Homo sapiens

<400> SEQUENCE: 273

Tyr Ile Ser Asp Arg Glu Ser Ala Thr Tyr Asn Pro Ser Leu Asn Ser
1               5                   10                  15

<210> SEQ ID NO 274
<211> LENGTH: 24
<212> TYPE: PRT
<213> ORGANISM: Homo sapiens

<400> SEQUENCE: 274

Ala Arg Arg Gly Gln Arg Ile Tyr Gly Val Val Ser Phe Gly Glu Phe
1               5                   10                  15

Phe Tyr Tyr Tyr Ser Met Asp Val
            20

<210> SEQ ID NO 275
<211> LENGTH: 11
<212> TYPE: PRT
<213> ORGANISM: Homo sapiens

<400> SEQUENCE: 275

Gly Arg Gln Ala Leu Gly Ser Arg Ala Val Gln
1               5                   10

<210> SEQ ID NO 276
<211> LENGTH: 7
<212> TYPE: PRT
<213> ORGANISM: Homo sapiens

<400> SEQUENCE: 276

Asn Asn Gln Asp Arg Pro Ser
1               5

<210> SEQ ID NO 277
<211> LENGTH: 12
<212> TYPE: PRT
<213> ORGANISM: Homo sapiens

<400> SEQUENCE: 277

His Met Trp Asp Ser Arg Ser Gly Phe Ser Trp Ser
1               5                   10

<210> SEQ ID NO 278
<211> LENGTH: 6
<212> TYPE: PRT
<213> ORGANISM: Homo sapiens

<400> SEQUENCE: 278

Asn Asn Tyr Tyr Trp Thr
1               5

<210> SEQ ID NO 279
<211> LENGTH: 16
<212> TYPE: PRT
<213> ORGANISM: Homo sapiens

<400> SEQUENCE: 279

Tyr Ile Ser Asp Arg Glu Ser Ala Thr Tyr Asn Pro Ser Leu Asn Ser
1 5 10 15

<210> SEQ ID NO 280
<211> LENGTH: 24
<212> TYPE: PRT
<213> ORGANISM: Homo sapiens

<400> SEQUENCE: 280

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 281
<211> LENGTH: 11
<212> TYPE: PRT
<213> ORGANISM: Homo sapiens

<400> SEQUENCE: 281

Gly Arg Gln Ala Leu Gly Ser Arg Ala Val Gln
1 5 10

<210> SEQ ID NO 282
<211> LENGTH: 7
<212> TYPE: PRT
<213> ORGANISM: Homo sapiens

<400> SEQUENCE: 282

Asn Asn Gln Asp Arg Pro Ser
1 5

<210> SEQ ID NO 283
<211> LENGTH: 12
<212> TYPE: PRT
<213> ORGANISM: Homo sapiens

<400> SEQUENCE: 283

His Met Trp Asp Ser Arg Ser Gly Phe Ser Trp Ser
1 5 10

<210> SEQ ID NO 284
<211> LENGTH: 6
<212> TYPE: PRT
<213> ORGANISM: Homo sapiens

<400> SEQUENCE: 284

Asn Asn Tyr Tyr Trp Thr
1 5

<210> SEQ ID NO 285
<211> LENGTH: 16
<212> TYPE: PRT
<213> ORGANISM: Homo sapiens

<400> SEQUENCE: 285

Tyr Ile Ser Asp Arg Glu Ser Ala Thr Tyr Asn Pro Ser Leu Asn Ser
1 5 10 15

<210> SEQ ID NO 286
<211> LENGTH: 24
<212> TYPE: PRT
<213> ORGANISM: Homo sapiens

<400> SEQUENCE: 286

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 287
<211> LENGTH: 11
<212> TYPE: PRT
<213> ORGANISM: Homo sapiens

<400> SEQUENCE: 287

Gly Arg Gln Ala Leu Gly Ser Arg Ala Val Gln
1 5 10

<210> SEQ ID NO 288
<211> LENGTH: 7
<212> TYPE: PRT
<213> ORGANISM: Homo sapiens

<400> SEQUENCE: 288

Asn Asn Gln Asp Arg Pro Ser
1 5

<210> SEQ ID NO 289
<211> LENGTH: 12
<212> TYPE: PRT
<213> ORGANISM: Homo sapiens

<400> SEQUENCE: 289

His Met Trp Asp Ser Arg Ser Gly Phe Ser Trp Ser
1 5 10

<210> SEQ ID NO 290
<211> LENGTH: 6
<212> TYPE: PRT
<213> ORGANISM: Homo sapiens

<400> SEQUENCE: 290

Asn Asn Tyr Tyr Trp Thr
1 5

<210> SEQ ID NO 291
<211> LENGTH: 16
<212> TYPE: PRT
<213> ORGANISM: Homo sapiens

<400> SEQUENCE: 291

Tyr Ile Ser Asp Arg Glu Ser Ala Thr Tyr Asn Pro Ser Leu Asn Ser
1 5 10 15

<210> SEQ ID NO 292
<211> LENGTH: 24
<212> TYPE: PRT
<213> ORGANISM: Homo sapiens

<400> SEQUENCE: 292

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 293

<211> LENGTH: 11
<212> TYPE: PRT
<213> ORGANISM: Homo sapiens

<400> SEQUENCE: 293

Gly Arg Gln Ala Leu Gly Ser Arg Ala Val Gln
1 5 10

<210> SEQ ID NO 294
<211> LENGTH: 7
<212> TYPE: PRT
<213> ORGANISM: Homo sapiens

<400> SEQUENCE: 294

Asn Asn Gln Asp Arg Pro Ser
1 5

<210> SEQ ID NO 295
<211> LENGTH: 12
<212> TYPE: PRT
<213> ORGANISM: Homo sapiens

<400> SEQUENCE: 295

His Met Trp Asp Ser Arg Ser Gly Phe Ser Trp Ser
1 5 10

<210> SEQ ID NO 296
<211> LENGTH: 6
<212> TYPE: PRT
<213> ORGANISM: Homo sapiens

<400> SEQUENCE: 296

Asn Asn Tyr Tyr Trp Thr
1 5

<210> SEQ ID NO 297
<211> LENGTH: 16
<212> TYPE: PRT
<213> ORGANISM: Homo sapiens

<400> SEQUENCE: 297

Tyr Ile Ser Asp Arg Glu Ser Ala Thr Tyr Asn Pro Ser Leu Asn Ser
1 5 10 15

<210> SEQ ID NO 298
<211> LENGTH: 24
<212> TYPE: PRT
<213> ORGANISM: Homo sapiens

<400> SEQUENCE: 298

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 299
<211> LENGTH: 11
<212> TYPE: PRT
<213> ORGANISM: Homo sapiens

<400> SEQUENCE: 299

Gly Arg Gln Ala Leu Gly Ser Arg Ala Val Gln
1 5 10

<210> SEQ ID NO 300
<211> LENGTH: 7
<212> TYPE: PRT
<213> ORGANISM: Homo sapiens

<400> SEQUENCE: 300

Asn Asn Gln Asp Arg Pro Ser
1 5

<210> SEQ ID NO 301
<211> LENGTH: 12
<212> TYPE: PRT
<213> ORGANISM: Homo sapiens

<400> SEQUENCE: 301

His Met Trp Asp Ser Arg Ser Gly Phe Ser Trp Ser
1 5 10

<210> SEQ ID NO 302
<211> LENGTH: 6
<212> TYPE: PRT
<213> ORGANISM: Homo sapiens

<400> SEQUENCE: 302

Asn Asn Tyr Tyr Trp Thr
1 5

<210> SEQ ID NO 303
<211> LENGTH: 16
<212> TYPE: PRT
<213> ORGANISM: Homo sapiens

<400> SEQUENCE: 303

Tyr Ile Ser Asp Arg Glu Ser Ala Thr Tyr Asn Pro Ser Leu Asn Ser
1 5 10 15

<210> SEQ ID NO 304
<211> LENGTH: 24
<212> TYPE: PRT
<213> ORGANISM: Homo sapiens

<400> SEQUENCE: 304

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 305
<211> LENGTH: 11
<212> TYPE: PRT
<213> ORGANISM: Homo sapiens

<400> SEQUENCE: 305

Gly Arg Gln Ala Leu Gly Ser Arg Ala Val Gln
1 5 10

<210> SEQ ID NO 306
<211> LENGTH: 7
<212> TYPE: PRT
<213> ORGANISM: Homo sapiens

<400> SEQUENCE: 306

Asn Asn Gln Asp Arg Pro Ser
1 5

<210> SEQ ID NO 307
<211> LENGTH: 12
<212> TYPE: PRT
<213> ORGANISM: Homo sapiens

<400> SEQUENCE: 307

His Met Trp Asp Ser Arg Ser Gly Phe Ser Trp Ser
1 5 10

<210> SEQ ID NO 308
<211> LENGTH: 6
<212> TYPE: PRT
<213> ORGANISM: Homo sapiens

<400> SEQUENCE: 308

Asn Asn Tyr Tyr Trp Thr
1 5

<210> SEQ ID NO 309
<211> LENGTH: 16
<212> TYPE: PRT
<213> ORGANISM: Homo sapiens

<400> SEQUENCE: 309

Tyr Ile Ser Asp Arg Glu Ser Ala Thr Tyr Asn Pro Ser Leu Asn Ser
1 5 10 15

<210> SEQ ID NO 310
<211> LENGTH: 24
<212> TYPE: PRT
<213> ORGANISM: Homo sapiens

<400> SEQUENCE: 310

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 311
<211> LENGTH: 11
<212> TYPE: PRT
<213> ORGANISM: Homo sapiens

<400> SEQUENCE: 311

Gly Arg Gln Ala Leu Gly Ser Arg Ala Val Gln
1 5 10

<210> SEQ ID NO 312
<211> LENGTH: 7
<212> TYPE: PRT
<213> ORGANISM: Homo sapiens

<400> SEQUENCE: 312

Asn Asn Gln Asp Arg Pro Ser
1 5

<210> SEQ ID NO 313
<211> LENGTH: 12
<212> TYPE: PRT
<213> ORGANISM: Homo sapiens

<400> SEQUENCE: 313

His Met Trp Asp Ser Arg Ser Gly Phe Ser Trp Ser
1 5 10

<210> SEQ ID NO 314
<211> LENGTH: 6
<212> TYPE: PRT
<213> ORGANISM: Homo sapiens

<400> SEQUENCE: 314

Asn Asn Tyr Tyr Trp Thr
1 5

<210> SEQ ID NO 315
<211> LENGTH: 16
<212> TYPE: PRT
<213> ORGANISM: Homo sapiens

<400> SEQUENCE: 315

Tyr Ile Ser Asp Arg Glu Ser Ala Thr Tyr Asn Pro Ser Leu Asn Ser
1 5 10 15

<210> SEQ ID NO 316
<211> LENGTH: 24
<212> TYPE: PRT
<213> ORGANISM: Homo sapiens

<400> SEQUENCE: 316

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 317
<211> LENGTH: 11
<212> TYPE: PRT
<213> ORGANISM: Homo sapiens

<400> SEQUENCE: 317

Gly Arg Gln Ala Leu Gly Ser Arg Ala Val Gln
1 5 10

<210> SEQ ID NO 318
<211> LENGTH: 7
<212> TYPE: PRT
<213> ORGANISM: Homo sapiens

<400> SEQUENCE: 318

Asn Asn Gln Asp Arg Pro Ser
1 5

<210> SEQ ID NO 319
<211> LENGTH: 12
<212> TYPE: PRT
<213> ORGANISM: Homo sapiens

<400> SEQUENCE: 319

His Met Trp Asp Ser Arg Ser Gly Phe Ser Trp Ser
1 5 10

<210> SEQ ID NO 320
<211> LENGTH: 6
<212> TYPE: PRT
<213> ORGANISM: Homo sapiens

<400> SEQUENCE: 320

Asn Asn Tyr Tyr Trp Thr 1 5

<210> SEQ ID NO 321
<211> LENGTH: 16
<212> TYPE: PRT
<213> ORGANISM: Homo sapiens

<400> SEQUENCE: 321

Tyr Ile Ser Asp Arg Glu Ser Ala Thr Tyr Asn Pro Ser Leu Asn Ser
1 5 10 15

<210> SEQ ID NO 322
<211> LENGTH: 24
<212> TYPE: PRT
<213> ORGANISM: Homo sapiens

<400> SEQUENCE: 322

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 323
<211> LENGTH: 11
<212> TYPE: PRT
<213> ORGANISM: Homo sapiens

<400> SEQUENCE: 323

Gly Arg Gln Ala Leu Gly Ser Arg Ala Val Gln
1 5 10

<210> SEQ ID NO 324
<211> LENGTH: 7
<212> TYPE: PRT
<213> ORGANISM: Homo sapiens

<400> SEQUENCE: 324

Asn Asn Gln Asp Arg Pro Ser
1 5

<210> SEQ ID NO 325
<211> LENGTH: 12
<212> TYPE: PRT
<213> ORGANISM: Homo sapiens

<400> SEQUENCE: 325

His Met Trp Asp Ser Arg Ser Gly Phe Ser Trp Ser
1 5 10

<210> SEQ ID NO 326
<211> LENGTH: 6
<212> TYPE: PRT
<213> ORGANISM: Homo sapiens

<400> SEQUENCE: 326

Asn Asn Tyr Tyr Trp Thr
1 5

<210> SEQ ID NO 327
<211> LENGTH: 16
<212> TYPE: PRT
<213> ORGANISM: Homo sapiens

<400> SEQUENCE: 327

Tyr Ile Ser Asp Arg Glu Ser Ala Thr Tyr Asn Pro Ser Leu Asn Ser
1 5 10 15

<210> SEQ ID NO 328
<211> LENGTH: 24
<212> TYPE: PRT
<213> ORGANISM: Homo sapiens

<400> SEQUENCE: 328

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 329
<211> LENGTH: 11
<212> TYPE: PRT
<213> ORGANISM: Homo sapiens

<400> SEQUENCE: 329

Gly Arg Gln Ala Leu Gly Ser Arg Ala Val Gln
1 5 10

<210> SEQ ID NO 330
<211> LENGTH: 7
<212> TYPE: PRT
<213> ORGANISM: Homo sapiens

<400> SEQUENCE: 330

Asn Asn Gln Asp Arg Pro Ser
1 5

<210> SEQ ID NO 331
<211> LENGTH: 12
<212> TYPE: PRT
<213> ORGANISM: Homo sapiens

<400> SEQUENCE: 331

His Met Trp Asp Ser Arg Ser Gly Phe Ser Trp Ser
1 5 10

<210> SEQ ID NO 332
<211> LENGTH: 6
<212> TYPE: PRT
<213> ORGANISM: Homo sapiens

<400> SEQUENCE: 332

Asn Asn Tyr Tyr Trp Thr
1 5

<210> SEQ ID NO 333
<211> LENGTH: 16
<212> TYPE: PRT
<213> ORGANISM: Homo sapiens

<400> SEQUENCE: 333

Tyr Ile Ser Asp Arg Glu Ser Ala Thr Tyr Asn Pro Ser Leu Asn Ser
1 5 10 15

<210> SEQ ID NO 334
<211> LENGTH: 24
<212> TYPE: PRT
<213> ORGANISM: Homo sapiens

<400> SEQUENCE: 334

```
Ala Arg Arg Gly Gln Arg Ile Tyr Gly Val Val Ser Phe Gly Glu Phe
1               5                   10                  15

Phe Tyr Tyr Tyr Ser Met Asp Val
            20


<210> SEQ ID NO 335
<211> LENGTH: 11
<212> TYPE: PRT
<213> ORGANISM: Homo sapiens

<400> SEQUENCE: 335

Gly Arg Gln Ala Leu Gly Ser Arg Ala Val Gln
1               5                   10


<210> SEQ ID NO 336
<211> LENGTH: 7
<212> TYPE: PRT
<213> ORGANISM: Homo sapiens

<400> SEQUENCE: 336

Asn Asn Gln Asp Arg Pro Ser
1               5


<210> SEQ ID NO 337
<211> LENGTH: 12
<212> TYPE: PRT
<213> ORGANISM: Homo sapiens

<400> SEQUENCE: 337

His Met Trp Asp Ser Arg Ser Gly Phe Ser Trp Ser
1               5                   10


<210> SEQ ID NO 338
<211> LENGTH: 6
<212> TYPE: PRT
<213> ORGANISM: Homo sapiens

<400> SEQUENCE: 338

Asn Asn Tyr Tyr Trp Thr
1               5


<210> SEQ ID NO 339
<211> LENGTH: 16
<212> TYPE: PRT
<213> ORGANISM: Homo sapiens

<400> SEQUENCE: 339

Tyr Ile Ser Asp Arg Glu Ser Ala Thr Tyr Asn Pro Ser Leu Asn Ser
1               5                   10                  15


<210> SEQ ID NO 340
<211> LENGTH: 24
<212> TYPE: PRT
<213> ORGANISM: Homo sapiens

<400> SEQUENCE: 340

Ala Arg Arg Gly Gln Arg Ile Tyr Gly Val Val Ser Phe Gly Glu Phe
1               5                   10                  15

Phe Tyr Tyr Tyr Ser Met Asp Val
            20


<210> SEQ ID NO 341
<211> LENGTH: 11
```

<212> TYPE: PRT
<213> ORGANISM: Homo sapiens

<400> SEQUENCE: 341

Gly Arg Gln Ala Leu Gly Ser Arg Ala Val Gln
1               5                   10

<210> SEQ ID NO 342
<211> LENGTH: 7
<212> TYPE: PRT
<213> ORGANISM: Homo sapiens

<400> SEQUENCE: 342

Asn Asn Gln Asp Arg Pro Ser
1               5

<210> SEQ ID NO 343
<211> LENGTH: 12
<212> TYPE: PRT
<213> ORGANISM: Homo sapiens

<400> SEQUENCE: 343

His Met Trp Asp Ser Arg Ser Gly Phe Ser Trp Ser
1               5                   10

<210> SEQ ID NO 344
<211> LENGTH: 6
<212> TYPE: PRT
<213> ORGANISM: Homo sapiens

<400> SEQUENCE: 344

Asn Asn Tyr Tyr Trp Thr
1               5

<210> SEQ ID NO 345
<211> LENGTH: 16
<212> TYPE: PRT
<213> ORGANISM: Homo sapiens

<400> SEQUENCE: 345

Tyr Ile Ser Asp Arg Glu Ser Ala Thr Tyr Asn Pro Ser Leu Asn Ser
1               5                   10                  15

<210> SEQ ID NO 346
<211> LENGTH: 24
<212> TYPE: PRT
<213> ORGANISM: Homo sapiens

<400> SEQUENCE: 346

Ala Arg Arg Gly Gln Arg Ile Tyr Gly Val Val Ser Phe Gly Glu Phe
1               5                   10                  15

Phe Tyr Tyr Tyr Ser Met Asp Val
            20

<210> SEQ ID NO 347
<211> LENGTH: 11
<212> TYPE: PRT
<213> ORGANISM: Homo sapiens

<400> SEQUENCE: 347

Gly Arg Gln Ala Leu Gly Ser Arg Ala Val Gln
1               5                   10

<210> SEQ ID NO 348

<211> LENGTH: 7
<212> TYPE: PRT
<213> ORGANISM: Homo sapiens

<400> SEQUENCE: 348

Asn Asn Gln Asp Arg Pro Ser
1 5

<210> SEQ ID NO 349
<211> LENGTH: 12
<212> TYPE: PRT
<213> ORGANISM: Homo sapiens

<400> SEQUENCE: 349

His Met Trp Asp Ser Arg Ser Gly Phe Ser Trp Ser
1 5 10

<210> SEQ ID NO 350
<211> LENGTH: 6
<212> TYPE: PRT
<213> ORGANISM: Homo sapiens

<400> SEQUENCE: 350

Asn Asn Tyr Tyr Trp Thr
1 5

<210> SEQ ID NO 351
<211> LENGTH: 16
<212> TYPE: PRT
<213> ORGANISM: Homo sapiens

<400> SEQUENCE: 351

Tyr Ile Ser Asp Arg Glu Ser Ala Thr Tyr Asn Pro Ser Leu Asn Ser
1 5 10 15

<210> SEQ ID NO 352
<211> LENGTH: 24
<212> TYPE: PRT
<213> ORGANISM: Homo sapiens

<400> SEQUENCE: 352

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 353
<211> LENGTH: 11
<212> TYPE: PRT
<213> ORGANISM: Homo sapiens

<400> SEQUENCE: 353

Gly Arg Gln Ala Leu Gly Ser Arg Ala Val Gln
1 5 10

<210> SEQ ID NO 354
<211> LENGTH: 7
<212> TYPE: PRT
<213> ORGANISM: Homo sapiens

<400> SEQUENCE: 354

Asn Asn Gln Asp Arg Pro Ser
1 5

<210> SEQ ID NO 355
<211> LENGTH: 12
<212> TYPE: PRT
<213> ORGANISM: Homo sapiens

<400> SEQUENCE: 355

His Met Trp Asp Ser Arg Ser Gly Phe Ser Trp Ser
1 5 10

<210> SEQ ID NO 356
<211> LENGTH: 6
<212> TYPE: PRT
<213> ORGANISM: Homo sapiens

<400> SEQUENCE: 356

Asn Asn Tyr Tyr Trp Thr
1 5

<210> SEQ ID NO 357
<211> LENGTH: 16
<212> TYPE: PRT
<213> ORGANISM: Homo sapiens

<400> SEQUENCE: 357

Tyr Ile Ser Asp Arg Glu Ser Ala Thr Tyr Asn Pro Ser Leu Asn Ser
1 5 10 15

<210> SEQ ID NO 358
<211> LENGTH: 24
<212> TYPE: PRT
<213> ORGANISM: Homo sapiens

<400> SEQUENCE: 358

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 359
<211> LENGTH: 11
<212> TYPE: PRT
<213> ORGANISM: Homo sapiens

<400> SEQUENCE: 359

Gly Arg Gln Ala Leu Gly Ser Arg Ala Val Gln
1 5 10

<210> SEQ ID NO 360
<211> LENGTH: 7
<212> TYPE: PRT
<213> ORGANISM: Homo sapiens

<400> SEQUENCE: 360

Asn Asn Gln Asp Arg Pro Ser
1 5

<210> SEQ ID NO 361
<211> LENGTH: 12
<212> TYPE: PRT
<213> ORGANISM: Homo sapiens

<400> SEQUENCE: 361

His Met Trp Asp Ser Arg Ser Gly Phe Ser Trp Ser
1 5 10

<210> SEQ ID NO 362
<211> LENGTH: 6
<212> TYPE: PRT
<213> ORGANISM: Homo sapiens

<400> SEQUENCE: 362

Asn Asn Tyr Tyr Trp Thr
1 5

<210> SEQ ID NO 363
<211> LENGTH: 16
<212> TYPE: PRT
<213> ORGANISM: Homo sapiens

<400> SEQUENCE: 363

Tyr Ile Ser Asp Arg Glu Ser Ala Thr Tyr Asn Pro Ser Leu Asn Ser
1 5 10 15

<210> SEQ ID NO 364
<211> LENGTH: 24
<212> TYPE: PRT
<213> ORGANISM: Homo sapiens

<400> SEQUENCE: 364

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 365
<211> LENGTH: 11
<212> TYPE: PRT
<213> ORGANISM: Homo sapiens

<400> SEQUENCE: 365

Gly Arg Gln Ala Leu Gly Ser Arg Ala Val Gln
1 5 10

<210> SEQ ID NO 366
<211> LENGTH: 7
<212> TYPE: PRT
<213> ORGANISM: Homo sapiens

<400> SEQUENCE: 366

Asn Asn Gln Asp Arg Pro Ser
1 5

<210> SEQ ID NO 367
<211> LENGTH: 12
<212> TYPE: PRT
<213> ORGANISM: Homo sapiens

<400> SEQUENCE: 367

His Met Trp Asp Ser Arg Ser Gly Phe Ser Trp Ser
1 5 10

<210> SEQ ID NO 368
<211> LENGTH: 6
<212> TYPE: PRT
<213> ORGANISM: Homo sapiens

<400> SEQUENCE: 368

Asn Asn Tyr Tyr Trp Thr
1 5

<210> SEQ ID NO 369
<211> LENGTH: 16
<212> TYPE: PRT
<213> ORGANISM: Homo sapiens

<400> SEQUENCE: 369

Tyr Ile Ser Asp Arg Glu Ser Ala Thr Tyr Asn Pro Ser Leu Asn Ser
1 5 10 15

<210> SEQ ID NO 370
<211> LENGTH: 24
<212> TYPE: PRT
<213> ORGANISM: Homo sapiens

<400> SEQUENCE: 370

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 371
<211> LENGTH: 11
<212> TYPE: PRT
<213> ORGANISM: Homo sapiens

<400> SEQUENCE: 371

Gly Arg Gln Ala Leu Gly Ser Arg Ala Val Gln
1 5 10

<210> SEQ ID NO 372
<211> LENGTH: 7
<212> TYPE: PRT
<213> ORGANISM: Homo sapiens

<400> SEQUENCE: 372

Asn Asn Gln Asp Arg Pro Ser
1 5

<210> SEQ ID NO 373
<211> LENGTH: 12
<212> TYPE: PRT
<213> ORGANISM: Homo sapiens

<400> SEQUENCE: 373

His Met Trp Asp Ser Arg Ser Gly Phe Ser Trp Ser
1 5 10

<210> SEQ ID NO 374
<211> LENGTH: 6
<212> TYPE: PRT
<213> ORGANISM: Homo sapiens

<400> SEQUENCE: 374

Asn Asn Tyr Tyr Trp Thr
1 5

<210> SEQ ID NO 375
<211> LENGTH: 16
<212> TYPE: PRT
<213> ORGANISM: Homo sapiens

<400> SEQUENCE: 375

Tyr Ile Ser Asp Arg Glu Ser Ala Thr Tyr Asn Pro Ser Leu Asn Ser 1 5 10 15

<210> SEQ ID NO 376
<211> LENGTH: 24
<212> TYPE: PRT
<213> ORGANISM: Homo sapiens

<400> SEQUENCE: 376

Ala Arg Arg Gly Gln Arg Ile Tyr Gly Val Val Ser Phe Gly Glu Phe
1 5 10 15

Phe Tyr Tyr Tyr Ser Met Asp Val
20

<210> SEQ ID NO 377
<211> LENGTH: 699
<212> TYPE: DNA
<213> ORGANISM: Homo sapiens

<400> SEQUENCE: 377
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 378
<211> LENGTH: 699
<212> TYPE: DNA
<213> ORGANISM: Homo sapiens

<400> SEQUENCE: 378
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 379
<211> LENGTH: 699
<212> TYPE: DNA
<213> ORGANISM: Homo sapiens

<400> SEQUENCE: 379
atgggatgga gctgtatcat cctgttcctc gtggccacag caaccggtgt acattcttcc 60
cctgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 380
<211> LENGTH: 699
<212> TYPE: DNA
<213> ORGANISM: Homo sapiens

<400> SEQUENCE: 380
atgggatgga gctgtatcat cctgttcctc gtggccacag caaccggtgt acattcttcc 60
tatgtgccac cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 381
<211> LENGTH: 699
<212> TYPE: DNA
<213> ORGANISM: Homo sapiens

<400> SEQUENCE: 381
atgggatgga gctgtatcat cctgttcctc gtggccacag caaccggtgt acattcttcc 60
tatgtgcgca gcctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 382
<211> LENGTH: 699
<212> TYPE: DNA
<213> ORGANISM: Homo sapiens

<400> SEQUENCE: 382
atgggatgga gctgtatcat cctgttcctc gtggccacag caaccggtgt acattcttcc 60
tatgtgcgcc cgctgtcagt ggccctgggg cagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 383
<211> LENGTH: 699
<212> TYPE: DNA
<213> ORGANISM: Homo sapiens

<400> SEQUENCE: 383
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacagaggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 384
<211> LENGTH: 699
<212> TYPE: DNA
<213> ORGANISM: Homo sapiens

<400> SEQUENCE: 384
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcaccaat 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 385
<211> LENGTH: 699
<212> TYPE: DNA
<213> ORGANISM: Homo sapiens

<400> SEQUENCE: 385
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gattccaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 386
<211> LENGTH: 699
<212> TYPE: DNA
<213> ORGANISM: Homo sapiens

<400> SEQUENCE: 386
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattggct ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 387
<211> LENGTH: 699
<212> TYPE: DNA
<213> ORGANISM: Homo sapiens

<400> SEQUENCE: 387
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccac cgccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 388
<211> LENGTH: 699
<212> TYPE: DNA
<213> ORGANISM: Homo sapiens

<400> SEQUENCE: 388
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggagagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600

```
ctgacgcctg agcagtggaa gtcccacaga agctacagct gccaggtcac gcatgaaggg    660

agcaccgtgg agaagacagt ggcccctaca gaatgttca                           699
```

<210> SEQ ID NO 389
<211> LENGTH: 699
<212> TYPE: DNA
<213> ORGANISM: Homo sapiens

<400> SEQUENCE: 389

```
atgggatgga gctgtatcat cctgttcctc gtggccacag caaccggtgt acattcttcc     60

tatgtgcgcc cgctgtcagt ggccctgggg gagacggcca ggatttcctg tggacgacag    120

gcccttggaa gtagagctgt tcagtggtat caacataggc caggccaggc ccctatattg    180

ctcatttata ataatcaaga ccggccctca gggatccctg agcgattctc tggcacccct    240

gatattaatt ttgggaccag ggccaccctg accatcagcg gggtcgaagc cggggatgaa    300

gccgactatt actgtcacat gtgggatagt agaagtggct tcagttggtc tttcggcggg    360

ggaaccaggc tgaccgtcct aggtcagccc aaggctgccc cctcggtcac tctgttcccg    420

ccctcctctg aggagcttca agccaacaag gccacactgg tgtgtctcat aagtgacttc    480

tacccgggag ccgtgacagt ggcctggaag gcagatagca gccccgtcaa ggcgggagtg    540

gagaccacca caccctccaa acaaagcaac aacaagtacg cggccagcag ctatctgagc    600

ctgacgcctg agcagtggaa gtcccacaga agctacagct gccaggtcac gcatgaaggg    660

agcaccgtgg agaagacagt ggcccctaca gaatgttca                           699
```

<210> SEQ ID NO 390
<211> LENGTH: 699
<212> TYPE: DNA
<213> ORGANISM: Homo sapiens

<400> SEQUENCE: 390

```
atgggatgga gctgtatcat cctgttcctc gtggccacag caaccggtgt acattcttcc     60

tatgtgcgcc cgctgtcagt ggccctgggg gagacggcca ggatttcctg tggacgacag    120

gcccttggaa gtagagctgt tcagtggtat caacataggc caggccaggc ccctatattg    180

ctcatttata ataatcaaga ccggccctca gggatccctg agcgattctc tggcacccct    240

gatattaatt ttgggaccag ggccaccctg accatcagcg gggtcgaagc cggggatgaa    300

gccgactatt actgtcacat gtgggatagt agaagtggct tcagttggtc tttcggcggg    360

gcgaccaggc tgaccgtcct aggtcagccc aaggctgccc cctcggtcac tctgttcccg    420

ccctcctctg aggagcttca agccaacaag gccacactgg tgtgtctcat aagtgacttc    480

tacccgggag ccgtgacagt ggcctggaag gcagatagca gccccgtcaa ggcgggagtg    540

gagaccacca caccctccaa acaaagcaac aacaagtacg cggccagcag ctatctgagc    600

ctgacgcctg agcagtggaa gtcccacaga agctacagct gccaggtcac gcatgaaggg    660

agcaccgtgg agaagacagt ggcccctaca gaatgttca                           699
```

<210> SEQ ID NO 391
<211> LENGTH: 699
<212> TYPE: DNA
<213> ORGANISM: Homo sapiens

<400> SEQUENCE: 391

```
atgggatgga gctgtatcat cctgttcctc gtggccacag caaccggtgt acattcttcc     60
```

tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg ggtcgaagc cggggatgaa 300 gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 392
<211> LENGTH: 699
<212> TYPE: DNA
<213> ORGANISM: Homo sapiens

<400> SEQUENCE: 392
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg ggtcgaagc cggggatgaa 300 gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 393
<211> LENGTH: 699
<212> TYPE: DNA
<213> ORGANISM: Homo sapiens

<400> SEQUENCE: 393
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg ggtcgaagc cggggatgaa 300 gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 394
<211> LENGTH: 699
<212> TYPE: DNA
<213> ORGANISM: Homo sapiens

<400> SEQUENCE: 394
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 395
<211> LENGTH: 699
<212> TYPE: DNA
<213> ORGANISM: Homo sapiens

<400> SEQUENCE: 395
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 396
<211> LENGTH: 699
<212> TYPE: DNA
<213> ORGANISM: Homo sapiens

<400> SEQUENCE: 396
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg ggtcgaagc cggggatgaa 300 gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 397
<211> LENGTH: 699
<212> TYPE: DNA
<213> ORGANISM: Homo sapiens

<400> SEQUENCE: 397
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg ggtcgaagc cggggatgaa 300 gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 398
<211> LENGTH: 699
<212> TYPE: DNA
<213> ORGANISM: Homo sapiens

<400> SEQUENCE: 398
atgggatgga gctgtatcat cctgttcctc gtggccacag caaccggtgt acattcttcc 60
cctgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg ggtcgaagc cggggatgaa 300 gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 399
<211> LENGTH: 699
<212> TYPE: DNA
<213> ORGANISM: Homo sapiens

<400> SEQUENCE: 399
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg ggtcgaagc cggggatgaa 300 gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 400
<211> LENGTH: 699
<212> TYPE: DNA
<213> ORGANISM: Homo sapiens

<400> SEQUENCE: 400
atgggatgga gctgtatcat cctgttcctc gtggccacag caaccggtgt acattcttcc 60
cctgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg ggtcgaagc cggggatgaa 300 gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 401
<211> LENGTH: 699
<212> TYPE: DNA
<213> ORGANISM: Homo sapiens

<400> SEQUENCE: 401
atgggatgga gctgtatcat cctgttcctc gtggccacag caaccggtgt acattcttcc 60
cctgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 402
<211> LENGTH: 699
<212> TYPE: DNA
<213> ORGANISM: Homo sapiens

<400> SEQUENCE: 402
atgggatgga gctgtatcat cctgttcctc gtggccacag caaccggtgt acattcttcc 60
cctgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 403
<211> LENGTH: 699
<212> TYPE: DNA
<213> ORGANISM: Homo sapiens

<400> SEQUENCE: 403
atgggatgga gctgtatcat cctgttcctc gtggccacag caaccggtgt acattcttcc 60
cctgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 404
<211> LENGTH: 699
<212> TYPE: DNA
<213> ORGANISM: Homo sapiens

<400> SEQUENCE: 404
atgggatgga gctgtatcat cctgttcctc gtggccacag caaccggtgt acattcttcc 60
cctgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 405
<211> LENGTH: 699
<212> TYPE: DNA
<213> ORGANISM: Homo sapiens

<400> SEQUENCE: 405
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 406
<211> LENGTH: 699
<212> TYPE: DNA

<213> ORGANISM: Homo sapiens

<400> SEQUENCE: 406
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 407
<211> LENGTH: 699
<212> TYPE: DNA
<213> ORGANISM: Homo sapiens

<400> SEQUENCE: 407
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 408
<211> LENGTH: 699
<212> TYPE: DNA
<213> ORGANISM: Homo sapiens

<400> SEQUENCE: 408
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 409
<211> LENGTH: 699
<212> TYPE: DNA
<213> ORGANISM: Homo sapiens

<400> SEQUENCE: 409
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 410
<211> LENGTH: 699
<212> TYPE: DNA
<213> ORGANISM: Homo sapiens

<400> SEQUENCE: 410
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 411

<211> LENGTH: 699
<212> TYPE: DNA
<213> ORGANISM: Homo sapiens

<400> SEQUENCE: 411

```
atgggatgga gctgtatcat cctgttcctc gtggccacag caaccggtgt acattcttcc     60

cctgtgcgcc cgctgtcagt ggccctgggg gagacggcca ggatttcctg tggacgacag    120

gcccttggaa gtagagctgt tcagtggtat caacataggc caggccaggc ccctatattg    180

ctcatttata ataatcaaga ccggccctca gggatccctg agcgattctc tggcacccct    240

gatattaatt ttgggaccag ggccaccctg accatcagcg ggtcgaagc cggggatgaa    300

gccgactatt actgtcacat gtgggatagt agaagtggct tcagttggtc tttcggcggg    360

gcgaccaggc tgaccgtcct aggtcagccc aaggctgccc cctcggtcac tctgttcccg    420

ccctcctctg aggagcttca agccaacaag gccacactgg tgtgtctcat aagtgacttc    480

tacccgggag ccgtgacagt ggcctggaag gcagatagca gccccgtcaa ggcgggagtg    540

gagaccacca caccctccaa acaaagcaac aacaagtacg cggccagcag ctatctgagc    600

ctgacgcctg agcagtggaa gtcccacaga agctacagct gccaggtcac gcatgaaggg    660

agcaccgtgg agaagacagt ggcccctaca gaatgttca                           699
```

<210> SEQ ID NO 412
<211> LENGTH: 699
<212> TYPE: DNA
<213> ORGANISM: Homo sapiens

<400> SEQUENCE: 412

```
atgggatgga gctgtatcat cctgttcctc gtggccacag caaccggtgt acattcttcc     60

cctgtgcgcc cgctgtcagt ggccctgggg gagacggcca ggatttcctg tggacgacag    120

gcccttggaa gtagagctgt tcagtggtat caacataggc caggccaggc ccctatattg    180

ctcatttata ataatcaaga ccggccctca gggatccctg agcgattctc tggcacccct    240

gatattaatt ttgggaccag ggccaccctg accatcagcg ggtcgaagc cggggatgaa    300

gccgactatt actgtcacat gtgggatagt agaagtggct tcagttggtc tttcggcggg    360

gcgaccaggc tgaccgtcct aggtcagccc aaggctgccc cctcggtcac tctgttcccg    420

ccctcctctg aggagcttca agccaacaag gccacactgg tgtgtctcat aagtgacttc    480

tacccgggag ccgtgacagt ggcctggaag gcagatagca gccccgtcaa ggcgggagtg    540

gagaccacca caccctccaa acaaagcaac aacaagtacg cggccagcag ctatctgagc    600

ctgacgcctg agcagtggaa gtcccacaga agctacagct gccaggtcac gcatgaaggg    660

agcaccgtgg agaagacagt ggcccctaca gaatgttca                           699
```

<210> SEQ ID NO 413
<211> LENGTH: 699
<212> TYPE: DNA
<213> ORGANISM: Homo sapiens

<400> SEQUENCE: 413

```
atgggatgga gctgtatcat cctgttcctc gtggccacag caaccggtgt acattcttcc     60

cctgtgcgcc cgctgtcagt ggccctgggg gagacggcca ggatttcctg tggacgacag    120

gcccttggaa gtagagctgt tcagtggtat caacataggc caggccaggc ccctatattg    180

ctcatttata ataatcaaga ccggccctca gggatccctg agcgattctc tggcacccct    240

gatattaatt ttgggaccag ggccaccctg accatcagcg ggtcgaagc cggggatgaa    300
```

gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 414
<211> LENGTH: 699
<212> TYPE: DNA
<213> ORGANISM: Homo sapiens

<400> SEQUENCE: 414
atgggatgga gctgtatcat cctgttcctc gtggccacag caaccggtgt acattcttcc 60
cctgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 415
<211> LENGTH: 699
<212> TYPE: DNA
<213> ORGANISM: Homo sapiens

<400> SEQUENCE: 415
atgggatgga gctgtatcat cctgttcctc gtggccacag caaccggtgt acattcttcc 60
cctgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 416
<211> LENGTH: 699
<212> TYPE: DNA
<213> ORGANISM: Homo sapiens

<400> SEQUENCE: 416
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 417
<211> LENGTH: 699
<212> TYPE: DNA
<213> ORGANISM: Homo sapiens

<400> SEQUENCE: 417
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 418
<211> LENGTH: 699
<212> TYPE: DNA
<213> ORGANISM: Homo sapiens

<400> SEQUENCE: 418
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 419
<211> LENGTH: 699
<212> TYPE: DNA
<213> ORGANISM: Homo sapiens

<400> SEQUENCE: 419
atgggatgga gctgtatcat cctgttcctc gtggccacag caaccggtgt acattcttcc 60
cctgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 420
<211> LENGTH: 699
<212> TYPE: DNA
<213> ORGANISM: Homo sapiens

<400> SEQUENCE: 420
atgggatgga gctgtatcat cctgttcctc gtggccacag caaccggtgt acattcttcc 60
cctgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 421
<211> LENGTH: 699
<212> TYPE: DNA
<213> ORGANISM: Homo sapiens

<400> SEQUENCE: 421
atgggatgga gctgtatcat cctgttcctc gtggccacag caaccggtgt acattcttcc 60
cctgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg ggtcgaagc cggggatgaa 300 gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 422
<211> LENGTH: 699
<212> TYPE: DNA
<213> ORGANISM: Homo sapiens

<400> SEQUENCE: 422
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg ggtcgaagc cggggatgaa 300 gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 423
<211> LENGTH: 699
<212> TYPE: DNA
<213> ORGANISM: Homo sapiens

<400> SEQUENCE: 423
atgggatgga gctgtatcat cctgttcctc gtggccacag caaccggtgt acattcttcc 60
cctgtgcgcc cgctgtcagt ggccctgggg gagacggcca ggatttcctg tggacgacag 120
gcccttggaa gtagagctgt tcagtggtat caacataggc caggccaggc ccctatattg 180

```
ctcatttata ataatcaaga ccggccctca gggatccctg agcgattctc tggcacccct    240
gatattaatt ttgggaccag ggccaccctg accatcagcg gggtcgaagc cggggatgaa    300
gccgactatt actgtcacat gtgggatagt agaagtggct tcagttggtc tttcggcggg    360
gcgaccaggc tgaccgtcct aggtcagccc aaggctgccc cctcggtcac tctgttcccg    420
ccctcctctg aggagcttca agccaacaag gccacactgg tgtgtctcat aagtgacttc    480
tacccgggag ccgtgacagt ggcctggaag gcagatagca gccccgtcaa ggcgggagtg    540
gagaccacca caccctccaa acaaagcaac aacaagtacg cggccagcag ctatctgagc    600
ctgacgcctg agcagtggaa gtcccacaga agctacagct gccaggtcac gcatgaaggg    660
agcaccgtgg agaagacagt ggcccctaca gaatgttca                          699
```

<210> SEQ ID NO 424
<211> LENGTH: 1443
<212> TYPE: DNA
<213> ORGANISM: Homo sapiens

<400> SEQUENCE: 424

```
atgggatggt catgtatcat ccttttttcta gtagcaactg caaccggtgt acactcgcag     60
gtgcagctgc aggagtcggg cccaggactg gtgaaacctt cggagaccct gtccgtcacc    120
tgcagtgtct ctggagattc catgaataat tactactgga cttggatccg gcagtccccc    180
ggaaagggac tggagtggat aggctatatc tctgacagag aatcagcgac ttacaacccc    240
tccctcaata gtcgagtcgt catatcacga gacacgtcga aaaaccaatt gtccctaaaa    300
ttaaactccg tcacccctgc ggacacggcc gtctattact gtgcgacagc gcgccgagga    360
cagaggattt atggagtggt ttcctttgga gagttcttct actactactc catggacgtc    420
tggggcaagg ggaccacggt caccgtctcc tcagctagca ccaagggccc atcggtcttc    480
cccctggcac cctcctccaa gagcacctct gggggcacag cggccctggg ctgcctggtc    540
aaggactact tccccgagcc ggtgacggtg tcgtggaact caggcgccct gaccagcggc    600
gtgcacacct tcccggctgt cctacagtcc tcaggactct actccctcag cagcgtggtg    660
accgtgccct ccagcagctt gggcacccag acctacatct gcaacgtgaa tcacaagccc    720
agcaacacca aggtggacaa gaaagttgag cccaaatctt gtgacaaaac tcacacatgc    780
ccaccgtgcc cagcacctga actcctgggg ggaccgtcag tcttcctctt ccccccaaaa    840
cccaaggaca ccctcatgat ctcccggacc cctgaggtca catgcgtggt ggtggacgtg    900
agccacgaag accctgaggt caagttcaac tggtacgtgg acggcgtgga ggtgcataat    960
gccaagacaa agccgcggga ggagcagtac aacagcacgt accgtgtggt cagcgtcctc   1020
accgtcctgc accaggactg gctgaatggc aaggagtaca agtgcaaggt ctccaacaaa   1080
gccctcccag cccccatcga gaaaaccatc tccaaagcca aagggcagcc ccgagaacca   1140
caggtgtaca ccctgccccc atcccgggat gagctgacca agaaccaggt cagcctgacc   1200
tgcctggtca aaggcttcta tcccagcgac atcgccgtgg agtgggagag caatgggcag   1260
ccggagaaca actacaagac cacgcctccc gtgctggact ccgacggctc cttcttcctc   1320
tacagcaagc tcaccgtgga caagagcagg tggcagcagg ggaacgtctt ctcatgctcc   1380
gtgatgcatg aggctctgca caaccactac acgcagaaga gcctctccct gtctccgggt   1440
aaa                                                                 1443
```

<210> SEQ ID NO 425

<211> LENGTH: 1443
<212> TYPE: DNA
<213> ORGANISM: Homo sapiens

<400> SEQUENCE: 425
atgggatggt catgtatcat cctttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcgt catatcacga gacacgtcga aaaaccaatt gtccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 426
<211> LENGTH: 1443
<212> TYPE: DNA
<213> ORGANISM: Homo sapiens

<400> SEQUENCE: 426
atgggatggt catgtatcat cctttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcgt catatcacga gacacgtcga aaaaccaatt gtccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 427
<211> LENGTH: 1443
<212> TYPE: DNA
<213> ORGANISM: Homo sapiens

<400> SEQUENCE: 427
atgggatggt catgtatcat ccttttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcgt catatcacga gacacgtcga aaaaccaatt gtccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080

```
gccctcccag cccccatcga gaaaaccatc tccaaagcca aagggcagcc ccgagaacca   1140

caggtgtaca ccctgccccc atcccgggat gagctgacca agaaccaggt cagcctgacc   1200

tgcctggtca aaggcttcta tcccagcgac atcgccgtgg agtgggagag caatgggcag   1260

ccggagaaca actacaagac cacgcctccc gtgctggact ccgacggctc cttcttcctc   1320

tacagcaagc tcaccgtgga caagagcagg tggcagcagg ggaacgtctt ctcatgctcc   1380

gtgctgcatg aggctctgca ctcccactac acgcagaaga gcctctccct gtctccgggt   1440

aaa                                                                 1443
```

<210> SEQ ID NO 428
<211> LENGTH: 1443
<212> TYPE: DNA
<213> ORGANISM: Homo sapiens

<400> SEQUENCE: 428

```
atgggatggt catgtatcat cctttttcta gtagcaactg caaccggtgt acactcgcag     60

gtgcagctgc aggagtcggg cccaggactg gtgaaacctt cggagaccct gtccgtcacc    120

tgcagtgtct ctggagattc catgaataat tactactgga cttggatccg gcagtccccc    180

ggaaagggac tggagtggat aggctatatc tctgacagag aatcagcgac ttacaacccc    240

tccctcaata gtcgagtcgt catatcacga gacacgtcga aaaaccaatt gtccctaaaa    300

ttaaactccg tcacccctgc ggacacggcc gtctattact gtgcgacagc gcgccgagga    360

cagaggattt atggagtggt ttcctttgga gagttcttct actactactc catggacgtc    420

tggggcaagg ggaccacggt caccgtctcc tcagctagca ccaagggccc atcggtcttc    480

cccctggcac cctcctccaa gagcacctct gggggcacag cggccctggg ctgcctggtc    540

aaggactact tccccgagcc ggtgacggtg tcgtggaact caggcgccct gaccagcggc    600

gtgcacacct tcccggctgt cctacagtcc tcaggactct actccctcag cagcgtggtg    660

accgtgccct ccagcagctt gggcacccag acctacatct gcaacgtgaa tcacaagccc    720

agcaacacca aggtggacaa gaaagttgag cccaaatctt gtgacaaaac tcacacatgc    780

ccaccgtgcc cagcacctga actcctgggg ggaccgtcag tcttcctctt ccccccaaaa    840

cccaaggaca ccctcatgat ctcccggacc cctgaggtca catgcgtggt ggtggacgtg    900

agccacgaag accctgaggt caagttcaac tggtacgtgg acggcgtgga ggtgcataat    960

gccaagacaa agccgcggga ggagcagtac aacagcacgt accgtgtggt cagcgtcctc   1020

accgtcctgc accaggactg gctgaatggc aaggagtaca agtgcaaggt ctccaacaaa   1080

gccctcccag cccccatcga gaaaaccatc tccaaagcca aagggcagcc ccgagaacca   1140

caggtgtaca ccctgccccc atcccgggat gagctgacca agaaccaggt cagcctgacc   1200

tgcctggtca aaggcttcta tcccagcgac atcgccgtgg agtgggagag caatgggcag   1260

ccggagaaca actacaagac cacgcctccc gtgctggact ccgacggctc cttcttcctc   1320

tacagcaagc tcaccgtgga caagagcagg tggcagcagg ggaacgtctt ctcatgctcc   1380

gtgctgcatg aggctctgca ctcccactac acgcagaaga gcctctccct gtctccgggt   1440

aaa                                                                 1443
```

<210> SEQ ID NO 429
<211> LENGTH: 1443
<212> TYPE: DNA
<213> ORGANISM: Homo sapiens

<400> SEQUENCE: 429

```
atgggatggt catgtatcat cctttttcta gtagcaactg caaccggtgt acactcgcag      60
gtgcagctgc aggagtcggg cccaggactg gtgaaacctt cggagaccct gtccgtcacc     120
tgcagtgtct ctggagattc catgaataat tactactgga cttggatccg gcagtccccc     180
ggaaagggac tggagtggat aggctatatc tctgacagag aatcagcgac ttacaacccc     240
tccctcaata gtcgagtcgt catatcacga gacacgtcga aaaaccaatt gtccctaaaa     300
ttaaactccg tcacccctgc ggacacggcc gtctattact gtgcgacagc gcgccgagga     360
cagaggattt atggagtggt ttcctttgga gagttcttct actactactc catggacgtc     420
tggggcaagg ggaccacggt caccgtctcc tcagctagca ccaagggccc atcggtcttc     480
cccctggcac cctcctccaa gagcacctct gggggcacag cggccctggg ctgcctggtc     540
aaggactact tccccgagcc ggtgacggtg tcgtggaact caggcgccct gaccagcggc     600
gtgcacacct tcccggctgt cctacagtcc tcaggactct actccctcag cagcgtggtg     660
accgtgccct ccagcagctt gggcacccag acctacatct gcaacgtgaa tcacaagccc     720
agcaacacca aggtggacaa gaaagttgag cccaaatctt gtgacaaaac tcacacatgc     780
ccaccgtgcc cagcacctga actcctgggg ggaccgtcag tcttcctctt ccccccaaaa     840
cccaaggaca ccctcatgat ctcccggacc cctgaggtca catgcgtggt ggtggacgtg     900
agccacgaag accctgaggt caagttcaac tggtacgtgg acggcgtgga ggtgcataat     960
gccaagacaa agccgcggga ggagcagtac aacagcacgt accgtgtggt cagcgtcctc    1020
accgtcctgc accaggactg gctgaatggc aaggagtaca agtgcaaggt ctccaacaaa    1080
gccctcccag cccccatcga gaaaaccatc tccaaagcca aagggcagcc ccgagaacca    1140
caggtgtaca ccctgccccc atcccgggat gagctgacca agaaccaggt cagcctgacc    1200
tgcctggtca aaggcttcta tcccagcgac atcgccgtgg agtgggagag caatgggcag    1260
ccggagaaca actacaagac cacgcctccc gtgctggact ccgacggctc cttcttcctc    1320
tacagcaagc tcaccgtgga caagagcagg tggcagcagg ggaacgtctt ctcatgctcc    1380
gtgctgcatg aggctctgca ctcccactac acgcagaaga gcctctccct gtctccgggt    1440
aaa                                                                  1443
```

<210> SEQ ID NO 430
<211> LENGTH: 1443
<212> TYPE: DNA
<213> ORGANISM: Homo sapiens

<400> SEQUENCE: 430

```
atgggatggt catgtatcat cctttttcta gtagcaactg caaccggtgt acactcgcag      60
gtgcagctgc aggagtcggg cccaggactg gtgaaacctt cggagaccct gtccgtcacc     120
tgcagtgtct ctggagattc catgaataat tactactgga cttggatccg gcagtccccc     180
ggaaagggac tggagtggat aggctatatc tctgacagag aatcagcgac ttacaacccc     240
tccctcaata gtcgagtcgt catatcacga gacacgtcga aaaaccaatt gtccctaaaa     300
ttaaactccg tcacccctgc ggacacggcc gtctattact gtgcgacagc gcgccgagga     360
cagaggattt atggagtggt ttcctttgga gagttcttct actactactc catggacgtc     420
tggggcaagg ggaccacggt caccgtctcc tcagctagca ccaagggccc atcggtcttc     480
cccctggcac cctcctccaa gagcacctct gggggcacag cggccctggg ctgcctggtc     540
aaggactact tccccgagcc ggtgacggtg tcgtggaact caggcgccct gaccagcggc     600
```

```
gtgcacacct tcccggctgt cctacagtcc tcaggactct actccctcag cagcgtggtg     660
accgtgccct ccagcagctt gggcacccag acctacatct gcaacgtgaa tcacaagccc     720
agcaacacca aggtggacaa gaaagttgag cccaaatctt gtgacaaaac tcacacatgc     780
ccaccgtgcc cagcacctga actcctgggg ggaccgtcag tcttcctctt ccccccaaaa     840
cccaaggaca ccctcatgat ctcccggacc cctgaggtca catgcgtggt ggtggacgtg     900
agccacgaag accctgaggt caagttcaac tggtacgtgg acggcgtgga ggtgcataat     960
gccaagacaa agccgcggga ggagcagtac aacagcacgt accgtgtggt cagcgtcctc    1020
accgtcctgc accaggactg gctgaatggc aaggagtaca agtgcaaggt ctccaacaaa    1080
gccctcccag cccccatcga gaaaaccatc tccaaagcca aagggcagcc ccgagaacca    1140
caggtgtaca ccctgccccc atcccgggat gagctgacca agaaccaggt cagcctgacc    1200
tgcctggtca aaggcttcta tcccagcgac atcgccgtgg agtgggagag caatgggcag    1260
ccggagaaca actacaagac cacgcctccc gtgctggact ccgacggctc cttcttcctc    1320
tacagcaagc tcaccgtgga caagagcagg tggcagcagg ggaacgtctt ctcatgctcc    1380
gtgctgcatg aggctctgca ctcccactac acgcagaaga gcctctccct gtctccgggt    1440
aaa                                                                  1443
```

```
<210> SEQ ID NO 431
<211> LENGTH: 1443
<212> TYPE: DNA
<213> ORGANISM: Homo sapiens

<400> SEQUENCE: 431

atgggatggt catgtatcat cctttttcta gtagcaactg caaccggtgt acactcgcag      60
gtgcagctgc aggagtcggg cccaggactg gtgaaacctt cggagaccct gtccgtcacc     120
tgcagtgtct ctggagattc catgaataat tactactgga cttggatccg gcagtccccc     180
ggaaagggac tggagtggat aggctatatc tctgacagag aatcagcgac ttacaacccc     240
tccctcaata gtcgagtcgt catatcacga gacacgtcga aaaaccaatt gtccctaaaa     300
ttaaactccg tcacccctgc ggacacggcc gtctattact gtgcgacagc gcgccgagga     360
cagaggattt atggagtggt ttcctttgga gagttcttct actactactc catggacgtc     420
tggggcaagg ggaccacggt caccgtctcc tcagctagca ccaagggccc atcggtcttc     480
cccctggcac cctcctccaa gagcacctct gggggcacag cggccctggg ctgcctggtc     540
aaggactact tccccgagcc ggtgacggtg tcgtggaact caggcgccct gaccagcggc     600
gtgcacacct tcccggctgt cctacagtcc tcaggactct actccctcag cagcgtggtg     660
accgtgccct ccagcagctt gggcacccag acctacatct gcaacgtgaa tcacaagccc     720
agcaacacca aggtggacaa gaaagttgag cccaaatctt gtgacaaaac tcacacatgc     780
ccaccgtgcc cagcacctga actcctgggg ggaccgtcag tcttcctctt ccccccaaaa     840
cccaaggaca ccctcatgat ctcccggacc cctgaggtca catgcgtggt ggtggacgtg     900
agccacgaag accctgaggt caagttcaac tggtacgtgg acggcgtgga ggtgcataat     960
gccaagacaa agccgcggga ggagcagtac aacagcacgt accgtgtggt cagcgtcctc    1020
accgtcctgc accaggactg gctgaatggc aaggagtaca agtgcaaggt ctccaacaaa    1080
gccctcccag cccccatcga gaaaaccatc tccaaagcca aagggcagcc ccgagaacca    1140
caggtgtaca ccctgccccc atcccgggat gagctgacca agaaccaggt cagcctgacc    1200
tgcctggtca aaggcttcta tcccagcgac atcgccgtgg agtgggagag caatgggcag    1260
```

ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 432
<211> LENGTH: 1443
<212> TYPE: DNA
<213> ORGANISM: Homo sapiens

<400> SEQUENCE: 432
atgggatggt catgtatcat ccttttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcgt catatcacga gacacgtcga aaaaccaatt gtccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 433
<211> LENGTH: 1443
<212> TYPE: DNA
<213> ORGANISM: Homo sapiens

<400> SEQUENCE: 433
atgggatggt catgtatcat ccttttttcta gtagcaactg caaccggtgt acactcgcag 60
gtgcagctgc aggagtcggg cccaggactg gtgaaacctt cggagaccct gtccgtcacc 120

```
tgcagtgtct ctggagattc catgaataat tactactgga cttggatccg gcagtccccc    180

ggaaagggac tggagtggat aggctatatc tctgacagag aatcagcgac ttacaacccc    240

tccctcaata gtcgagtcgt catatcacga gacacgtcga aaaaccaatt gtccctaaaa    300

ttaaactccg tcacccctgc ggacacggcc gtctattact gtgcgacagc gcgccgagga    360

cagaggattt atggagtggt ttcctttgga gagttcttct actactactc catggacgtc    420

tggggcaagg ggaccacggt caccgtctcc tcagctagca ccaagggccc atcggtcttc    480

cccctggcac cctcctccaa gagcacctct gggggcacag cggccctggg ctgcctggtc    540

aaggactact tccccgagcc ggtgacggtg tcgtggaact caggcgccct gaccagcggc    600

gtgcacacct tcccggctgt cctacagtcc tcaggactct actccctcag cagcgtggtg    660

accgtgccct ccagcagctt gggcacccag acctacatct gcaacgtgaa tcacaagccc    720

agcaacacca aggtggacaa gaaagttgag cccaaatctt gtgacaaaac tcacacatgc    780

ccaccgtgcc cagcacctga actcctgggg ggaccgtcag tcttcctctt ccccccaaaa    840

cccaaggaca ccctcatgat ctcccggacc cctgaggtca catgcgtggt ggtggacgtg    900

agccacgaag accctgaggt caagttcaac tggtacgtgg acggcgtgga ggtgcataat    960

gccaagacaa agccgcggga ggagcagtac aacagcacgt accgtgtggt cagcgtcctc   1020

accgtcctgc accaggactg gctgaatggc aaggagtaca agtgcaaggt ctccaacaaa   1080

gccctcccag cccccatcga gaaaaccatc tccaaagcca aagggcagcc ccgagaacca   1140

caggtgtaca ccctgccccc atcccgggat gagctgacca agaaccaggt cagcctgacc   1200

tgcctggtca aaggcttcta tcccagcgac atcgccgtgg agtgggagag caatgggcag   1260

ccggagaaca actacaagac cacgcctccc gtgctggact ccgacggctc cttcttcctc   1320

tacagcaagc tcaccgtgga caagagcagg tggcagcagg ggaacgtctt ctcatgctcc   1380

gtgctgcatg aggctctgca ctcccactac acgcagaaga gcctctccct gtctccgggt   1440

aaa                                                                 1443
```

<210> SEQ ID NO 434
<211> LENGTH: 1443
<212> TYPE: DNA
<213> ORGANISM: Homo sapiens

<400> SEQUENCE: 434

```
atgggatggt catgtatcat cctttttcta gtagcaactg caaccggtgt acactcgcag     60

gtgcagctgc aggagtcggg cccaggactg gtgaaacctt cggagaccct gtccgtcacc    120

tgcagtgtct ctggagattc catgaataat tactactgga cttggatccg gcagtccccc    180

ggaaagggac tggagtggat aggctatatc tctgacagag aatcagcgac ttacaacccc    240

tccctcaata gtcgagtcgt catatcacga gacacgtcga aaaaccaatt gtccctaaaa    300

ttaaactccg tcacccctgc ggacacggcc gtctattact gtgcgacagc gcgccgagga    360

cagaggattt atggagtggt ttcctttgga gagttcttct actactactc catggacgtc    420

tggggcaagg ggaccacggt caccgtctcc tcagctagca ccaagggccc atcggtcttc    480

cccctggcac cctcctccaa gagcacctct gggggcacag cggccctggg ctgcctggtc    540

aaggactact tccccgagcc ggtgacggtg tcgtggaact caggcgccct gaccagcggc    600

gtgcacacct tcccggctgt cctacagtcc tcaggactct actccctcag cagcgtggtg    660

accgtgccct ccagcagctt gggcacccag acctacatct gcaacgtgaa tcacaagccc    720

agcaacacca aggtggacaa gaaagttgag cccaaatctt gtgacaaaac tcacacatgc    780
```

```
ccaccgtgcc cagcacctga actcctgggg ggaccgtcag tcttcctctt ccccccaaaa    840

cccaaggaca ccctcatgat ctcccggacc cctgaggtca catgcgtggt ggtggacgtg    900

agccacgaag accctgaggt caagttcaac tggtacgtgg acggcgtgga ggtgcataat    960

gccaagacaa agccgcggga ggagcagtac aacagcacgt accgtgtggt cagcgtcctc   1020

accgtcctgc accaggactg gctgaatggc aaggagtaca agtgcaaggt ctccaacaaa   1080

gccctcccag cccccatcga gaaaaccatc tccaaagcca aagggcagcc ccgagaacca   1140

caggtgtaca ccctgccccc atcccgggat gagctgacca agaaccaggt cagcctgacc   1200

tgcctggtca aaggcttcta tcccagcgac atcgccgtgg agtgggagag caatgggcag   1260

ccggagaaca actacaagac cacgcctccc gtgctggact ccgacggctc cttcttcctc   1320

tacagcaagc tcaccgtgga caagagcagg tggcagcagg ggaacgtctt ctcatgctcc   1380

gtgctgcatg aggctctgca ctcccactac acgcagaaga gcctctccct gtctccgggt   1440

aaa                                                                 1443
```

```
<210> SEQ ID NO 435
<211> LENGTH: 1443
<212> TYPE: DNA
<213> ORGANISM: Homo sapiens

<400> SEQUENCE: 435

atgggatggt catgtatcat cctttttcta gtagcaactg caaccggtgt acactcgcag     60

gtgcagctgc aggagtcggg cccaggactg gtgaaacctt cggagaccct gtccgtcacc    120

tgcagtgtct ctggagattc catgaataat tactactgga cttggatccg gcagtccccc    180

ggaaagggac tggagtggat aggctatatc tctgacagag aatcagcgac ttacaacccc    240

tccctcaata gtcgagtcgt catatcacga gacacgtcga aaaaccaatt gtccctaaaa    300

ttaaactccg tcacccctgc ggacacggcc gtctattact gtgcgacagc gcgccgagga    360

cagaggattt atggagtggt ttcctttgga gagttcttct actactactc catggacgtc    420

tggggcaagg ggaccacggt caccgtctcc tcagctagca ccaagggccc atcggtcttc    480

cccctggcac cctcctccaa gagcacctct gggggcacag cggccctggg ctgcctggtc    540

aaggactact tccccgagcc ggtgacggtg tcgtggaact caggcgccct gaccagcggc    600

gtgcacacct tcccggctgt cctacagtcc tcaggactct actccctcag cagcgtggtg    660

accgtgccct ccagcagctt gggcacccag acctacatct gcaacgtgaa tcacaagccc    720

agcaacacca aggtggacaa gaaagttgag cccaaatctt gtgacaaaac tcacacatgc    780

ccaccgtgcc cagcacctga actcctgggg ggaccgtcag tcttcctctt ccccccaaaa    840

cccaaggaca ccctcatgat ctcccggacc cctgaggtca catgcgtggt ggtggacgtg    900

agccacgaag accctgaggt caagttcaac tggtacgtgg acggcgtgga ggtgcataat    960

gccaagacaa agccgcggga ggagcagtac aacagcacgt accgtgtggt cagcgtcctc   1020

accgtcctgc accaggactg gctgaatggc aaggagtaca agtgcaaggt ctccaacaaa   1080

gccctcccag cccccatcga gaaaaccatc tccaaagcca aagggcagcc ccgagaacca   1140

caggtgtaca ccctgccccc atcccgggat gagctgacca agaaccaggt cagcctgacc   1200

tgcctggtca aaggcttcta tcccagcgac atcgccgtgg agtgggagag caatgggcag   1260

ccggagaaca actacaagac cacgcctccc gtgctggact ccgacggctc cttcttcctc   1320

tacagcaagc tcaccgtgga caagagcagg tggcagcagg ggaacgtctt ctcatgctcc   1380
```

gtgctgcatg aggctctgca ctcccactac acgcagaaga gcctctccct gtctccgggt 1440
aaa 1443

<210> SEQ ID NO 436
<211> LENGTH: 1443
<212> TYPE: DNA
<213> ORGANISM: Homo sapiens

<400> SEQUENCE: 436
atgggatggt catgtatcat ccttttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcgt catatcacga gacacgtcga aaaaccaatt gtccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 437
<211> LENGTH: 1443
<212> TYPE: DNA
<213> ORGANISM: Homo sapiens

<400> SEQUENCE: 437
atgggatggt catgtatcat ccttttttcta gtagcaactg caaccggtgt acactcgcag 60
gtgcagctgc aggagtcggg cccaggactg gtgaaacctt cggagaccct gtccgtcacc 120
tgcagtgtct ctggaggttc catgaataat tactactgga cttggatccg gcagtccccc 180
ggaaagggac tggagtggat aggctatatc tctgacagag aatcagcgac ttacaacccc 240
tccctcaata gtcgagtcgt catatcacga gacacgtcga aaaaccaatt gtccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 438
<211> LENGTH: 1443
<212> TYPE: DNA
<213> ORGANISM: Homo sapiens

<400> SEQUENCE: 438
atgggatggt catgtatcat cctttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagccaccc 180
ggaaagggac tggagtggat aggctatatc tctgacagag aatcagcgac ttacaacccc 240
tccctcaata gtcgagtcgt catatcacga gacacgtcga aaaaccaatt gtccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 439
<211> LENGTH: 1443
<212> TYPE: DNA
<213> ORGANISM: Homo sapiens

<400> SEQUENCE: 439
atgggatggt catgtatcat cctttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcac catatcacga gacacgtcga aaaaccaatt gtccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 440
<211> LENGTH: 1443
<212> TYPE: DNA
<213> ORGANISM: Homo sapiens

<400> SEQUENCE: 440
atgggatggt catgtatcat ccttttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcgt catatcagtt gacacgtcga aaaaccaatt gtccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 441
<211> LENGTH: 1443
<212> TYPE: DNA
<213> ORGANISM: Homo sapiens

<400> SEQUENCE: 441
atgggatggt catgtatcat ccttttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcgt catatcacga gacacgtcga aaaaccaatt ttccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420

```
tggggcaagg ggaccacggt caccgtctcc tcagctagca ccaagggccc atcggtcttc    480

cccctggcac cctcctccaa gagcacctct gggggcacag cggccctggg ctgcctggtc    540

aaggactact tccccgagcc ggtgacggtg tcgtggaact caggcgccct gaccagcggc    600

gtgcacacct tcccggctgt cctacagtcc tcaggactct actccctcag cagcgtggtg    660

accgtgccct ccagcagctt gggcacccag acctacatct gcaacgtgaa tcacaagccc    720

agcaacacca aggtggacaa gaaagttgag cccaaatctt gtgacaaaac tcacacatgc    780

ccaccgtgcc cagcacctga actcctgggg ggaccgtcag tcttcctctt ccccccaaaa    840

cccaaggaca ccctcatgat ctcccggacc cctgaggtca catgcgtggt ggtggacgtg    900

agccacgaag accctgaggt caagttcaac tggtacgtgg acggcgtgga ggtgcataat    960

gccaagacaa agccgcggga ggagcagtac aacagcacgt accgtgtggt cagcgtcctc   1020

accgtcctgc accaggactg gctgaatggc aaggagtaca agtgcaaggt ctccaacaaa   1080

gccctcccag cccccatcga gaaaaccatc tccaaagcca aagggcagcc ccgagaacca   1140

caggtgtaca ccctgccccc atcccgggat gagctgacca agaaccaggt cagcctgacc   1200

tgcctggtca aaggcttcta tcccagcgac atcgccgtgg agtgggagag caatgggcag   1260

ccggagaaca actacaagac cacgcctccc gtgctggact ccgacggctc cttcttcctc   1320

tacagcaagc tcaccgtgga caagagcagg tggcagcagg ggaacgtctt ctcatgctcc   1380

gtgctgcatg aggctctgca ctcccactac acgcagaaga gcctctccct gtctccgggt   1440

aaa                                                                 1443
```

```
<210> SEQ ID NO 442
<211> LENGTH: 1443
<212> TYPE: DNA
<213> ORGANISM: Homo sapiens

<400> SEQUENCE: 442

atgggatggt catgtatcat cctttttcta gtagcaactg caaccggtgt acactcgcag     60

gtgcagctgc aggagtcggg cccaggactg gtgaaacctt cggagaccct gtccgtcacc    120

tgcagtgtct ctggagattc catgaataat tactactgga cttggatccg gcagtccccc    180

ggaaagggac tggagtggat aggctatatc tctgacagag aatcagcgac ttacaacccc    240

tccctcaata gtcgagtcgt catatcacga gacacgtcga aaaaccaatt gtccctaaaa    300

ttaaactccg tcacccctgc ggacacggcc gtctattact gtgcgcgcgc gcgccgagga    360

cagaggattt atggagtggt ttcctttgga gagttcttct actactactc catggacgtc    420

tggggcaagg ggaccacggt caccgtctcc tcagctagca ccaagggccc atcggtcttc    480

cccctggcac cctcctccaa gagcacctct gggggcacag cggccctggg ctgcctggtc    540

aaggactact tccccgagcc ggtgacggtg tcgtggaact caggcgccct gaccagcggc    600

gtgcacacct tcccggctgt cctacagtcc tcaggactct actccctcag cagcgtggtg    660

accgtgccct ccagcagctt gggcacccag acctacatct gcaacgtgaa tcacaagccc    720

agcaacacca aggtggacaa gaaagttgag cccaaatctt gtgacaaaac tcacacatgc    780

ccaccgtgcc cagcacctga actcctgggg ggaccgtcag tcttcctctt ccccccaaaa    840

cccaaggaca ccctcatgat ctcccggacc cctgaggtca catgcgtggt ggtggacgtg    900

agccacgaag accctgaggt caagttcaac tggtacgtgg acggcgtgga ggtgcataat    960

gccaagacaa agccgcggga ggagcagtac aacagcacgt accgtgtggt cagcgtcctc   1020

accgtcctgc accaggactg gctgaatggc aaggagtaca agtgcaaggt ctccaacaaa   1080
```

gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 443
<211> LENGTH: 1443
<212> TYPE: DNA
<213> ORGANISM: Homo sapiens

<400> SEQUENCE: 443
atgggatggt catgtatcat cctttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcgt catatcacga gacacgtcga aaaaccaatt gtccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420
tggggccagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 444
<211> LENGTH: 1443
<212> TYPE: DNA
<213> ORGANISM: Homo sapiens

<400> SEQUENCE: 444
atgggatggt catgtatcat ccttttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctccaaa gtcgagtcgt catatcacga gacacgtcga aaaaccaatt gtccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 445
<211> LENGTH: 1443
<212> TYPE: DNA
<213> ORGANISM: Homo sapiens

<400> SEQUENCE: 445
atgggatggt catgtatcat ccttttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcgt catatcagtt gacacgtcga aaaaccaatt gtccctaaaa 300
ttaaactccg tcacccctgc ggacacggcc gtctattact gtgcgcgcgc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 446
<211> LENGTH: 1443
<212> TYPE: DNA
<213> ORGANISM: Homo sapiens

<400> SEQUENCE: 446
atgggatggt catgtatcat cctttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcac catatcacga gacacgtcga aaaaccaatt ttccctaaaa 300
ttaaactccg tcacccctgc ggacacggcc gtctattact gtgcgcgcgc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 447
<211> LENGTH: 1443
<212> TYPE: DNA
<213> ORGANISM: Homo sapiens

<400> SEQUENCE: 447
atgggatggt catgtatcat cctttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcac catatcacga gacacgtcga aaaaccaatt ttccctaaaa 300
ttaaactccg tcacccctgc ggacacggcc gtctattact gtgcgcgcgc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 448
<211> LENGTH: 1443
<212> TYPE: DNA
<213> ORGANISM: Homo sapiens

<400> SEQUENCE: 448
atgggatggt catgtatcat cctttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcac catatcacga gacacgtcga aaaaccaatt gtccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 449
<211> LENGTH: 1443
<212> TYPE: DNA
<213> ORGANISM: Homo sapiens

<400> SEQUENCE: 449
atgggatggt catgtatcat cctttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcgt catatcagtt gacacgtcga aaaaccaatt gtccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720

```
agcaacacca aggtggacaa gaaagttgag cccaaatctt gtgacaaaac tcacacatgc    780

ccaccgtgcc cagcacctga actcctgggg ggaccgtcag tcttcctctt ccccccaaaa    840

cccaaggaca ccctcatgat ctcccggacc cctgaggtca catgcgtggt ggtggacgtg    900

agccacgaag accctgaggt caagttcaac tggtacgtgg acggcgtgga ggtgcataat    960

gccaagacaa agccgcggga ggagcagtac aacagcacgt accgtgtggt cagcgtcctc   1020

accgtcctgc accaggactg gctgaatggc aaggagtaca agtgcaaggt ctccaacaaa   1080

gccctcccag cccccatcga gaaaaccatc tccaaagcca aagggcagcc ccgagaacca   1140

caggtgtaca ccctgccccc atcccgggat gagctgacca agaaccaggt cagcctgacc   1200

tgcctggtca aaggcttcta tcccagcgac atcgccgtgg agtgggagag caatgggcag   1260

ccggagaaca actacaagac cacgcctccc gtgctggact ccgacggctc cttcttcctc   1320

tacagcaagc tcaccgtgga caagagcagg tggcagcagg ggaacgtctt ctcatgctcc   1380

gtgctgcatg aggctctgca ctcccactac acgcagaaga gcctctccct gtctccgggt   1440

aaa                                                                 1443
```

<210> SEQ ID NO 450
<211> LENGTH: 1443
<212> TYPE: DNA
<213> ORGANISM: Homo sapiens

<400> SEQUENCE: 450

```
atgggatggt catgtatcat cctttttcta gtagcaactg caaccggtgt acactcgcag     60

gtgcagctgc aggagtcggg cccaggactg gtgaaacctt cggagaccct gtccgtcacc    120

tgcagtgtct ctggagattc catgaataat tactactgga cttggatccg gcagtccccc    180

ggaaagggac tggagtggat aggctatatc tctgacagag aatcagcgac ttacaacccc    240

tccctcaata gtcgagtcgt catatcacga gacacgtcga aaaaccaatt ttccctaaaa    300

ttaaactccg tcacccctgc ggacacggcc gtctattact gtgcgacagc gcgccgagga    360

cagaggattt atggagtggt ttcctttgga gagttcttct actactactc catggacgtc    420

tggggcaagg ggaccacggt caccgtctcc tcagctagca ccaagggccc atcggtcttc    480

cccctggcac cctcctccaa gagcacctct gggggcacag cggccctggg ctgcctggtc    540

aaggactact tccccgagcc ggtgacggtg tcgtggaact caggcgccct gaccagcggc    600

gtgcacacct tcccggctgt cctacagtcc tcaggactct actccctcag cagcgtggtg    660

accgtgccct ccagcagctt gggcacccag acctacatct gcaacgtgaa tcacaagccc    720

agcaacacca aggtggacaa gaaagttgag cccaaatctt gtgacaaaac tcacacatgc    780

ccaccgtgcc cagcacctga actcctgggg ggaccgtcag tcttcctctt ccccccaaaa    840

cccaaggaca ccctcatgat ctcccggacc cctgaggtca catgcgtggt ggtggacgtg    900

agccacgaag accctgaggt caagttcaac tggtacgtgg acggcgtgga ggtgcataat    960

gccaagacaa agccgcggga ggagcagtac aacagcacgt accgtgtggt cagcgtcctc   1020

accgtcctgc accaggactg gctgaatggc aaggagtaca agtgcaaggt ctccaacaaa   1080

gccctcccag cccccatcga gaaaaccatc tccaaagcca aagggcagcc ccgagaacca   1140

caggtgtaca ccctgccccc atcccgggat gagctgacca agaaccaggt cagcctgacc   1200

tgcctggtca aaggcttcta tcccagcgac atcgccgtgg agtgggagag caatgggcag   1260

ccggagaaca actacaagac cacgcctccc gtgctggact ccgacggctc cttcttcctc   1320

tacagcaagc tcaccgtgga caagagcagg tggcagcagg ggaacgtctt ctcatgctcc   1380
```

gtgctgcatg aggctctgca ctcccactac acgcagaaga gcctctccct gtctccgggt 1440
aaa 1443

<210> SEQ ID NO 451
<211> LENGTH: 1443
<212> TYPE: DNA
<213> ORGANISM: Homo sapiens

<400> SEQUENCE: 451
atgggatggt catgtatcat cctttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcgt catatcacga gacacgtcga aaaaccaatt gtccctaaaa 300
ttaaactccg tcacccctgc ggacacggcc gtctattact gtgcgcgcgc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 452
<211> LENGTH: 1443
<212> TYPE: DNA
<213> ORGANISM: Homo sapiens

<400> SEQUENCE: 452
atgggatggt catgtatcat cctttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcac catatcagtt gacacgtcga aaaaccaatt gtccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 453
<211> LENGTH: 1443
<212> TYPE: DNA
<213> ORGANISM: Homo sapiens

<400> SEQUENCE: 453
atgggatggt catgtatcat cctttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcac catatcacga gacacgtcga aaaaccaatt ttccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900

```
agccacgaag accctgaggt caagttcaac tggtacgtgg acggcgtgga ggtgcataat    960
gccaagacaa agccgcggga ggagcagtac aacagcacgt accgtgtggt cagcgtcctc   1020
accgtcctgc accaggactg gctgaatggc aaggagtaca agtgcaaggt ctccaacaaa   1080
gccctcccag cccccatcga gaaaaccatc tccaaagcca aagggcagcc ccgagaacca   1140
caggtgtaca ccctgccccc atcccgggat gagctgacca agaaccaggt cagcctgacc   1200
tgcctggtca aaggcttcta tcccagcgac atcgccgtgg agtgggagag caatgggcag   1260
ccggagaaca actacaagac cacgcctccc gtgctggact ccgacggctc cttcttcctc   1320
tacagcaagc tcaccgtgga caagagcagg tggcagcagg ggaacgtctt ctcatgctcc   1380
gtgctgcatg aggctctgca ctcccactac acgcagaaga gcctctccct gtctccgggt   1440
aaa                                                                 1443
```

<210> SEQ ID NO 454
<211> LENGTH: 1443
<212> TYPE: DNA
<213> ORGANISM: Homo sapiens

<400> SEQUENCE: 454

```
atgggatggt catgtatcat cctttttcta gtagcaactg caaccggtgt acactcgcag     60
gtgcagctgc aggagtcggg cccaggactg gtgaaacctt cggagaccct gtccgtcacc    120
tgcagtgtct ctggagattc catgaataat tactactgga cttggatccg gcagtccccc    180
ggaaagggac tggagtggat aggctatatc tctgacagag aatcagcgac ttacaacccc    240
tccctcaata gtcgagtcac catatcacga gacacgtcga aaaaccaatt gtccctaaaa    300
ttaaactccg tcacccctgc ggacacggcc gtctattact gtgcgcgcgc gcgccgagga    360
cagaggattt atggagtggt ttcctttgga gagttcttct actactactc catggacgtc    420
tggggcaagg ggaccacggt caccgtctcc tcagctagca ccaagggccc atcggtcttc    480
cccctggcac cctcctccaa gagcacctct gggggcacag cggccctggg ctgcctggtc    540
aaggactact tccccgagcc ggtgacggtg tcgtggaact caggcgccct gaccagcggc    600
gtgcacacct tcccggctgt cctacagtcc tcaggactct actccctcag cagcgtggtg    660
accgtgccct ccagcagctt gggcacccag acctacatct gcaacgtgaa tcacaagccc    720
agcaacacca aggtggacaa gaaagttgag cccaaatctt gtgacaaaac tcacacatgc    780
ccaccgtgcc cagcacctga actcctgggg ggaccgtcag tcttcctctt ccccccaaaa    840
cccaaggaca ccctcatgat ctcccggacc cctgaggtca catgcgtggt ggtggacgtg    900
agccacgaag accctgaggt caagttcaac tggtacgtgg acggcgtgga ggtgcataat    960
gccaagacaa agccgcggga ggagcagtac aacagcacgt accgtgtggt cagcgtcctc   1020
accgtcctgc accaggactg gctgaatggc aaggagtaca agtgcaaggt ctccaacaaa   1080
gccctcccag cccccatcga gaaaaccatc tccaaagcca aagggcagcc ccgagaacca   1140
caggtgtaca ccctgccccc atcccgggat gagctgacca agaaccaggt cagcctgacc   1200
tgcctggtca aaggcttcta tcccagcgac atcgccgtgg agtgggagag caatgggcag   1260
ccggagaaca actacaagac cacgcctccc gtgctggact ccgacggctc cttcttcctc   1320
tacagcaagc tcaccgtgga caagagcagg tggcagcagg ggaacgtctt ctcatgctcc   1380
gtgctgcatg aggctctgca ctcccactac acgcagaaga gcctctccct gtctccgggt   1440
aaa                                                                 1443
```

<210> SEQ ID NO 455
<211> LENGTH: 1443
<212> TYPE: DNA
<213> ORGANISM: Homo sapiens

<400> SEQUENCE: 455
atgggatggt catgtatcat ccttttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcgt catatcagtt gacacgtcga aaaaccaatt ttccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 456
<211> LENGTH: 1443
<212> TYPE: DNA
<213> ORGANISM: Homo sapiens

<400> SEQUENCE: 456
atgggatggt catgtatcat ccttttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcgt catatcagtt gacacgtcga aaaaccaatt gtccctaaaa 300
ttaaactccg tcacccctgc ggacacggcc gtctattact gtgcgcgcgc gcgccgagga 360
cagaggattt atggagtggt ttcctttgga gagttcttct actactactc catggacgtc 420

```
tggggcaagg ggaccacggt caccgtctcc tcagctagca ccaagggccc atcggtcttc    480

cccctggcac cctcctccaa gagcacctct gggggcacag cggccctggg ctgcctggtc    540

aaggactact tccccgagcc ggtgacggtg tcgtggaact caggcgccct gaccagcggc    600

gtgcacacct tcccggctgt cctacagtcc tcaggactct actccctcag cagcgtggtg    660

accgtgccct ccagcagctt gggcacccag acctacatct gcaacgtgaa tcacaagccc    720

agcaacacca aggtggacaa gaaagttgag cccaaatctt gtgacaaaac tcacacatgc    780

ccaccgtgcc cagcacctga actcctgggg ggaccgtcag tcttcctctt ccccccaaaa    840

cccaaggaca ccctcatgat ctcccggacc cctgaggtca catgcgtggt ggtggacgtg    900

agccacgaag accctgaggt caagttcaac tggtacgtgg acggcgtgga ggtgcataat    960

gccaagacaa agccgcggga ggagcagtac aacagcacgt accgtgtggt cagcgtcctc   1020

accgtcctgc accaggactg gctgaatggc aaggagtaca agtgcaaggt ctccaacaaa   1080

gccctcccag cccccatcga gaaaaccatc tccaaagcca aagggcagcc ccgagaacca   1140

caggtgtaca ccctgccccc atcccgggat gagctgacca agaaccaggt cagcctgacc   1200

tgcctggtca aaggcttcta tcccagcgac atcgccgtgg agtgggagag caatgggcag   1260

ccggagaaca actacaagac cacgcctccc gtgctggact ccgacggctc cttcttcctc   1320

tacagcaagc tcaccgtgga caagagcagg tggcagcagg ggaacgtctt ctcatgctcc   1380

gtgctgcatg aggctctgca ctcccactac acgcagaaga gcctctccct gtctccgggt   1440

aaa                                                                 1443
```

<210> SEQ ID NO 457
<211> LENGTH: 1443
<212> TYPE: DNA
<213> ORGANISM: Homo sapiens

<400> SEQUENCE: 457

```
atgggatggt catgtatcat ccttttttcta gtagcaactg caaccggtgt acactcgcag     60

gtgcagctgc aggagtcggg cccaggactg gtgaaacctt cggagaccct gtccgtcacc    120

tgcagtgtct ctggagattc catgaataat tactactgga cttggatccg gcagtccccc    180

ggaaagggac tggagtggat aggctatatc tctgacagag aatcagcgac ttacaacccc    240

tccctcaata gtcgagtcgt catatcacga gacacgtcga aaaaccaatt ttccctaaaa    300

ttaaactccg tcacccctgc ggacacggcc gtctattact gtgcgcgcgc gcgccgagga    360

cagaggattt atggagtggt ttcctttgga gagttcttct actactactc catggacgtc    420

tggggcaagg ggaccacggt caccgtctcc tcagctagca ccaagggccc atcggtcttc    480

cccctggcac cctcctccaa gagcacctct gggggcacag cggccctggg ctgcctggtc    540

aaggactact tccccgagcc ggtgacggtg tcgtggaact caggcgccct gaccagcggc    600

gtgcacacct tcccggctgt cctacagtcc tcaggactct actccctcag cagcgtggtg    660

accgtgccct ccagcagctt gggcacccag acctacatct gcaacgtgaa tcacaagccc    720

agcaacacca aggtggacaa gaaagttgag cccaaatctt gtgacaaaac tcacacatgc    780

ccaccgtgcc cagcacctga actcctgggg ggaccgtcag tcttcctctt ccccccaaaa    840

cccaaggaca ccctcatgat ctcccggacc cctgaggtca catgcgtggt ggtggacgtg    900

agccacgaag accctgaggt caagttcaac tggtacgtgg acggcgtgga ggtgcataat    960

gccaagacaa agccgcggga ggagcagtac aacagcacgt accgtgtggt cagcgtcctc   1020
```

accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 458
<211> LENGTH: 1443
<212> TYPE: DNA
<213> ORGANISM: Homo sapiens

<400> SEQUENCE: 458
atgggatggt catgtatcat cctttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcac catatcagtt gacacgtcga aaaaccaatt gtccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 459
<211> LENGTH: 1443
<212> TYPE: DNA
<213> ORGANISM: Homo sapiens

<400> SEQUENCE: 459
atgggatggt catgtatcat cctttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcac catatcacga gacacgtcga aaaaccaatt ttccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 460
<211> LENGTH: 1443
<212> TYPE: DNA
<213> ORGANISM: Homo sapiens

<400> SEQUENCE: 460
atgggatggt catgtatcat cctttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcac catatcacga gacacgtcga aaaaccaatt gtccctaaaa 300
ttaaactccg tcacccctgc ggacacggcc gtctattact gtgcgcgcgc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540

```
aaggactact tccccgagcc ggtgacggtg tcgtggaact caggcgccct gaccagcggc    600

gtgcacacct tcccggctgt cctacagtcc tcaggactct actccctcag cagcgtggtg    660

accgtgccct ccagcagctt gggcacccag acctacatct gcaacgtgaa tcacaagccc    720

agcaacacca aggtggacaa gaaagttgag cccaaatctt gtgacaaaac tcacacatgc    780

ccaccgtgcc cagcacctga actcctgggg ggaccgtcag tcttcctctt ccccccaaaa    840

cccaaggaca ccctcatgat ctcccggacc cctgaggtca catgcgtggt ggtggacgtg    900

agccacgaag accctgaggt caagttcaac tggtacgtgg acggcgtgga ggtgcataat    960

gccaagacaa agccgcggga ggagcagtac aacagcacgt accgtgtggt cagcgtcctc   1020

accgtcctgc accaggactg gctgaatggc aaggagtaca agtgcaaggt ctccaacaaa   1080

gccctcccag cccccatcga gaaaaccatc tccaaagcca aagggcagcc ccgagaacca   1140

caggtgtaca ccctgccccc atcccgggat gagctgacca agaaccaggt cagcctgacc   1200

tgcctggtca aaggcttcta tcccagcgac atcgccgtgg agtgggagag caatgggcag   1260

ccggagaaca actacaagac cacgcctccc gtgctggact ccgacggctc cttcttcctc   1320

tacagcaagc tcaccgtgga caagagcagg tggcagcagg ggaacgtctt ctcatgctcc   1380

gtgctgcatg aggctctgca ctcccactac acgcagaaga gcctctccct gtctccgggt   1440

aaa                                                                 1443
```

<210> SEQ ID NO 461
<211> LENGTH: 1443
<212> TYPE: DNA
<213> ORGANISM: Homo sapiens

<400> SEQUENCE: 461

```
atgggatggt catgtatcat cctttttcta gtagcaactg caaccggtgt acactcgcag     60

gtgcagctgc aggagtcggg cccaggactg gtgaaacctt cggagaccct gtccgtcacc    120

tgcagtgtct ctggagattc catgaataat tactactgga cttggatccg gcagtccccc    180

ggaaagggac tggagtggat aggctatatc tctgacagag aatcagcgac ttacaacccc    240

tccctcaata gtcgagtcgt catatcagtt gacacgtcga aaaaccaatt ttccctaaaa    300

ttaaactccg tcacccctgc ggacacggcc gtctattact gtgcgacagc gcgccgagga    360

cagaggattt atggagtggt ttcctttgga gagttcttct actactactc catggacgtc    420

tggggcaagg ggaccacggt caccgtctcc tcagctagca ccaagggccc atcggtcttc    480

cccctggcac cctcctccaa gagcacctct gggggcacag cggccctggg ctgcctggtc    540

aaggactact tccccgagcc ggtgacggtg tcgtggaact caggcgccct gaccagcggc    600

gtgcacacct tcccggctgt cctacagtcc tcaggactct actccctcag cagcgtggtg    660

accgtgccct ccagcagctt gggcacccag acctacatct gcaacgtgaa tcacaagccc    720

agcaacacca aggtggacaa gaaagttgag cccaaatctt gtgacaaaac tcacacatgc    780

ccaccgtgcc cagcacctga actcctgggg ggaccgtcag tcttcctctt ccccccaaaa    840

cccaaggaca ccctcatgat ctcccggacc cctgaggtca catgcgtggt ggtggacgtg    900

agccacgaag accctgaggt caagttcaac tggtacgtgg acggcgtgga ggtgcataat    960

gccaagacaa agccgcggga ggagcagtac aacagcacgt accgtgtggt cagcgtcctc   1020

accgtcctgc accaggactg gctgaatggc aaggagtaca agtgcaaggt ctccaacaaa   1080

gccctcccag cccccatcga gaaaaccatc tccaaagcca aagggcagcc ccgagaacca   1140

caggtgtaca ccctgccccc atcccgggat gagctgacca agaaccaggt cagcctgacc   1200
```

```
tgcctggtca aaggcttcta tcccagcgac atcgccgtgg agtgggagag caatgggcag   1260

ccggagaaca actacaagac cacgcctccc gtgctggact ccgacggctc cttcttcctc   1320

tacagcaagc tcaccgtgga caagagcagg tggcagcagg ggaacgtctt ctcatgctcc   1380

gtgctgcatg aggctctgca ctcccactac acgcagaaga gcctctccct gtctccgggt   1440

aaa                                                                 1443
```

<210> SEQ ID NO 462
<211> LENGTH: 1443
<212> TYPE: DNA
<213> ORGANISM: Homo sapiens

<400> SEQUENCE: 462

```
atgggatggt catgtatcat cctttttcta gtagcaactg caaccggtgt acactcgcag     60

gtgcagctgc aggagtcggg cccaggactg gtgaaacctt cggagaccct gtccgtcacc    120

tgcagtgtct ctggagattc catgaataat tactactgga cttggatccg gcagtccccc    180

ggaaagggac tggagtggat aggctatatc tctgacagag aatcagcgac ttacaacccc    240

tccctcaata gtcgagtcgt catatcacga gacacgtcga aaaaccaatt ttccctaaaa    300

ttaaactccg tcacccctgc ggacacggcc gtctattact gtgcgcgcgc gcgccgagga    360

cagaggattt atggagtggt ttcctttgga gagttcttct actactactc catggacgtc    420

tggggcaagg ggaccacggt caccgtctcc tcagctagca ccaagggccc atcggtcttc    480

cccctggcac cctcctccaa gagcacctct gggggcacag cggccctggg ctgcctggtc    540

aaggactact tccccgagcc ggtgacggtg tcgtggaact caggcgccct gaccagcggc    600

gtgcacacct tcccggctgt cctacagtcc tcaggactct actccctcag cagcgtggtg    660

accgtgccct ccagcagctt gggcacccag acctacatct gcaacgtgaa tcacaagccc    720

agcaacacca aggtggacaa gaaagttgag cccaaatctt gtgacaaaac tcacacatgc    780

ccaccgtgcc cagcacctga actcctgggg ggaccgtcag tcttcctctt ccccccaaaa    840

cccaaggaca ccctcatgat ctcccggacc cctgaggtca catgcgtggt ggtggacgtg    900

agccacgaag accctgaggt caagttcaac tggtacgtgg acggcgtgga ggtgcataat    960

gccaagacaa agccgcggga ggagcagtac aacagcacgt accgtgtggt cagcgtcctc   1020

accgtcctgc accaggactg gctgaatggc aaggagtaca agtgcaaggt ctccaacaaa   1080

gccctcccag cccccatcga gaaaaccatc tccaaagcca aagggcagcc ccgagaacca   1140

caggtgtaca ccctgccccc atcccgggat gagctgacca agaaccaggt cagcctgacc   1200

tgcctggtca aaggcttcta tcccagcgac atcgccgtgg agtgggagag caatgggcag   1260

ccggagaaca actacaagac cacgcctccc gtgctggact ccgacggctc cttcttcctc   1320

tacagcaagc tcaccgtgga caagagcagg tggcagcagg ggaacgtctt ctcatgctcc   1380

gtgctgcatg aggctctgca ctcccactac acgcagaaga gcctctccct gtctccgggt   1440

aaa                                                                 1443
```

<210> SEQ ID NO 463
<211> LENGTH: 1443
<212> TYPE: DNA
<213> ORGANISM: Homo sapiens

<400> SEQUENCE: 463

```
atgggatggt catgtatcat cctttttcta gtagcaactg caaccggtgt acactcgcag     60
```

```
gtgcagctgc aggagtcggg cccaggactg gtgaaacctt cggagaccct gtccgtcacc    120

tgcagtgtct ctggagattc catgaataat tactactgga cttggatccg gcagtccccc    180

ggaaagggac tggagtggat aggctatatc tctgacagag aatcagcgac ttacaacccc    240

tccctcaata gtcgagtcac catatcagtt gacacgtcga aaaaccaatt ttccctaaaa    300

ttaaactccg tcacccctgc ggacacggcc gtctattact gtgcgacagc gcgccgagga    360

cagaggattt atggagtggt ttcctttgga gagttcttct actactactc catggacgtc    420

tggggcaagg ggaccacggt caccgtctcc tcagctagca ccaagggccc atcggtcttc    480

cccctggcac cctcctccaa gagcacctct gggggcacag cggccctggg ctgcctggtc    540

aaggactact tccccgagcc ggtgacggtg tcgtggaact caggcgccct gaccagcggc    600

gtgcacacct tcccggctgt cctacagtcc tcaggactct actccctcag cagcgtggtg    660

accgtgccct ccagcagctt gggcacccag acctacatct gcaacgtgaa tcacaagccc    720

agcaacacca aggtggacaa gaaagttgag cccaaatctt gtgacaaaac tcacacatgc    780

ccaccgtgcc cagcacctga actcctgggg ggaccgtcag tcttcctctt ccccccaaaa    840

cccaaggaca ccctcatgat ctcccggacc cctgaggtca catgcgtggt ggtggacgtg    900

agccacgaag accctgaggt caagttcaac tggtacgtgg acggcgtgga ggtgcataat    960

gccaagacaa agccgcggga ggagcagtac aacagcacgt accgtgtggt cagcgtcctc   1020

accgtcctgc accaggactg gctgaatggc aaggagtaca agtgcaaggt ctccaacaaa   1080

gccctcccag cccccatcga gaaaaccatc tccaaagcca aagggcagcc ccgagaacca   1140

caggtgtaca ccctgccccc atcccgggat gagctgacca agaaccaggt cagcctgacc   1200

tgcctggtca aaggcttcta tcccagcgac atcgccgtgg agtgggagag caatgggcag   1260

ccggagaaca actacaagac cacgcctccc gtgctggact ccgacggctc cttcttcctc   1320

tacagcaagc tcaccgtgga caagagcagg tggcagcagg ggaacgtctt ctcatgctcc   1380

gtgctgcatg aggctctgca ctcccactac acgcagaaga gcctctccct gtctccgggt   1440

aaa                                                                 1443
```

<210> SEQ ID NO 464
<211> LENGTH: 1443
<212> TYPE: DNA
<213> ORGANISM: Homo sapiens

<400> SEQUENCE: 464

```
atgggatggt catgtatcat cctttttcta gtagcaactg caaccggtgt acactcgcag     60

gtgcagctgc aggagtcggg cccaggactg gtgaaacctt cggagaccct gtccgtcacc    120

tgcagtgtct ctggagattc catgaataat tactactgga cttggatccg gcagtccccc    180

ggaaagggac tggagtggat aggctatatc tctgacagag aatcagcgac ttacaacccc    240

tccctcaata gtcgagtcac catatcagtt gacacgtcga aaaaccaatt gtccctaaaa    300

ttaaactccg tcacccctgc ggacacggcc gtctattact gtgcgcgcgc gcgccgagga    360

cagaggattt atggagtggt ttcctttgga gagttcttct actactactc catggacgtc    420

tggggcaagg ggaccacggt caccgtctcc tcagctagca ccaagggccc atcggtcttc    480

cccctggcac cctcctccaa gagcacctct gggggcacag cggccctggg ctgcctggtc    540

aaggactact tccccgagcc ggtgacggtg tcgtggaact caggcgccct gaccagcggc    600

gtgcacacct tcccggctgt cctacagtcc tcaggactct actccctcag cagcgtggtg    660

accgtgccct ccagcagctt gggcacccag acctacatct gcaacgtgaa tcacaagccc    720
```

```
agcaacacca aggtggacaa gaaagttgag cccaaatctt gtgacaaaac tcacacatgc    780
ccaccgtgcc cagcacctga actcctgggg ggaccgtcag tcttcctctt ccccccaaaa    840
cccaaggaca ccctcatgat ctcccggacc cctgaggtca catgcgtggt ggtggacgtg    900
agccacgaag accctgaggt caagttcaac tggtacgtgg acggcgtgga ggtgcataat    960
gccaagacaa agccgcggga ggagcagtac aacagcacgt accgtgtggt cagcgtcctc   1020
accgtcctgc accaggactg gctgaatggc aaggagtaca agtgcaaggt ctccaacaaa   1080
gccctcccag cccccatcga gaaaaccatc tccaaagcca aagggcagcc ccgagaacca   1140
caggtgtaca ccctgccccc atcccgggat gagctgacca agaaccaggt cagcctgacc   1200
tgcctggtca aaggcttcta tcccagcgac atcgccgtgg agtgggagag caatgggcag   1260
ccggagaaca actacaagac cacgcctccc gtgctggact ccgacggctc cttcttcctc   1320
tacagcaagc tcaccgtgga caagagcagg tggcagcagg ggaacgtctt ctcatgctcc   1380
gtgctgcatg aggctctgca ctcccactac acgcagaaga gcctctccct gtctccgggt   1440
aaa                                                                 1443
```

<210> SEQ ID NO 465
<211> LENGTH: 1443
<212> TYPE: DNA
<213> ORGANISM: Homo sapiens

<400> SEQUENCE: 465

```
atgggatggt catgtatcat cctttttcta gtagcaactg caaccggtgt acactcgcag     60
gtgcagctgc aggagtcggg cccaggactg gtgaaacctt cggagaccct gtccgtcacc    120
tgcagtgtct ctggagattc catgaataat tactactgga cttggatccg gcagtccccc    180
ggaaagggac tggagtggat aggctatatc tctgacagag aatcagcgac ttacaacccc    240
tccctcaata gtcgagtcgt catatcagtt gacacgtcga aaaaccaatt ttccctaaaa    300
ttaaactccg tcacccctgc ggacacggcc gtctattact gtgcgcgcgc gcgccgagga    360
cagaggattt atggagtggt ttcctttgga gagttcttct actactactc catggacgtc    420
tggggcaagg ggaccacggt caccgtctcc tcagctagca ccaagggccc atcggtcttc    480
cccctggcac cctcctccaa gagcacctct gggggcacag cggccctggg ctgcctggtc    540
aaggactact tccccgagcc ggtgacggtg tcgtggaact caggcgccct gaccagcggc    600
gtgcacacct tcccggctgt cctacagtcc tcaggactct actccctcag cagcgtggtg    660
accgtgccct ccagcagctt gggcacccag acctacatct gcaacgtgaa tcacaagccc    720
agcaacacca aggtggacaa gaaagttgag cccaaatctt gtgacaaaac tcacacatgc    780
ccaccgtgcc cagcacctga actcctgggg ggaccgtcag tcttcctctt ccccccaaaa    840
cccaaggaca ccctcatgat ctcccggacc cctgaggtca catgcgtggt ggtggacgtg    900
agccacgaag accctgaggt caagttcaac tggtacgtgg acggcgtgga ggtgcataat    960
gccaagacaa agccgcggga ggagcagtac aacagcacgt accgtgtggt cagcgtcctc   1020
accgtcctgc accaggactg gctgaatggc aaggagtaca agtgcaaggt ctccaacaaa   1080
gccctcccag cccccatcga gaaaaccatc tccaaagcca aagggcagcc ccgagaacca   1140
caggtgtaca ccctgccccc atcccgggat gagctgacca agaaccaggt cagcctgacc   1200
tgcctggtca aaggcttcta tcccagcgac atcgccgtgg agtgggagag caatgggcag   1260
ccggagaaca actacaagac cacgcctccc gtgctggact ccgacggctc cttcttcctc   1320
```

tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 466
<211> LENGTH: 1443
<212> TYPE: DNA
<213> ORGANISM: Homo sapiens

<400> SEQUENCE: 466
atgggatggt catgtatcat cctttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcac catatcagtt gacacgtcga aaaaccaatt ttccctaaaa 300
ttaaactccg tcacccctgc ggacacggcc gtctattact gtgcgacagc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 467
<211> LENGTH: 1443
<212> TYPE: DNA
<213> ORGANISM: Homo sapiens

<400> SEQUENCE: 467
atgggatggt catgtatcat cctttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcac catatcagtt gacacgtcga aaaaccaatt gtccctaaaa 300
ttaaactccg tcacccctgc ggacacggcc gtctattact gtgcgcgcgc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 468
<211> LENGTH: 1443
<212> TYPE: DNA
<213> ORGANISM: Homo sapiens

<400> SEQUENCE: 468
atgggatggt catgtatcat cctttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcgt catatcagtt gacacgtcga aaaaccaatt ttccctaaaa 300
ttaaactccg tcacccctgc ggacacggcc gtctattact gtgcgcgcgc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840

```
cccaaggaca ccctcatgat ctcccggacc cctgaggtca catgcgtggt ggtggacgtg    900

agccacgaag accctgaggt caagttcaac tggtacgtgg acggcgtgga ggtgcataat    960

gccaagacaa agccgcggga ggagcagtac aacagcacgt accgtgtggt cagcgtcctc   1020

accgtcctgc accaggactg gctgaatggc aaggagtaca agtgcaaggt ctccaacaaa   1080

gccctcccag cccccatcga gaaaaccatc tccaaagcca aagggcagcc ccgagaacca   1140

caggtgtaca ccctgccccc atcccgggat gagctgacca agaaccaggt cagcctgacc   1200

tgcctggtca aaggcttcta tcccagcgac atcgccgtgg agtgggagag caatgggcag   1260

ccggagaaca actacaagac cacgcctccc gtgctggact ccgacggctc cttcttcctc   1320

tacagcaagc tcaccgtgga caagagcagg tggcagcagg ggaacgtctt ctcatgctcc   1380

gtgctgcatg aggctctgca ctcccactac acgcagaaga gcctctccct gtctccgggt   1440

aaa                                                                 1443
```

<210> SEQ ID NO 469
<211> LENGTH: 1443
<212> TYPE: DNA
<213> ORGANISM: Homo sapiens

<400> SEQUENCE: 469

```
atgggatggt catgtatcat cctttttcta gtagcaactg caaccggtgt acactcgcag     60

gtgcagctgc aggagtcggg cccaggactg gtgaaacctt cggagaccct gtccgtcacc    120

tgcagtgtct ctggagattc catgaataat tactactgga cttggatccg gcagtccccc    180

ggaaagggac tggagtggat aggctatatc tctgacagag aatcagcgac ttacaacccc    240

tccctcaata gtcgagtcac catatcagtt gacacgtcga aaaaccaatt ttccctaaaa    300

ttaaactccg tcacccctgc ggacacggcc gtctattact gtgcgcgcgc gcgccgagga    360

cagaggattt atggagtggt ttcctttgga gagttcttct actactactc catggacgtc    420

tggggcaagg ggaccacggt caccgtctcc tcagctagca ccaagggccc atcggtcttc    480

cccctggcac cctcctccaa gagcacctct gggggcacag cggccctggg ctgcctggtc    540

aaggactact tccccgagcc ggtgacggtg tcgtggaact caggcgccct gaccagcggc    600

gtgcacacct tcccggctgt cctacagtcc tcaggactct actccctcag cagcgtggtg    660

accgtgccct ccagcagctt gggcacccag acctacatct gcaacgtgaa tcacaagccc    720

agcaacacca aggtggacaa gaaagttgag cccaaatctt gtgacaaaac tcacacatgc    780

ccaccgtgcc cagcacctga actcctgggg ggaccgtcag tcttcctctt ccccccaaaa    840

cccaaggaca ccctcatgat ctcccggacc cctgaggtca catgcgtggt ggtggacgtg    900

agccacgaag accctgaggt caagttcaac tggtacgtgg acggcgtgga ggtgcataat    960

gccaagacaa agccgcggga ggagcagtac aacagcacgt accgtgtggt cagcgtcctc   1020

accgtcctgc accaggactg gctgaatggc aaggagtaca agtgcaaggt ctccaacaaa   1080

gccctcccag cccccatcga gaaaaccatc tccaaagcca aagggcagcc ccgagaacca   1140

caggtgtaca ccctgccccc atcccgggat gagctgacca agaaccaggt cagcctgacc   1200

tgcctggtca aaggcttcta tcccagcgac atcgccgtgg agtgggagag caatgggcag   1260

ccggagaaca actacaagac cacgcctccc gtgctggact ccgacggctc cttcttcctc   1320

tacagcaagc tcaccgtgga caagagcagg tggcagcagg ggaacgtctt ctcatgctcc   1380

gtgctgcatg aggctctgca ctcccactac acgcagaaga gcctctccct gtctccgggt   1440

aaa                                                                 1443
```

<210> SEQ ID NO 470
<211> LENGTH: 1443
<212> TYPE: DNA
<213> ORGANISM: Homo sapiens

<400> SEQUENCE: 470
atgggatggt catgtatcat ccttttttcta gtagcaactg caaccggtgt acactcgcag 60
gtgcagctgc aggagtcggg cccaggactg gtgaaacctt cggagaccct gtccgtcacc 120
tgcagtgtct ctggagattc catgaataat tactactgga cttggatccg gcagtccccc 180
ggaaagggac tggagtggat aggctatatc tctgacagag aatcagcgac ttacaacccc 240
tccctcaata gtcgagtcac catatcagtt gacacgtcga aaaaccaatt ttccctaaaa 300
ttaaactccg tcacccctgc ggacacggcc gtctattact gtgcgcgcgc gcgccgagga 360
cagaggattt atggagtggt ttcctttgga gagttcttct actactactc catggacgtc 420
tggggcaagg ggaccacggt caccgtctcc tcagctagca ccaagggccc atcggtcttc 480
cccctggcac cctcctccaa gagcacctct gggggcacag cggccctggg ctgcctggtc 540
aaggactact tccccgagcc ggtgacggtg tcgtggaact caggcgccct gaccagcggc 600
gtgcacacct tcccggctgt cctacagtcc tcaggactct actccctcag cagcgtggtg 660
accgtgccct ccagcagctt gggcacccag acctacatct gcaacgtgaa tcacaagccc 720
agcaacacca aggtggacaa gaaagttgag cccaaatctt gtgacaaaac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atcccgggat gagctgacca agaaccaggt cagcctgacc 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgctgcatg aggctctgca ctcccactac acgcagaaga gcctctccct gtctccgggt 1440
aaa 1443

<210> SEQ ID NO 471
<211> LENGTH: 699
<212> TYPE: DNA
<213> ORGANISM: Homo sapiens

<400> SEQUENCE: 471
atgggatgga gctgtatcat cctgttcctc gtggccacag caaccggtgt acattcttcc 60
tatgtgcgcc cgctgtcagt ggccctgggg gagacggcca ggatttcctg tggacgacag 120
gcccttggaa gtagagctgt tcagtggtat caacataggc caggccaggc ccctatattg 180
ctcatttata ataatcaaga ccggccctca gggatccctg agcgattctc tggcacccct 240
gatattaatt ttgggaccag ggccaccctg accatcagcg gggtcgaagc cggggatgaa 300
gccgactatt actgtcacat gtgggatagt agaagtggct tcagttggtc tttcggcggg 360
gcgaccaggc tgaccgtcct aggtcagccc aaggctgccc cctcggtcac tctgttcccg 420
ccctcctctg aggagcttca agccaacaag gccacactgg tgtgtctcat aagtgacttc 480
tacccgggag ccgtgacagt ggcctggaag gcagatagca gccccgtcaa ggcgggagtg 540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttca 699

<210> SEQ ID NO 472
<211> LENGTH: 33
<212> TYPE: DNA
<213> ORGANISM: Homo sapiens

<400> SEQUENCE: 472
ggacgacagg cccttggaag tagagctgtt cag 33

<210> SEQ ID NO 473
<211> LENGTH: 21
<212> TYPE: DNA
<213> ORGANISM: Homo sapiens

<400> SEQUENCE: 473
aataatcaag accggccctc a 21

<210> SEQ ID NO 474
<211> LENGTH: 36
<212> TYPE: DNA
<213> ORGANISM: Homo sapiens

<400> SEQUENCE: 474
cacatgtggg atagtagaag tggcttcagt tggtct 36

<210> SEQ ID NO 475
<211> LENGTH: 18
<212> TYPE: DNA
<213> ORGANISM: Homo sapiens

<400> SEQUENCE: 475
aataattact actggact 18

<210> SEQ ID NO 476
<211> LENGTH: 48
<212> TYPE: DNA
<213> ORGANISM: Homo sapiens

<400> SEQUENCE: 476
tatatctctg acagagaatc agcgacttac aacccctccc tcaatagt 48

<210> SEQ ID NO 477
<211> LENGTH: 72
<212> TYPE: DNA
<213> ORGANISM: Homo sapiens

<400> SEQUENCE: 477
gcgcgccgag gacagaggat ttatggagtg gtttcctttg gagagttctt ctactactac 60
tccatggacg tc 72

<210> SEQ ID NO 478
<211> LENGTH: 33
<212> TYPE: DNA
<213> ORGANISM: Homo sapiens

<400> SEQUENCE: 478
ggacgacagg cccttggaag tagagctgtt cag 33

<210> SEQ ID NO 479
<211> LENGTH: 21
<212> TYPE: DNA
<213> ORGANISM: Homo sapiens

<400> SEQUENCE: 479
aataatcaag accggccctc a 21

<210> SEQ ID NO 480
<211> LENGTH: 36
<212> TYPE: DNA
<213> ORGANISM: Homo sapiens

<400> SEQUENCE: 480
cacatgtggg atagtagaag tggcttcagt tggtct 36

<210> SEQ ID NO 481
<211> LENGTH: 18
<212> TYPE: DNA
<213> ORGANISM: Homo sapiens

<400> SEQUENCE: 481
aataattact actggact 18

<210> SEQ ID NO 482
<211> LENGTH: 48
<212> TYPE: DNA
<213> ORGANISM: Homo sapiens

<400> SEQUENCE: 482
tatatctctg acagagaatc agcgacttac aacccctccc tcaatagt 48

<210> SEQ ID NO 483
<211> LENGTH: 72
<212> TYPE: DNA
<213> ORGANISM: Homo sapiens

<400> SEQUENCE: 483
gcgcgccgag gacagaggat ttatggagtg gtttcctttg gagagttctt ctactactac 60
tccatggacg tc 72

<210> SEQ ID NO 484
<211> LENGTH: 33
<212> TYPE: DNA
<213> ORGANISM: Homo sapiens

<400> SEQUENCE: 484
ggacgacagg cccttggaag tagagctgtt cag 33

<210> SEQ ID NO 485
<211> LENGTH: 21
<212> TYPE: DNA
<213> ORGANISM: Homo sapiens

<400> SEQUENCE: 485
aataatcaag accggccctc a 21

<210> SEQ ID NO 486

<211> LENGTH: 36
<212> TYPE: DNA
<213> ORGANISM: Homo sapiens

<400> SEQUENCE: 486
cacatgtggg atagtagaag tggcttcagt tggtct 36

<210> SEQ ID NO 487
<211> LENGTH: 18
<212> TYPE: DNA
<213> ORGANISM: Homo sapiens

<400> SEQUENCE: 487
aataattact actggact 18

<210> SEQ ID NO 488
<211> LENGTH: 48
<212> TYPE: DNA
<213> ORGANISM: Homo sapiens

<400> SEQUENCE: 488
tatatctctg acagagaatc agcgacttac aacccctccc tcaatagt 48

<210> SEQ ID NO 489
<211> LENGTH: 72
<212> TYPE: DNA
<213> ORGANISM: Homo sapiens

<400> SEQUENCE: 489
gcgcgccgag gacagaggat ttatggagtg gtttcctttg gagagttctt ctactactac 60
tccatggacg tc 72

<210> SEQ ID NO 490
<211> LENGTH: 33
<212> TYPE: DNA
<213> ORGANISM: Homo sapiens

<400> SEQUENCE: 490
ggacgacagg cccttggaag tagagctgtt cag 33

<210> SEQ ID NO 491
<211> LENGTH: 21
<212> TYPE: DNA
<213> ORGANISM: Homo sapiens

<400> SEQUENCE: 491
aataatcaag accggccctc a 21

<210> SEQ ID NO 492
<211> LENGTH: 36
<212> TYPE: DNA
<213> ORGANISM: Homo sapiens

<400> SEQUENCE: 492
cacatgtggg atagtagaag tggcttcagt tggtct 36

<210> SEQ ID NO 493
<211> LENGTH: 18
<212> TYPE: DNA
<213> ORGANISM: Homo sapiens

<400> SEQUENCE: 493
aataattact actggact 18

<210> SEQ ID NO 494
<211> LENGTH: 48
<212> TYPE: DNA
<213> ORGANISM: Homo sapiens

<400> SEQUENCE: 494
tatatctctg acagagaatc agcgacttac aacccctccc tcaatagt 48

<210> SEQ ID NO 495
<211> LENGTH: 72
<212> TYPE: DNA
<213> ORGANISM: Homo sapiens

<400> SEQUENCE: 495
gcgcgccgag gacagaggat ttatggagtg gtttcctttg gagagttctt ctactactac 60
tccatggacg tc 72

<210> SEQ ID NO 496
<211> LENGTH: 33
<212> TYPE: DNA
<213> ORGANISM: Homo sapiens

<400> SEQUENCE: 496
ggacgacagg cccttggaag tagagctgtt cag 33

<210> SEQ ID NO 497
<211> LENGTH: 21
<212> TYPE: DNA
<213> ORGANISM: Homo sapiens

<400> SEQUENCE: 497
aataatcaag accggccctc a 21

<210> SEQ ID NO 498
<211> LENGTH: 36
<212> TYPE: DNA
<213> ORGANISM: Homo sapiens

<400> SEQUENCE: 498
cacatgtggg atagtagaag tggcttcagt tggtct 36

<210> SEQ ID NO 499
<211> LENGTH: 18
<212> TYPE: DNA
<213> ORGANISM: Homo sapiens

<400> SEQUENCE: 499
aataattact actggact 18

<210> SEQ ID NO 500
<211> LENGTH: 48
<212> TYPE: DNA
<213> ORGANISM: Homo sapiens

<400> SEQUENCE: 500
tatatctctg acagagaatc agcgacttac aacccctccc tcaatagt 48

<210> SEQ ID NO 501
<211> LENGTH: 72
<212> TYPE: DNA
<213> ORGANISM: Homo sapiens

<400> SEQUENCE: 501
gcgcgccgag gacagaggat ttatggagtg gtttcctttg gagagttctt ctactactac 60
tccatggacg tc 72

<210> SEQ ID NO 502
<211> LENGTH: 33
<212> TYPE: DNA
<213> ORGANISM: Homo sapiens

<400> SEQUENCE: 502
ggacgacagg cccttggaag tagagctgtt cag 33

<210> SEQ ID NO 503
<211> LENGTH: 21
<212> TYPE: DNA
<213> ORGANISM: Homo sapiens

<400> SEQUENCE: 503
aataatcaag accggccctc a 21

<210> SEQ ID NO 504
<211> LENGTH: 36
<212> TYPE: DNA
<213> ORGANISM: Homo sapiens

<400> SEQUENCE: 504
cacatgtggg atagtagaag tggcttcagt tggtct 36

<210> SEQ ID NO 505
<211> LENGTH: 18
<212> TYPE: DNA
<213> ORGANISM: Homo sapiens

<400> SEQUENCE: 505
aataattact actggact 18

<210> SEQ ID NO 506
<211> LENGTH: 48
<212> TYPE: DNA
<213> ORGANISM: Homo sapiens

<400> SEQUENCE: 506
tatatctctg acagagaatc agcgacttac aacccctccc tcaatagt 48

<210> SEQ ID NO 507
<211> LENGTH: 72
<212> TYPE: DNA
<213> ORGANISM: Homo sapiens

<400> SEQUENCE: 507
gcgcgccgag gacagaggat ttatggagtg gtttcctttg gagagttctt ctactactac 60
tccatggacg tc 72

<210> SEQ ID NO 508
<211> LENGTH: 33
<212> TYPE: DNA
<213> ORGANISM: Homo sapiens

<400> SEQUENCE: 508
ggacgacagg cccttggaag tagagctgtt cag 33

<210> SEQ ID NO 509
<211> LENGTH: 21
<212> TYPE: DNA
<213> ORGANISM: Homo sapiens

<400> SEQUENCE: 509
aataatcaag accggccctc a 21

<210> SEQ ID NO 510
<211> LENGTH: 36
<212> TYPE: DNA
<213> ORGANISM: Homo sapiens

<400> SEQUENCE: 510
cacatgtggg atagtagaag tggcttcagt tggtct 36

<210> SEQ ID NO 511
<211> LENGTH: 18
<212> TYPE: DNA
<213> ORGANISM: Homo sapiens

<400> SEQUENCE: 511
aataattact actggact 18

<210> SEQ ID NO 512
<211> LENGTH: 48
<212> TYPE: DNA
<213> ORGANISM: Homo sapiens

<400> SEQUENCE: 512
tatatctctg acagagaatc agcgacttac aacccctccc tcaatagt 48

<210> SEQ ID NO 513
<211> LENGTH: 72
<212> TYPE: DNA
<213> ORGANISM: Homo sapiens

<400> SEQUENCE: 513
gcgcgccgag gacagaggat ttatggagtg gtttcctttg gagagttctt ctactactac 60
tccatggacg tc 72

<210> SEQ ID NO 514
<211> LENGTH: 33
<212> TYPE: DNA
<213> ORGANISM: Homo sapiens

<400> SEQUENCE: 514
ggacgacagg cccttggaag tagagctgtt cag 33

<210> SEQ ID NO 515
<211> LENGTH: 21
<212> TYPE: DNA
<213> ORGANISM: Homo sapiens

<400> SEQUENCE: 515
aataatcaag accggccctc a 21

<210> SEQ ID NO 516
<211> LENGTH: 36
<212> TYPE: DNA
<213> ORGANISM: Homo sapiens

<400> SEQUENCE: 516
cacatgtggg atagtagaag tggcttcagt tggtct 36

<210> SEQ ID NO 517
<211> LENGTH: 18
<212> TYPE: DNA
<213> ORGANISM: Homo sapiens

<400> SEQUENCE: 517
aataattact actggact 18

<210> SEQ ID NO 518
<211> LENGTH: 48
<212> TYPE: DNA
<213> ORGANISM: Homo sapiens

<400> SEQUENCE: 518
tatatctctg acagagaatc agcgacttac aacccctccc tcaatagt 48

<210> SEQ ID NO 519
<211> LENGTH: 72
<212> TYPE: DNA
<213> ORGANISM: Homo sapiens

<400> SEQUENCE: 519
gcgcgccgag gacagaggat ttatggagtg gtttcctttg gagagttctt ctactactac 60
tccatggacg tc 72

<210> SEQ ID NO 520
<211> LENGTH: 33
<212> TYPE: DNA
<213> ORGANISM: Homo sapiens

<400> SEQUENCE: 520
ggacgacagg cccttggaag tagagctgtt cag 33

<210> SEQ ID NO 521
<211> LENGTH: 21
<212> TYPE: DNA
<213> ORGANISM: Homo sapiens

<400> SEQUENCE: 521
aataatcaag accggccctc a 21

<210> SEQ ID NO 522
<211> LENGTH: 36
<212> TYPE: DNA
<213> ORGANISM: Homo sapiens

<400> SEQUENCE: 522
cacatgtggg atagtagaag tggcttcagt tggtct 36

<210> SEQ ID NO 523
<211> LENGTH: 18
<212> TYPE: DNA
<213> ORGANISM: Homo sapiens

<400> SEQUENCE: 523
aataattact actggact 18

<210> SEQ ID NO 524
<211> LENGTH: 48
<212> TYPE: DNA
<213> ORGANISM: Homo sapiens

<400> SEQUENCE: 524
tatatctctg acagagaatc agcgacttac aacccctccc tcaatagt 48

<210> SEQ ID NO 525
<211> LENGTH: 72
<212> TYPE: DNA
<213> ORGANISM: Homo sapiens

<400> SEQUENCE: 525
gcgcgccgag gacagaggat ttatggagtg gtttcctttg gagagttctt ctactactac 60
tccatggacg tc 72

<210> SEQ ID NO 526
<211> LENGTH: 33
<212> TYPE: DNA
<213> ORGANISM: Homo sapiens

<400> SEQUENCE: 526
ggacgacagg cccttggaag tagagctgtt cag 33

<210> SEQ ID NO 527
<211> LENGTH: 21
<212> TYPE: DNA
<213> ORGANISM: Homo sapiens

<400> SEQUENCE: 527
aataatcaag accggccctc a 21

<210> SEQ ID NO 528
<211> LENGTH: 36
<212> TYPE: DNA
<213> ORGANISM: Homo sapiens

<400> SEQUENCE: 528
cacatgtggg atagtagaag tggcttcagt tggtct 36

<210> SEQ ID NO 529
<211> LENGTH: 18
<212> TYPE: DNA
<213> ORGANISM: Homo sapiens

<400> SEQUENCE: 529
aataattact actggact 18

<210> SEQ ID NO 530
<211> LENGTH: 48
<212> TYPE: DNA
<213> ORGANISM: Homo sapiens

<400> SEQUENCE: 530
tatatctctg acagagaatc agcgacttac aacccctccc tcaatagt 48

<210> SEQ ID NO 531
<211> LENGTH: 72
<212> TYPE: DNA
<213> ORGANISM: Homo sapiens

<400> SEQUENCE: 531
gcgcgccgag gacagaggat ttatggagtg gtttcctttg gagagttctt ctactactac 60
tccatggacg tc 72

<210> SEQ ID NO 532
<211> LENGTH: 33
<212> TYPE: DNA
<213> ORGANISM: Homo sapiens

<400> SEQUENCE: 532
ggacgacagg cccttggaag tagagctgtt cag 33

<210> SEQ ID NO 533
<211> LENGTH: 21
<212> TYPE: DNA
<213> ORGANISM: Homo sapiens

<400> SEQUENCE: 533
aataatcaag accggccctc a 21

<210> SEQ ID NO 534
<211> LENGTH: 36
<212> TYPE: DNA
<213> ORGANISM: Homo sapiens

<400> SEQUENCE: 534
cacatgtggg atagtagaag tggcttcagt tggtct 36

<210> SEQ ID NO 535
<211> LENGTH: 18
<212> TYPE: DNA
<213> ORGANISM: Homo sapiens

<400> SEQUENCE: 535
aataattact actggact 18

<210> SEQ ID NO 536
<211> LENGTH: 48
<212> TYPE: DNA
<213> ORGANISM: Homo sapiens

<400> SEQUENCE: 536
tatatctctg acagagaatc agcgacttac aacccctccc tcaatagt 48

<210> SEQ ID NO 537
<211> LENGTH: 72
<212> TYPE: DNA
<213> ORGANISM: Homo sapiens

<400> SEQUENCE: 537
gcgcgccgag gacagaggat ttatggagtg gtttcctttg gagagttctt ctactactac 60
tccatggacg tc 72

<210> SEQ ID NO 538
<211> LENGTH: 33
<212> TYPE: DNA
<213> ORGANISM: Homo sapiens

<400> SEQUENCE: 538
ggacgacagg cccttggaag tagagctgtt cag 33

<210> SEQ ID NO 539
<211> LENGTH: 21
<212> TYPE: DNA
<213> ORGANISM: Homo sapiens

<400> SEQUENCE: 539
aataatcaag accggccctc a 21

<210> SEQ ID NO 540
<211> LENGTH: 36
<212> TYPE: DNA
<213> ORGANISM: Homo sapiens

<400> SEQUENCE: 540
cacatgtggg agagtagaag tggcttcagt tggtct 36

<210> SEQ ID NO 541
<211> LENGTH: 18
<212> TYPE: DNA
<213> ORGANISM: Homo sapiens

<400> SEQUENCE: 541
aataattact actggact 18

<210> SEQ ID NO 542
<211> LENGTH: 48
<212> TYPE: DNA
<213> ORGANISM: Homo sapiens

<400> SEQUENCE: 542
tatatctctg acagagaatc agcgacttac aacccctccc tcaatagt 48

<210> SEQ ID NO 543
<211> LENGTH: 72
<212> TYPE: DNA
<213> ORGANISM: Homo sapiens

<400> SEQUENCE: 543
gcgcgccgag gacagaggat ttatggagtg gtttcctttg gagagttctt ctactactac 60
tccatggacg tc 72

<210> SEQ ID NO 544
<211> LENGTH: 33
<212> TYPE: DNA
<213> ORGANISM: Homo sapiens

<400> SEQUENCE: 544
ggacgacagg cccttggaag tagagctgtt cag 33

<210> SEQ ID NO 545
<211> LENGTH: 21
<212> TYPE: DNA
<213> ORGANISM: Homo sapiens

<400> SEQUENCE: 545
aataatcaag accggccctc a 21

<210> SEQ ID NO 546
<211> LENGTH: 36
<212> TYPE: DNA
<213> ORGANISM: Homo sapiens

<400> SEQUENCE: 546
cacatgtggg atagtagaag tggcttcagt tggtct 36

<210> SEQ ID NO 547
<211> LENGTH: 18
<212> TYPE: DNA

<213> ORGANISM: Homo sapiens

<400> SEQUENCE: 547
aataattact actggact 18

<210> SEQ ID NO 548
<211> LENGTH: 48
<212> TYPE: DNA
<213> ORGANISM: Homo sapiens

<400> SEQUENCE: 548
tatatctctg acagagaatc agcgacttac aacccctccc tcaatagt 48

<210> SEQ ID NO 549
<211> LENGTH: 72
<212> TYPE: DNA
<213> ORGANISM: Homo sapiens

<400> SEQUENCE: 549
gcgcgccgag gacagaggat ttatggagtg gtttcctttg gagagttctt ctactactac 60
tccatggacg tc 72

<210> SEQ ID NO 550
<211> LENGTH: 33
<212> TYPE: DNA
<213> ORGANISM: Homo sapiens

<400> SEQUENCE: 550
ggacgacagg cccttggaag tagagctgtt cag 33

<210> SEQ ID NO 551
<211> LENGTH: 21
<212> TYPE: DNA
<213> ORGANISM: Homo sapiens

<400> SEQUENCE: 551
aataatcaag accggccctc a 21

<210> SEQ ID NO 552
<211> LENGTH: 36
<212> TYPE: DNA
<213> ORGANISM: Homo sapiens

<400> SEQUENCE: 552
cacatgtggg atagtagaag tggcttcagt tggtct 36

<210> SEQ ID NO 553
<211> LENGTH: 18
<212> TYPE: DNA
<213> ORGANISM: Homo sapiens

<400> SEQUENCE: 553
aataattact actggact 18

<210> SEQ ID NO 554
<211> LENGTH: 48
<212> TYPE: DNA
<213> ORGANISM: Homo sapiens

<400> SEQUENCE: 554
tatatctctg acagagaatc agcgacttac aacccctccc tcaatagt 48

<210> SEQ ID NO 555
<211> LENGTH: 72
<212> TYPE: DNA
<213> ORGANISM: Homo sapiens

<400> SEQUENCE: 555
gcgcgccgag gacagaggat ttatggagtg gtttcctttg gagagttctt ctactactac 60
tccatggacg tc 72

<210> SEQ ID NO 556
<211> LENGTH: 33
<212> TYPE: DNA
<213> ORGANISM: Homo sapiens

<400> SEQUENCE: 556
ggacgacagg cccttggaag tagagctgtt cag 33

<210> SEQ ID NO 557
<211> LENGTH: 21
<212> TYPE: DNA
<213> ORGANISM: Homo sapiens

<400> SEQUENCE: 557
aataatcaag accggccctc a 21

<210> SEQ ID NO 558
<211> LENGTH: 36
<212> TYPE: DNA
<213> ORGANISM: Homo sapiens

<400> SEQUENCE: 558
cacatgtggg atagtagaag tggcttcagt tggtct 36

<210> SEQ ID NO 559
<211> LENGTH: 18
<212> TYPE: DNA
<213> ORGANISM: Homo sapiens

<400> SEQUENCE: 559
aataattact actggact 18

<210> SEQ ID NO 560
<211> LENGTH: 48
<212> TYPE: DNA
<213> ORGANISM: Homo sapiens

<400> SEQUENCE: 560
tatatctctg acagagaatc agcgacttac aacccctccc tcaatagt 48

<210> SEQ ID NO 561
<211> LENGTH: 72
<212> TYPE: DNA
<213> ORGANISM: Homo sapiens

<400> SEQUENCE: 561
gcgcgccgag gacagaggat ttatggagtg gtttcctttg gagagttctt ctactactac 60
tccatggacg tc 72

<210> SEQ ID NO 562
<211> LENGTH: 33
<212> TYPE: DNA
<213> ORGANISM: Homo sapiens

<400> SEQUENCE: 562
ggacgacagg cccttggaag tagagctgtt cag 33

<210> SEQ ID NO 563
<211> LENGTH: 21
<212> TYPE: DNA
<213> ORGANISM: Homo sapiens

<400> SEQUENCE: 563
aataatcaag accggccctc a 21

<210> SEQ ID NO 564
<211> LENGTH: 36
<212> TYPE: DNA
<213> ORGANISM: Homo sapiens

<400> SEQUENCE: 564
cacatgtggg atagtagaag tggcttcagt tggtct 36

<210> SEQ ID NO 565
<211> LENGTH: 18
<212> TYPE: DNA
<213> ORGANISM: Homo sapiens

<400> SEQUENCE: 565
aataattact actggact 18

<210> SEQ ID NO 566
<211> LENGTH: 48
<212> TYPE: DNA
<213> ORGANISM: Homo sapiens

<400> SEQUENCE: 566
tatatctctg acagagaatc agcgacttac aacccctccc tcaatagt 48

<210> SEQ ID NO 567
<211> LENGTH: 72
<212> TYPE: DNA
<213> ORGANISM: Homo sapiens

<400> SEQUENCE: 567
gcgcgccgag gacagaggat ttatggagtg gtttcctttg gagagttctt ctactactac 60
tccatggacg tc 72

<210> SEQ ID NO 568
<211> LENGTH: 33
<212> TYPE: DNA
<213> ORGANISM: Homo sapiens

<400> SEQUENCE: 568
ggacgacagg cccttggaag tagagctgtt cag 33

<210> SEQ ID NO 569
<211> LENGTH: 21
<212> TYPE: DNA
<213> ORGANISM: Homo sapiens

<400> SEQUENCE: 569
aataatcaag accggccctc a 21

<210> SEQ ID NO 570
<211> LENGTH: 36

<212> TYPE: DNA
<213> ORGANISM: Homo sapiens

<400> SEQUENCE: 570
cacatgtggg atagtagaag tggcttcagt tggtct 36

<210> SEQ ID NO 571
<211> LENGTH: 18
<212> TYPE: DNA
<213> ORGANISM: Homo sapiens

<400> SEQUENCE: 571
aataattact actggact 18

<210> SEQ ID NO 572
<211> LENGTH: 48
<212> TYPE: DNA
<213> ORGANISM: Homo sapiens

<400> SEQUENCE: 572
tatatctctg acagagaatc agcgacttac aacccctccc tcaatagt 48

<210> SEQ ID NO 573
<211> LENGTH: 72
<212> TYPE: DNA
<213> ORGANISM: Homo sapiens

<400> SEQUENCE: 573
gcgcgccgag gacagaggat ttatggagtg gtttcctttg gagagttctt ctactactac 60
tccatggacg tc 72

<210> SEQ ID NO 574
<211> LENGTH: 33
<212> TYPE: DNA
<213> ORGANISM: Homo sapiens

<400> SEQUENCE: 574
ggacgacagg cccttggaag tagagctgtt cag 33

<210> SEQ ID NO 575
<211> LENGTH: 21
<212> TYPE: DNA
<213> ORGANISM: Homo sapiens

<400> SEQUENCE: 575
aataatcaag accggccctc a 21

<210> SEQ ID NO 576
<211> LENGTH: 36
<212> TYPE: DNA
<213> ORGANISM: Homo sapiens

<400> SEQUENCE: 576
cacatgtggg atagtagaag tggcttcagt tggtct 36

<210> SEQ ID NO 577
<211> LENGTH: 18
<212> TYPE: DNA
<213> ORGANISM: Homo sapiens

<400> SEQUENCE: 577
aataattact actggact 18

<210> SEQ ID NO 578
<211> LENGTH: 48
<212> TYPE: DNA
<213> ORGANISM: Homo sapiens

<400> SEQUENCE: 578
tatatctctg acagagaatc agcgacttac aacccctccc tcaatagt 48

<210> SEQ ID NO 579
<211> LENGTH: 72
<212> TYPE: DNA
<213> ORGANISM: Homo sapiens

<400> SEQUENCE: 579
gcgcgccgag gacagaggat ttatggagtg gtttcctttg gagagttctt ctactactac 60
tccatggacg tc 72

<210> SEQ ID NO 580
<211> LENGTH: 33
<212> TYPE: DNA
<213> ORGANISM: Homo sapiens

<400> SEQUENCE: 580
ggacgacagg cccttggaag tagagctgtt cag 33

<210> SEQ ID NO 581
<211> LENGTH: 21
<212> TYPE: DNA
<213> ORGANISM: Homo sapiens

<400> SEQUENCE: 581
aataatcaag accggccctc a 21

<210> SEQ ID NO 582
<211> LENGTH: 36
<212> TYPE: DNA
<213> ORGANISM: Homo sapiens

<400> SEQUENCE: 582
cacatgtggg atagtagaag tggcttcagt tggtct 36

<210> SEQ ID NO 583
<211> LENGTH: 18
<212> TYPE: DNA
<213> ORGANISM: Homo sapiens

<400> SEQUENCE: 583
aataattact actggact 18

<210> SEQ ID NO 584
<211> LENGTH: 48
<212> TYPE: DNA
<213> ORGANISM: Homo sapiens

<400> SEQUENCE: 584
tatatctctg acagagaatc agcgacttac aacccctccc tcaatagt 48

<210> SEQ ID NO 585
<211> LENGTH: 72
<212> TYPE: DNA
<213> ORGANISM: Homo sapiens

<400> SEQUENCE: 585
gcgcgccgag gacagaggat ttatggagtg gtttcctttg gagagttctt ctactactac 60
tccatggacg tc 72

<210> SEQ ID NO 586
<211> LENGTH: 33
<212> TYPE: DNA
<213> ORGANISM: Homo sapiens

<400> SEQUENCE: 586
ggacgacagg cccttggaag tagagctgtt cag 33

<210> SEQ ID NO 587
<211> LENGTH: 21
<212> TYPE: DNA
<213> ORGANISM: Homo sapiens

<400> SEQUENCE: 587
aataatcaag accggccctc a 21

<210> SEQ ID NO 588
<211> LENGTH: 36
<212> TYPE: DNA
<213> ORGANISM: Homo sapiens

<400> SEQUENCE: 588
cacatgtggg atagtagaag tggcttcagt tggtct 36

<210> SEQ ID NO 589
<211> LENGTH: 18
<212> TYPE: DNA
<213> ORGANISM: Homo sapiens

<400> SEQUENCE: 589
aataattact actggact 18

<210> SEQ ID NO 590
<211> LENGTH: 48
<212> TYPE: DNA
<213> ORGANISM: Homo sapiens

<400> SEQUENCE: 590
tatatctctg acagagaatc agcgacttac aacccctccc tcaatagt 48

<210> SEQ ID NO 591
<211> LENGTH: 72
<212> TYPE: DNA
<213> ORGANISM: Homo sapiens

<400> SEQUENCE: 591
gcgcgccgag gacagaggat ttatggagtg gtttcctttg gagagttctt ctactactac 60
tccatggacg tc 72

<210> SEQ ID NO 592
<211> LENGTH: 33
<212> TYPE: DNA
<213> ORGANISM: Homo sapiens

<400> SEQUENCE: 592
ggacgacagg cccttggaag tagagctgtt cag 33

<210> SEQ ID NO 593

<211> LENGTH: 21
<212> TYPE: DNA
<213> ORGANISM: Homo sapiens

<400> SEQUENCE: 593
aataatcaag accggccctc a 21

<210> SEQ ID NO 594
<211> LENGTH: 36
<212> TYPE: DNA
<213> ORGANISM: Homo sapiens

<400> SEQUENCE: 594
cacatgtggg atagtagaag tggcttcagt tggtct 36

<210> SEQ ID NO 595
<211> LENGTH: 18
<212> TYPE: DNA
<213> ORGANISM: Homo sapiens

<400> SEQUENCE: 595
aataattact actggact 18

<210> SEQ ID NO 596
<211> LENGTH: 48
<212> TYPE: DNA
<213> ORGANISM: Homo sapiens

<400> SEQUENCE: 596
tatatctctg acagagaatc agcgacttac aacccctccc tccaaagt 48

<210> SEQ ID NO 597
<211> LENGTH: 72
<212> TYPE: DNA
<213> ORGANISM: Homo sapiens

<400> SEQUENCE: 597
gcgcgccgag gacagaggat ttatggagtg gtttcctttg gagagttctt ctactactac 60
tccatggacg tc 72

<210> SEQ ID NO 598
<211> LENGTH: 33
<212> TYPE: DNA
<213> ORGANISM: Homo sapiens

<400> SEQUENCE: 598
ggacgacagg cccttggaag tagagctgtt cag 33

<210> SEQ ID NO 599
<211> LENGTH: 21
<212> TYPE: DNA
<213> ORGANISM: Homo sapiens

<400> SEQUENCE: 599
aataatcaag accggccctc a 21

<210> SEQ ID NO 600
<211> LENGTH: 36
<212> TYPE: DNA
<213> ORGANISM: Homo sapiens

<400> SEQUENCE: 600
cacatgtggg atagtagaag tggcttcagt tggtct 36

<210> SEQ ID NO 601
<211> LENGTH: 18
<212> TYPE: DNA
<213> ORGANISM: Homo sapiens

<400> SEQUENCE: 601
aataattact actggact 18

<210> SEQ ID NO 602
<211> LENGTH: 48
<212> TYPE: DNA
<213> ORGANISM: Homo sapiens

<400> SEQUENCE: 602
tatatctctg acagagaatc agcgacttac aacccctccc tcaatagt 48

<210> SEQ ID NO 603
<211> LENGTH: 72
<212> TYPE: DNA
<213> ORGANISM: Homo sapiens

<400> SEQUENCE: 603
gcgcgccgag gacagaggat ttatggagtg gtttcctttg gagagttctt ctactactac 60
tccatggacg tc 72

<210> SEQ ID NO 604
<211> LENGTH: 33
<212> TYPE: DNA
<213> ORGANISM: Homo sapiens

<400> SEQUENCE: 604
ggacgacagg cccttggaag tagagctgtt cag 33

<210> SEQ ID NO 605
<211> LENGTH: 21
<212> TYPE: DNA
<213> ORGANISM: Homo sapiens

<400> SEQUENCE: 605
aataatcaag accggccctc a 21

<210> SEQ ID NO 606
<211> LENGTH: 36
<212> TYPE: DNA
<213> ORGANISM: Homo sapiens

<400> SEQUENCE: 606
cacatgtggg atagtagaag tggcttcagt tggtct 36

<210> SEQ ID NO 607
<211> LENGTH: 18
<212> TYPE: DNA
<213> ORGANISM: Homo sapiens

<400> SEQUENCE: 607
aataattact actggact 18

<210> SEQ ID NO 608
<211> LENGTH: 48
<212> TYPE: DNA
<213> ORGANISM: Homo sapiens

<400> SEQUENCE: 608
tatatctctg acagagaatc agcgacttac aacccctccc tcaatagt 48

<210> SEQ ID NO 609
<211> LENGTH: 72
<212> TYPE: DNA
<213> ORGANISM: Homo sapiens

<400> SEQUENCE: 609
gcgcgccgag gacagaggat ttatggagtg gtttcctttg gagagttctt ctactactac 60
tccatggacg tc 72

<210> SEQ ID NO 610
<211> LENGTH: 33
<212> TYPE: DNA
<213> ORGANISM: Homo sapiens

<400> SEQUENCE: 610
ggacgacagg cccttggaag tagagctgtt cag 33

<210> SEQ ID NO 611
<211> LENGTH: 21
<212> TYPE: DNA
<213> ORGANISM: Homo sapiens

<400> SEQUENCE: 611
aataatcaag accggccctc a 21

<210> SEQ ID NO 612
<211> LENGTH: 36
<212> TYPE: DNA
<213> ORGANISM: Homo sapiens

<400> SEQUENCE: 612
cacatgtggg atagtagaag tggcttcagt tggtct 36

<210> SEQ ID NO 613
<211> LENGTH: 18
<212> TYPE: DNA
<213> ORGANISM: Homo sapiens

<400> SEQUENCE: 613
aataattact actggact 18

<210> SEQ ID NO 614
<211> LENGTH: 48
<212> TYPE: DNA
<213> ORGANISM: Homo sapiens

<400> SEQUENCE: 614
tatatctctg acagagaatc agcgacttac aacccctccc tcaatagt 48

<210> SEQ ID NO 615
<211> LENGTH: 72
<212> TYPE: DNA
<213> ORGANISM: Homo sapiens

<400> SEQUENCE: 615
gcgcgccgag gacagaggat ttatggagtg gtttcctttg gagagttctt ctactactac 60
tccatggacg tc 72

<210> SEQ ID NO 616
<211> LENGTH: 33
<212> TYPE: DNA
<213> ORGANISM: Homo sapiens

<400> SEQUENCE: 616
ggacgacagg cccttggaag tagagctgtt cag 33

<210> SEQ ID NO 617
<211> LENGTH: 21
<212> TYPE: DNA
<213> ORGANISM: Homo sapiens

<400> SEQUENCE: 617
aataatcaag accggccctc a 21

<210> SEQ ID NO 618
<211> LENGTH: 36
<212> TYPE: DNA
<213> ORGANISM: Homo sapiens

<400> SEQUENCE: 618
cacatgtggg atagtagaag tggcttcagt tggtct 36

<210> SEQ ID NO 619
<211> LENGTH: 18
<212> TYPE: DNA
<213> ORGANISM: Homo sapiens

<400> SEQUENCE: 619
aataattact actggact 18

<210> SEQ ID NO 620
<211> LENGTH: 48
<212> TYPE: DNA
<213> ORGANISM: Homo sapiens

<400> SEQUENCE: 620
tatatctctg acagagaatc agcgacttac aacccctccc tcaatagt 48

<210> SEQ ID NO 621
<211> LENGTH: 72
<212> TYPE: DNA
<213> ORGANISM: Homo sapiens

<400> SEQUENCE: 621
gcgcgccgag gacagaggat ttatggagtg gtttcctttg gagagttctt ctactactac 60
tccatggacg tc 72

<210> SEQ ID NO 622
<211> LENGTH: 33
<212> TYPE: DNA
<213> ORGANISM: Homo sapiens

<400> SEQUENCE: 622
ggacgacagg cccttggaag tagagctgtt cag 33

<210> SEQ ID NO 623
<211> LENGTH: 21
<212> TYPE: DNA
<213> ORGANISM: Homo sapiens

<400> SEQUENCE: 623
aataatcaag accggccctc a 21

<210> SEQ ID NO 624
<211> LENGTH: 36
<212> TYPE: DNA
<213> ORGANISM: Homo sapiens

<400> SEQUENCE: 624
cacatgtggg atagtagaag tggcttcagt tggtct 36

<210> SEQ ID NO 625
<211> LENGTH: 18
<212> TYPE: DNA
<213> ORGANISM: Homo sapiens

<400> SEQUENCE: 625
aataattact actggact 18

<210> SEQ ID NO 626
<211> LENGTH: 48
<212> TYPE: DNA
<213> ORGANISM: Homo sapiens

<400> SEQUENCE: 626
tatatctctg acagagaatc agcgacttac aacccctccc tcaatagt 48

<210> SEQ ID NO 627
<211> LENGTH: 72
<212> TYPE: DNA
<213> ORGANISM: Homo sapiens

<400> SEQUENCE: 627
gcgcgccgag gacagaggat ttatggagtg gtttcctttg gagagttctt ctactactac 60
tccatggacg tc 72

<210> SEQ ID NO 628
<211> LENGTH: 33
<212> TYPE: DNA
<213> ORGANISM: Homo sapiens

<400> SEQUENCE: 628
ggacgacagg cccttggaag tagagctgtt cag 33

<210> SEQ ID NO 629
<211> LENGTH: 21
<212> TYPE: DNA
<213> ORGANISM: Homo sapiens

<400> SEQUENCE: 629
aataatcaag accggccctc a 21

<210> SEQ ID NO 630
<211> LENGTH: 36
<212> TYPE: DNA
<213> ORGANISM: Homo sapiens

<400> SEQUENCE: 630
cacatgtggg atagtagaag tggcttcagt tggtct 36

<210> SEQ ID NO 631
<211> LENGTH: 18
<212> TYPE: DNA
<213> ORGANISM: Homo sapiens

<400> SEQUENCE: 631
aataattact actggact 18

<210> SEQ ID NO 632
<211> LENGTH: 48
<212> TYPE: DNA
<213> ORGANISM: Homo sapiens

<400> SEQUENCE: 632
tatatctctg acagagaatc agcgacttac aacccctccc tcaatagt 48

<210> SEQ ID NO 633
<211> LENGTH: 72
<212> TYPE: DNA
<213> ORGANISM: Homo sapiens

<400> SEQUENCE: 633
gcgcgccgag gacagaggat ttatggagtg gtttcctttg gagagttctt ctactactac 60
tccatggacg tc 72

<210> SEQ ID NO 634
<211> LENGTH: 33
<212> TYPE: DNA
<213> ORGANISM: Homo sapiens

<400> SEQUENCE: 634
ggacgacagg cccttggaag tagagctgtt cag 33

<210> SEQ ID NO 635
<211> LENGTH: 21
<212> TYPE: DNA
<213> ORGANISM: Homo sapiens

<400> SEQUENCE: 635
aataatcaag accggccctc a 21

<210> SEQ ID NO 636
<211> LENGTH: 36
<212> TYPE: DNA
<213> ORGANISM: Homo sapiens

<400> SEQUENCE: 636
cacatgtggg atagtagaag tggcttcagt tggtct 36

<210> SEQ ID NO 637
<211> LENGTH: 18
<212> TYPE: DNA
<213> ORGANISM: Homo sapiens

<400> SEQUENCE: 637
aataattact actggact 18

<210> SEQ ID NO 638
<211> LENGTH: 48
<212> TYPE: DNA
<213> ORGANISM: Homo sapiens

<400> SEQUENCE: 638
tatatctctg acagagaatc agcgacttac aacccctccc tcaatagt 48

<210> SEQ ID NO 639

<211> LENGTH: 72
<212> TYPE: DNA
<213> ORGANISM: Homo sapiens

<400> SEQUENCE: 639
gcgcgccgag gacagaggat ttatggagtg gtttcctttg gagagttctt ctactactac 60
tccatggacg tc 72

<210> SEQ ID NO 640
<211> LENGTH: 33
<212> TYPE: DNA
<213> ORGANISM: Homo sapiens

<400> SEQUENCE: 640
ggacgacagg cccttggaag tagagctgtt cag 33

<210> SEQ ID NO 641
<211> LENGTH: 21
<212> TYPE: DNA
<213> ORGANISM: Homo sapiens

<400> SEQUENCE: 641
aataatcaag accggccctc a 21

<210> SEQ ID NO 642
<211> LENGTH: 36
<212> TYPE: DNA
<213> ORGANISM: Homo sapiens

<400> SEQUENCE: 642
cacatgtggg atagtagaag tggcttcagt tggtct 36

<210> SEQ ID NO 643
<211> LENGTH: 18
<212> TYPE: DNA
<213> ORGANISM: Homo sapiens

<400> SEQUENCE: 643
aataattact actggact 18

<210> SEQ ID NO 644
<211> LENGTH: 48
<212> TYPE: DNA
<213> ORGANISM: Homo sapiens

<400> SEQUENCE: 644
tatatctctg acagagaatc agcgacttac aacccctccc tcaatagt 48

<210> SEQ ID NO 645
<211> LENGTH: 72
<212> TYPE: DNA
<213> ORGANISM: Homo sapiens

<400> SEQUENCE: 645
gcgcgccgag gacagaggat ttatggagtg gtttcctttg gagagttctt ctactactac 60
tccatggacg tc 72

<210> SEQ ID NO 646
<211> LENGTH: 33
<212> TYPE: DNA
<213> ORGANISM: Homo sapiens

<400> SEQUENCE: 646
ggacgacagg cccttggaag tagagctgtt cag 33

<210> SEQ ID NO 647
<211> LENGTH: 21
<212> TYPE: DNA
<213> ORGANISM: Homo sapiens

<400> SEQUENCE: 647
aataatcaag accggccctc a 21

<210> SEQ ID NO 648
<211> LENGTH: 36
<212> TYPE: DNA
<213> ORGANISM: Homo sapiens

<400> SEQUENCE: 648
cacatgtggg atagtagaag tggcttcagt tggtct 36

<210> SEQ ID NO 649
<211> LENGTH: 18
<212> TYPE: DNA
<213> ORGANISM: Homo sapiens

<400> SEQUENCE: 649
aataattact actggact 18

<210> SEQ ID NO 650
<211> LENGTH: 48
<212> TYPE: DNA
<213> ORGANISM: Homo sapiens

<400> SEQUENCE: 650
tatatctctg acagagaatc agcgacttac aacccctccc tcaatagt 48

<210> SEQ ID NO 651
<211> LENGTH: 72
<212> TYPE: DNA
<213> ORGANISM: Homo sapiens

<400> SEQUENCE: 651
gcgcgccgag gacagaggat ttatggagtg gtttcctttg gagagttctt ctactactac 60
tccatggacg tc 72

<210> SEQ ID NO 652
<211> LENGTH: 33
<212> TYPE: DNA
<213> ORGANISM: Homo sapiens

<400> SEQUENCE: 652
ggacgacagg cccttggaag tagagctgtt cag 33

<210> SEQ ID NO 653
<211> LENGTH: 21
<212> TYPE: DNA
<213> ORGANISM: Homo sapiens

<400> SEQUENCE: 653
aataatcaag accggccctc a 21

<210> SEQ ID NO 654
<211> LENGTH: 36
<212> TYPE: DNA

<213> ORGANISM: Homo sapiens

<400> SEQUENCE: 654
cacatgtggg atagtagaag tggcttcagt tggtct 36

<210> SEQ ID NO 655
<211> LENGTH: 18
<212> TYPE: DNA
<213> ORGANISM: Homo sapiens

<400> SEQUENCE: 655
aataattact actggact 18

<210> SEQ ID NO 656
<211> LENGTH: 48
<212> TYPE: DNA
<213> ORGANISM: Homo sapiens

<400> SEQUENCE: 656
tatatctctg acagagaatc agcgacttac aacccctccc tcaatagt 48

<210> SEQ ID NO 657
<211> LENGTH: 72
<212> TYPE: DNA
<213> ORGANISM: Homo sapiens

<400> SEQUENCE: 657
gcgcgccgag gacagaggat ttatggagtg gtttcctttg gagagttctt ctactactac 60
tccatggacg tc 72

<210> SEQ ID NO 658
<211> LENGTH: 33
<212> TYPE: DNA
<213> ORGANISM: Homo sapiens

<400> SEQUENCE: 658
ggacgacagg cccttggaag tagagctgtt cag 33

<210> SEQ ID NO 659
<211> LENGTH: 21
<212> TYPE: DNA
<213> ORGANISM: Homo sapiens

<400> SEQUENCE: 659
aataatcaag accggccctc a 21

<210> SEQ ID NO 660
<211> LENGTH: 36
<212> TYPE: DNA
<213> ORGANISM: Homo sapiens

<400> SEQUENCE: 660
cacatgtggg atagtagaag tggcttcagt tggtct 36

<210> SEQ ID NO 661
<211> LENGTH: 18
<212> TYPE: DNA
<213> ORGANISM: Homo sapiens

<400> SEQUENCE: 661
aataattact actggact 18

<210> SEQ ID NO 662
<211> LENGTH: 48
<212> TYPE: DNA
<213> ORGANISM: Homo sapiens

<400> SEQUENCE: 662
tatatctctg acagagaatc agcgacttac aacccctccc tcaatagt 48

<210> SEQ ID NO 663
<211> LENGTH: 72
<212> TYPE: DNA
<213> ORGANISM: Homo sapiens

<400> SEQUENCE: 663
gcgcgccgag gacagaggat ttatggagtg gtttcctttg gagagttctt ctactactac 60
tccatggacg tc 72

<210> SEQ ID NO 664
<211> LENGTH: 33
<212> TYPE: DNA
<213> ORGANISM: Homo sapiens

<400> SEQUENCE: 664
ggacgacagg cccttggaag tagagctgtt cag 33

<210> SEQ ID NO 665
<211> LENGTH: 21
<212> TYPE: DNA
<213> ORGANISM: Homo sapiens

<400> SEQUENCE: 665
aataatcaag accggccctc a 21

<210> SEQ ID NO 666
<211> LENGTH: 36
<212> TYPE: DNA
<213> ORGANISM: Homo sapiens

<400> SEQUENCE: 666
cacatgtggg atagtagaag tggcttcagt tggtct 36

<210> SEQ ID NO 667
<211> LENGTH: 18
<212> TYPE: DNA
<213> ORGANISM: Homo sapiens

<400> SEQUENCE: 667
aataattact actggact 18

<210> SEQ ID NO 668
<211> LENGTH: 48
<212> TYPE: DNA
<213> ORGANISM: Homo sapiens

<400> SEQUENCE: 668
tatatctctg acagagaatc agcgacttac aacccctccc tcaatagt 48

<210> SEQ ID NO 669
<211> LENGTH: 72
<212> TYPE: DNA
<213> ORGANISM: Homo sapiens

<400> SEQUENCE: 669
gcgcgccgag gacagaggat ttatggagtg gtttcctttg gagagttctt ctactactac 60
tccatggacg tc 72

<210> SEQ ID NO 670
<211> LENGTH: 33
<212> TYPE: DNA
<213> ORGANISM: Homo sapiens

<400> SEQUENCE: 670
ggacgacagg cccttggaag tagagctgtt cag 33

<210> SEQ ID NO 671
<211> LENGTH: 21
<212> TYPE: DNA
<213> ORGANISM: Homo sapiens

<400> SEQUENCE: 671
aataatcaag accggccctc a 21

<210> SEQ ID NO 672
<211> LENGTH: 36
<212> TYPE: DNA
<213> ORGANISM: Homo sapiens

<400> SEQUENCE: 672
cacatgtggg atagtagaag tggcttcagt tggtct 36

<210> SEQ ID NO 673
<211> LENGTH: 18
<212> TYPE: DNA
<213> ORGANISM: Homo sapiens

<400> SEQUENCE: 673
aataattact actggact 18

<210> SEQ ID NO 674
<211> LENGTH: 48
<212> TYPE: DNA
<213> ORGANISM: Homo sapiens

<400> SEQUENCE: 674
tatatctctg acagagaatc agcgacttac aacccctccc tcaatagt 48

<210> SEQ ID NO 675
<211> LENGTH: 72
<212> TYPE: DNA
<213> ORGANISM: Homo sapiens

<400> SEQUENCE: 675
gcgcgccgag gacagaggat ttatggagtg gtttcctttg gagagttctt ctactactac 60
tccatggacg tc 72

<210> SEQ ID NO 676
<211> LENGTH: 33
<212> TYPE: DNA
<213> ORGANISM: Homo sapiens

<400> SEQUENCE: 676
ggacgacagg cccttggaag tagagctgtt cag 33

<210> SEQ ID NO 677
<211> LENGTH: 21

<212> TYPE: DNA
<213> ORGANISM: Homo sapiens

<400> SEQUENCE: 677
aataatcaag accggccctc a 21

<210> SEQ ID NO 678
<211> LENGTH: 36
<212> TYPE: DNA
<213> ORGANISM: Homo sapiens

<400> SEQUENCE: 678
cacatgtggg atagtagaag tggcttcagt tggtct 36

<210> SEQ ID NO 679
<211> LENGTH: 18
<212> TYPE: DNA
<213> ORGANISM: Homo sapiens

<400> SEQUENCE: 679
aataattact actggact 18

<210> SEQ ID NO 680
<211> LENGTH: 48
<212> TYPE: DNA
<213> ORGANISM: Homo sapiens

<400> SEQUENCE: 680
tatatctctg acagagaatc agcgacttac aacccctccc tcaatagt 48

<210> SEQ ID NO 681
<211> LENGTH: 72
<212> TYPE: DNA
<213> ORGANISM: Homo sapiens

<400> SEQUENCE: 681
gcgcgccgag gacagaggat ttatggagtg gtttcctttg gagagttctt ctactactac 60
tccatggacg tc 72

<210> SEQ ID NO 682
<211> LENGTH: 33
<212> TYPE: DNA
<213> ORGANISM: Homo sapiens

<400> SEQUENCE: 682
ggacgacagg cccttggaag tagagctgtt cag 33

<210> SEQ ID NO 683
<211> LENGTH: 21
<212> TYPE: DNA
<213> ORGANISM: Homo sapiens

<400> SEQUENCE: 683
aataatcaag accggccctc a 21

<210> SEQ ID NO 684
<211> LENGTH: 36
<212> TYPE: DNA
<213> ORGANISM: Homo sapiens

<400> SEQUENCE: 684
cacatgtggg atagtagaag tggcttcagt tggtct 36

<210> SEQ ID NO 685
<211> LENGTH: 18
<212> TYPE: DNA
<213> ORGANISM: Homo sapiens

<400> SEQUENCE: 685
aataattact actggact 18

<210> SEQ ID NO 686
<211> LENGTH: 48
<212> TYPE: DNA
<213> ORGANISM: Homo sapiens

<400> SEQUENCE: 686
tatatctctg acagagaatc agcgacttac aacccctccc tcaatagt 48

<210> SEQ ID NO 687
<211> LENGTH: 72
<212> TYPE: DNA
<213> ORGANISM: Homo sapiens

<400> SEQUENCE: 687
gcgcgccgag gacagaggat ttatggagtg gtttcctttg gagagttctt ctactactac 60
tccatggacg tc 72

<210> SEQ ID NO 688
<211> LENGTH: 33
<212> TYPE: DNA
<213> ORGANISM: Homo sapiens

<400> SEQUENCE: 688
ggacgacagg cccttggaag tagagctgtt cag 33

<210> SEQ ID NO 689
<211> LENGTH: 21
<212> TYPE: DNA
<213> ORGANISM: Homo sapiens

<400> SEQUENCE: 689
aataatcaag accggccctc a 21

<210> SEQ ID NO 690
<211> LENGTH: 36
<212> TYPE: DNA
<213> ORGANISM: Homo sapiens

<400> SEQUENCE: 690
cacatgtggg atagtagaag tggcttcagt tggtct 36

<210> SEQ ID NO 691
<211> LENGTH: 18
<212> TYPE: DNA
<213> ORGANISM: Homo sapiens

<400> SEQUENCE: 691
aataattact actggact 18

<210> SEQ ID NO 692
<211> LENGTH: 48
<212> TYPE: DNA
<213> ORGANISM: Homo sapiens

<400> SEQUENCE: 692
tatatctctg acagagaatc agcgacttac aacccctccc tcaatagt 48

<210> SEQ ID NO 693
<211> LENGTH: 72
<212> TYPE: DNA
<213> ORGANISM: Homo sapiens

<400> SEQUENCE: 693
gcgcgccgag gacagaggat ttatggagtg gtttcctttg gagagttctt ctactactac 60
tccatggacg tc 72

<210> SEQ ID NO 694
<211> LENGTH: 33
<212> TYPE: DNA
<213> ORGANISM: Homo sapiens

<400> SEQUENCE: 694
ggacgacagg cccttggaag tagagctgtt cag 33

<210> SEQ ID NO 695
<211> LENGTH: 21
<212> TYPE: DNA
<213> ORGANISM: Homo sapiens

<400> SEQUENCE: 695
aataatcaag accggccctc a 21

<210> SEQ ID NO 696
<211> LENGTH: 36
<212> TYPE: DNA
<213> ORGANISM: Homo sapiens

<400> SEQUENCE: 696
cacatgtggg atagtagaag tggcttcagt tggtct 36

<210> SEQ ID NO 697
<211> LENGTH: 18
<212> TYPE: DNA
<213> ORGANISM: Homo sapiens

<400> SEQUENCE: 697
aataattact actggact 18

<210> SEQ ID NO 698
<211> LENGTH: 48
<212> TYPE: DNA
<213> ORGANISM: Homo sapiens

<400> SEQUENCE: 698
tatatctctg acagagaatc agcgacttac aacccctccc tcaatagt 48

<210> SEQ ID NO 699
<211> LENGTH: 72
<212> TYPE: DNA
<213> ORGANISM: Homo sapiens

<400> SEQUENCE: 699
gcgcgccgag gacagaggat ttatggagtg gtttcctttg gagagttctt ctactactac 60
tccatggacg tc 72

<210> SEQ ID NO 700

<211> LENGTH: 33
<212> TYPE: DNA
<213> ORGANISM: Homo sapiens

<400> SEQUENCE: 700
ggacgacagg cccttggaag tagagctgtt cag 33

<210> SEQ ID NO 701
<211> LENGTH: 21
<212> TYPE: DNA
<213> ORGANISM: Homo sapiens

<400> SEQUENCE: 701
aataatcaag accggccctc a 21

<210> SEQ ID NO 702
<211> LENGTH: 36
<212> TYPE: DNA
<213> ORGANISM: Homo sapiens

<400> SEQUENCE: 702
cacatgtggg atagtagaag tggcttcagt tggtct 36

<210> SEQ ID NO 703
<211> LENGTH: 18
<212> TYPE: DNA
<213> ORGANISM: Homo sapiens

<400> SEQUENCE: 703
aataattact actggact 18

<210> SEQ ID NO 704
<211> LENGTH: 48
<212> TYPE: DNA
<213> ORGANISM: Homo sapiens

<400> SEQUENCE: 704
tatatctctg acagagaatc agcgacttac aacccctccc tcaatagt 48

<210> SEQ ID NO 705
<211> LENGTH: 72
<212> TYPE: DNA
<213> ORGANISM: Homo sapiens

<400> SEQUENCE: 705
gcgcgccgag gacagaggat ttatggagtg gtttcctttg gagagttctt ctactactac 60
tccatggacg tc 72

<210> SEQ ID NO 706
<211> LENGTH: 33
<212> TYPE: DNA
<213> ORGANISM: Homo sapiens

<400> SEQUENCE: 706
ggacgacagg cccttggaag tagagctgtt cag 33

<210> SEQ ID NO 707
<211> LENGTH: 21
<212> TYPE: DNA
<213> ORGANISM: Homo sapiens

<400> SEQUENCE: 707
aataatcaag accggccctc a 21

<210> SEQ ID NO 708
<211> LENGTH: 36
<212> TYPE: DNA
<213> ORGANISM: Homo sapiens

<400> SEQUENCE: 708
cacatgtggg atagtagaag tggcttcagt tggtct 36

<210> SEQ ID NO 709
<211> LENGTH: 18
<212> TYPE: DNA
<213> ORGANISM: Homo sapiens

<400> SEQUENCE: 709
aataattact actggact 18

<210> SEQ ID NO 710
<211> LENGTH: 48
<212> TYPE: DNA
<213> ORGANISM: Homo sapiens

<400> SEQUENCE: 710
tatatctctg acagagaatc agcgacttac aacccctccc tcaatagt 48

<210> SEQ ID NO 711
<211> LENGTH: 72
<212> TYPE: DNA
<213> ORGANISM: Homo sapiens

<400> SEQUENCE: 711
gcgcgccgag gacagaggat ttatggagtg gtttcctttg gagagttctt ctactactac 60
tccatggacg tc 72

<210> SEQ ID NO 712
<211> LENGTH: 33
<212> TYPE: DNA
<213> ORGANISM: Homo sapiens

<400> SEQUENCE: 712
ggacgacagg cccttggaag tagagctgtt cag 33

<210> SEQ ID NO 713
<211> LENGTH: 21
<212> TYPE: DNA
<213> ORGANISM: Homo sapiens

<400> SEQUENCE: 713
aataatcaag accggccctc a 21

<210> SEQ ID NO 714
<211> LENGTH: 36
<212> TYPE: DNA
<213> ORGANISM: Homo sapiens

<400> SEQUENCE: 714
cacatgtggg atagtagaag tggcttcagt tggtct 36

<210> SEQ ID NO 715
<211> LENGTH: 18
<212> TYPE: DNA
<213> ORGANISM: Homo sapiens

<400> SEQUENCE: 715
aataattact actggact 18

<210> SEQ ID NO 716
<211> LENGTH: 48
<212> TYPE: DNA
<213> ORGANISM: Homo sapiens

<400> SEQUENCE: 716
tatatctctg acagagaatc agcgacttac aacccctccc tcaatagt 48

<210> SEQ ID NO 717
<211> LENGTH: 72
<212> TYPE: DNA
<213> ORGANISM: Homo sapiens

<400> SEQUENCE: 717
gcgcgccgag gacagaggat ttatggagtg gtttcctttg gagagttctt ctactactac 60
tccatggacg tc 72

<210> SEQ ID NO 718
<211> LENGTH: 33
<212> TYPE: DNA
<213> ORGANISM: Homo sapiens

<400> SEQUENCE: 718
ggacgacagg cccttggaag tagagctgtt cag 33

<210> SEQ ID NO 719
<211> LENGTH: 21
<212> TYPE: DNA
<213> ORGANISM: Homo sapiens

<400> SEQUENCE: 719
aataatcaag accggccctc a 21

<210> SEQ ID NO 720
<211> LENGTH: 36
<212> TYPE: DNA
<213> ORGANISM: Homo sapiens

<400> SEQUENCE: 720
cacatgtggg atagtagaag tggcttcagt tggtct 36

<210> SEQ ID NO 721
<211> LENGTH: 18
<212> TYPE: DNA
<213> ORGANISM: Homo sapiens

<400> SEQUENCE: 721
aataattact actggact 18

<210> SEQ ID NO 722
<211> LENGTH: 48
<212> TYPE: DNA
<213> ORGANISM: Homo sapiens

<400> SEQUENCE: 722
tatatctctg acagagaatc agcgacttac aacccctccc tcaatagt 48

<210> SEQ ID NO 723
<211> LENGTH: 72

<212> TYPE: DNA
<213> ORGANISM: Homo sapiens

<400> SEQUENCE: 723
gcgcgccgag gacagaggat ttatggagtg gtttcctttg gagagttctt ctactactac 60
tccatggacg tc 72

<210> SEQ ID NO 724
<211> LENGTH: 33
<212> TYPE: DNA
<213> ORGANISM: Homo sapiens

<400> SEQUENCE: 724
ggacgacagg cccttggaag tagagctgtt cag 33

<210> SEQ ID NO 725
<211> LENGTH: 21
<212> TYPE: DNA
<213> ORGANISM: Homo sapiens

<400> SEQUENCE: 725
aataatcaag accggccctc a 21

<210> SEQ ID NO 726
<211> LENGTH: 36
<212> TYPE: DNA
<213> ORGANISM: Homo sapiens

<400> SEQUENCE: 726
cacatgtggg atagtagaag tggcttcagt tggtct 36

<210> SEQ ID NO 727
<211> LENGTH: 18
<212> TYPE: DNA
<213> ORGANISM: Homo sapiens

<400> SEQUENCE: 727
aataattact actggact 18

<210> SEQ ID NO 728
<211> LENGTH: 48
<212> TYPE: DNA
<213> ORGANISM: Homo sapiens

<400> SEQUENCE: 728
tatatctctg acagagaatc agcgacttac aacccctccc tcaatagt 48

<210> SEQ ID NO 729
<211> LENGTH: 72
<212> TYPE: DNA
<213> ORGANISM: Homo sapiens

<400> SEQUENCE: 729
gcgcgccgag gacagaggat ttatggagtg gtttcctttg gagagttctt ctactactac 60
tccatggacg tc 72

<210> SEQ ID NO 730
<211> LENGTH: 33
<212> TYPE: DNA
<213> ORGANISM: Homo sapiens

<400> SEQUENCE: 730
ggacgacagg cccttggaag tagagctgtt cag 33

<210> SEQ ID NO 731
<211> LENGTH: 21
<212> TYPE: DNA
<213> ORGANISM: Homo sapiens

<400> SEQUENCE: 731
aataatcaag accggccctc a 21

<210> SEQ ID NO 732
<211> LENGTH: 36
<212> TYPE: DNA
<213> ORGANISM: Homo sapiens

<400> SEQUENCE: 732
cacatgtggg atagtagaag tggcttcagt tggtct 36

<210> SEQ ID NO 733
<211> LENGTH: 18
<212> TYPE: DNA
<213> ORGANISM: Homo sapiens

<400> SEQUENCE: 733
aataattact actggact 18

<210> SEQ ID NO 734
<211> LENGTH: 48
<212> TYPE: DNA
<213> ORGANISM: Homo sapiens

<400> SEQUENCE: 734
tatatctctg acagagaatc agcgacttac aacccctccc tcaatagt 48

<210> SEQ ID NO 735
<211> LENGTH: 72
<212> TYPE: DNA
<213> ORGANISM: Homo sapiens

<400> SEQUENCE: 735
gcgcgccgag gacagaggat ttatggagtg gtttcctttg gagagttctt ctactactac 60
tccatggacg tc 72

<210> SEQ ID NO 736
<211> LENGTH: 33
<212> TYPE: DNA
<213> ORGANISM: Homo sapiens

<400> SEQUENCE: 736
ggacgacagg cccttggaag tagagctgtt cag 33

<210> SEQ ID NO 737
<211> LENGTH: 21
<212> TYPE: DNA
<213> ORGANISM: Homo sapiens

<400> SEQUENCE: 737
aataatcaag accggccctc a 21

<210> SEQ ID NO 738
<211> LENGTH: 36
<212> TYPE: DNA
<213> ORGANISM: Homo sapiens

<400> SEQUENCE: 738
cacatgtggg atagtagaag tggcttcagt tggtct 36

<210> SEQ ID NO 739
<211> LENGTH: 18
<212> TYPE: DNA
<213> ORGANISM: Homo sapiens

<400> SEQUENCE: 739
aataattact actggact 18

<210> SEQ ID NO 740
<211> LENGTH: 48
<212> TYPE: DNA
<213> ORGANISM: Homo sapiens

<400> SEQUENCE: 740
tatatctctg acagagaatc agcgacttac aacccctccc tcaatagt 48

<210> SEQ ID NO 741
<211> LENGTH: 72
<212> TYPE: DNA
<213> ORGANISM: Homo sapiens

<400> SEQUENCE: 741
gcgcgccgag gacagaggat ttatggagtg gtttcctttg gagagttctt ctactactac 60
tccatggacg tc 72

<210> SEQ ID NO 742
<211> LENGTH: 33
<212> TYPE: DNA
<213> ORGANISM: Homo sapiens

<400> SEQUENCE: 742
ggacgacagg cccttggaag tagagctgtt cag 33

<210> SEQ ID NO 743
<211> LENGTH: 21
<212> TYPE: DNA
<213> ORGANISM: Homo sapiens

<400> SEQUENCE: 743
aataatcaag accggccctc a 21

<210> SEQ ID NO 744
<211> LENGTH: 36
<212> TYPE: DNA
<213> ORGANISM: Homo sapiens

<400> SEQUENCE: 744
cacatgtggg atagtagaag tggcttcagt tggtct 36

<210> SEQ ID NO 745
<211> LENGTH: 18
<212> TYPE: DNA
<213> ORGANISM: Homo sapiens

<400> SEQUENCE: 745
aataattact actggact 18

<210> SEQ ID NO 746

<211> LENGTH: 48
<212> TYPE: DNA
<213> ORGANISM: Homo sapiens

<400> SEQUENCE: 746
tatatctctg acagagaatc agcgacttac aacccctccc tcaatagt 48

<210> SEQ ID NO 747
<211> LENGTH: 72
<212> TYPE: DNA
<213> ORGANISM: Homo sapiens

<400> SEQUENCE: 747
gcgcgccgag gacagaggat ttatggagtg gtttcctttg gagagttctt ctactactac 60
tccatggacg tc 72

<210> SEQ ID NO 748
<211> LENGTH: 33
<212> TYPE: DNA
<213> ORGANISM: Homo sapiens

<400> SEQUENCE: 748
ggacgacagg cccttggaag tagagctgtt cag 33

<210> SEQ ID NO 749
<211> LENGTH: 21
<212> TYPE: DNA
<213> ORGANISM: Homo sapiens

<400> SEQUENCE: 749
aataatcaag accggccctc a 21

<210> SEQ ID NO 750
<211> LENGTH: 36
<212> TYPE: DNA
<213> ORGANISM: Homo sapiens

<400> SEQUENCE: 750
cacatgtggg atagtagaag tggcttcagt tggtct 36

<210> SEQ ID NO 751
<211> LENGTH: 18
<212> TYPE: DNA
<213> ORGANISM: Homo sapiens

<400> SEQUENCE: 751
aataattact actggact 18

<210> SEQ ID NO 752
<211> LENGTH: 48
<212> TYPE: DNA
<213> ORGANISM: Homo sapiens

<400> SEQUENCE: 752
tatatctctg acagagaatc agcgacttac aacccctccc tcaatagt 48

<210> SEQ ID NO 753
<211> LENGTH: 72
<212> TYPE: DNA

-continued

```
<213> ORGANISM: Homo sapiens

<400> SEQUENCE: 753

gcgcgccgag gacagaggat ttatggagtg gtttcctttg gagagttctt ctactactac     60

tccatggacg tc                                                          72
```

ANTI-HIV ANTIBODY 10-1074 VARIANTS

CROSS-REFERENCE TO RELATED APPLICATIONS

This application claims priority under 35 U.S.C. § 119(e) to U.S. Provisional Patent Application No. 62/731,356, filed Sep. 14, 2018. The foregoing application is incorporated by reference herein in its entirety.

STATEMENT REGARDING FEDERALLY SPONSORED RESEARCH

This invention was made with government support under Grant No. P01 AI081677 awarded the NIH. The government has certain rights in the invention.

FIELD OF THE INVENTION

This invention relates generally to broad and potent antibodies against Human Immunodeficiency Virus ("HIV") and more specifically to anti-HIV antibody 10-1074 variants and the use thereof.

BACKGROUND OF THE INVENTION

HIV causes acquired immunodeficiency syndrome (AIDS), a condition in humans characterized by clinical features including wasting syndromes, central nervous system degeneration and profound immunosuppression that results in life-threatening opportunistic infections and malignancies. Since its discovery in 1981, HIV type 1 (HIV-1) has led to the death of at least 25 million people worldwide. It is predicted that 20-60 million people will become infected over the next two decades even if there is a 2.5% annual decrease in HIV infections. There is a need for therapeutic agents and methods for treatment or inhibition of HIV infection.

Some HIV infected individuals show broadly neutralizing IgG antibodies in their serum. Yet, little is known regarding the specificity and activity of these antibodies, despite their potential importance in designing effective vaccines. In animal models, passive transfer of neutralizing antibodies can contribute to protection against virus challenge. Neutralizing antibody responses also can be developed in HIV-infected individuals, but the detailed composition of the serologic response is yet to be fully uncovered.

SUMMARY OF INVENTION

The present disclosure relates to a new category of broadly-neutralizing anti-HIV antibodies, having modified light chain variable regions and/or heavy chain variable regions leading to improved biophysical characteristics, as well as methods of production and methods of use thereof.

Accordingly, in a first aspect, the present disclosure provides an isolated anti-HIV antibody, or antigen-binding portion thereof, including a light chain variable region having a light chain amino acid sequence that is at least 75% identical to a polypeptide sequence selected from the group consisting of the light chain variable regions of SEQ ID NOs: 3-13, 22, 24-28, 35-39, 43-45, and 47. The isolated anti-HIV antibody, or antigen-binding portion thereof includes one or more light chain substitutions at one or more residues located within or outside the light chain variable region. The one or more residues are selected from the group consisting of LmdV:Y2, LmdV:R7, LmdV:P9, LmdV:E17, LmdV:H46, LmdV:P81.1, LmdV:I81.3, LmdV:N82, LmdV:R88, LmdV:D110, and LmdV:A142.

In another aspect, the present disclosure provides an isolated anti-HIV antibody, or antigen-binding portion thereof, including a heavy chain variable region having a heavy chain amino acid sequence that is at least 75% identical to a polypeptide sequence selected from the group consisting of the heavy chain variable regions of SEQ ID NOs: 61-94. The isolated anti-HIV antibody, or antigen-binding portion thereof includes one or more heavy chain substitutions at one or more residues located within or outside of the heavy chain variable region. The one or more residues are selected from the group consisting of HV:D29, HV:S47, HV:N75, HV:V79, HV:R82, HV:L89, HV:T108, and HV:K141.

In another aspect, the present disclosure provides an isolated anti-HIV antibody, or antigen-binding portion thereof, including a light chain variable region having a light chain amino acid sequence that is at least 75% identical to a polypeptide sequence selected from the group consisting of the light chain variable regions of SEQ ID NOs: 3-13, 22, 24-28, 35-39, 43-45, and 47. The isolated anti-HIV antibody, or antigen-binding portion thereof includes one or more light chain substitutions at one or more residues selected from the group consisting of LmdV:Y2, LmdV:R7, LmdV:P9, LmdV:E17, LmdV:H46, LmdV:P81.1, LmdV:I81.3, LmdV:N82, LmdV:R88, LmdV:D110, and LmdV:A142. The anti-HIV antibody, or antigen-binding portion thereof, further includes a heavy chain variable region having a heavy chain amino acid sequence is at least 75% identical to a polypeptide sequence selected from the group consisting of the heavy chain variable regions of SEQ ID NOs: 61-94. The isolated anti-HIV antibody, or antigen-binding portion thereof includes one or more heavy chain substitutions at one or more residues selected from the group consisting of HV:D29, HV:S47, HV:N75, HV:V79, HV:R82, HV:L89, HV:T108, and HV:K141.

In some embodiments, the isolated anti-HIV antibody, or antigen-binding portion thereof includes the one or more light chain substitutions selected from the group consisting of LmdV:Y2P, LmdV:R7P, LmdV:P9S, LmdV:E17Q, LmdV:H46Q, LmdV:P81.1N, LmdV:I81.3S, LmdV:N82G, LmdV:R88T, LmdV:D110E, and LmdV:A142G or conservative substitutions thereof (i.e., LmdV:P9C, LmdV:P9T, LmdV:E17N, LmdV:H46N, LmdV:P81.1Q, LmdV:R88C, LmdV:R88S).

In some embodiments, the isolated anti-HIV antibody, or antigen-binding portion thereof includes the one or more heavy chain substitutions selected from the group consisting of HV:D29G, HV:S47P, HV:N75Q, HV:V79T, HV:R82V, HV:L89F, HV:T108R, and HV:K141Q or conservative substitutions thereof (i.e., HV:L89W, HV:L89Y, HV:T108H, HV:T108K, HV:K141N).

In some embodiments, the isolated anti-HIV antibody, or antigen-binding portion thereof, includes the one or more light chain substitutions selected from the group consisting of LmdV:Y2P, LmdV:R7P, LmdV:P9S, LmdV:E17Q, LmdV:H46Q, LmdV:P81.1N, LmdV:I81.3S, LmdV:N82G, LmdV:R88T, LmdV:D110E, and LmdV:A142G or conservative substitutions thereof (i.e., LmdV:P9C, LmdV:P9T, LmdV:E17N, LmdV:H46N, LmdV:P81.1Q, LmdV:R88C, LmdV:R88S) and the one or more heavy chain substitutions selected from the group consisting of HV:D29G, HV:S47P, HV:N75Q, HV:V79T, HV:R82V, HV:L89F, HV:T108R, and HV:K141Q or conservative substitutions thereof (i.e., HV:L89W, HV:L89Y, HV:T108H, HV:T108K, HV:K141N).

In some embodiments, the light chain amino acid sequence is at least 75% identical to the light chain variable region of SEQ ID NO.: 3 and includes a LmdV:Y2P substitution or a conservative substitution of proline at LmdV:Y2.

In some embodiments, the heavy chain amino acid sequence is at least 75% identical to to the heavy chain variable region of SEQ ID NO.: 63 and includes an HV:V79T substitution or a conservative substitution of threonine at HV:V79.

In some embodiments, the heavy chain amino acid sequence is at least 75% identical to to the heavy chain variable region of SEQ ID NO.: 64 and includes an HV:R82V substitution or a conservative substitution of valine at HV:R82.

In some embodiments, the heavy chain amino acid sequence is at least 75% identical to to the heavy chain variable region of SEQ ID NO.: 65 and includes an HV:L89F substitution or a conservative substitution of phenylalanine of HV:L89.

In some embodiments, the heavy chain amino acid sequence is at least 75% identical to to the heavy chain variable region of SEQ ID NO.: 66 and includes an HV:T108R substitution or a conservative substitution of arginine at HV:T108.

In some embodiments, the light chain amino acid sequence is at least 75% identical to the light chain variable region of SEQ ID NO.: 22 and includes a LmdV:Y2P substitution or a conservative substitution of proline at LmdV:Y2, and the heavy chain amino acid sequence is at least 75% identical to the heavy chain variable region of SEQ ID NO.: 69 and includes an HV:R82V substitution or a conservative substitution of valine at HV:R82, and an HV:T108R substitution or a conservative substitution of arginine at HV:T108.

In some embodiments, the heavy chain amino acid sequence is at least 75% identical to the heavy chain variable region of SEQ ID NO.: 70 and includes an HV:V79T substitution or a conservative substitutions of threonine at HV:V79, an HV:L89F substitution or a conservative substitution of phenylalanine at HV:L89, and an HV:T108R substitution or a conservative substitution of arginine at HV:T108.

In some embodiments, the light chain amino acid sequence is at least 75% identical to the light chain variable region of SEQ ID NO.: 24 and comprises a LmdV:Y2P substitution or a conservative substitution of proline at LmdV:Y2, and the heavy chain amino acid sequence is at least 75% identical to the heavy chain variable region of SEQ ID NO.: 71 and includes an HV:V79T substitution or a conservative substitution of threonine at HV:V79, an HV:L89F substitution or a conservative substitution of phenylalanine at HV:L89, and an HV:T108R substitution or a conservative substitution of arginine at HV:T108.

In some embodiments, the isolated anti-HIV antibody, or antigen-binding portion thereof includes SEQ NO.: 3. In some embodiments, the isolated anti-HIV antibody, or antigen-binding portion thereof includes SEQ NO.: 63, 64, 65, 66, or 70. In some embodiments, the light chain variable region includes the light chain variable region of SEQ NO.: 22 and the heavy chain variable region includes the heavy chain variable region of SEQ No.: 69. In some embodiments, the light chain variable region includes the light chain variable region of SEQ NO.: 24 and the heavy chain variable region includes the heavy chain variable region of SEQ No.: 71.

In another aspect, the present disclosure also provides a pharmaceutical composition having the above-presented anti-HIV antibody or antigen-binding portion and a pharmaceutically acceptable carrier or excipient. In some embodiments, the pharmaceutical composition further includes a second therapeutic agent. In some embodiments, the second therapeutic agent is an anti-HIV-1 broadly neutralizing antibody, such as 3BNC117.

In another aspect, the present disclosure additionally provides a nucleic acid, or a codon-optimized nucleic acid, encoding the above-presented anti-HIV antibody or antigen-binding portion thereof. Also provided is a vector or vector system having at least one above-presented nucleic acid and a cell having at least one above-presented nucleic acid.

In another aspect, the present disclosure provides a method of making recombinant anti-HIV antibody, or antigen-binding portion thereof. The method includes, among others, obtaining the cultured cell mentioned above, culturing the cell in a medium under conditions permitting expression of a polypeptide encoded by the vector and assembling of an antibody or fragment thereof, and purifying the antibody or fragment from the cultured cell or the medium of the cell.

In another aspect, the present disclosure provides a method of preventing or treating an HIV infection or an HIV-related disease. The method includes, among others, identifying a patient in need of such prevention or treatment, and administering to said patient a first therapeutic agent having a therapeutically effective amount of at least one above presented anti-HIV antibody of or an antigen-binding portion thereof. The method can further include administering a second therapeutic agent. The second therapeutic agent can be administered before, concurrently with or after the administration of the anti-HIV antibody or antigen-binding portion thereof. In some embodiments, the second therapeutic agent is an anti-HIV-1 broadly neutralizing antibody, such as 3BNC117.

In another aspect, the present disclosure further provides a kit having a pharmaceutically acceptable dose unit of a pharmaceutically effective amount of at least one isolated anti-HIV antibody presented above or antigen-binding portion thereof. The kit can further include a pharmaceutically acceptable dose unit of a pharmaceutically effective amount of an anti-HIV agent. The two pharmaceutically acceptable dose units can optionally take the form of a single pharmaceutically acceptable dose unit. An exemplary anti-HIV agent can be selected from the group consisting of a non-nucleoside reverse transcriptase inhibitor, a protease inhibitor, an entry or fusion inhibitor, and an integrase inhibitor. In some embodiments, the anti-HIV agent is an anti-HIV broadly neutralizing antibody, such as 3BNC117.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

BRIEF DESCRIPTION OF THE DRAWINGS

FIG. 5A shows the study design of the Phase 1b clinical trial in which a combination of 3BNC117 and 10-1074, two potent monoclonal anti-HIV-1 broadly neutralizing antibodies that target independent sites on the HIV-1 envelope spike, was administered during ATI. Red and blue triangles represent 3BNC117 and 10-1074 infusions, respectively. FIG. 5B shows plasma HIV-1 RNA levels (black; left y-axis) and bNAb serum concentrations (3BNC117, red; 10-1074, blue; right y-axis) in the 9 bNAb-sensitive participants (left) and the 2 participants with pre-existing resistance against one of the antibodies (right). Red and blue triangles indicate 3BNC117 and 10-1074 infusions, respectively. Serum antibody concentrations were determined by TZM-bl assay. Grey shaded areas indicate time on ART. Lower limit of detection of HIV-1 RNA was 20 copies/ml. FIG. 5C shows Kaplan-Meier plots summarizing time to viral rebound for the participants with HIV-1 RNA<20 copies/ml 2 weeks before and at the start of ATI (n=11, left), for the participants sensitive to both antibodies (n=9, center), and for the participants that showed pre-existing resistance to one of the antibodies (n=2, right). Y-axis indicates percentage of participants that maintain viral suppression. X-axis indicates weeks after start of ATI. Participants receiving the combination of 3BNC117+10-1074 are indicated by the blue line. Dotted red lines indicate a cohort of individuals receiving 3BNC117 alone during ATI (n=13) and dotted black lines indicate a cohort of participants who underwent ATI without intervention (n=52).

FIGS. 6A, 6B, 6C, 6D, 6E, and 6F (collectively "FIG. 6") show demographics, $CD4^+$ T cells during study period in participants and pharamacokinetics of 3BNC117 and 10-1074. FIG. 6A is a table showing baseline participant demographics. *NNRTI—Non-nucleoside reverse transcriptase inhibitor. FIG. 6B shows absolute $CD4^+$ T cell counts and percentage of $CD4^+$ T cells among $CD3^+$ T cells at screening (n=15), day 0 (n=15), at the time of viral rebound (n=13) and at the end of the study are shown (n=15) (see also Supplementary Table 2). The last available time point after resuppression was used as end of the study time point for the participants that reinitiated ART. Red lines indicate mean, and error bars indicate standard deviation. P values were obtained using a two-tailed paired t-test comparing $CD4^+$ T cell counts between day 0 and the time of viral rebound. FIGS. 6C and 6D show 3BNC117 (red) and 10-1074 (blue) levels in serum (n=15) as determined by TZM-bl assay (FIG. 6C) and ELISA (FIG. 6D). Curves indicate mean serum antibody concentrations and error bars represent standard deviation. Red and blue triangles indicate 3BNC117 and 10-1074 infusions, respectively. In the TZM-bl assay, lower limits of detection were 0.46 μg/ml and 0.01 μg/ml for 3BNC117 and 10-1074, respectively (FIG. 6C). In the ELISA, lower limits of detection were 0.78 μg/ml and 0.41 μg/ml, respectively (FIG. 6D). In cases where participants only received 2 infusions due to early viral rebound (9245, 9249 and 9253), only antibody concentrations up to the second infusion were included. The half-life of each bNAb is indicated in days. FIGS. 6E and 6F show half-lives of both antibodies as measured by TZM-bl assay (FIG. 6E) and ELISA (FIG. 6F). Each dot represents a single participant. The half-lives of both antibodies from the 15 participants enrolled in the study are represented. Black lines indicate the mean value and standard deviation (n=15). P values were obtained using a two-tailed unpaired t-test comparing the two antibodies.

FIG. 7A is a set of charts showing Env contact sites of 10-1074 at the G(D/N) IR motif (positions 324-327, according to HXB2 numbering) and the glycan at the potential N-linked glycosylation site at position 332 (N×S/T motif at positions 332-334). The diagram shows the 7 bNAb-sensitive participants that rebounded before week 30 (left) and the 2 individuals with preexisting resistance to one of the 2 antibodies (right). LR indicates latent reservoir viruses isolated by $Q^2$VOA, and RB indicates rebound viruses isolated by SGA (plasma) or viral outgrowth (PBMCs). Each amino acid is represented by a color, and the frequency of each amino acid is indicated by the height of the rectangle. Shaded rectangles indicate the lack of variation between latent reservoir virus and rebound virus at the indicated position. Full-color rectangles represent amino acid residues with changes in distribution between reservoir and rebound viruses. FIGS. 7B and 7C are dot plots indicating IC80 (μg/ml) of 3BNC117 (FIG. 7B, left panel) and 10-1074 (FIG. 7C, right panel) against latent and rebound viruses determined by TZM-bl neutralization assay. $Q^2$VOA-derived latent viruses from week −2 and week 12 are shown as black and grey circles, respectively. For outgrowth culture-derived rebound viruses, the highest IC80 determined is shown as red circle. For 9246, 9252, 9245 and 9251 viruses could not be obtained from rebound outgrowth cultures and pseudoviruses were made from env sequences from $Q^2$VOA and plasma SGA.

FIG. 9A is a set of Venn diagrams showing sequence identity between env sequences obtained from $Q^2$VOA at week −2 (blue) and week 12 (grey), and plasma SGA or rebound PBMC outgrowth culture at the time of viral rebound (red). Area of overlap is proportional to the number of identical sequences. Number of sequences obtained is indicated. FIG. 9B shows infectious units per million (IUPM) $CD4^+$ T cells at weeks −2 and 12 as determined by $Q^2$VOA. Participants with IUPMs higher and lower than 0.1 are shown on the top and bottom, respectively. The 2 time points were not statistically different (P=0.078 (paired t-test)).

DETAILED DESCRIPTION OF THE INVENTION

Figure 1A:
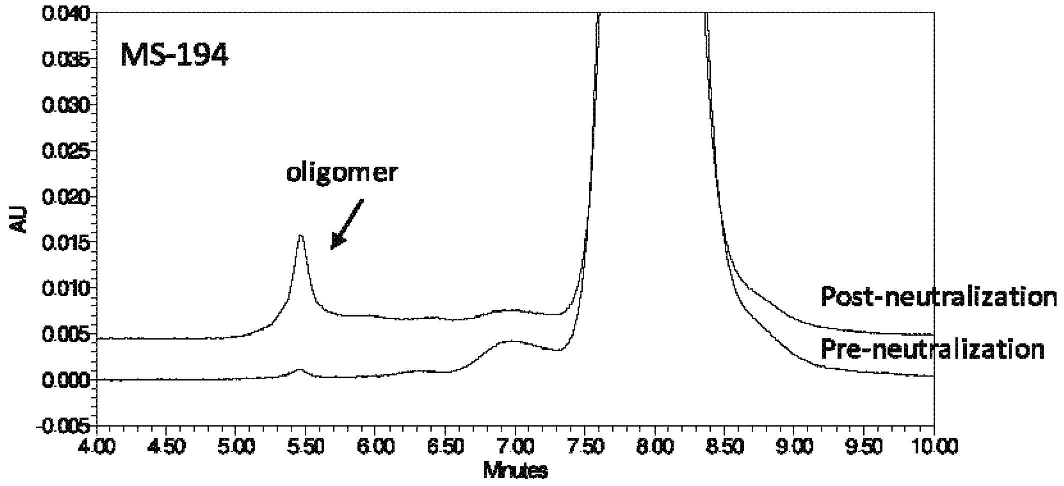
FIGS. 1A and 1B (collectively "FIG. 1") show the characterization of anti-HIV antibody 10-1074 variants MS-194 (FIG. 1A) and MS-203 (FIG. 1B) by high-performance size exclusion chromatography ("HP-SEC") before and after viral neutralization. Peaks in the HP-SEC profiles corresponding to the oligomeric species formed during viral inactivation are indicated by arrows.

This disclosure is based, at least in part, on an unexpected discovery of a new category of broadly neutralizing antibodies (bNAbs) against HIV that can recognize carbohydrate-dependent epitopes, including complex-type N-glycan, on gp120.

Antibodies are essential for the success of most vaccines, and antibodies against HIV appear to be the only correlate of protection in the recent RV144 anti-HIV vaccine trial. Some HIV-1 infected patients develop broadly neutralizing serologic activity against the gp160 viral spike 2-4 years after infection, but these antibodies do not generally protect infected humans because autologous viruses escape through mutation. Nevertheless, broadly neutralizing activity puts selective pressure on the virus and passive transfer of broadly neutralizing antibodies (bNAbs) to macaques protects against SHIV infection. It has therefore been proposed that vaccines that elicit such antibodies may be protective against HIV infection in humans.

The development of single cell antibody cloning techniques revealed that bNAbs target several different epitopes on the HIV-1 gp160 spike. The most potent HIV-1 bNAbs recognize the CD4 binding site (CD4bs) (Science 333 (6049):1633-1637; Nature 477(7365):466-470; Science 334 (6060):1289-1293) and carbohydrate-dependent epitopes associated with the variable loops (Nature 477(7365):466-470; Science 326(5950):285-289; Science 334(6059):1097-1103; Nature 480(7377):336-343), including the V1/V2 (PG9/PG16) (Science 326(5950):285-289) and V3 loops (PGTs) (Nature 477(7365):466-470). Less is known about carbohydrate-dependent epitopes because the antibodies studied to date are either unique examples or members of small clonal families.

To better understand the neutralizing antibody response to HIV-1 and the epitope targeted by PGT antibodies, members of a large clonal family dominating the gp160-specific IgG memory response from the clade A-infected patient who produced PGT121 have been isolated. The isolation of PGT121 is described in greater details in PCT/US13/65696. PGT121 antibodies can be divided into two groups, a PGT121-like and a 10-1074-like group, according to sequence, binding affinity, neutralizing activity and recognition of carbohydrates and the V3 loop. 10-1074 and related family members exhibit unusual potent neutralization, including broad reactivity against newly-transmitted viruses. Unlike previously-characterized carbohydrate-dependent bNAbs, PGT121 binds to complex-type, rather than high-mannose, N-glycans in glycan microarray experiments. The 10-1074 group exhibits remarkable potency and breadth despite not binding detectably to protein-free glycans. Crystal structures of un-liganded PGT121, 10-1074, and their germline precursor reveal that differential carbohydrate recognition maps to a cleft between CDRH2 and CDRH3, which was occupied by a complex-type N-glycan in a separate PGT121 structure. Swapping glycan contact residues between PGT121 and 10-1074 confirmed the importance of these residues in neutralizing activities.

Because the biophysical stability of monoclonal antibodies is an important determinant of their usefulness and commercial value, this disclosure presents the processes to optimize biophysical characteristics of the 10-1074 broadly neutralizing antibody. For example, a series of substitutions were carried out to identify potentially destabilizing residues in the Fv region of the 10-1074 broadly neutralizing antibody. These residues may, by themselves or in combination, lead to instability at low pH, increase susceptibility to chemical degradation, or lead to aggregation during production or long-term storage. Based on this analysis, a series of variants are designed for maintaining potency while optimizing desired characteristics using combinatorial residue replacement techniques. The optimization process is divided into different stages with the first being identification of single residues in the framework region which are potentially responsible for destabilization. Specifically, anti-HIV 10-1074 antibody variants (shown in Tables 2-7 and 9) were produced by transient expression, each containing a single residue modification of the identified amino acids. The variants were characterized for retention of neutralization activity and for desired biophysical characteristics as shown in Tables 8-16. Five distinct amino acid residues, LmdV:Y2, HV:V79, HV:R82, HV:L89, and HV:T108, were identified that showed an increase in desirable biophysical characteristics and did not impact neutralization. The residues were used to produce a library of variants (shown in Tables 2-7 and 12) encompassing all possible combinations of the five amino acids. The variants were again produced by transient expression, and the purified combinatorial variants were analyzed for retention of neutralization activity and desired biophysical characteristics. From the combinatorial library three variants, MS-200, MS-201, and MS-202 were identified for more in-depth analysis including expression, purification, and storage stability to identify combinatorial variants with optimized characteristics which included increased thermal stability, increased resistance to chemical unfolding, increased solubility, and increased resistance to aggregation during storage.

Isolated Anti-HIV Antibodies, Pharmaceutical Compositions, and Kits

Accordingly, in one aspect, this disclosure provides an isolated anti-HIV antibody, or antigen-binding portion thereof, including a light chain variable region having a light chain amino acid sequence that is at least 75% (i.e., 80%, 85%, 90%, 95%, 97%, 98%, 99%) identical to a polypeptide sequence selected from the group consisting of the light chain variable regions of SEQ ID NOs: 3-13, 22, 24-28, 35-39, 43-45, and 47 (Table 2). The isolated anti-HIV antibody, or antigen-binding portion thereof may include one or more light chain substitutions at one or more residues located within or outside the light chain variable region. The residues for substitution are can be one or more of LmdV: Y2, LmdV:R7, LmdV:P9, LmdV:E17, LmdV:H46, LmdV: P81.1, LmdV:I81.3, LmdV:N82, LmdV:R88, LmdV:D110, and LmdV:A142.

Also provided is an isolated anti-HIV antibody, or antigen-binding portion thereof, including a heavy chain variable region having a heavy chain amino acid sequence that is at least 75% (i.e., 80%, 85%, 90%, 95%, 97%, 98%, 99%) identical to a polypeptide sequence selected from the group consisting of the heavy chain variable regions of SEQ ID NOs: 61-94 (Table 3). The isolated anti-HIV antibody, or antigen-binding portion thereof includes one or more heavy chain substitutions at one or more residues located within or outside of the heavy chain variable region. The residues for substitution can be one or more of HV:D29, HV:S47, HV:N75, HV:V79, HV:R82, HV:L89, HV:T108, and HV:K141.

In another aspect, the present disclosure provides an isolated anti-HIV antibody, or antigen-binding portion thereof, including a light chain variable region having a light chain amino acid sequence that is at least 75% (i.e., 80%, 85%, 90%, 95%, 97%, 98%, 99%) identical to a polypeptide sequence selected from the group consisting of the light chain variable regions of SEQ ID NOs: 3-13, 22, 24-28, 35-39, 43-45, and 47 (Table 2). The isolated anti-HIV antibody, or antigen-binding portion thereof includes one or more light chain substitutions at one or more residues of LmdV:Y2, LmdV:R7, LmdV:P9, LmdV:E17, LmdV:H46, LmdV:P81.1, LmdV:I81.3, LmdV:N82, LmdV:R88, LmdV:D110, and LmdV:A142. The anti-HIV antibody, or antigen-binding portion thereof, further includes a heavy chain variable region having a heavy chain amino acid sequence is at least 75% (i.e., 80%, 85%, 90%, 95%, 97%, 98%, 99%) identical to a polypeptide sequence selected from the group consisting of the heavy chain variable regions of SEQ ID NOs: 61-94 (Table 3). The isolated anti-HIV antibody, or antigen-binding portion thereof includes one or more heavy chain substitutions at one or more residues of HV:D29, HV:S47, HV:N75, HV:V79, HV:R82, HV:L89, HV:T108, and HV:K141.

In some embodiments, the isolated anti-HIV antibody, or antigen-binding portion thereof includes the one or more light chain substitutions of LmdV:Y2P, LmdV:R7P, LmdV:P9S, LmdV:E17Q, LmdV:H46Q, LmdV:P81.1N, LmdV:I81.3S, LmdV:N82G, LmdV:R88T, LmdV:D110E, and LmdV:A142G or conservative substitutions thereof (i.e., LmdV:P9C, LmdV:P9T, LmdV:E17N, LmdV:H46N, LmdV:P81.1Q, LmdV:R88C, LmdV:R88S).

In some embodiments, the isolated anti-HIV antibody, or antigen-binding portion thereof includes the one or more heavy chain substitutions of HV:D29G, HV:S47P, HV:N75Q, HV:V79T, HV:R82V, HV:L89F, HV:T108R, and HV:K141Q or conservative substitutions thereof (i.e., HV:L89W, HV:L89Y, HV:T108H, HV:T108K, HV:K141N).

In some embodiments, the isolated anti-HIV antibody, or antigen-binding portion thereof, includes the one or more light chain substitutions of LmdV:Y2P, LmdV:R7P, LmdV:P9S, LmdV:E17Q, LmdV:H46Q, LmdV:P81.1N, LmdV:I81.3S, LmdV:N82G, LmdV:R88T, LmdV:D110E, and LmdV:A142G or conservative substitutions thereof (i.e., LmdV:P9C, LmdV:P9T, LmdV:E17N, LmdV:H46N, LmdV:P81.1Q, LmdV:R88C, LmdV:R88S) and the one or more heavy chain substitutions of HV:D29G, HV:S47P, HV:N75Q, HV:V79T, HV:R82V, HV:L89F, HV:T108R, and HV:K141Q or conservative substitutions thereof (i.e., HV:L89W, HV:L89Y, HV:T108H, HV:T108K, HV:K141N).

In some embodiments, the light chain amino acid sequence is at least 75% (i.e., 80%, 85%, 90%, 95%, 97%, 98%, 99%) identical to the light chain variable region of SEQ ID NO.: 3 and includes a LmdV:Y2P substitution or a conservative substitution of proline at LmdV:Y2.

In some embodiments, the heavy chain amino acid sequence is at least 75% (i.e., 80%, 85%, 90%, 95%, 97%, 98%, 99%) identical to the heavy chain variable region of SEQ ID NO.: 63 and includes an HV:V79T substitution or a conservative substitution of threonine at HV:V79.

In some embodiments, the heavy chain amino acid sequence is at least 75% (i.e., 80%, 85%, 90%, 95%, 97%, 98%, 99%) identical to the heavy chain variable region of SEQ ID NO.: 64 and includes an HV:R82V substitution or a conservative substitution of valine at HV:R82.

In some embodiments, the heavy chain amino acid sequence is at least 75% (i.e., 80%, 85%, 90%, 95%, 97%, 98%, 99%) identical to the heavy chain variable region of SEQ ID NO.: 65 and includes an HV:L89F substitution or a conservative substitution of phenylalanine of HV:L89.

In some embodiments, the heavy chain amino acid sequence is at least 75% (i.e., 80%, 85%, 90%, 95%, 97%, 98%, 99%) identical to the heavy chain variable region of SEQ ID NO.: 66 and includes an HV:T108R substitution or a conservative substitution of arginine at HV:T108.

In some embodiments, the light chain amino acid sequence is at least 75% (i.e., 80%, 85%, 90%, 95%, 97%, 98%, 99%) identical to the light chain variable region of SEQ ID NO.: 22 and includes a LmdV:Y2P substitution or a conservative substitution of proline at LmdV:Y2, and the heavy chain amino acid sequence is at least 75% (i.e., 80%, 85%, 90%, 95%, 97%, 98%, 99%) identical to the heavy chain variable region of SEQ ID NO.: 69 and includes an HV:R82V substitution or a conservative substitution of valine at HV:R82, and an HV:T108R substitution or a conservative substitution of arginine at HV:T108.

In some embodiments, the heavy chain amino acid sequence is at least 75% (i.e., 80%, 85%, 90%, 95%, 97%, 98%, 99%) identical to the heavy chain variable region of SEQ ID NO.: 70 and includes an HV:V79T substitution or a conservative substitutions of threonine at HV:V79, an HV:L89F substitution or a conservative substitution of phenylalanine at HV:L89, and an HV:T108R substitution or a conservative substitution of arginine at HV:T108.

In some embodiments, the light chain amino acid sequence is at least 75% (i.e., 80%, 85%, 90%, 95%, 97%, 98%, 99%) identical to the light chain variable region of SEQ ID NO.: 24 and comprises a LmdV:Y2P substitution or a conservative substitution of proline at LmdV:Y2, and the heavy chain amino acid sequence is at least 75% (i.e., 80%, 85%, 90%, 95%, 97%, 98%, 99%) identical to the heavy chain variable region of SEQ ID NO.: 71 and includes an HV:V79T substitution or a conservative substitution of threonine at HV:V79, an HV:L89F substitution or a conservative substitution of phenylalanine at HV:L89, and an HV:T108R substitution or a conservative substitution of arginine at HV:T108.

In some embodiments, the isolated anti-HIV antibody, or antigen-binding portion thereof includes SEQ NO.: 3. In some embodiments, the isolated anti-HIV antibody, or antigen-binding portion thereof includes SEQ NO.: 63, 64, 65, 66, or 70. In some embodiments, the light chain variable region includes the light chain variable region of SEQ NO.: 22 and the heavy chain variable region includes the heavy chain variable region of SEQ No.: 69. In some embodiments, the light chain variable region includes the light chain variable region of SEQ NO.: 24 and the heavy chain variable region includes the heavy chain variable region of SEQ No.: 71.

Variable domain residue positions are numbered according to the AHo (Honegger, A., & Plückthun, A. (2001). Journal of Molecular Biology, 309(3), 657-70.) structure-based numbering system. An exemplary residue numbering of variable domains of MS-194 is shown in Table 1. The abbreviations used in Table 1 are described as follows. "Ldr" refers leader sequence (e.g., AKA signal sequence or signal peptide). "Mat. Linear" refers to the linear number of the mature form of protein chains. "LmdV" refers variable regions in light chains which are of the lambda type.

The term "antibody" (Ab) as used herein includes monoclonal antibodies, polyclonal antibodies, multispecific antibodies (for example, bispecific antibodies and polyreactive antibodies), and antibody fragments. Thus, the term "antibody" as used in any context within this specification is meant to include, but not be limited to, any specific binding member, immunoglobulin class and/or isotype (e.g., IgG1, IgG2, IgG3, IgG4, IgM, IgA, IgD, IgE and IgM); and biologically relevant fragment or specific binding member thereof, including but not limited to Fab, F(ab')2, Fv, and scFv (single chain or related entity). It is understood in the art that an antibody is a glycoprotein having at least two heavy (H) chains and two light (L) chains inter-connected by disulfide bonds, or an antigen-binding portion thereof. A heavy chain is comprised of a heavy chain variable region (VH) and a heavy chain constant region (CH1, CH2, and CH3). A light chain is comprised of a light chain variable region (VL) and a light chain constant region (CL). The variable regions of both the heavy and light chains comprise framework regions (FWR) and complementarity determining regions (CDR). The four FWR regions are relatively conserved while CDR regions (CDR1, CDR2, and CDR3) represent hypervariable regions and are arranged from NH2 terminus to the COOH terminus as follows: FWR1, CDR1, FWR2, CDR2, FWR3, CDR3, and FWR4. The variable regions of the heavy and light chains contain a binding domain that interacts with an antigen while, depending on the isotype, the constant region(s) may mediate the binding of the immunoglobulin to host tissues or factors.

Also included in the definition of "antibody" as used herein are chimeric antibodies, humanized antibodies, and recombinant antibodies, human antibodies generated from a transgenic non-human animal, as well as antibodies selected from libraries using enrichment technologies available to the artisan.

The term "variable" refers to the fact that certain segments of the variable (V) domains differ extensively in sequence among antibodies. The V domain mediates antigen-binding and defines specificity of a particular antibody for its particular antigen. However, the variability is not evenly distributed across the amino acid span of the variable regions. Instead, the V regions consist of relatively invariant stretches called framework regions (FRs) of 15-30 amino acids separated by shorter regions of extreme variability called "hypervariable regions" that may be 9-12 amino acids long. The variable regions of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see, for example, Kabat et al., Sequences of Proteins of Immunological Interest, 5th Ed. Public Health Service, National Institutes of Health, Bethesda, Md. (1991)).

The term "hypervariable region" as used herein refers to the amino acid residues of an antibody that are responsible for antigen binding. The hypervariable region generally comprises amino acid residues from a "complementarity determining region" ("CDR").

The term "monoclonal antibody" as used herein refers to an antibody obtained from a population of substantially homogeneous antibodies, i.e., the individual antibodies comprising the population are identical except for possible naturally occurring mutations that may be present in minor amounts. The term "polyclonal antibody" refers to preparations that include different antibodies directed against different determinants ("epitopes").

The monoclonal antibodies herein include "chimeric" antibodies in which a portion of the heavy and/or light chain is identical with, or homologous to, corresponding sequences in antibodies derived from a particular species or belonging to a particular antibody class or subclass, while the remainder of the chain(s) is identical with, or homologous to, corresponding sequences in antibodies derived from another species or belonging to another antibody class or subclass, as well as fragments of such antibodies, so long as they exhibit the desired biological activity (see, for example, U.S. Pat. No. 4,816,567; and Morrison et al., Proc. Natl. Acad. Sci. USA, 81:6851-6855 (1984)). The described invention provides variable region antigen-binding sequences derived from human antibodies. Accordingly, chimeric antibodies of primary interest herein include antibodies having one or more human antigen-binding sequences (for example, CDRs) and containing one or more sequences derived from a non-human antibody, for example, an FR or C region sequence. In addition, chimeric antibodies included herein are those comprising a human variable region antigen-binding sequence of one antibody class or subclass and another sequence, for example, FR or C region sequence, derived from another antibody class or subclass.

A "humanized antibody" generally is considered to be a human antibody that has one or more amino acid residues introduced into it from a source that is non-human. These non-human amino acid residues often are referred to as "import" residues, which typically are taken from an "import" variable region. Humanization may be performed following the method of Winter and co-workers (see, for example, Jones et al., Nature, 321:522-525 (1986); Reichmann et al., Nature, 332:323-327 (1988); Verhoeyen et al., Science, 239:1534-1536 (1988)), by substituting import hypervariable region sequences for the corresponding sequences of a human antibody. Accordingly, such "humanized" antibodies are chimeric antibodies (see, for example, U.S. Pat. No. 4,816,567), where substantially less than an intact human variable region has been substituted by the corresponding sequence from a non-human species.

An "antibody fragment" comprises a portion of an intact antibody, such as the antigen-binding or variable region of the intact antibody. Examples of antibody fragments include, but are not limited to, Fab, Fab', F(ab')2, and Fv fragments; diabodies; linear antibodies (see, for example, U.S. Pat. No. 5,641,870; Zapata et al., Protein Eng. 8(10): 1057-1062 [1995]); single-chain antibody molecules; and multispecific antibodies formed from antibody fragments.

"Fv" is the minimum antibody fragment that contains a complete antigen-recognition and antigen-binding site. This fragment contains a dimer of one heavy- and one light-chain variable region domain in tight, non-covalent association. From the folding of these two domains emanate six hypervariable regions (three loops each from the H and L chain) that contribute the amino acid residues for antigen-binding and confer antigen-binding specificity to the antibody. However, even a single variable region (or half of an Fv comprising only three CDRs specific for an antigen) has the ability to recognize and bind antigen, although at a lower affinity than the entire binding site.

"Single-chain Fv" ("sFv" or "scFv") are antibody fragments that comprise the VH and VL antibody domains connected into a single polypeptide chain. The sFv polypeptide can further comprise a polypeptide linker between the VH and VL domains that enables the sFv to form the desired structure for antigen binding. For a review of sFv, see, for example, Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments with short linkers (about 5-10 residues) between the VH and VL domains such that inter-chain but not the intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

Domain antibodies (dAbs), which can be produced in fully human form, are the smallest known antigen-binding fragments of antibodies, ranging from about 11 kDa to about 15 kDa. DAbs are the robust variable regions of the heavy and light chains of immunoglobulins (VH and VL, respectively). They are highly expressed in microbial cell culture, show favorable biophysical properties including, for example, but not limited to, solubility and temperature stability, and are well suited to selection and affinity maturation by in vitro selection systems such as, for example, phage display. DAbs are bioactive as monomers and, owing to their small size and inherent stability, can be formatted into larger molecules to create drugs with prolonged serum half-lives or other pharmacological activities. Examples of this technology have been described in, for example, WO9425591 for antibodies derived from Camelidae heavy chain Ig, as well in US20030130496 describing the isolation of single domain fully human antibodies from phage libraries.

Fv and sFv are the only species with intact combining sites that are devoid of constant regions. Thus, they are suitable for reduced nonspecific binding during in vivo use. sFv fusion proteins can be constructed to yield fusion of an effector protein at either the amino or the carboxy terminus of an sFv. See, for example, Antibody Engineering, ed. Borrebaeck, supra. The antibody fragment also can be a "linear antibody," for example, as described in U.S. Pat. No. 5,641,870 for example. Such linear antibody fragments can be monospecific or bispecific.

In certain embodiments, antibodies of the described invention are bispecific or multispecific. Bispecific antibodies are antibodies that have binding specificities for at least two different epitopes. Exemplary bispecific antibodies can bind to two different epitopes of a single antigen. Other such antibodies can combine a first antigen-binding site with a binding site for a second antigen. Alternatively, an anti-HIV arm can be combined with an arm that binds to a triggering molecule on a leukocyte, such as a T-cell receptor molecule (for example, CD3), or Fc receptors for IgG (Fc gamma R), such as Fc gamma RI (CD64), Fc gamma RII (CD32) and Fc gamma RIII (CD16), so as to focus and localize cellular defense mechanisms to the infected cell. Bispecific antibodies also can be used to localize cytotoxic agents to infected cells. Bispecific antibodies can be prepared as full-length antibodies or antibody fragments (for example, F(ab')2 bispecific antibodies). For example, WO 96/16673 describes a bispecific anti-ErbB2/anti-Fc gamma RIII antibody and U.S. Pat. No. 5,837,234 discloses a bispecific anti-ErbB2/anti-Fc gamma RI antibody. For example, a bispecific anti-ErbB2/Fc alpha antibody is reported in WO98/02463; U.S. Pat. No. 5,821,337 teaches a bispecific anti-ErbB2/anti-CD3 antibody. See also, for example, Mouquet et al., Polyreactivity Increases The Apparent Affinity Of Anti-HIV Antibodies By Heteroligation. Nature. 467, 591-5 (2010), and Mouquet et al., Enhanced HIV-1 neutralization by antibody heteroligation" Proc Natl Acad Sci USA. 2012 Jan. 17; 109(3):875-80.

Methods for making bispecific antibodies are known in the art. Traditional production of full-length bispecific antibodies is based on the co-expression of two immunoglobulin heavy chain-light chain pairs, where the two chains have different specificities (see, for example, Millstein et al., Nature, 305:537-539 (1983)). Similar procedures are disclosed in, for example, WO 93/08829, Traunecker et al., EMBO J., 10:3655-3659 (1991) and see also Mouquet et al., Enhanced HIV-1 neutralization by antibody heteroligation" Proc Natl Acad Sci USA. 2012 Jan. 17; 109(3):875-80.

Alternatively, antibody variable regions with the desired binding specificities (antibody-antigen combining sites) are fused to immunoglobulin constant domain sequences. The fusion is with an Ig heavy chain constant domain, comprising at least part of the hinge, CH2, and CH3 regions. According to some embodiments, the first heavy-chain constant region (CH1) containing the site necessary for light chain bonding, is present in at least one of the fusions. DNAs encoding the immunoglobulin heavy chain fusions and, if desired, the immunoglobulin light chain, are inserted into separate expression vectors and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

Techniques for generating bispecific antibodies from antibody fragments also have been described in the literature. For example, bispecific antibodies can be prepared using chemical linkage. For example, Brennan et al., Science, 229:81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated then are converted to thionitrobenzoate (TNB) derivatives. One of the Fab'-TNB derivatives then is reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Other modifications of the antibody are contemplated herein. For example, the antibody can be linked to one of a variety of nonproteinaceous polymers, for example, polyethylene glycol, polypropylene glycol, polyoxyalkylenes, or copolymers of polyethylene glycol and polypropylene glycol. The antibody also can be entrapped in microcapsules prepared, for example, by coacervation techniques or by interfacial polymerization (for example, hydroxymethyl cellulose or gelatin-microcapsules and poly-(methylmethacrylate) microcapsules, respectively), in colloidal drug delivery systems (for example, liposomes, albumin microspheres, microemulsions, nanoparticles and nanocapsules), or in macroemulsions. Such techniques are disclosed in, for example, Remington's Pharmaceutical Sciences, 16th edition, Oslo, A., Ed., (1980).

Typically, the antibodies of the described invention are produced recombinantly, using vectors and methods available in the art. Human antibodies also can be generated by in vitro activated B cells (see, for example, U.S. Pat. Nos. 5,567,610 and 5,229,275). General methods in molecular genetics and genetic engineering useful in the present disclosure are described in the current editions of Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, CA), "Guide to Protein Purification" in Methods in Enzymology (M. P. Deutscher, ed., (1990) Academic Press, Inc.); PCR Protocols: A Guide to Methods and Applications (Innis et al. 1990. Academic Press, San Diego, CA), Culture of Animal Cells: A Manual of Basic Technique, 2nd Ed. (R. I. Freshney. 1987. Liss, Inc. New York, NY), and Gene Transfer and Expression Protocols, pp. 109-128, ed. E. J. Murray, The Humana Press Inc., Clifton, N.J.). Reagents, cloning vectors, and kits for genetic manipulation are available from commercial vendors such as BioRad, Stratagene, Invitrogen, ClonTech and Sigma-Aldrich Co.

Human antibodies also can be produced in transgenic animals (for example, mice) that are capable of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice results in the production of human antibodies upon antigen challenge. See, for example, Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; and WO 97/17852. Such animals can be genetically engineered to produce human antibodies comprising a polypeptide of the described invention.

Various techniques have been developed for the production of antibody fragments. Traditionally, these fragments were derived via proteolytic digestion of intact antibodies (see, for example, Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Fab'-SH fragments can be directly recovered from *E. coli* and chemically coupled to form F(ab')2 fragments (see, for example, Carter et al., Bio/Technology 10:163-167 (1992)). According to another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046. Other techniques for the production of antibody fragments will be apparent to the skilled practitioner.

Other techniques that are known in the art for the selection of antibody fragments from libraries using enrichment technologies, including but not limited to phage display, ribosome display (Hanes and Pluckthun, 1997, *Proc. Nat. Acad. Sci.* 94: 4937-4942), bacterial display (Georgiou, et al., 1997, *Nature Biotechnology* 15: 29-34) and/or yeast display (Kieke, et al., 1997, *Protein Engineering* 10: 1303-1310) may be utilized as alternatives to previously discussed technologies to select single chain antibodies. Single-chain antibodies are selected from a library of single chain antibodies produced directly utilizing filamentous phage technology. Phage display technology is known in the art (e.g., see technology from Cambridge Antibody Technology (CAT)) as disclosed in U.S. Pat. Nos. 5,565,332; 5,733,743; 5,871,907; 5,872,215; 5,885,793; 5,962,255; 6,140,471; 6,225,447; 6,291650; 6,492,160; 6,521,404; 6,544,731; 6,555,313; 6,582,915; 6,593,081, as well as other U.S. family members, or applications which rely on priority filing GB 9206318, filed 24 May 1992; see also Vaughn, et al. 1996, *Nature Biotechnology* 14: 309-314). Single chain antibodies may also be designed and constructed using available recombinant DNA technology, such as a DNA amplification method (e.g., PCR), or possibly by using a respective hybridoma cDNA as a template.

Variant antibodies also are included within the scope of the invention. Thus, variants of the sequences recited in the application also are included within the scope of the invention. Further variants of the antibody sequences having improved affinity can be obtained using methods known in the art and are included within the scope of the invention. For example, amino acid substitutions can be used to obtain antibodies with further improved affinity. Alternatively, codon optimization of the nucleotide sequence can be used to improve the efficiency of translation in expression systems for the production of the antibody.

Such variant antibody sequences will share 70% or more (i.e., 75%, 80%, 85%, 90%, 95%, 97%, 98%, 99% or greater) sequence identity with the sequences disclosed in the application. Such sequence identity is calculated with regard to the full length of the reference sequence (i.e., the sequence recited in the application). Percentage identity, as referred to herein, is as determined using BLAST version 2.1.3 using the default parameters specified by the NCBI (the National Center for Biotechnology Information) [Blosum 62 matrix; gap open penalty=11 and gap extension penalty=1]. For example, peptide sequences provided by this disclosure include at least about 5, 10, 15, 20, 30, 40, 50, 75, 100, 150, or more contiguous peptides of one or more of the sequences disclosed herein as well as all intermediate lengths therebetween. As used herein, the term "intermediate lengths" is meant to describe any length between the quoted values, such as 7, 8, 9, 10, 11, 12, 13, 14, 15, 16, 17, 18, 19, etc.; 21, 22, 23, etc.; 30, 31, 32, etc.; 50, 51, 52, 53, etc.; 100, 101, 102, 103, etc.; 150, 151, 152, 153, etc.

The present disclosure provides for antibodies, either alone or in combination with other antibodies, such as, but not limited to, VRC01, anti-V3 loop, CD4bs, and CD4i antibodies as well as PG9/PG16-like antibodies, that have broad neutralizing activity in serum.

According to another embodiment, the present disclosure provides methods for the preparation and administration of an HIV antibody composition that is suitable for administration to a human or non-human primate patient having HIV infection, or at risk of HIV infection, in an amount and according to a schedule sufficient to induce a protective immune response against HIV, or reduction of the HIV virus, in a human.

According to another embodiment, the present disclosure provides a vaccine comprising at least one antibody of the disclosure and a pharmaceutically acceptable carrier. According to one embodiment, the vaccine is a vaccine comprising at least one antibody described herein and a pharmaceutically acceptable carrier. The vaccine can include a plurality of the antibodies having the characteristics described herein in any combination and can further include antibodies neutralizing to HIV as are known in the art.

It is to be understood that compositions can be a single or a combination of antibodies disclosed herein, which can be the same or different, in order to prophylactically or therapeutically treat the progression of various subtypes of HIV infection after vaccination. Such combinations can be selected according to the desired immunity. When an antibody is administered to an animal or a human, it can be combined with one or more pharmaceutically acceptable carriers, excipients or adjuvants as are known to one of ordinary skilled in the art. The composition can further include broadly neutralizing antibodies known in the art, including but not limited to, VRC01, b12, anti-V3 loop, CD4bs, and CD4i antibodies as well as PG9/PG16-like antibodies.

Further, with respect to determining the effective level in a patient for treatment of HIV, in particular, suitable animal models are available and have been widely implemented for evaluating the in vivo efficacy against HIV of various gene therapy protocols (Sarver et al. (1993b), supra). These models include mice, monkeys, and cats. Even though these animals are not naturally susceptible to HIV disease, chimeric mice models (for example, SCID, bg/nu/xid, NOD/SCID, SCID-hu, immunocompetent SCID-hu, bone marrow-ablated BALB/c) reconstituted with human peripheral blood mononuclear cells (PBMCs), lymph nodes, fetal liver/thymus or other tissues can be infected with lentiviral vector or HIV, and employed as models for HIV pathogenesis. Similarly, the simian immune deficiency virus (SIV)/monkey model can be employed, as can the feline immune deficiency virus (FIV)/cat model. The pharmaceutical composition can contain other pharmaceuticals, in conjunction with a vector according to the invention, when used to therapeutically treat AIDS. These other pharmaceuticals can be used in their traditional fashion (i.e., as agents to treat HIV infection).

According to another embodiment, the present disclosure provides an antibody-based pharmaceutical composition comprising an effective amount of an isolated HIV antibody, or an affinity matured version, which provides a prophylactic or therapeutic treatment choice to reduce infection of the HIV virus. The pharmaceutical composition may further include a second therapeutic agent. In some embodiments, the second therapeutic agent can be an anti-HIV-1 broadly neutralizing antibody. The anti-HIV-1 broadly neutralizing antibody can be one of 10-259, 10-303, 10-410, 10-847, 10-996, 10-1121, 10-1130, 10-1146, 10-1341, 10-1369, 10-1074GM, GL, 10E8, 12A12, 12A21, 2F5, 2G12, 35022, 3BC176, 3BNC117, 3BNC55, 3BNC60, 3BNC62, 447-52D, 4E10, 5H/11-BMV-D5, 8ANC195, b12, CAP256-VRC26.01, CAP256-VRC26.02, CAP256-VRC26.03, CAP256-VRC26.04, CAP256-VRC26.05, CAP256-VRC26.06, CAP256-VRC26.07, CAP256-VRC26.08, CAP256-VRC26.09, CAP256-VRC26.10, CAP256-VRC26.11, CAP256-VRC26.12, CH01, CH02, CH03, CH04, CH103, HGN194, HJ16, HK20, M66.6, NIH45-46, PCDN-33A, PCDN-33B, PCDN-38A, PG9, PG16, PGDM1400, PGDM1401, PGDM1402, PGDM1403, PGDM1404, PGDM1405, PGDM1406, PGDM1407, PGDM1408, PGDM1409, PGDM1410, PGDM1411, PGDM1412, PGT121, PGT122, PGT123, PGT125, PGT126, PGT127, PGT128, PGT130, PGT131, PGT135, PGT136, PGT137, PGT141, PGT142, PGT143, PGT145, PGT151, PGT152, VRC-CH30, VRC-CH31, VRC-CH32, VRC-CH33, VRC-CH34, VRC-PG04, VRC-CH04b, VRC-PG20, VRC01, VRC02, VRC03, VRC07, VRC23, and Z13. In some embodiments, the anti-HIV-1 broadly neutralizing antibody is 3BNC117. 3BNC117 is a next-generation bNAb that targets the CD4 binding site on HIV envelope gp160. It is a recombinant human IgG1 kappa monoclonal antibody cloned from an HIV-infected viremic controller. A long-acting version of 3BNC117 is known as 3BNC117-LS. 3BNC117 was described in US patent U.S. Pat. No. 9,783,594.

The antibody-based pharmaceutical composition of the present disclosure may be formulated by any number of strategies known in the art (e.g., see McGoff and Scher, 2000, Solution Formulation of Proteins/Peptides: In McNally, E. J., ed. Protein Formulation and Delivery. New York, NY: Marcel Dekker; pp. 139-158; Akers and Defilippis, 2000, Peptides and Proteins as Parenteral Solutions. In: Pharmaceutical Formulation Development of Peptides and Proteins. Philadelphia, PA: Talyor and Francis; pp. 145-177; Akers et al., 2002, Pharm. Biotechnol. 14:47-127). A pharmaceutically acceptable composition suitable for patient administration will contain an effective amount of the antibody in a formulation which both retains biological activity while also promoting maximal stability during storage within an acceptable temperature range. The pharmaceutical compositions can also include, depending on the formulation desired, pharmaceutically acceptable diluents, pharmaceutically acceptable carriers and/or pharmaceutically acceptable excipients, or any such vehicle commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. The amount of an excipient that is useful in the pharmaceutical composition or formulation of this disclosure is an amount that serves to uniformly distribute the antibody throughout the composition so that it can be uniformly dispersed when it is to be delivered to a subject in need thereof. It may serve to dilute the antibody to a concentration which provides the desired beneficial palliative or curative results while at the same time minimizing any adverse side effects that might occur from too high a concentration. It may also have a preservative effect. Thus, for the antibody having high physiological activity, more of the excipient will be employed. On the other hand, for any active ingredient(s) that exhibit a lower physiological activity, a lesser quantity of the excipient will be employed.

The above-described antibodies and antibody compositions or vaccine compositions, comprising at least one or a combination of the antibodies described herein, can be administered for the prophylactic and therapeutic treatment of HIV viral infection.

The present disclosure also relates to isolated polypeptides comprising the novel amino acid sequences of the light chain regions and heavy chain variable regions, listed in Tables 2-3. In other related embodiments, this disclosure provides polypeptide variants having the amino acid sequences of the light chain regions and heavy chain variable regions of the HIV antibodies that share at least 70%, 75%, 80%, 85%, 90%, 95%, 96%, 97%, 98%, or 99%, or greater sequence identity compared to a polypeptide sequence, listed in Tables 2-3, as determined using the methods described herein (i.e., BLAST analysis using standard parameters). One skilled in this art will recognize that these values can be appropriately adjusted to determine corresponding identity of proteins encoded by taking into amino acid similarity and the like. In other related embodiments, this disclosure provides polypeptide variants having the amino acid sequences of the light chain regions and heavy chain variable regions of the HIV antibodies that share at least 70%, 75%, 80%, 85%, 90%, 95%, 96%, 97%, 98%, or 99%, or greater sequence identity compared to a polypeptide sequence, listed in Tables 2-3, and having the amino acid sequences of the CDR regions identical or substantially identical to those listed in Table 4 or to the amino acid sequences of the CDR regions of the unmodified 10-1074-LS antibody (or MS-193). In other related embodiments, this disclosure provides polypeptide variants having the amino acid sequences of the light chain regions and heavy chain variable regions of the HIV antibodies that share at least 70%, 75%, 80%, 85%, 90%, 95%, 96%, 97%, 98%, or 99%, or greater sequence identity compared to a polypeptide sequence, listed in Tables 2-3, and having the amino acid sequences of the CDR regions identical or substantially identical to those listed in Table 4 or to the amino acid sequences of the CDR regions of the unmodified 10-1074-LS antibody (or MS-193), such that polypeptide variants retain 70%, 75%, 80%, 85%, 90%, 95%, 96%, 97%, 98%, or 99%, or greater binding affinity to the HIV virus. The term "substantially identical" refers to the identity of a sequence to another sequence greater than about 85%.

The term "polypeptide" is used in its conventional meaning, i.e., as a sequence of amino acids. The polypeptides are not limited to a specific length of the product. Peptides, oligopeptides, and proteins are included within the definition of polypeptide, and such terms can be used interchangeably herein unless specifically indicated otherwise. This term also includes post-expression modifications of the polypeptide, for example, glycosylations, acetylations, phosphorylations and the like, as well as other modifications known in the art, both naturally occurring and non-naturally occurring. A polypeptide can be an entire protein or a subsequence thereof. Particular polypeptides of interest in the context of this disclosure are amino acid subsequences comprising CDRs, VH, and VL, being capable of binding an antigen or HIV-infected cell.

A polypeptide "variant," as the term is used herein, is a polypeptide that typically differs from a polypeptide specifically disclosed herein in one or more substitutions, deletions, additions and/or insertions. Such variants can be naturally occurring or can be synthetically generated, for example, by modifying one or more of the above polypeptide sequences of the disclosure and evaluating one or more biological activities of the polypeptide as described herein and/or using any of some techniques well known in the art.

For example, certain amino acids can be substituted for other amino acids in a protein structure without appreciable loss of its ability to bind other polypeptides (for example, antigens) or cells. Since it is the binding capacity and nature of a protein that defines that protein's biological functional activity, certain amino acid sequence substitutions can be made in a protein sequence, and, accordingly, its underlying DNA coding sequence, whereby a protein with like properties is obtained. It is thus contemplated that various changes can be made in the peptide sequences of the disclosed compositions, or corresponding DNA sequences that encode said peptides without appreciable loss of their biological utility or activity.

Variant antibody sequences include those wherein conservative substitutions have been introduced by modification of polynucleotides encoding polypeptides of the invention. Amino acids can be classified according to physical properties and contribution to secondary and tertiary protein structure. A "conservative substitution" is recognized in the art as a substitution of one amino acid for another amino acid that has similar properties. Exemplary conservative substitutions are set out below:

CONSERVATIVE SUBSTITUTION I

| Side chain characteristic | Amino acid |
|---|---|
| Aliphatic | |
| Non-polar | G A P I L V |
| Polar - uncharged | C S T M N Q |
| Polar - charged | D E K R |
| Aromatic | H F W Y |
| Other | N Q D E |

Alternatively, conservative amino acids can be grouped as described in Lehninger, [Biochemistry, Second Edition; Worth Publishers, Inc. NY, N.Y. (1975), pp. 71-77] as set out below:

CONSERVATIVE SUBSTITUTION II

| Side chain characteristic | Amino acid |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still another alternative, exemplary conservative substitutions are set out below:

CONSERVATIVE SUBSTITUTIONS III

| Original residue | Exemplary substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

A conservative substitution of an existing substitution refers to a conservative substitution of the substituting residue. For example, a conservative substitution of LmdV:

Y2P refers to a conservative substitution (i.e., glycine (G)) of proline (P) at position LmdV:Y2. In another example, a conservative substitution of HV:V79T refers to a conservative substitution (i.e., serine (S), cysteine (C)) of threonine (T) at position HV:V79.

"Homology" or "sequence identity" refers to the percentage of residues in the polynucleotide or polypeptide sequence variant that are identical to the non-variant sequence after aligning the sequences and introducing gaps, if necessary, to achieve the maximum percent homology. In particular embodiments, polynucleotide and polypeptide variants have at least about 70%, at least about 75%, at least about 80%, at least about 90%, at least about 95%, at least about 98%, or at least about 99% polynucleotide or polypeptide homology with a polynucleotide or polypeptide described herein.

Such variant polypeptide sequences will share 70% or more (i.e. 80%, 85%, 90%, 95%, 97%, 98%, 99% or more) sequence identity with the sequences recited in the application. In additional embodiments, the described invention provides polypeptide fragments comprising various lengths of contiguous stretches of amino acid sequences disclosed herein. For example, peptide sequences provided by this disclosure include at least about 5, 10, 15, 20, 30, 40, 50, 75, 100, 150, or more contiguous peptides of one or more of the sequences disclosed herein as well as all intermediate lengths therebetween.

The disclosure also includes nucleic acid sequences encoding part or all of the light and heavy chains of the described inventive antibodies, and fragments thereof. Due to the redundancy of the genetic code, variants of these sequences will exist that encode the same amino acid sequences.

The present disclosure also includes isolated nucleic acid sequences encoding the polypeptides for the light and heavy chains of the HIV antibodies listed in Tables 2-3. In other related embodiments, the described invention provides polynucleotide variants that encode the peptide sequences of the heavy and light chains of the HIV antibodies listed in Tables 5-6. These polynucleotide variants have at least 70%, at least 75%, at least 80%, at least 85%, at least 90%, at least 95%, at least 96%, at least 97%, at least 98%, or at least 99%, or greater, sequence identity compared to a polynucleotide sequence of this disclosure, as determined using the methods described herein (i.e., BLAST analysis using standard parameters). One skilled in this art will recognize that these values can be appropriately adjusted to determine corresponding identity of proteins encoded by two nucleotide sequences by taking into account codon degeneracy, amino acid similarity, reading frame positioning, and the like.

The terms "nucleic acid" and "polynucleotide" are used interchangeably herein to refer to single-stranded or double-stranded RNA, DNA, or mixed polymers. Polynucleotides can include genomic sequences, extra-genomic and plasmid sequences, and smaller engineered gene segments that express, or can be adapted to express polypeptides.

An "isolated nucleic acid" is a nucleic acid that is substantially separated from other genome DNA sequences as well as proteins or complexes such as ribosomes and polymerases, which naturally accompany a native sequence. The term encompasses a nucleic acid sequence that has been removed from its naturally occurring environment and includes recombinant or cloned DNA isolates and chemically synthesized analogs or analogs biologically synthesized by heterologous systems. A substantially pure nucleic acid includes isolated forms of the nucleic acid. Accordingly, this refers to the nucleic acid as originally isolated and does not exclude genes or sequences later added to the isolated nucleic acid by the hand of man.

A polynucleotide "variant," as the term is used herein, is a polynucleotide that typically differs from a polynucleotide specifically disclosed herein in one or more substitutions, deletions, additions and/or insertions. Such variants can be naturally occurring or can be synthetically generated, for example, by modifying one or more of the polynucleotide sequences of the disclosure and evaluating one or more biological activities of the encoded polypeptide as described herein and/or using any of some techniques well known in the art.

Modifications can be made in the structure of the polynucleotides of the described invention and still obtain a functional molecule that encodes a variant or derivative polypeptide with desirable characteristics. When it is desired to alter the amino acid sequence of a polypeptide to create an equivalent or even an improved, variant or portion of a polypeptide of the invention, one skilled in the art typically will change one or more of the codons of the encoding DNA sequence.

Typically, polynucleotide variants contain one or more substitutions, additions, deletions and/or insertions, such that the immunogenic binding properties of the polypeptide encoded by the variant polynucleotide is not substantially diminished relative to a polypeptide encoded by a polynucleotide sequence specifically set forth herein.

In additional embodiments, the described invention provides polynucleotide fragments comprising various lengths of contiguous stretches of sequence identical to or complementary to one or more of the sequences disclosed herein. For example, polynucleotides are provided by this disclosure that comprise at least about 10, 15, 20, 30, 40, 50, 75, 100, 150, 200, 300, 400, 500 or 1000 or more contiguous nucleotides of one or more of the sequences disclosed herein as well as all intermediate lengths therebetween and encompass any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; and including all integers through 200-500; 500-1,000.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this disclosure with other polynucleotides include prewashing in a solution of 5×SSC, 0.5% SDS, 1.0 mM EDTA (pH 8.0); hybridizing at 50-60° C., 5×SSC, overnight; followed by washing twice at 65° C. for 20 minutes with each of 2×, 0.5×, and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, for example, to 60-65° C. or 65-70° C.

In some embodiments, the polypeptide encoded by the polynucleotide variant or fragment has the same binding specificity (i.e., specifically or preferentially binds to the same epitope or HIV strain) as the polypeptide encoded by the native polynucleotide. In some embodiments, the described polynucleotides, polynucleotide variants, fragments, and hybridizing sequences, encode polypeptides that have a level of binding activity of at least about 50%, at least about 70%, and at least about 90% of that for a polypeptide sequence specifically set forth herein.

The polynucleotides of the described invention, or fragments thereof, regardless of the length of the coding sequence itself, can be combined with other DNA sequences, such as promoters, polyadenylation signals, additional restriction enzyme sites, multiple cloning sites, other coding segments, and the like, such that their overall length can vary considerably. A nucleic acid fragment of almost any length is employed. For example, illustrative polynucleotide segments with total lengths of about 10000, about 5000, about 3000, about 2000, about 1000, about 500, about 200, about 100, about 50 base pairs in length, and the like, (including all intermediate lengths) are included in many implementations of this invention.

Further included within the scope of the invention are vectors such as expression vectors, comprising a nucleic acid sequence according to the invention. Cells transformed with such vectors also are included within the scope of the invention.

The present disclosure also provides vectors and host cells comprising a nucleic acid of the invention, as well as recombinant techniques for the production of a polypeptide of the invention. Vectors of the invention include those capable of replication in any type of cell or organism, including, for example, plasmids, phage, cosmids, and minichromosomes. In some embodiments, vectors comprising a polynucleotide of the described invention are vectors suitable for propagation or replication of the polynucleotide, or vectors suitable for expressing a polypeptide of the described invention. Such vectors are known in the art and commercially available.

"Vector" includes shuttle and expression vectors. Typically, the plasmid construct also will include an origin of replication (for example, the ColE1 origin of replication) and a selectable marker (for example, ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells.

As used herein, the term "cell" can be any cell, including, but not limited to, that of a eukaryotic, multicellular species (for example, as opposed to a unicellular yeast cell), such as, but not limited to, a mammalian cell or a human cell. A cell can be present as a single entity or can be part of a larger collection of cells. Such a "larger collection of cells" can comprise, for example, a cell culture (either mixed or pure), a tissue (for example, endothelial, epithelial, mucosa or other tissue), an organ (for example, lung, liver, muscle and other organs), an organ system (for example, circulatory system, respiratory system, gastrointestinal system, urinary system, nervous system, integumentary system or other organ system), or an organism (e.g., a bird, mammal, or the like).

Polynucleotides of the invention may be synthesized, in whole or in parts that are then combined, and inserted into a vector using routine molecular and cell biology techniques, including, for example, subcloning the polynucleotide into a linearized vector using appropriate restriction sites and restriction enzymes. Polynucleotides of the described invention are amplified by polymerase chain reaction using oligonucleotide primers complementary to each strand of the polynucleotide. These primers also include restriction enzyme cleavage sites to facilitate subcloning into a vector. The replicable vector components generally include but are not limited to, one or more of the following: a signal sequence, an origin of replication, and one or more marker or selectable genes.

In order to express a polypeptide of the invention, the nucleotide sequences encoding the polypeptide, or functional equivalents, may be inserted into an appropriate expression vector, i.e., a vector that contains the necessary elements for the transcription and translation of the inserted coding sequence. Methods well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

The present disclosure also provides kits useful in performing diagnostic and prognostic assays using the antibodies, polypeptides and nucleic acids of the present invention. Kits of the present invention include a suitable container comprising an HIV antibody, a polypeptide or a nucleic acid of the invention in either labeled or unlabeled form. In addition, when the antibody, polypeptide or nucleic acid is supplied in a labeled form suitable for an indirect binding assay, the kit further includes reagents for performing the appropriate indirect assay. For example, the kit may include one or more suitable containers including enzyme substrates or derivatizing agents, depending on the nature of the label. Control samples and/or instructions may also be included. The present disclosure also provides kits for detecting the presence of the HIV antibodies or the nucleotide sequence of the HIV antibody of the present disclosure in a biological sample by PCR or mass spectrometry.

In some embodiments, the kit includes a pharmaceutically acceptable dose unit of a pharmaceutically effective amount of at least one isolated anti-HIV antibody described herein or antigen-binding portion thereof. The kit can further include a pharmaceutically acceptable dose unit of a pharmaceutically effective amount of an anti-HIV agent. The two pharmaceutically acceptable dose units can optionally take the form of a single pharmaceutically acceptable dose unit. An exemplary anti-HIV agent can be selected from the group consisting of a non-nucleoside reverse transcriptase inhibitor, a protease inhibitor, an entry or fusion inhibitor, and an integrase inhibitor. In some embodiments, the anti-HIV agent is an anti-HIV broadly neutralizing antibody, such as 3BNC117.

"Label" as used herein refers to a detectable compound or composition that is conjugated directly or indirectly to the antibody so as to generate a "labeled" antibody. A label can also be conjugated to a polypeptide and/or a nucleic acid sequence disclosed herein. The label can be detectable by itself (for example, radioisotope labels or fluorescent labels) or, in the case of an enzymatic label, can catalyze chemical alteration of a substrate compound or composition that is detectable. Antibodies and polypeptides of the described invention also can be modified to include an epitope tag or label, for example, for use in purification or diagnostic applications. Suitable detection means include the use of labels such as, but not limited to, radionucleotides, enzymes, coenzymes, fluorescers, chemiluminescers, chromogens, enzyme substrates or co-factors, enzyme inhibitors, prosthetic group complexes, free radicals, particles, dyes, and the like.

According to another embodiment, the present disclosure provides diagnostic methods. Diagnostic methods generally involve contacting a biological sample obtained from a patient, such as, for example, blood, serum, saliva, urine, sputum, a cell swab sample, or a tissue biopsy, with an HIV antibody and determining whether the antibody preferentially binds to the sample as compared to a control sample or predetermined cut-off value, thereby indicating the presence of the HIV virus.

According to another embodiment, the present disclosure provides methods to detect the presence of the HIV antibodies of the present disclosure in a biological sample from a patient. Detection methods generally involve obtaining a biological sample from a patient, such as, for example, blood, serum, saliva, urine, sputum, a cell swab sample, or a tissue biopsy and isolating HIV antibodies or fragments thereof, or the nucleic acids that encode an HIV antibody, and assaying for the presence of an HIV antibody in the biological sample. Also, the present disclosure provides methods to detect the nucleotide sequence of an HIV antibody in a cell. The nucleotide sequence of an HIV antibody may also be detected using the primers disclosed herein. The presence of the HIV antibody in a biological sample from a patient may be determined by utilizing known recombinant techniques and/or the use of a mass spectrometer.

In another embodiment, the present disclosure provides a method for detecting an HIV antibody comprising a heavy chain comprising a highly conserved consensus sequence and a light chain comprising a highly conserved consensus sequence in a biological sample, comprising obtaining an immunoglobulin-containing biological sample from a mammalian subject, isolating an HIV antibody from said sample, and identifying the highly conserved consensus sequences of the heavy chain and the light chain. The biological sample may be blood, serum, saliva, urine, sputum, a cell swab sample, or a tissue biopsy. The amino acid sequences may be determined by methods known in the art including, for example, PCR and mass spectrometry.

The term "assessing" includes any form of measurement, and includes determining if an element is present or not. The terms "determining," "measuring," "evaluating," "assessing" and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

Method of Reducing Viral Replication

Methods for reducing an increase in HIV virus titer, virus replication, virus proliferation or an amount of an HIV viral protein in a subject are further provided. According to another aspect, a method includes administering to the subject an amount of an HIV antibody effective to reduce an increase in HIV titer, virus replication or an amount of an HIV protein of one or more HIV strains or isolates in the subject.

According to another embodiment, the present disclosure provides a method of reducing viral replication or spread of HIV infection to additional host cells or tissues comprising contacting a mammalian cell with the antibody, or a portion thereof, which binds to an antigenic epitope on gp120.

Method of Treatment

According to another embodiment, the present disclosure provides a method for treating a mammal infected with a virus infection, such as, for example, HIV, comprising administering to said mammal a pharmaceutical composition comprising the HIV antibodies disclosed herein. According to one embodiment, the method for treating a mammal infected with HIV comprises administering to said mammal a pharmaceutical composition that comprises an antibody of the present disclosure, or a fragment thereof. The compositions of the disclosure can include more than one antibody having the characteristics disclosed (for example, a plurality or pool of antibodies). It also can include other HIV neutralizing antibodies as are known in the art, for example, but not limited to, 10-259, 10-303, 10-410, 10-847, 10-996, 10-1121, 10-1130, 10-1146, 10-1341, 10-1369, 10-1074GM, GL, 10E8, 12A12, 12A21, 2F5, 2G12, 35022, 3BC176, 3BNC117, 3BNC55, 3BNC60, 3BNC62, 447-52D, 4E10, 5H/11-BMV-D5, 8ANC195, b12, CAP256-VRC26.01, CAP256-VRC26.02, CAP256-VRC26.03, CAP256-VRC26.04, CAP256-VRC26.05, CAP256-VRC26.06, CAP256-VRC26.07, CAP256-VRC26.08, CAP256-VRC26.09, CAP256-VRC26.10, CAP256-VRC26.11, CAP256-VRC26.12, CH01, CH02, CH03, CH04, CH103, HGN194, HJ16, HK20, M66.6, NIH45-46, PCDN-33A, PCDN-33B, PCDN-38A, PG9, PG16, PGDM1400, PGDM1401, PGDM1402, PGDM1403, PGDM1404, PGDM1405, PGDM1406, PGDM1407, PGDM1408, PGDM1409, PGDM1410, PGDM1411, PGDM1412, PGT121, PGT122, PGT123, PGT125, PGT126, PGT127, PGT128, PGT130, PGT131, PGT135, PGT136, PGT137, PGT141, PGT142, PGT143, PGT145, PGT151, PGT152, VRC-CH30, VRC-CH31, VRC-CH32, VRC-CH33, VRC-CH34, VRC-PG04, VRC-CH04b, VRC-PG20, VRC01, VRC02, VRC03, VRC07, VRC23, and Z13.

The method can further include administering a second therapeutic agent, such as a therapeutically effective amount of the second therapeutic agent. The second therapeutic agent can be administered before, concurrently with or after the administration of the anti-HIV antibody or antigen-binding portion thereof. In some embodiments, the second therapeutic agent is an anti-HIV-1 broadly neutralizing antibody. Examples of anti-HIV-1 broadly neutralizing antibodies are provided above. In some embodiments, the anti-HIV-1 broadly neutralizing antibody is 3BNC117.

Passive immunization has proven to be an effective and safe strategy for the prevention and treatment of viral diseases. (See, for example, Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999). Passive immunization using human monoclonal antibodies provides an immediate treatment strategy for emergency prophylaxis and treatment of HIV.

Subjects at risk for HIV-related diseases or disorders include patients who have come into contact with an infected person or who have been exposed to HIV in some other way. Administration of a prophylactic agent can occur prior to the manifestation of symptoms characteristic of HIV-related disease or disorder, such that a disease or disorder is prevented or, alternatively, delayed in its progression.

For in vivo treatment of human and non-human patients, the patient is administered or provided a pharmaceutical formulation including an HIV antibody of this disclosure. When used for in vivo therapy, the antibodies of this disclosure are administered to the patient in therapeutically effective amounts (i.e., amounts that eliminate or reduce the patient's viral burden). The antibodies are administered to a human patient, in accord with known methods, such as intravenous administration, for example, as a bolus or by continuous infusion over a period of time, by intramuscular, intraperitoneal, intracerobrospinal, subcutaneous, intraarticular, intrasynovial, intrathecal, oral, topical, or inhalation routes. The antibodies can be administered parenterally, when possible, at the target cell site, or intravenously. In some embodiments, the antibody is administered by an intravenous or subcutaneous administration. Therapeutic compositions of the disclosure may be administered to a patient or subject systemically, parenterally, or locally. The above parameters for assessing successful treatment and improvement in the disease are readily measurable by routine procedures familiar to a physician.

For parenteral administration, the antibodies may be formulated in a unit dosage injectable form (solution, suspension, emulsion) in association with a pharmaceutically acceptable, parenteral vehicle. Examples of such vehicles include, but are not limited, water, saline, Ringer's solution, dextrose solution, and 5% human serum albumin. Nonaqueous vehicles include, but are not limited to, fixed oils and ethyl oleate. Liposomes can be used as carriers. The vehicle may contain minor amounts of additives such as substances that enhance isotonicity and chemical stability, such as, for example, buffers and preservatives. The antibodies can be formulated in such vehicles at concentrations of about 1 mg/ml to 150 mg/ml.

The dose and dosage regimen depends upon a variety of factors readily determined by a physician, such as the nature of the infection, for example, its therapeutic index, the patient, and the patient's history. Generally, a therapeutically effective amount of an antibody is administered to a patient. In some embodiments, the amount of antibody administered is in the range of about 0.1 mg/kg to about 50 mg/kg of patient body weight. Depending on the type and severity of the infection, about 0.1 mg/kg to about 50 mg/kg body weight (for example, about 0.1-15 mg/kg/dose) of antibody is an initial candidate dosage for administration to the patient, whether, for example, by one or more separate administrations, or by continuous infusion. The progress of this therapy is readily monitored by conventional methods and assays and based on criteria known to the physician or other persons of skill in the art. The above parameters for assessing successful treatment and improvement in the disease are readily measurable by routine procedures familiar to a physician.

Other therapeutic regimens may be combined with the administration of the HIV antibody of the present disclosure. The combined administration includes co-administration, using separate formulations or a single pharmaceutical formulation, and consecutive administration in either order, wherein preferably there is a time period while both (or all) active agents simultaneously exert their biological activities. Such combined therapy can result in a synergistic therapeutic effect. The above parameters for assessing successful treatment and improvement in the disease are readily measurable by routine procedures familiar to a physician.

The terms "treating" or "treatment" or "alleviation" are used interchangeably and refer to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present disclosure, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

The term "effective amount," "effective dose," or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A "prophylactically effective amount" or a "prophylactically effective dosage" of a drug is an amount of the drug that, when administered alone or in combination with another therapeutic agent to a subject at risk of developing a disease or of suffering a recurrence of disease, inhibits the development or recurrence of the disease. The ability of a therapeutic or prophylactic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

Administration "in combination with" one or more further therapeutic agents includes simultaneous (concurrent) and consecutive administration in any order.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include, but not limited to, buffers such as phosphate, citrate, acetate and other organic acids; antioxidants including, but not limited to, ascorbic acid; low molecular weight (less than about 10 residues) polypeptide; proteins, such as, but not limited to, serum albumin, gelatin, or immunoglobulins; hydrophilic polymers such as, but not limited to, polyvinylpyrrolidone; amino acids such as, but not limited to, glycine, glutamine, asparagine, arginine, proline or lysine; monosaccharides, disaccharides, and other carbohydrates including, but not limited to, glucose, mannose, or dextrins; chelating agents such as, but not limited to, EDTA; sugar alcohols such as, but not limited to, mannitol, sorbitol, sucrose or trehalose; salt-forming counterions such as, but not limited to, sodium; and/or nonionic surfactants such as, but not limited to, TWEEN; polyethylene glycol (PEG), poloxamers, i.e. Pluronic F-68 and polysorbates, i.e. polysorbate 20 or polysorbate 80

Definitions

To aid in understanding the detailed description of the compositions and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

The term "recombinant" when made in reference to a nucleic acid molecule refers to a nucleic acid molecule which is comprised of segments of nucleic acid joined together by means of molecular biological techniques. The term "recombinant," when made in reference to a protein or a polypeptide, refers to a protein molecule which is expressed using a recombinant nucleic acid molecule.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

As used herein, the term "in vitro" refers to events that occur in an artificial environment, e.g., in a test tube or reaction vessel, in cell culture, etc., rather than within a multi-cellular organism.

As used herein, the term "in vivo" refers to events that occur within a multi-cellular organism such as a non-human animal.

The terms "prevent," "preventing," "prevention," "prophylactic treatment" and the like refer to reducing the probability of developing a disorder or condition in a subject, who does not have, but is at risk of or susceptible to developing a disorder or condition.

As used herein, "administering" refers to the physical introduction of a composition comprising a therapeutic agent to a subject, using any of the various methods and delivery systems known to those skilled in the art. Routes of administration described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, a composition described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. The activity of such agents may render it suitable as a "therapeutic agent," which is a biologically, physiologically, or pharmacologically active substance (or substances) that acts locally or systemically in a subject.

The terms "therapeutic agent," "therapeutic capable agent," or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

"Combination" therapy, as used herein, unless otherwise clear from the context, is meant to encompass administration of two or more therapeutic agents in a coordinated fashion, and includes, but is not limited to, concurrent dosing. Specifically, combination therapy encompasses both co-administration (e.g., administration of a co-formulation or simultaneous administration of separate therapeutic compositions) and serial or sequential administration, provided that administration of one therapeutic agent is conditioned in some way on administration of another therapeutic agent. For example, one therapeutic agent may be administered only after a different therapeutic agent has been administered and allowed to act for a prescribed period of time. See, e.g., Kohrt et al. (2011) *Blood* 117:2423.

Where a value of ranges is provided, it is understood that each intervening value, to the tenth of the unit of the lower limit unless the context clearly dictates otherwise, between the upper and lower limit of that range and any other stated or intervening value in that stated range is encompassed within the disclosure. The upper and lower limits of these smaller ranges which may independently be included in the smaller ranges is also encompassed within the disclosure, subject to any specifically excluded limit in the stated range. Where the stated range includes one or both of the limits, ranges excluding either both of those included limits are also included in the disclosure.

It is noted here that, as used in this specification and the appended claims, the singular forms "a," "an," and "the" include plural reference unless the context clearly dictates otherwise.

The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

The word "substantially" does not exclude "completely," e.g., a composition which is "substantially free" from Y may be completely free from Y. Where necessary, the word "substantially" may be omitted from the definition of the invention.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise.

In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates, which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1

Identification and Characterization of the Variants of the 10-1074 Broadly Neutralizing Antibody—Round 1

The first round variants, including MS-203, MS-204, MS-205, MS-206, MS-207, MS-208, MS-209, MS-210, MS-211, MS-212, MS-213, MS-214, MS-215, MS-216, MS-217, MS-218, MS-219, MS-220, and MS-224, as shown in Table 9, were produced using transient expression in HEK293 cells and purified by protein A chromatography. The characterization methods used to analyze the variants are listed in Table 8, including size exclusion chromatography (SEC), differential scanning fluorimetry (DSF), low pH stability, and relative solubility assay (RSA). The antibodies were buffer exchanged into phosphate-buffered saline and used for analysis. Assays used for analysis of the first round variants included SEC to quantify monomer and high molecular weight species following purification, DSF to characterize stability of the CH2 and Fab domains during thermal ramping, and retention of neutralization capacity.

The monomer content of the variants ranged from a low of 60.8% to a high of 96.3%. The monomer content of the unmodified 10-1074-LS (or MS-194) was 91.5% with the remainder of material for all variants being high molecular weight species (HMW). Variants with less than 10% HMW were considered for the second round combinatorial variants. In addition to SEC analysis, differential scanning fluorimetry was used to define molecules with increased thermodynamic stability. For the 10-1074-LS (or MS-194) parental molecule, only a single Tm was measured indicating that the CH2 and Fab domains unfolded at the same temperature. Similar results were observed for some of the variants. A few, though, also showed the presence of both a Tm1 and a second melting transition termed Tm2, because modifications that help to stabilize the Fab domain were made in the Fv domain of the antibodies, resulting in the increased thermal transition. Antibodies that did not show a consistent Tm2 for both replicates of the DSF analysis were not considered for Round 2 combinations.

Neutralization activity was also measured to ensure retention of activity of the bnAb variants. Results are shown in Table 10 for neutralization against six pseudoviruses of HIV (e.g., Du156.12, WIT04160.33, CNE17, CNE30, CAAN5342.A2, Du172.17), which are representative of the broader set of viruses against which 10-1074 is active. Antibodies with more than a 3-fold increase in the IC50 or IC80 value for a particular pseudovirus were considered inactive and discarded from further consideration. As evidenced by the data, only one variant, MS-208, lost neutralization activity and was not selected for further development.

The final set of amino acids for further development was based on the combination of amount purified, percent high molecular weight, increase in thermodynamic stability by DSF, and retention of neutralization activity. An example of the reasoning for the selection of residues for combinatorial analysis is described in Table 11. Five amino acid residues selected for further development are MS-203 (LmdV: Y2P), MS-216 (HV: V79T), MS-217 (HV: R82V), MS-218 (HV: L89F) and MS-219 (HV: T108R).

Example 2

Identification and Characterization of the Variants of the 10-1074 Broadly Neutralizing Antibody—Round 2

The second round combinatorial variants were designed based on the first round variants as described in the prior section. The combinatorial variants tested in the second round of optimization are shown in Table 12 and consist of ten double combinations, ten triple combinations, five quadruples and one quintuple combination consisting of all five amino acid modifications. These variants include MS-200, MS-201, MS-202, MS-225, MS-226, MS-227, MS-228, MS-229, MS-230, MS-231, MS-232, MS-233, MS-234, MS-235, MS-236, MS-237, MS-238, MS-239, MS-240, MS-241, MS-242, MS-243, MS-244, and MS-245. The combinatorial variants were produced using transient expression in HEK293 cells and purified by protein A chromatography. The antibodies were buffer exchanged into phosphate-buffered saline before being used for analysis. Assays used for analysis of the second round variants included SEC to quantify monomer and high molecular weight species following purification, differential scanning fluorimetry to characterize stability of the CH2 and Fab domains during thermal ramping, chemical unfolding, low pH stability, solubility, and retention of neutralization capacity.

Results of the initial screening consisting of SEC analysis for dimer and oligomer content and DSF for increased thermodynamic stability are shown in Table 13. For example, MS-200 has lower HMW than the control variant MS-194. MS-200 also has a Tm1=70.15° C. and a Tm2=74.62° C., suggesting it has improved thermal stability. Separation of the HMW species into dimer and oligomer species, with HMW species eluting earlier than dimer, provides a more refined view of the data. The data show that the dimer content was relatively unchanged from 10-1074-LS (or MS-194), while the oligomer content of the variants both increased up to 2-fold for a few variants and decreased up to approximately 7-fold for others. The variants were also characterized by DSF to identify those with increased thermodynamic stability as evidenced by the presence of distinct Tm2 unfolding temperatures.

To better differentiate the variants by DSF, an alternative analysis of the data was devised which took advantage of the change between Tm1 and Tm2 and the area under the thermal unfolding curves. As indicated by the data in Table 14 termed DSF Shoulder Score, the variants may have similar Tm2 values, but different shoulder score values with the increased values indicative of greater stability. For example, the DSF Shoulder Score values for MS-200, MS-201, and MS-202 are 16.12, 29.39, and 22.49, respectively, which are significantly larger than the Shoulder Score value, 7.65, of the control antibody variant MS-194, suggesting the variants MS-200, MS-201, and MS-203 are more stable than the control antibody variant MS-194. Thermodynamic stability was also assessed by chemical unfolding which asses the intrinsic resistance of the native state against unfolding as measured by the mid-point of the denaturation curve. The higher the value, the greater the stability. Together with the DSF shoulder score, a much finer differentiation of the intrinsic thermodynamic stability of the antibodies was obtained. In addition to the intrinsic stability, the resistance to aggregation during low pH incubation, neutralization, and solubility of the variants was also analyzed. While the parental 10-1074-LS (or MS-194) aggregated with up to 40% HMW formation, some variants showed only 2-3% HMW formation. Solubility was also increased for some variants, with up to a 42% increase in solubility over the parental molecule.

The neutralization capacity of a subset of the combinatorial variants was also examined to ensure no loss in neutralization occurred. As shown in Table 15, a reduced set of variants were tested against a representative set of 12 pseudoviruses, including SC422661.8, WITO4160.33, CAAN5342.A2, DU156.12, DU172.17, CNE17, CNE30, CNE53, 235-47, X1193_c1, X1254_c3, and 3301.v1.c24. Variants with a Tm2 were selected for the testing. Of the variants that were tested they all retained neutralization activity against the set of pseudoviruses examined.

The final set of variants for in-depth biophysical analysis was defined based on the biophysical attributes since the reduced set of antibodies defined in Table 15 all retained neutralization activity. The specific reasons for exclusion of bnAbs from the set for in-depth analysis are described in Table 16, and the final set is shown below.

| | ORIGINAL NAME | LIGHT CHAIN MODIFICATIONS | HEAVY CHAIN MODIFICATIONS |
|---|---|---|---|
| MS-200 | 10-1074_ROUND2_XTEND.015 | LMDV: Y2P | HV: R82V, HV: T108R |
| MS-201 | 10-1074_ROUND2_XTEND.019 | | HV: V79T, HV: L89F, HV: T108R |
| MS-202 | 10-1074_ROUND2_XTEND.023 | LMDV: Y2P | HV: V79T, HV: L89F, HV: T108R |

In-Depth Analysis of the Final Variant Set

Figure 2:
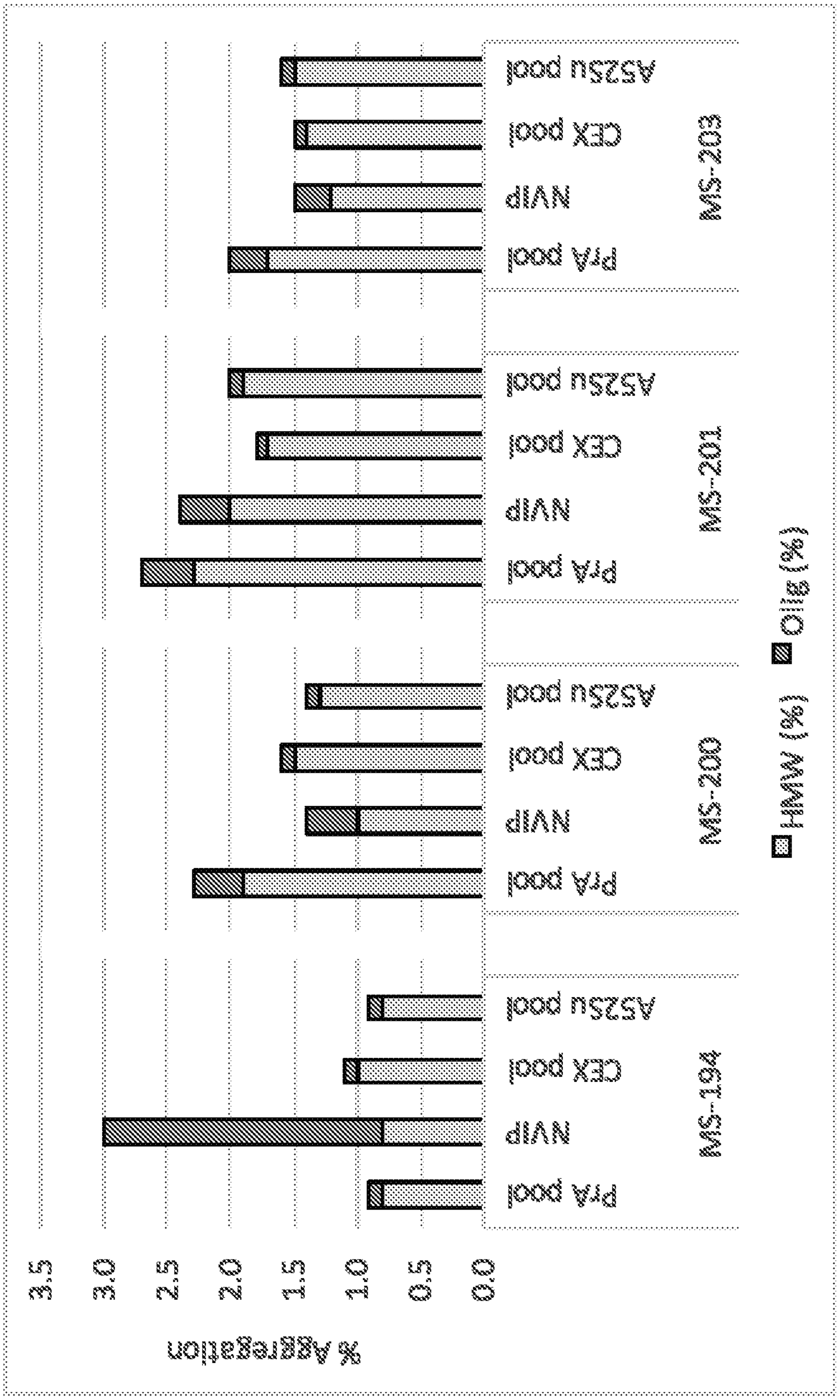
FIG. 2 shows quantification of the degree of aggregation represented by the level of high molecular weight ("HMW") and oligomeric species following each of the purification steps for the 10-1074 antibody variants MS-194, MS-200, MS-201, and MS-203.
Figure 3:
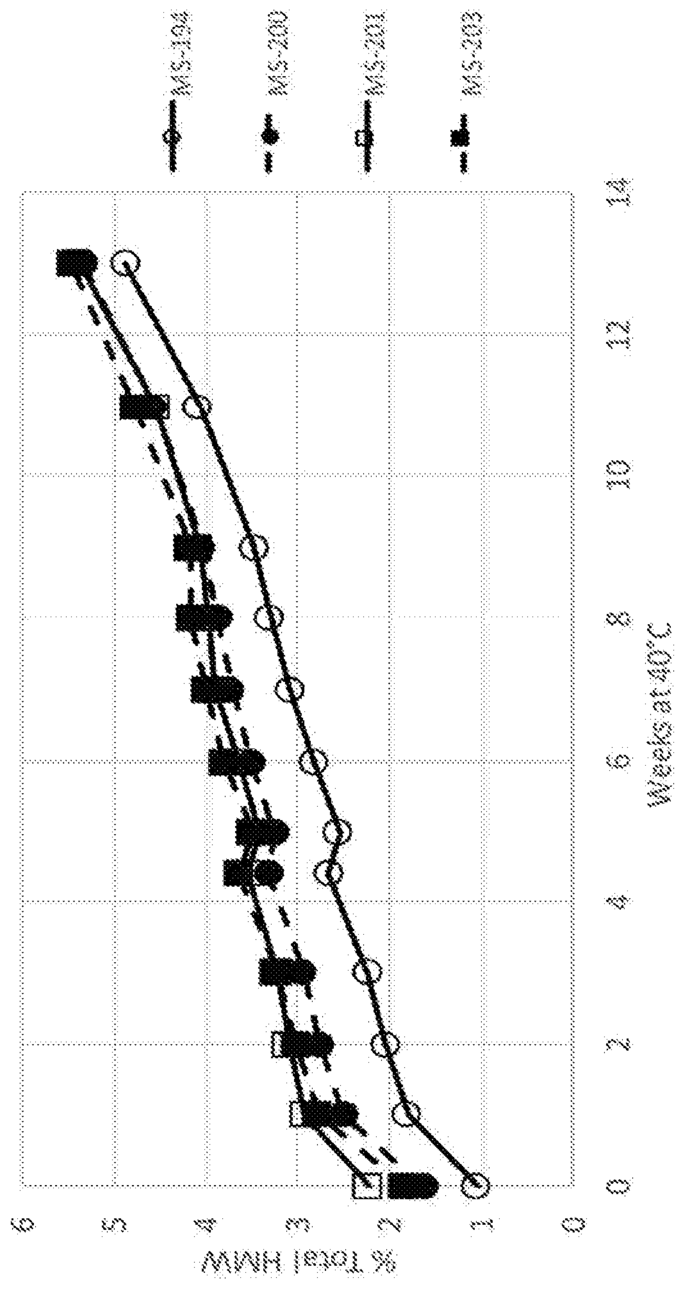
FIG. 3 shows the level of HMW during incubation at 40° C. for up to 13 weeks for the 10-1074 antibody variants MS-194, MS-200, MS-201, and MS-203.
Figure 4:
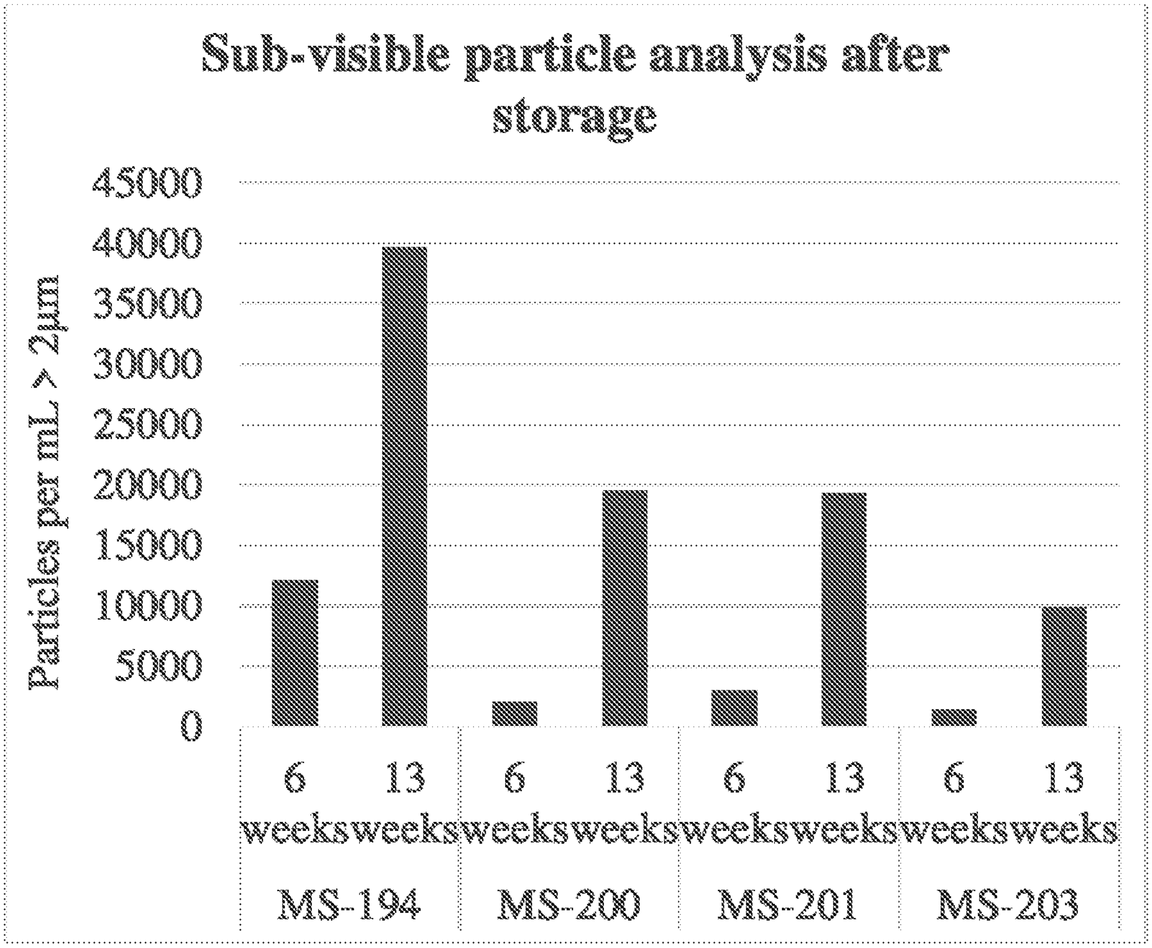
FIG. 4 shows the level of sub-visible particle formation during 6 weeks and 13 weeks for the 10-1074 antibody variants MS-194, MS-200, MS-201, and MS-203.

The final optimized variant was based on the final variant set defined above. Analysis performed was downstream purification (FIGS. 1-2), accelerated stability (FIGS. 3-4). For the downstream purification analysis and accelerated stability, molecules were produced using transient expression in a CHO-S cell line.

The results from the in-depth analysis indicate that MS-202 was the best performing molecule of the optimized variants. While both MS-200, MS-201, and MS-202 have similar rates of dimer formation at 40° C., MS-202 shows better resistance to sub-visible particle formation over a 13 week period.

Production of Antibodies

Antibody materials were cloned and produced as previously described (Durocher, Y., Perret, S., & Kamen, A. (2002). *Nucleic Acids Research,* 30(2), E9). bNAbs antibody materials were generated from transient expression of two suspension cell lines, Human Embryonic Kidney 293 (HEK293) and Chinese Hamster Ovary (CHO). The pTT5 mammalian expression vectors containing either a light chain (LC) or heavy chain (HC) coding region were co-transfected into HEK293 cells at a viable cell density (VCD) of 1*10^6 cells/mL using polyethyleneimine (PEI) (Durocher, Perret, & Kamen, 2002) then two-fold diluted with pre-warmed medium to ⅕ shake flask volume. Expression duration was 5-7 days at 37° C., 5% $CO_2$, and 85% humidity at a shaking speed of 130 RPM with an orbit of 19 mm. The ExpiCHO-S™ "max titer" method was followed essentially as described by ThermoFisher (catalog number A29133, document part number A29518). The pcDNA3.4 expression vectors containing either LC or HC coding regions were co-transfected into CHO-S cells at a VCD of 6*10^6 using expifectamine. The expression duration was 12 days at 32° C., 5% $CO_2$, and 85% humidity at a shaking speed of 130 RPM with an orbit of 19 mm. All clarified supernatants were produced by pelleting the cells at 3000 g for 20 minutes followed by 0.22 m filtration. Antibodies were purified from the clarified supernatants using Mab Select SuRe protein A resin. A sodium phosphate, sodium chloride buffer system with an arginine wash and an acetate pH 3.5 elution was utilized. Protein A elutions were neutralized with tris and buffer exchanged into 20 mM sodium phosphate, 150 mM NaCl, pH 7.4.

Neutralization Assays

Virus neutralization was evaluated using a luciferase-based assayin TZM.bl cells (J Virol 79(16):10108-10125). The HIV-1 pseudoviruses tested contained mostly tier-2 and tier-3 viruses (Journal of Virology 84(3):1439-1452). High-mannose-only pseudoviruses were produced in wild-type cells treated with 25 μM kifunensine (Enzo Life Sciences) or in HEK 293S $GnTI^{-/-}$ cells. Non-linear regression analysis was used to calculate concentrations at which half-maximal inhibition was observed ($IC_{50}$ values). Neutralization activities were also evaluated with a previously characterized PBMC-based assay using infection with primary HIV-1 variants (n=95) isolated from clade B-infected donors with known seroconversion dates either between 1985 and 1989 ("historical seroconverters", n=14) or between 2003 and 2006 ("contemporary seroconverters", n=21) (Journal of Virology 85(14):7236-7245; Nat Med 16(9):995-997). Neutralization activity for each antibody was calculated using GraphPad Prism software (v5.0b) as the area under the best-fit curve, which fits the proportion of viruses neutralized over $IC_{50}$ values ranging from 0.001 to 50 μg/ml.

HP-SEC

High-Performance Size Exclusion Chromatography ("HP-SEC") separates proteins based on differences in their hydrodynamic volumes. Molecules with larger hydrodynamic protein volumes elute earlier than molecules with smaller volumes. Undiluted samples were loaded onto a Waters XBridge Protein BEH SEC 200 Å column (3.5 μm, 7.8×300 mm), separated isocratically with a 100 mM sodium phosphate, 250 mM sodium chloride, pH 6.8 running buffer, and the eluent was monitored by UV absorbance at 280 nm. Purity was determined by calculating the percentage of each separated component as compared to the total integrated area.

DSF

The DSF technique consists of measuring the fluorescence intensity of a hydrophobic probe at gradually increasing temperatures to determine the transition temperature and exposure of the hydrophobic regions of a protein. The measurements from this technique, reported as transition temperatures, correlate well with data obtained from differential scanning calorimetry (DSC). DSF is a high throughput technique that is used to estimate a protein's relative thermodynamic stability and by ranking the results, can be used as a tool to select candidates with more favorable stability properties. Thermal transition temperature(s) by DSF were measured according to the method previously described (Feng H, et al. J Pharm Sci, 2010; 99:4, 1707-1720). The analysis was carried out in PBS buffer (20 mM sodium phosphate and 150 mM sodium chloride pH 7.1) at a final protein concentration of 0.15 mg/mL and a final Sypro Orange concentration of 3×. Protein and Sypro Orange were mixed at a 1:1 volumetric ratio in a 96 well PCR plate and analyzed using a Roche Light Cycler 480 instrument equipped with Thermal Shift Analysis Software. Thermal curves were generated by heating the samples from 20-95° C. at a ramp rate of 4.4° C./s and 10 acquisitions per ° C., at Ex=465 nm Em=580 nm. Transition temperatures and shoulder scores were determined using the first derivative of the melting curve.

Low pH Stability

The pH of protein samples at 1 mg/mL in 20 mM PBS was lowered to approximately pH 3.3 using 2 M acetic acid. After a 30 minute incubation, samples were neutralized to approximately pH 5 using 2 M Tris base. Samples were measured for high molecular weight species using the SE-HPLC method and measured in duplicate. As a control, protein samples had PBS added that was the same volume of the 2 M acetic acid and 2 M Tris base and measured for high molecular weight species.

Relative Solubility

Solubility was assessed according to the method previously described (Vishal M. Toprani, Sangeeta B. Joshi, Lisa A. Kueltzo, Richard M. Schwartz, C. Russell Middaugh, David B. Volkin). A micro-polyethylene glycol precipitation assay as a relative solubility screening tool for monoclonal antibody design and formulation development (J. Pharm. Sci 2016; 105:8: 2319-2327). Analysis was done in PBS buffer (20 mM sodium phosphate and 150 mM sodium chloride pH 7.1) and a final PEG 10,000 concentration of 7.9%. Protein at 1 mg/mL was diluted into the PEG solution at a 1:4 ratio and incubated at room temperature overnight in a 96 well 0.22 m filter plate. After PEG incubation, samples are passed through the filter by centrifugation and the remaining soluble protein is measured by a protein A titer assay.

Chemical Unfolding

Thirty-two guanidine hydrochloride (GND) concentrations in PBS ranging from 0 to 6 M GND were prepared using a liquid handling robot. Then, the protein samples at 1 mg/mL in 20 mM PBS were transferred to each GND concentration to achieve a final protein concentration of 0.05 mg/mL. After a 24 hr incubation, the samples were measured on a SpectraMax M5 plate reader (excitation: 280 nm, emission: 300-450 nm). The measured fluorescence intensity at 373 nm was corrected for scattering and stray light by subtraction of a small amount of the summed intensity measured between 300 and 320 nm (used as a surrogate for signal due to scattering) and then ratioed to the total intensity measured between 320 and 440 nm to correct for total intensity fluctuations. Then, the chemical unfolding curve was generated by graphing each corrected intensity against the GND concentration. The inflection point of the curve was calculated and reported for each protein sample from this curve. Samples were completed in triplicate.

Sub-Visible Particle Analysis

Sub-visible particles were measured using a Flowcam 8100 benchtop microflow imaging system equipped with an 80 μm flow cell and a 10× magnification lens and controlled by the Visual Spreadsheet software. Samples were equilibrated to room temperature and gently swirled to mix thoroughly. Single readings of 100 μl per sample were collected, and total particle concentration above 2 μm was recorded.

Example 3

Figure 1B:
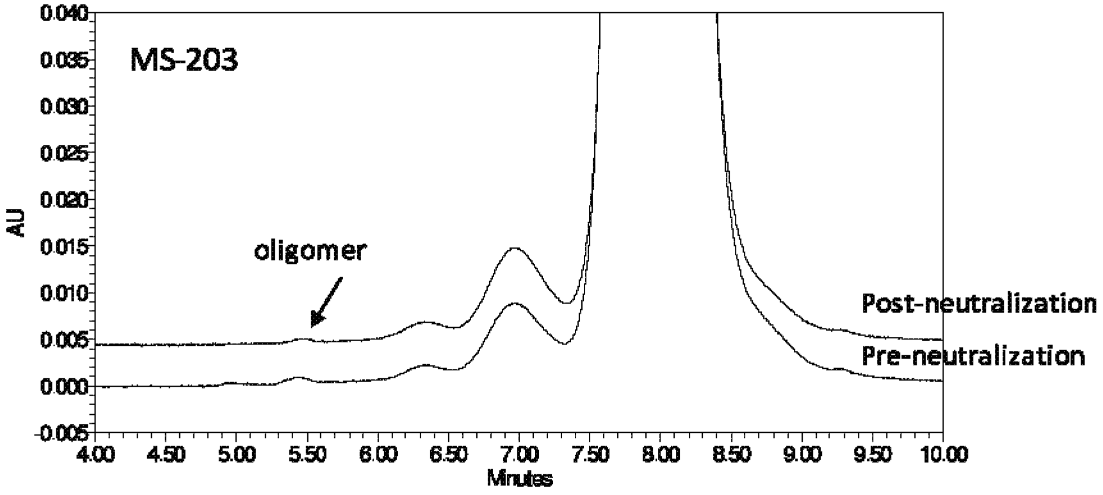

Characterization for the Formation of Oligomeric Species and HMW of the 10-1074 Variants During Viral Inactivation and the Purification Steps FIG. 1 shows the characterization of anti-HIV antibody 10-1074 variants MS-194 (FIG. 1A) and MS-203 (FIG. 1B) by high-performance size exclusion chromatography ("HP-SEC") before and after viral neutralization. Peaks in the HP-SEC profiles corresponding to the oligomeric species formed during viral inactivation are indicated by arrows. FIG. 2 shows quantification of the degree of aggregation represented by the level of high molecular weight ("HMW") and oligomeric species following each of the purification steps for the 10-1074 antibody variants MS-194, MS-200, MS-201, and MS-203.

Molecules MS-194, MS-200, MS-201, and MS-203, were produced using the ExpiCHO-S™ "max titer" method essentially as described by ThermoFisher (catalog number A29133, document part number A29518). The pcDNA3.4 expression vectors containing either light chain or heavy chain coding regions were co-transfected into CHO-S cells at a VCD of 6*10^6 using expifectamine. The expression duration was 12 days at 32° C., 5% $CO_2$ and 85% humidity at a shaking speed of 130 RPM with an orbit of 19 mm. All clarified supernatants were produced by pelleting the cells at 3000 g for 20 minutes followed by 0.22 μm filtration.

Antibodies were purified from the clarified supernatants using MabSelect SuRe protein A resin. Equilibrated with a Tris and sodium chloride buffer. Following loading of the column, the column was washed with a Tris buffer containing 0.5M sodium chloride. Bound mAb was eluted with a 0.1 M acetate buffer at pH 3.6 and neutralized. The stability of each molecule during viral inactivation was ascertained by titrating the eluate to pH 3.5, followed by incubating for 1 hour followed by neutralization with Tris buffer. The remainder of the Protein A elutions were also neutralized with a tris buffer system immediately following elution. Further purification was achieved by loading the neutralized eluent onto a Fractogel $SO_3^-$ cation-exchange resin (EMD Millipore Corporation) and eluting with a sodium chloride gradient. The peak containing the mAb was collected, concentrated to 20 mg/mL, and buffer exchanged into 10 mM acetate, 9% sucrose, pH 5.2.

The percent high molecular weight and oligomer were determined for each sample using HP-SEC analysis as previously described. As shown in FIGS. 1A and 1B and quantified in FIG. 2 the MS-194 antibody shows a significant increase in oligomer during the low pH viral inactivation while molecules MS-200, MS-201, and MS-203 showed no increase in HMW or oligomer content during the viral inactivation process.

Example 4

Characterization of Stability of the 10-1074 Variants

FIG. 3 shows the level of HMW during incubation at 40° C. for up to 13 weeks for the 10-1074 antibody variants MS-194, MS-200, MS-201, and MS-203. The figure shows a similar rate of dimer formation during incubation at 40° C. for up to 13 weeks. FIG. 4 shows the level of sub-visible particle formation during 6 weeks and 13 weeks for the 10-1074 antibody variants MS-194, MS-200, MS-201, and MS-203. The figure shows that antibodies MS-200, MS-201 and MS-203 particulated to a much smaller degree than MS-194. After 6 weeks, MS-194 showed 6× more particles than MS-200, MS-201, and MS-203, while after 13 weeks MS-200 and MS-203 had approximately 2× less than MS-194 and MS-203 showed 4× less particle formation.

Monoclonal antibodies MS-194, MS-200, MS-201 and MS-203 purified by cation-exchange chromatography and buffer exchanged as previously described were buffer exchanged into 20 mM acetate, 9% sucrose and concentrated to 100 mg/mL at a final pH of 5.2. A 500 μL aliquot of each sample was placed in a 4 mL Type I glass vial, sealed with a rubber stopper and aluminum crimp seal. The samples were incubated for up to 13 weeks at 40° C. Samples were removed at the indicated time points and the vials resealed and placed back in the incubator. The % HMW was determined using HP-SEC and sub-visible particles determined using the FlowCam instrument as described above.

Example 5

Combination Therapy with Anti-HIV-1 Antibodies

Although anti-HIV-1 antibodies constitute a potential alternative to ARTS, treatment of viremic individuals with a single antibody also results in emergence of resistant viral variants ((Caskey, M. et al. Nature 522, 487-491 (2015); Caskey, M. et al. Nat. Med. 23, 185-191 (2017); Lynch, R. M. et al. Sci. Transl. Med. 7, 319ra206 (2015)). Moreover, combinations of first-generation anti-HIV-1 broadly neutralizing antibodies (bNAbs) had little measurable effect on the infection. This disclosure presents the results from a phase 1b clinical trial (NCT02825797) in which a combination of 3BNC117 and 10-1074, two potent monoclonal anti-HIV-1 broadly neutralizing antibodies that target independent sites on the HIV-1 envelope spike, was administered during analytical treatment interruption (ATI) (Mendoza et al., Nature. 2018 September; 561(7724): 479-484; Bar-On et al., Nature Medicine 24:1701-1707 (2018)). Participants received three infusions of 30 mg/kg of each antibody at 0, 3, and 6 weeks. Infusions of the two antibodies were generally well tolerated. The nine enrolled individuals with antibody-sensitive latent viral reservoirs maintained suppression for 15 to >30 weeks (median=21 weeks). In the four individuals with dual antibody-sensitive viruses, immunotherapy resulted in an average reduction in HIV-1 viral load of 2.05 $\log_{10}$ copies per ml that remained significantly reduced for three months following the first of up to three infusions. In addition, none developed viruses resistant to both antibodies. It was concluded that the combination of anti-HIV-1 monoclonal antibodies 3BNC117 and 10-1074 could maintain long-term suppression in the absence of ART in individuals with antibody-sensitive viral reservoirs.

Study Design

An open-label phase 1b study was conducted in HIV-1-infected participants who were virologically suppressed on antiretroviral therapy (ART) (http://www.clinicaltrials.gov; NCT02825797; EudraCT: 2016-002803-25) (Mendoza et al., Nature. 2018 September; 561(7724): 479-484; Bar-On et al., Nature Medicine 24:1701-1707 (2018)). Study participants were enrolled sequentially according to eligibility criteria. Participants received 3BNC117 and 10-1074 intravenously at a dose of 30 mg/kg body weight of each antibody, at weeks 0, 3, and 6, unless viral rebound occurred. ART was discontinued 2 days after the first infusion of antibodies (day 2). Plasma HIV-1 viral RNA levels were monitored weekly and ART was resumed if viral load increased to ≥200 copies/ml or $CD4^+$ T cell counts decreased to <350 cells/μl in two consecutive measurements. Time of viral rebound was determined by the first viral load >200 copies/ml. Study participants were followed for 30 weeks after the first infusion. Safety data are reported until the end of study follow-up. All participants provided written informed consent before participation in the study, and the study was conducted in accordance with Good Clinical Practice (GCP). The protocol was approved by the Federal Drug Administration (FDA) in the USA, the Paul-Ehrlich-Institute in Germany, and the Institutional Review Boards (IRBs) at the Rockefeller University and the University of Cologne.

Study Participants

Study participants were recruited at the Rockefeller University Hospital, New York, USA, and the University Hospital Cologne, Cologne, Germany. Eligible participants were adults aged 18-65 years, HIV-1-infected, on ART for a minimum of 24 months, with plasma HIV-1 RNA levels of <50 copies/ml for at least 18 months (one viral blip of >50 but <500 copies/ml during this 18-month period was allowed), plasma HIV-1 RNA levels <20 copies/ml at the screening visit, and a current $CD4^+$ T cell count >500 cells/μl. In addition, participants were pre-screened for sensitivity of latent proviruses against 3BNC117 and 10-1074 by bulk PBMC viral outgrowth culture as described below. Sensitivity was defined as an IC50<2 μg/ml for both 3BNC117 and 10-1074 against outgrowth virus. Participants on an NNRTI-based ART regimen were switched to an integrase inhibitor-based regimen (dolutegravir plus tenofovir disoproxil fumarate/emtricitabine) 4 weeks before treatment interruption due to the prolonged half-life of NNRTIs. Exclusion criteria included reported $CD4^+$ T cell nadir of <200 cells/μl, concomitant hepatitis B or C infection, previous receipt of monoclonal antibodies of any kind, clinically relevant physical findings, medical conditions or laboratory abnormalities, and pregnancy or lactation.

Study Procedures

3BNC117 and 10-1074 were administered intravenously at a dose level of 30 mg/kg (Mendoza et al., Nature. 2018 September; 561(7724): 479-484; Bar-On et al., Nature Medicine 24:1701-1707 (2018)). The appropriate stock volume of 3BNC117 and 10-1074 was calculated according to body weight and diluted in sterile normal saline to a total volume of 250 ml per antibody. Monoclonal antibody infusions were administered sequentially and intravenously over 60 minutes. Study participants were observed at the Rockefeller University Hospital or the University Hospital Cologne for one hour after the last antibody infusion. Participants returned for weekly follow-up visits during the ATI period for safety assessments, which included physical examination and measurements of clinical laboratory parameters such as hematology, chemistries, urinalysis, and pregnancy tests (for women). Plasma HIV-1 RNA levels were monitored weekly during the ATI period, and $CD4^+$ T cell counts were measured every 1 to 2 weeks. After ART was re-initiated, participants returned for follow up every 2 weeks until viral re-suppression was achieved, and every 8 weeks thereafter. Study investigators evaluated and graded adverse events according to the DAIDS AE Grading Table (version 2.0, November 2014) and determined causality. Leukapheresis was performed at the Rockefeller University Hospital or at the University Hospital Cologne at week −2 and week 12. Blood samples were collected before and at multiple times after 3BNC117 and 10-1074 infusions. Samples were processed within 4 h of collection, and serum and plasma samples were stored at −80° C. Peripheral blood mononuclear cells (PBMCs) were isolated by density gradient centrifugation. The absolute number of PBMCs was determined by an automated cell counter (Vi-Cell XR; Beckman Coulter) or manually, and cells were cryopreserved in fetal bovine serum plus 10% DMSO.

Plasma HIV-1 RNA Levels

HIV-1 RNA levels in plasma were measured at the time of screening, at week −2, day 0 (before infusion), weekly during ATI, and every two weeks to every eight weeks after viral rebound had occurred. HIV-1 RNA levels were determined using the Roche COBAS AmpliPrep/COBAS TaqMan HIV-1 Assay (version 2.0) or the Roche COBAS HIV-1 quantitative nucleic acid test (COBAS 6800), which quantitate HIV-1 RNA over a range of $2\times10^1$ to $1\times10^7$ copies/ml. These assays were performed at LabCorp or at the University Hospital Cologne.

$CD4^+$ T Cells $CD4^+$ T-cell counts were determined by a clinical flow cytometry assay, performed at LabCorp or at the University Hospital Cologne, at screening, week 0 (before infusion), weeks 2, 3, 5, 6, 8, 10, and weekly thereafter, while participants remained off ART.

Determination of Baseline Neutralizing Antibody Activity

Purified IgG (Protein G Sepharose 4 Fast Flow, GE Life Sciences) obtained before antibody infusions was tested against a panel of 12 HIV-1 pseudoviruses as described previously (Schoofs T et al. Science 352, 997-1001 (2016)).

Measurement of 3BNC117 and 10-1074 Serum Levels

Blood samples were collected before, at the end of each 3BNC117 infusion and at the end of each 10-1074 infusion at weeks 0, 3, and 6, and weekly during the ATI period, up to week 30. Serum levels of 3BNC117 and 10-1074 were determined by a TZM-bl assay and by ELISA from samples obtained before and after each antibody infusion, and approximately every three weeks during follow up as well as at the time of viral rebound.

3BNC117 and 10-1074 serum concentrations were measured by a validated sandwich ELISA. High bind polystyrene plates were coated with 4 µg/ml of an anti-idiotypic antibody specifically recognizing 3BNC117 (anti-ID 1F1-2E3 mAb) or 2 µg/ml of an anti-idiotypic antibody specifically recognizing 10-1074 (anti-ID 3A1-4E11 mAb), and incubated overnight at 2-8° C. After washing, plates were blocked with 5% Milk Blotto (w/v), 5% NGS (v/v), and 0.05% Tween 20 (v/v) in PBS. Serum samples, QCs and standards were added (1:50 minimum dilution in 5% Milk Blotto (w/v), 5% NGS (v/v), and 0.05% Tween 20 (v/v) in PBS) and incubated at room temperature. 3BNC117 or 10-1074 were detected using a horseradish peroxidase (HRP)-conjugated mouse anti-human IgG kappa-chain-specific antibody (Abcam) for 3BNC117 or an HRP-conjugated goat antihuman IgG Fc-specific antibody for 10-1074 (Jackson ImmunoResearch) and the HRP substrate tetra-methylbenzidine. 3BNC117 and 10-1074 concentrations were then calculated from a standard curve of 3BNC117 or 10-1074 run on the same plate using a 5-PL curve-fitting algorithm (Softmax Pro, v5.4.5). Standard curves and positive controls were created from the drug product lots of 3BNC117 and 10-1074 used in the clinical study. The capture anti-idiotypic mAbs were produced using a stable hybridoma cell line (Duke Protein Production Facility). The lower limit of quantitation for the 3BNC117 ELISA is 0.78 µg/ml and for the 10-1074 ELISA is 0.41 µg/ml. The lower limit of detection was determined to be 0.51 µg/ml and 0.14 µg/ml in HIV-1 seropositive serum for the 3BNC117 and 10-1074 ELISA, respectively. For values that were detectable (i.e., positive for mAb) but were below the lower limit of quantitation, values are reported as <0.78 µg/ml and <0.41 µg/ml for 3BNC117 and 10-1074 ELISA, respectively. If day 0 baseline samples had measurable levels of antibody by the respective assays, the background measured antibody level was subtracted from subsequent results. In addition, samples with antibody levels measured to be within 3-fold from background were excluded from the analysis of PK parameters.

Serum concentrations of active 3BNC117 and 10-1074 were also measured using a validated luciferase-based neutralization assay in TZM-bl cells as previously described (Sarzotti-Kelsoe M et al. J Immunol Methods 409, 131-146 (2014)). Briefly, serum samples were tested using a primary 1:20 dilution with a 5-fold titration series against HIV-1 Env pseudoviruses Q769.d22 and X2088_c9, which are highly sensitive to neutralization by 3BNC117 and 10-1074, respectively, while fully resistant against the other administered antibody. In the case of the post-infusion time points of 10-1074, instances where serum ID50 titers against X2088_c9 were >100,000, serum samples were also tested against a less sensitive strain, Du422. To generate standard curves, 3BNC117 and 10-1074 clinical drug products were included in every assay set-up using a primary concentration of 10 µg/ml with a 5-fold titration series. Serum concentrations of 3BNC117 and 10-1074 for each sample were calculated as follows: serum ID50 titer (dilution)× $3BNC117_{IC50}$ or 10-1074 IC50 titer (µg/ml)=serum concentration of 3BNC117 or 10-1074 (µg/ml). Env pseudoviruses were produced using an ART-resistant backbone vector that reduces background inhibitory activity of antiretroviral drugs if present in the serum sample (SG3ΔEnv/K101P.Q148H.Y181C). Virus pseudotyped with the envelope protein of murine leukemia virus (MuLV) was utilized as a negative control. Antibody concentrations were calculated using the serum ID80 titer and monoclonal antibody IC80 if non-specific activity against MuLV was detected (ID50>20; 9246, week 30; 9248, baseline, d0, wk 18). All assays were performed in a laboratory meeting GCLP standards.

Pre-Screening Bulk PBMC Culture

To test HIV-1 viral strains for sensitivity to 3BNC117 and 10-1074, bulk viral outgrowth cultures were performed by co-culturing isolated $CD4^+$ T cells with MOLT-4/CCR-5 cells or $CD8^+$ T cell-depleted donor lymphoblasts. PBMCs for pre-screening were obtained up to 72 weeks (range 54-505 days) before enrollment under separate protocols approved by the IRBs of The Rockefeller University and the University of Cologne. Sensitivity was determined by TZM-bl neutralization assay as described below. Culture supernatants with IC50<2 μg/ml were deemed sensitive.

Quantitative and Qualitative Viral Outgrowth Assay ($Q^2$VOA)

The quantitative and qualitative viral outgrowth assay ($Q^2$VOA) was performed using isolated PBMCs from leukapheresis at week −2 and week 12 as previously described (Lorenzi J C et al. PNAS 113, E7908-E7916 (2016)). Briefly, isolated $CD4^+$ T cells were activated with 1 μg/ml phytohemagglutinin (Life Technologies) and 100 U/ml IL-2 (Peprotech) and co-cultured with $1\times10^6$ irradiated PBMCs from a healthy donor in 24-well plates. A total of $6\times10^7$-$6.2\times10^8$ cells were assayed for each individual at each of the 2 time points. After 24 hours, PHA was removed and $0.1\times10^6$ MOLT-4/CCR5 cells were added to each well. Cultures were maintained for 2 weeks, splitting by half the MOLT-4/CCR5 cells 7 days after the initiation of the culture and every other day after that. Positive wells were detected by measuring p24 by ELISA. The frequency of latently infected cells was calculated through the infectious units per million (IUPM) algorithm developed by the Siliciano lab (http://silicianolab.johnshopkins.edu).

Rebound Outgrowth Cultures $CD4^+$ T cells isolated from PBMCs from the rebound time points were cultured at limiting dilution exactly as described for $Q^2$VOA. $CD4^+$ T cells were activated with T cell activation beads (Miltenyi) at a concentration of $0.5\times10^6$ beads per $10^6$ $CD4^+$ T cells and 20 U/ml of IL-2. Rebound outgrowth was performed using PBMCS from the highest viral load sample (usually the repeat measurement ≥200 copies/ml). Viruses whose sequences matched the SGA env sequences, and therefore were identical to those present in plasma, as opposed to potentially reactivated PBMC-derived latent reservoir viruses, were selected to test for neutralization.

Viral Sensitivity Testing

Supernatants from p24-positive bulk PBMC cultures, rebound PBMC outgrowth cultures and $Q^2$VOA wells were tested for sensitivity to 3BNC117 and 10-1074 by TZM-bl neutralization assay as previously described (Sarzotti-Kelsoe M et al. J Immunol Methods 409, 131-146 (2014)).

Sequencing

HIV-1 RNA extraction and single genome amplification were performed as previously described (Salazar-Gonzalez J F et al. J Virol 82, 3952-3970 (2008)). In brief, HIV-1 RNA was extracted from plasma samples or $Q^2$VOA-derived virus supernatants using the MinElute Virus Spin kit (Qiagen) followed by first strand cDNA synthesis using SuperScript III reverse transcriptase (Invitrogen). cDNA synthesis for plasma-derived HIV-1 RNA was performed using the antisense primer envB3out Fidelity Platinum Taq (Invitrogen) and run at 94° C. for 2 min; 35 cycles of 94° C. for 15 s, 55° C. for 30 s, and 68° C. for 4 min; and 68° C. for 15 min. Second round PCR was performed with 1 μl of first PCR product as template and High Fidelity Platinum Taq at 94° C. for 2 min; 45 cycles of 94° C. for 15 s, 55° C. for 30 s, and 68° C. for 4 min; and 68° C. for 15 min. cDNA synthesis for $Q^2$VOA-derived HIV-1 RNA was performed using the antisense primer R3B6R Study Outcomes Combination bNab Infusion is Well Tolerated To evaluate the effects of the combination of 3BNC117 and 10-1074 on maintaining HIV-1 suppression during ATI, a Phase 1b clinical trial was conducted (FIG. 5A) (Mendoza et al., Nature. 2018 September; 561(7724): 479-484). HIV-1-infected individuals on ART were pre-screened for 3BNC117 and 10-1074 sensitivity of bulk outgrowth culture-derived viruses using the TZM-bl neutralization assay. Consistent with previous results, 64% and 71% of the outgrowth viruses were sensitive to 3BNC117 and 10-1074, respectively, and 48% were sensitive to both (IC50≤2 μg/ml).

Figure 5A:
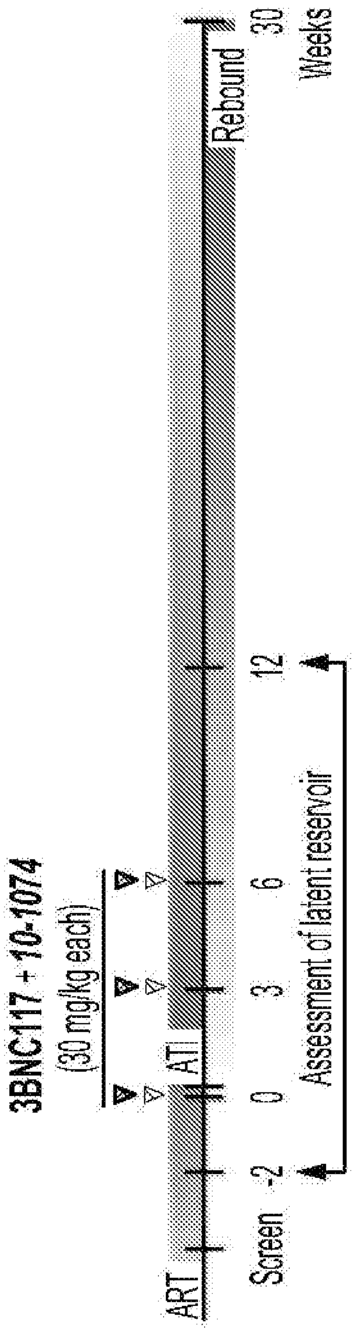
FIGS. 5A, 5B, and 5C (collectively "FIG. 5") show delayed viral rebound with 3BNC117 and 10-1074 combination therapy during analytical treatment interruption (ATI).

Study eligibility criteria included ongoing ART for at least 24 months with plasma HIV-1 RNA levels of <50 copies/ml for at least 18 months (with one blip <500 copies/ml allowed) and <20 copies/ml at screening, as well as $CD4^+$ T cell counts >500 cells/μl. Enrolled participants received 3 infusions of 30 mg/kg each of 3BNC117+10-1074 at 3-week intervals beginning 2 days before treatment interruption (FIG. 5A). Individuals whose regimens contained non-nucleoside reverse transcriptase inhibitors were switched to an integrase inhibitor-based regimen 4 weeks before discontinuing ART (FIG. 6A). Viral load and $CD4^+$ T cell counts were monitored every 1-2 weeks. ART was reinitiated, and antibody infusions were discontinued if viremia of >200 copies/ml was confirmed. Time of viral rebound was defined as the first of two consecutive viral loads >200 copies/ml. Fifteen individuals were enrolled, but four of them showed viral loads of >20 copies/ml two weeks before or at the time of the first bNAb infusion, and they were excluded from efficacy analyses.

Figure 6B:
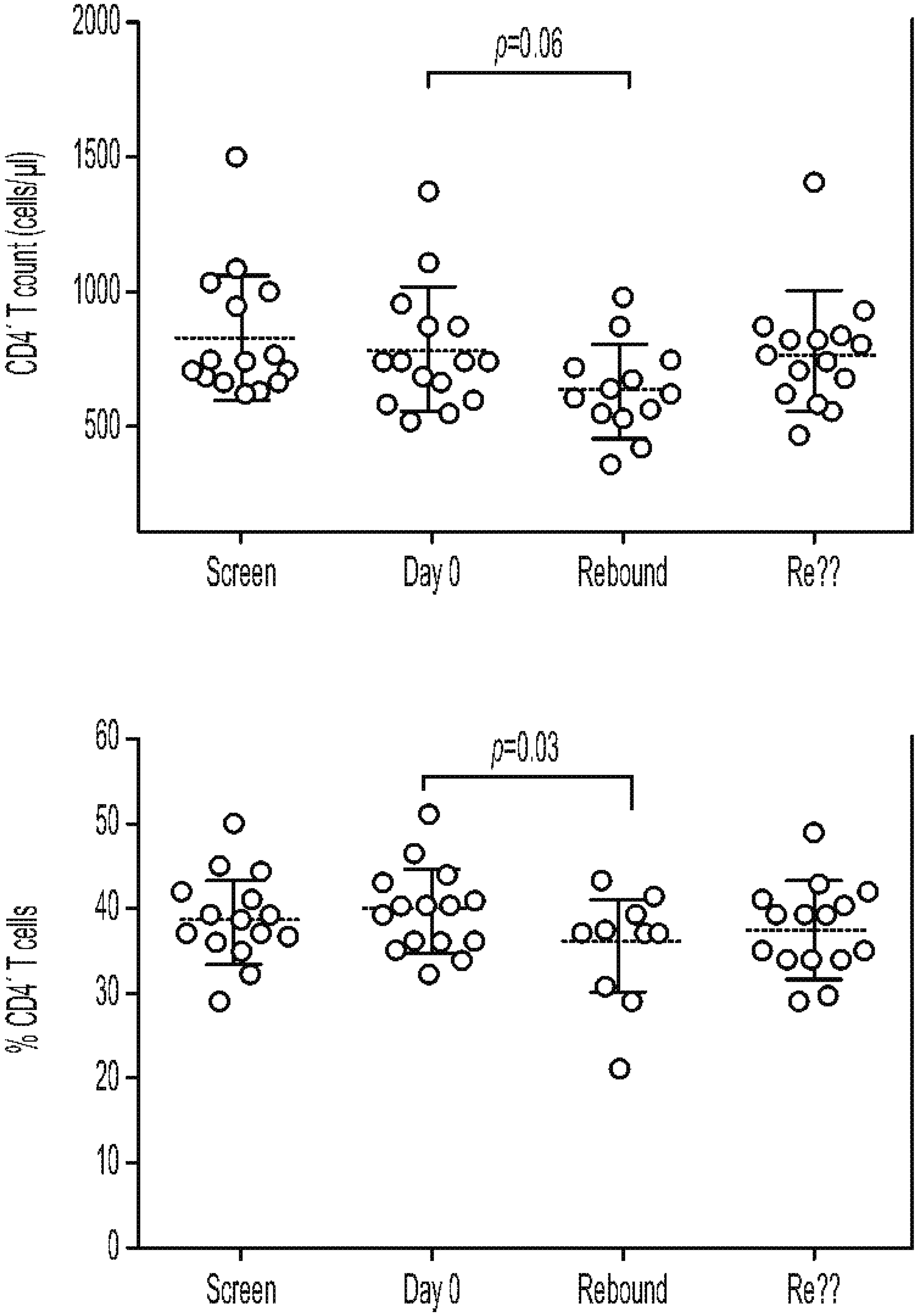
Figure 6C:
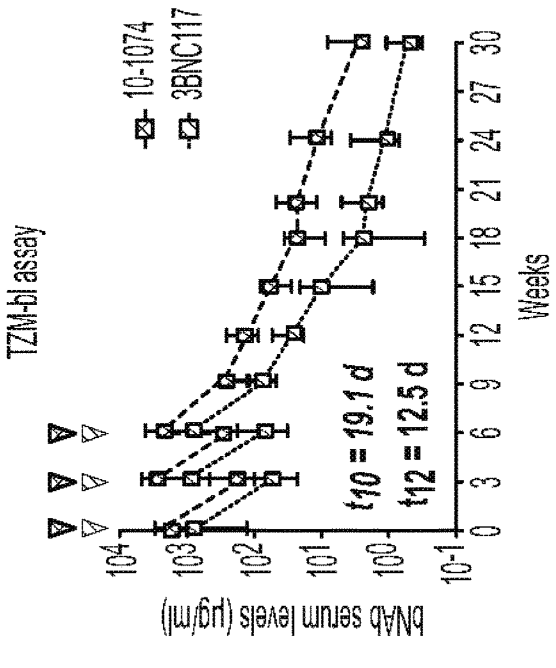
Figure 6D:
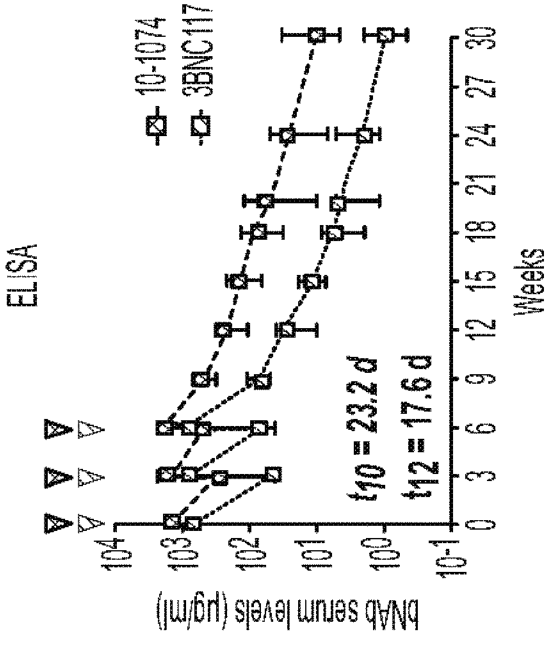
Figure 6E:
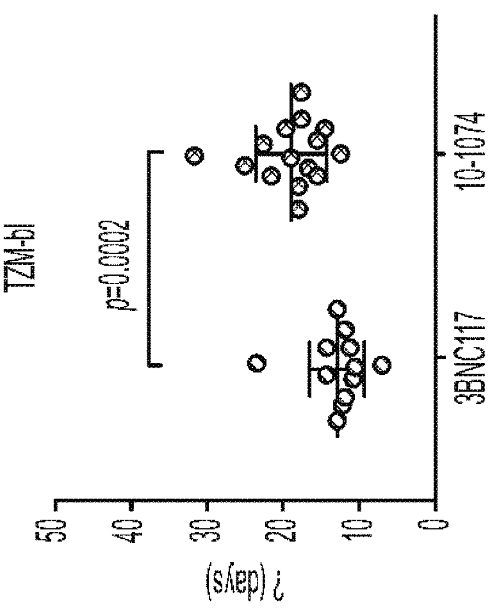
Figure 6F:
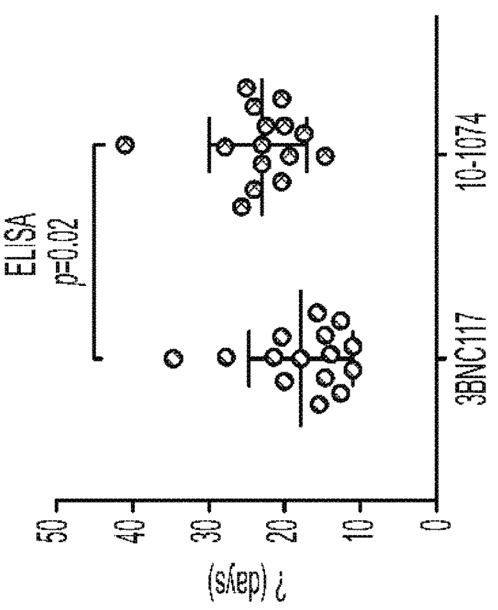

Antibody infusions were generally safe and well-tolerated with no reported serious adverse events or antibody-related adverse events except for mild fatigue in two participants. The mean $CD4^+$ T cell count was 685 and 559 cells/μl at the time of first antibody infusion and at rebound, respectively (FIG. 6B). Re-initiation of ART after viral rebound resulted in resuppression of viremia. It was concluded that combination therapy with 3BNC117+10-1074 is generally safe and well-tolerated.

Combination bNAbs Maintain Viral Suppression

Figure 5B:
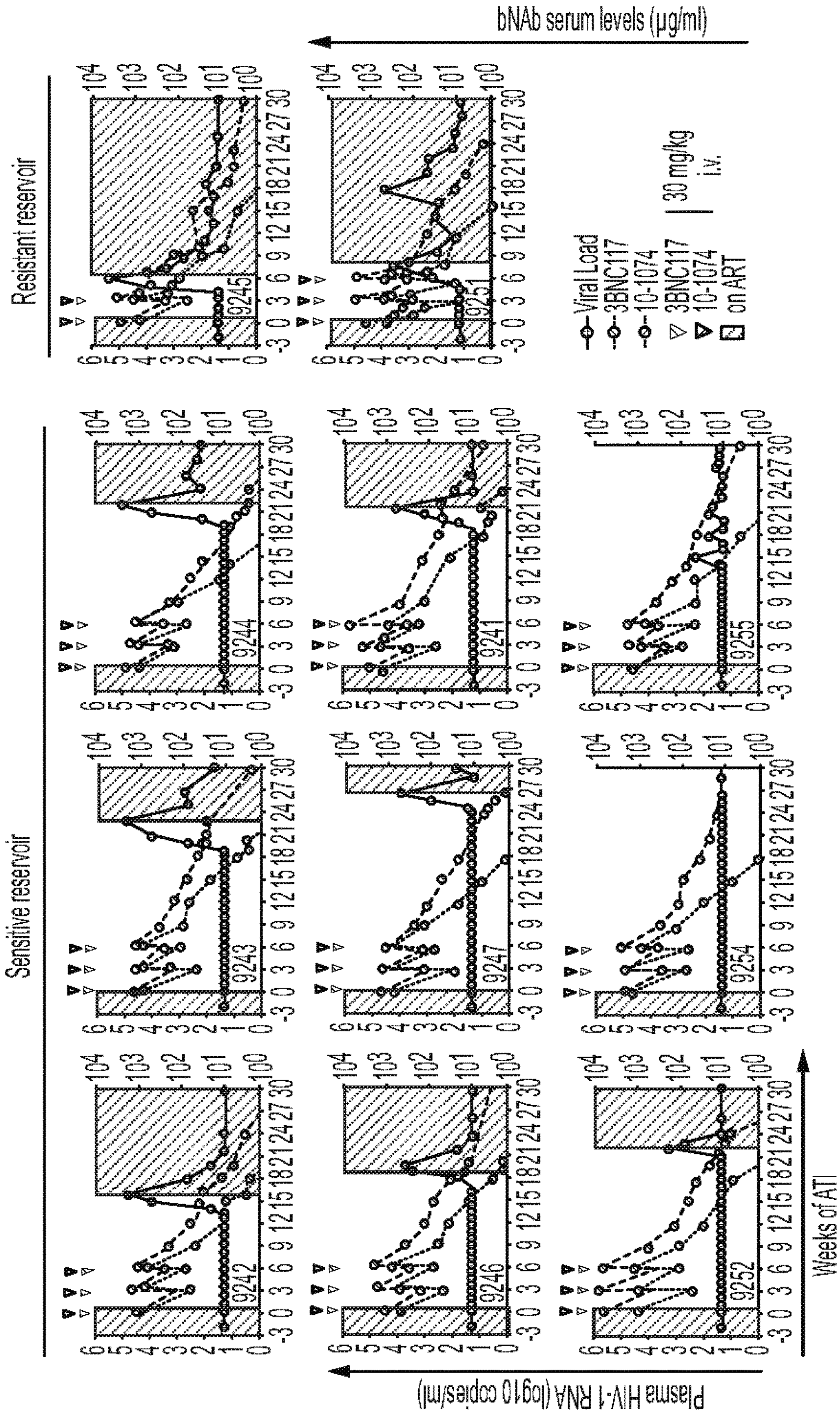
Figure 5C:
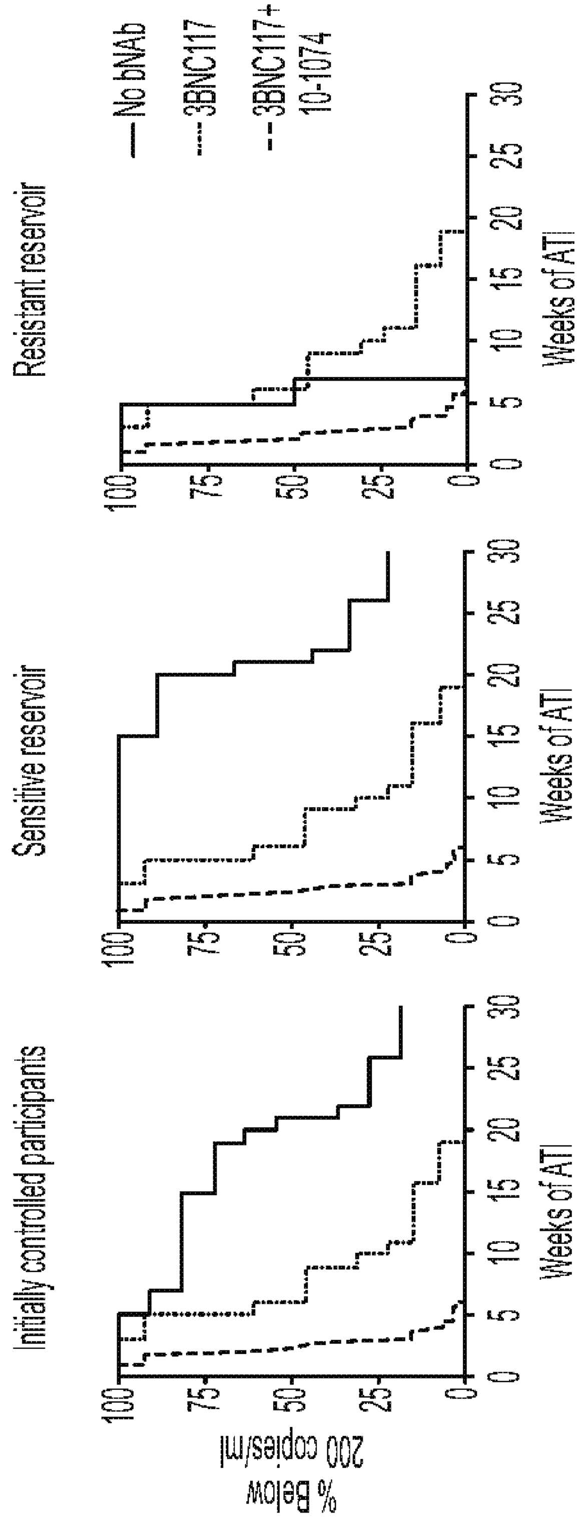

For the 11 individuals who had complete viral suppression (HIV-1 RNA<20 copies/ml) during the screening period and at day 0, combination antibody therapy was associated with maintenance of viral suppression for 5 to >30 weeks (FIGS. 5B and 5C) (Mendoza et al., Nature. 2018 September; 561(7724): 479-484). The median time to rebound was 21 weeks compared to 2.3 weeks for historical controls who participated in non-interventional ATI studies and 6-10 weeks for monotherapy with 3BNC117 (FIG. 5C). Altogether, 9 of the 11 participants maintained viral suppression for over 15 weeks, while 2 rebounded at weeks 5 and 7 (FIGS. 5B and 5C).

Figure 7A:
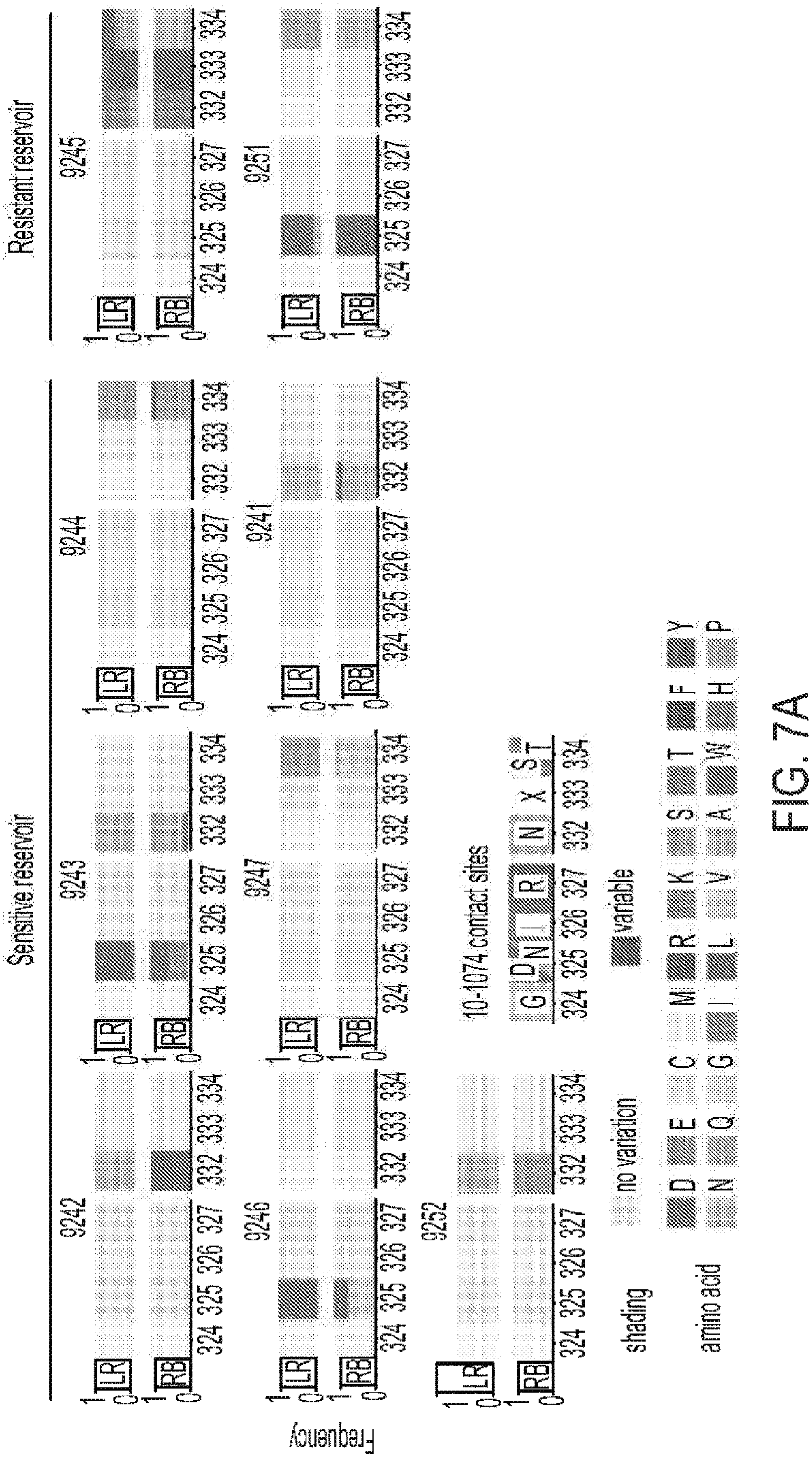
FIGS. 7A, 7B, and 7C (collectively "FIG. 7") show amino acid variants at 10-1074 contact sites and bNAb sensitivity of reactivated latent and rebound viruses.

Quantitative and qualitative viral outgrowth assays ($Q^2$VOA) were used to retrospectively analyze the replication-competent latent viral reservoir in all individuals. Phylogenetic analysis showed that the trial participants were infected with epidemiologically distinct clade B viruses. $Q^2$VOA analysis revealed that the pre-infusion latent reservoir in the two individuals rebounding early, 9245 and 9251, harbored 10-1074- or 3BNC117-resistant viruses, respectively (FIG. 7). Therefore, these two individuals were effectively subjected to antibody monotherapy because there was pre-existing resistance in the reservoir to one of the two bNAbs. Consistent with this idea, the delay in rebound in these two participants was within the range anticipated for antibody monotherapy (FIG. 5C). In addition, all four of the individuals excluded from the analysis due to incomplete viral suppression showed pre-existing resistance or viruses that were not fully neutralized by one or both of the antibodies and these individuals rebounded before week 12.

Figure 7C:
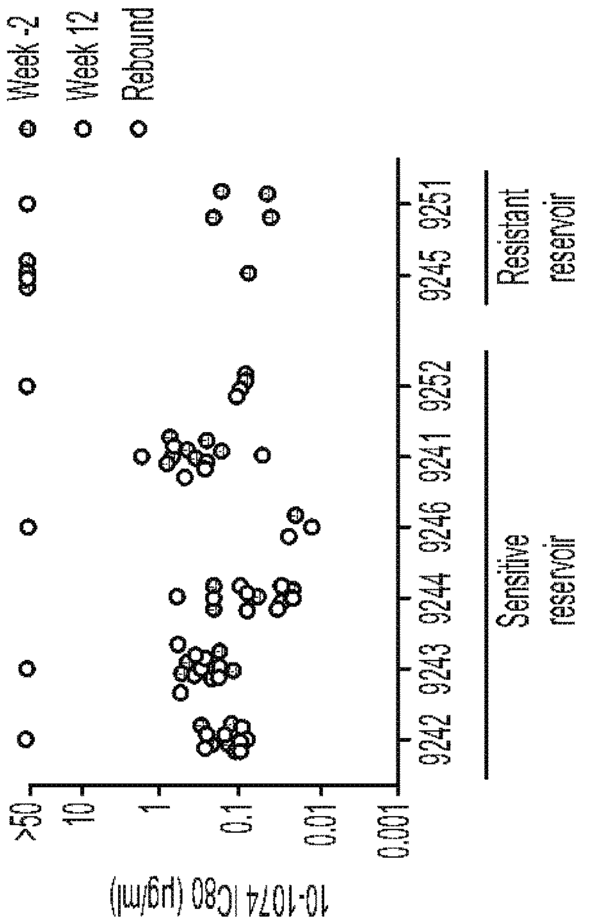
Figure 7B:
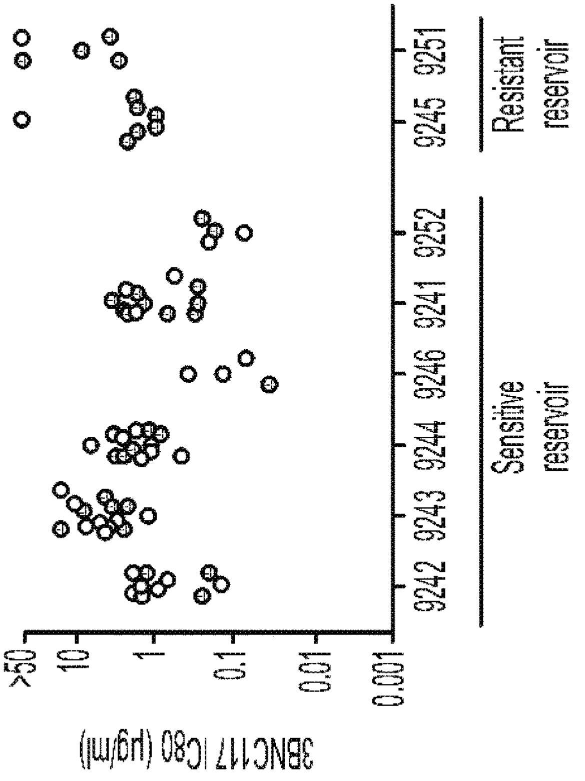

To examine the viruses arising in the early rebounding individuals, single genome analysis (SGA) on rebound plasma was performed. Pseudoviruses constructed from plasma SGA were tested for bNAb sensitivity in the TZM-bl assay. In addition to the pre-existing sequences associated with resistance in the 10-1074 target site (N332T+S334N, FIG. 7A), rebound viruses in 9245 also carried an extended V5 loop and potential N-linked glycosylation sites that could interfere with 3BNC117 binding. Conversely, genetic features associated with resistance to 3BNC117 were found in the pre-infusion reservoir of 9251 and were accompanied by mutations in the 10-1074 target site in the rebounding viruses (S334N, FIG. 7A). For both individuals, resistance of rebound viruses to both antibodies was confirmed by the TZM-bl neutralization assay (FIGS. 7B and 7C). Thus, bulk outgrowth cultures used for screening failed to detect pre-existing resistance in the reservoir of 2 of the 11 individuals studied. This result is not surprising given that bulk cultures are dominated by a limited number of rapidly growing viral species which may not be representative of the diversity in the latent reservoir.

Similarly, participant 91C33, who failed to respond to antibody infusions, had preexisting circulating viruses that were resistant to both antibodies (Bar-On et al., Nature Medicine 24:1701-1707 (2018)). These viruses carried mutations in 3BNC117 contact sites (N280S and A281H) and in 10-1074 contact sites (N332T and S334N). Two individuals, 91C35 and 9341, responded to antibody therapy with a decrease in viremia of −1.58 and −1.32 $\log_{10}$ copies per ml but HIV-1 RNA levels returned to baseline within 3 and 4 weeks, respectively. 91C35 was found to have pre-infusion circulating viruses with reduced sensitivity to 3BNC117, and carried a CD4 contact residue mutation (A281T) that was associated with viral escape from 3BNC11720. Pre-infusion viruses derived from bulk $CD4^+$ T cell outgrowth cultures of 9341 showed a 10-1074 IC80 that was 1.3 $\log_{10}$ higher than the geometric mean IC80 of all other enrolled viremic individuals. In both of these cases, rebounding viruses were resistant to both antibodies and carried mutations resulting in the loss of the potential N-linked glycosylation site at position 332 that is critical for 10-1074 binding. In addition, rebound viruses from 91C35 and 9341 contained G471E and N276D mutations, respectively, that are associated with increased resistance to 3BNC117. These mutations were not found in the pre-infusion circulating viruses described above or in the additional 113 pre-infusion env sequences that were analyzed from these two participants. Thus, 91C35 and 9341 were infected with viruses with reduced sensitivity to one of the two antibodies and resemble individuals that received antibody monotherapy, both in the magnitude of the drop in viremia and time required to return to baseline viremia. It was concluded that the bulk outgrowth cultures used for initial screening failed to detect partial or complete preexisting resistance against one or both of the antibodies in three of the seven individuals studied.

The four remaining individuals showed no detectable pre-existing resistant viruses in circulation and experienced significantly suppressed viremia until day 94 after the first antibody infusion with an average maximum drop in viral load of −2.05 $\log_{10}$ copies per ml (Bar-On et al., Nature Medicine 24:1701-1707 (2018)). The individual in this group with the highest initial viral load (97,800 copies per ml; patient 9343) was the first to rebound at eight weeks. The two individuals with the lowest initial viral loads, 91C22 and 9342 (750 and 2,550 copies per ml, respectively), demonstrated suppression to near or below the limit of detection for 12 and 16 weeks, respectively. Finally, viremia in participant 91C34 was reduced for a period of 12 weeks, however it never dropped below 810 copies per ml. Despite the persistent viremia, no resistance against both antibodies developed in this individual for as long as bNAb serum levels were above 10 μg/ml. In three of the four initially sensitive individuals, rebound viremia was associated with the appearance of viruses that were resistant to 10-1074, but these individuals remained sensitive to 3BNC117. This is consistent with the relatively shorter half-life of 3BNC117, which means that participants were effectively exposed to 10-1074 monotherapy at the end of the observation period. In accordance with the increased resistance to 10-1074, rebound viruses carried mutations in 10-1074 contact sites. By contrast, there was no accumulation of de novo mutations in 3BNC117 contact sites. 91C22, the participant with the lowest initial viral load, only returned to baseline viremia after both antibodies were below the limit of detection, and rebound viruses remained sensitive to both antibodies. Overall none of the four participants that were initially sensitive to the two antibodies developed de novo resistance to 3BNC117 over a cumulative observation period of over one year (56 weeks), despite the residual viremia observed in three of these participants and frequent recombination events between circulating viruses.

The median time to rebound in the 7 individuals that had no detectable resistant viruses in the pre-infusion latent reservoir, and rebounded during the study period, was also 21 weeks and different from 6-10 weeks for monotherapy with 3BNC117 (FIG. 5C) (Mendoza et al., Nature. 2018 September; 561(7724): 479-484). In these participants, viral suppression was maintained for 15 to 26 weeks after ART discontinuation. The two remaining participants (9254 and 9255) completed the study follow-up at 30 weeks without experiencing rebound. Notably, viral rebound never occurred when the concentration of both administered antibodies was above 10 μg/ml. The average 3BNC117 serum concentration (determined by TZM-bl assay) at the time of rebound in sensitive individuals that rebounded during study follow-up was 1.9 μg/ml (FIG. 5B). In contrast, the average serum concentration of 10-1074 at rebound was 14.8 μg/ml (FIG. 5B). The difference in the antibody concentrations at the time of rebound is consistent with the longer half-life of 10-1074 which resulted in a period of 10-1074 monotherapy (FIG. 5B). Finally, these 9 individuals showed little or no preexisting neutralizing antibodies against a diagnostic panel of viruses before bNAb infusion.

Rebound and Latent Viruses

Figure 8:
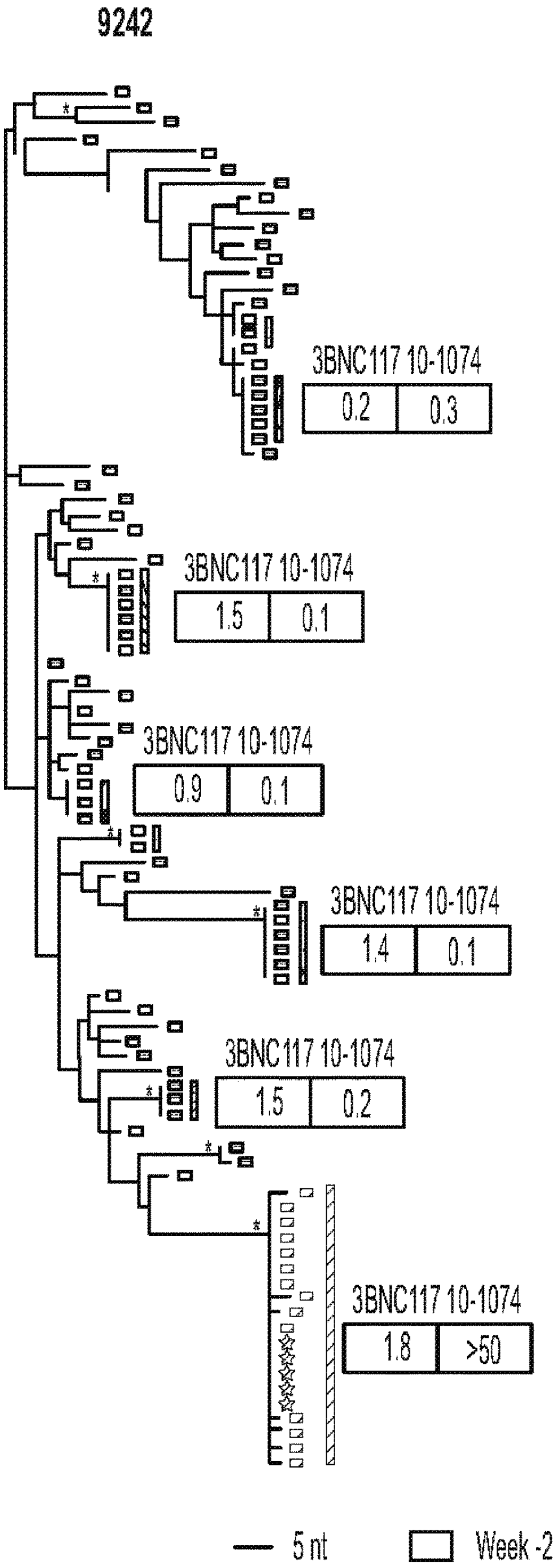
FIG. 8 shows a comparison of the circulating latent reservoir and rebound viruses. Maximum likelihood phylogenetic trees of full-length env sequences of viruses isolated from $Q^2$VOA, rebound plasma SGA, and rebound PBMC outgrowth cultures from 3 out of 7 participants (9242, 9243 and 9252) that rebounded before week 30. Open and closed black rectangles indicate $Q^2$VOA-derived viruses from week −2 and week 12, respectively. Viruses obtained at the time of rebound are indicated by red rectangles (plasma SGA) and red stars (rebound PBMC outgrowth cultures). Asterisks indicate nodes with significant bootstrap values (bootstrap support ≥70%). Boxes indicate IC80s (μg/ml) of 3BNC117 and 10-1074 against representative viruses throughout the phylogenetic tree and clones, when possible. Asterisks in boxes indicate IC100 values of >50 μg/ml.
Figure 8:
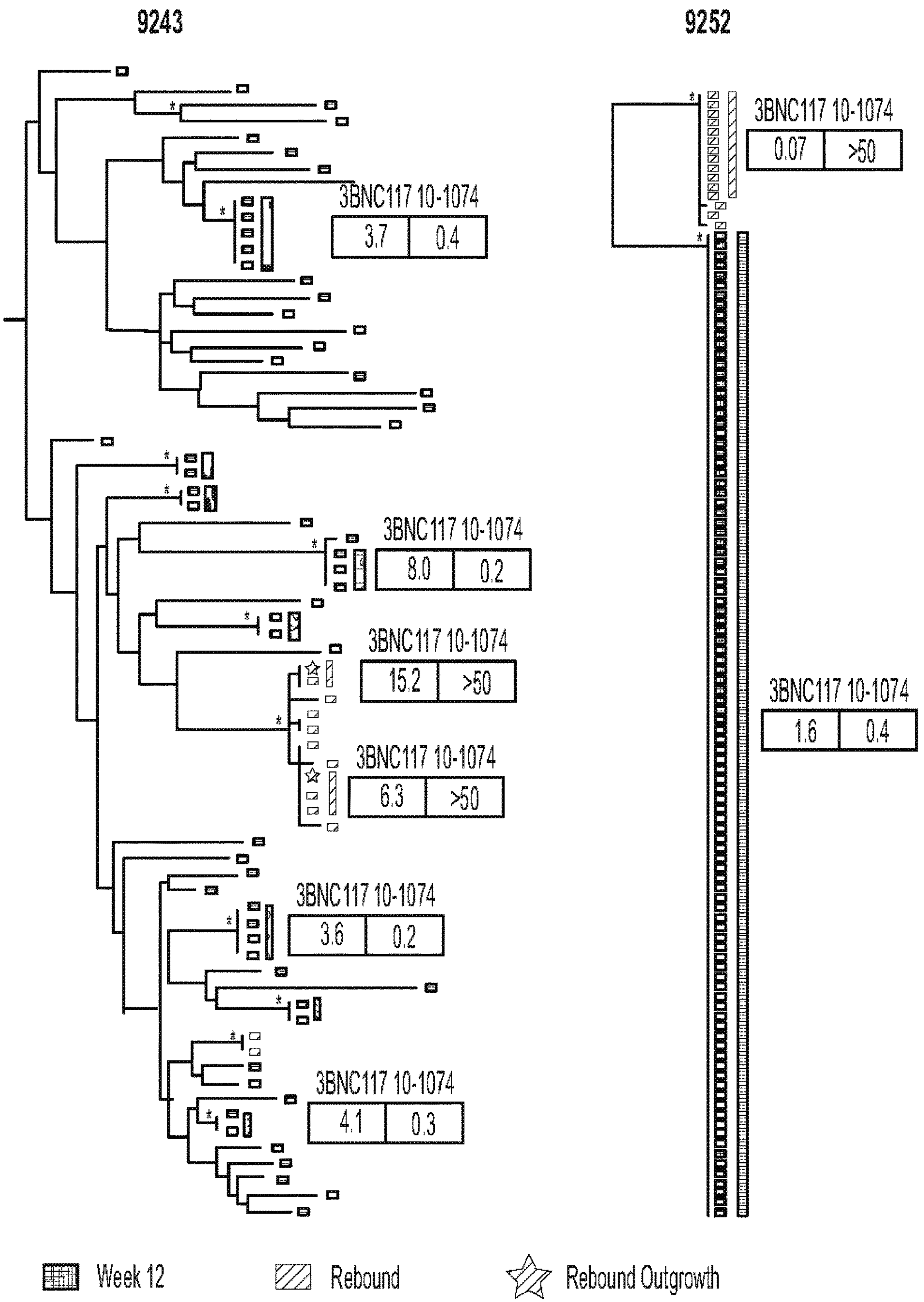
Figure 9A:
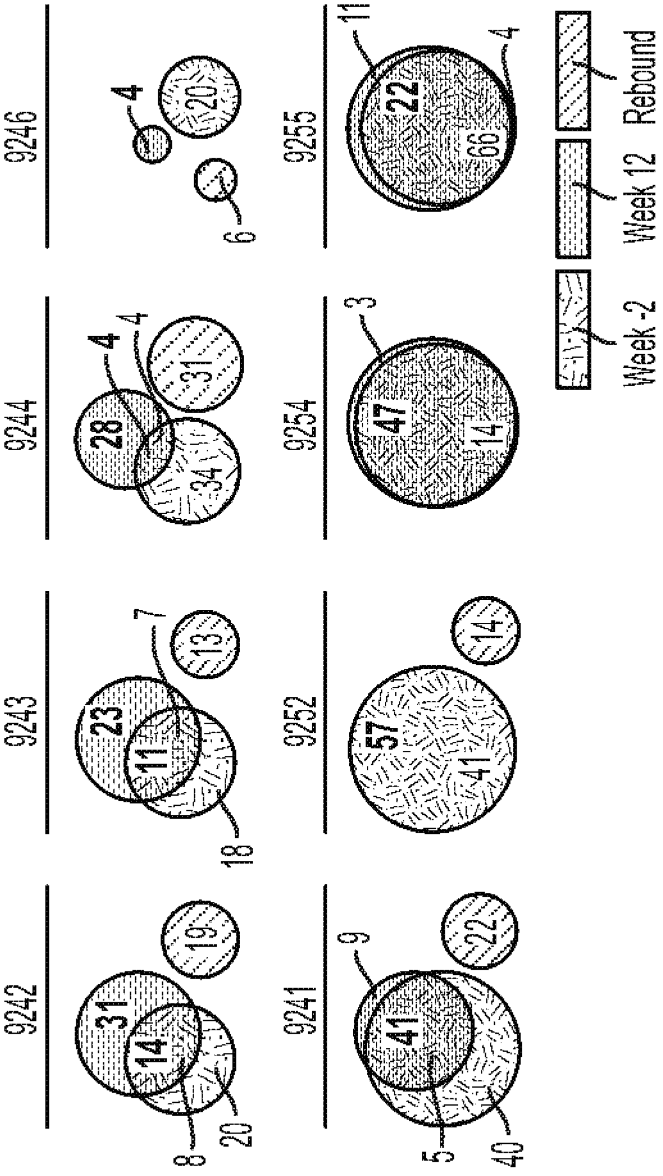
FIGS. 9A and 9B (collectively "FIG. 9") show distribution of the circulating latent reservoir and rebound viruses.

To examine the relationship between rebound viruses and the circulating latent reservoir, env sequences obtained from plasma rebound viruses were compared by SGA with sequences obtained by $Q^2$VOA from both pre-infusion and week 12 samples. In addition, sensitivity of rebound outgrowth viruses and/or pseudoviruses to 3BNC117 and 10-1074 was measured by the TZM-bl neutralization assay (FIGS. 7B and 7C). A total of 154 viral env sequences obtained by plasma SGA were analyzed and compared to 408 sequences obtained from the latent reservoir by $Q^2$VOA. Although rebound and reservoir viruses clustered together for each individual, no identical sequences between the two compartments in any of the individuals studied were found (FIGS. 8 and 9A). The difference could be accounted for by distinct requirements for HIV-1 reactivation in vitro and in vivo, compartmentalization of reservoir viruses, HIV-1 mutation during the course of the trial, and/or by viral recombination in some individuals. Whether or not bNAb therapy influences selection for recombination events remains to be determined.

Similar to 3BNC117 monotherapy, the vast majority of rebounding viruses clustered within low diversity lineages consistent with expansion of 1-2 recrudescent viruses (FIG. 8). In contrast, rebound viruses are consistently polyclonal during ATI in the absence of antibody therapy. Thus, the antibodies restrict the outgrowth of latent viruses in vivo.

The emerging viruses in 6 of the 7 individuals that rebounded when the mean 3BNC117 and 10-1074 concentrations were 1.9 and 14.8 μg/ml, respectively, carried resistance-associated mutations in the 10-1074 target site (FIGS. 5B and 8A). Consistent with the sequence data, these rebound viruses were generally resistant to 10-1074 by the TZM-bl neutralization assay but remained sensitive to 3BNC117 (FIGS. 7B and 7C). The level of sensitivity to 3BNC117 in these emerging viruses was similar to that found in the reservoir viruses in each of the individuals (FIG. 7B). One individual, 9244, showed rebound viruses that remained sensitive to both antibodies in TZM-bl neutralization assays. Rebound occurred when 3BNC117 and 10-1074 concentrations in serum of this individual were undetectable and 11.6 μg/ml, respectively (FIG. 5B). The sensitivity of the plasma rebound viruses was similar to that of latent pre-infusion and week 12 viruses obtained in viral outgrowth cultures (FIGS. 7B and 7C). Therefore, this individual did not develop resistance to either of the antibodies despite prolonged exposure to both. In conclusion, none of the 9 individuals with pre-infusion reservoirs containing viruses that were sensitive to both antibodies developed double resistance during the observation period.

The Latent Reservoir

Figure 9B:
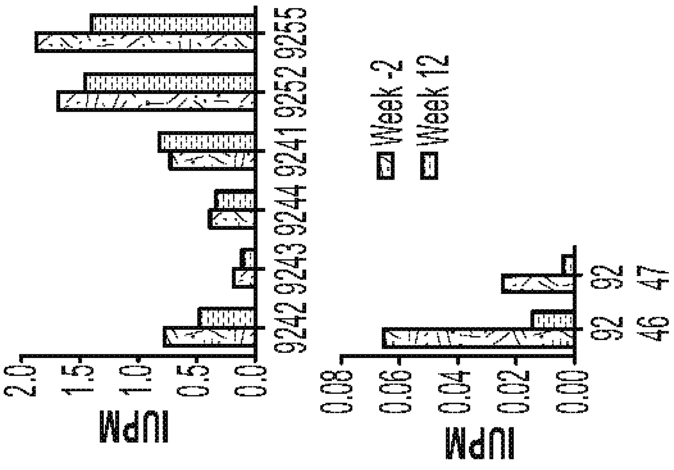

To determine whether there were changes in the circulating reservoir during the observation period, the results of $Q^2$VOA assays performed at entry and 12 weeks after the start of ATI for 8 of the 9 individuals that remained suppressed for at least 12 weeks were compared (FIG. 9). Similar to previous reports, 63% of all viruses obtained by $Q^2$VOA belonged to expanded clones. Comparison of the env sequences of the viruses that emerged in outgrowth cultures revealed that 60% of the sequences could be found at both time points. However, there were numerous examples of clones that appeared or disappeared between the time points, and some of these changes were significant. To determine the number of infectious units per million (IUPM, http://silicianolab.johnshopkins.edu/), $6.0\times10^7$-$6.2\times10^8$ $CD4^+$ T cells were assayed by $Q^2$VOA for each time point for each individual (FIG. 9B). The difference between the 2 time points was never greater than 6.5-fold for any individual, and the 2 time points were not statistically different (P=0.078). Moreover, time to rebound was not directly correlated with IUPM. Additional time points would be required to calculate the half-life of the reservoir in individuals receiving immunotherapy.

Discussion

First generation anti-HIV-1 bNAbs were generally ineffective in suppressing viremia in animal models and humans leading to the conclusion that this approach should not be pursued. bNAb monotherapy with 3BNC117 or VRC01 was not enough to maintain control during ATI in HIV-1-infected humans. In contrast, the combination of 3BNC117 and 10-1074 was sufficient to maintain viral suppression in sensitive individuals when the concentration of both antibodies remains above a certain level in serum, for example, above 10 μg/ml. Rebound occurred when 3BNC117 levels dropped below 10 μg/ml effectively leading to 10-1074 monotherapy, from which nearly all individuals rapidly escaped by mutations in the 10-1074 contact site. The observation that 9 individuals infected with distinct viruses were unable to develop double resistant viruses over a median 21 week period suggests that viral replication was severely limited by this antibody combination.

In human studies, monotherapy with 3BNC117 is associated with enhanced humoral immunity and accelerated clearance of HIV-1-infected cells. In addition, when administered early to SHIVAD8-infected macaques, combined 3BNC117+10-1074 immunotherapy induced host $CD8^+$ T cell responses that contributed to the control of viremia in nearly 50% of the animals. However, virus-specific $CD8^+$ T cells responsible for control of viremia in these macaques were not detected in the circulation, and their contribution to viral suppression was only documented after $CD8^+$ T cell depletion. In most controller macaques, complete viral suppression was only established after rebound viremia that followed antibody clearance.

Two individuals in this study remained suppressed for over 30 weeks after ATI, 9254 and 9255. Neither one had detectable levels of ART in the blood or carried the B*27 and B*57 HLA alleles that are most frequently associated with elite control (Walker B D & Yu X G. Nat Rev Immunol 13, 487-498 (2013)). The first, 9254, reports starting ART within 4-5 months after probable exposure to the virus with an initial viral load of 860,000 copies/ml. Despite relatively early therapy and excellent virological control for 21 years on therapy, this individual had an IUPM of 0.68 by $Q^2$VOA at the 12-week time point. The second individual, 9255, showed several viral blips that were spontaneously controlled beginning 15 weeks after ATI when antibody levels were waning. This individual was infected for at least 7 months before starting ART with an initial viral load of 85,800 copies/ml and had an IUPM of 1.4 at the 12-week time point. A small fraction of individuals on ART show spontaneous prolonged virologic control after ART was discontinued, and this number appears to increase when ART treatment was initiated during the acute phase of infection.

A significant fraction of the circulating latent reservoir is composed of expanded clones of infected T cells. These T cell clones appear to be dynamic in that the specific contribution of individual clones of circulating latently infected $CD4^+$ T cells to the reservoir of individuals receiving ART fluctuates over time. Individuals that maintain viral suppression by antibody therapy appear to show similar fluctuations in reservoir clones that do not appear to be associated with antibody sensitivity. Whether the apparent differences observed in the reservoir during immunotherapy lead to changes in the reservoir half-life cannot be determined from the available data and will require reservoir assessments in additional individuals at multiple time points over an extended observation period.

Individuals harboring viruses sensitive to 3BNC117 and 10-1074 maintained viral suppression during ATI for a median of almost 4 months after the final antibody administration. In macaques, the therapeutic efficacy of anti-HIV-1 antibodies is directly related to their half-life, which can be extended by mutations that enhance Fc domain interactions with the neonatal Fc receptor. The mutations can increase the half-life of antibodies in humans by 2-4-fold. The data suggest that a single administration of combinations of bNAbs with extended half-lives could maintain suppression for 6-12 months in individuals harboring sensitive viruses.

TABLE 1

| Residue numbering of anti-HIV antibody 10-1074 variant MS-194 | | | | | | | |
|---|---|---|---|---|---|---|---|
| MS-194_LC | | | | MS-194_HC | | | |
| Residue | Linear # | Mat. Linear # | ASN # | Residue | Linear # | Mat. Linear # | ASN # |
| M | 1 | | Ldr: −19 | M | 1 | | Ldr: −19 |
| G | 2 | | Ldr: −18 | G | 2 | | Ldr: −18 |
| W | 3 | | Ldr: −17 | W | 3 | | Ldr: −17 |
| S | 4 | | Ldr: −16 | S | 4 | | Ldr: −16 |
| C | 5 | | Ldr: −15 | C | 5 | | Ldr: −15 |
| I | 6 | | Ldr: −14 | I | 6 | | Ldr: −14 |
| I | 7 | | Ldr: −13 | I | 7 | | Ldr: −13 |
| L | 8 | | Ldr: −12 | L | 8 | | Ldr: −12 |
| F | 9 | | Ldr: −11 | F | 9 | | Ldr: −11 |
| L | 10 | | Ldr: −10 | L | 10 | | Ldr: −10 |
| V | 11 | | Ldr: −9 | V | 11 | | Ldr: −9 |
| A | 12 | | Ldr: −8 | A | 12 | | Ldr: −8 |
| T | 13 | | Ldr: −7 | T | 13 | | Ldr: −7 |
| A | 14 | | Ldr: −6 | A | 14 | | Ldr: −6 |
| T | 15 | | Ldr: −5 | T | 15 | | Ldr: −5 |
| G | 16 | | Ldr: −4 | G | 16 | | Ldr: −4 |
| V | 17 | | Ldr: −3 | V | 17 | | Ldr: −3 |
| H | 18 | | Ldr: −2 | H | 18 | | Ldr: −2 |
| S | 19 | | Ldr: −1 | S | 19 | | Ldr: −1 |
| S | 20 | 1 | LmdV: 1 | Q | 20 | 1 | HV: 1 |
| Y | 21 | 2 | LmdV: 2 | V | 21 | 2 | HV: 2 |
| V | 22 | 3 | LmdV: 3 | Q | 22 | 3 | HV: 3 |
| — | 22.1 | 3.1 | LmdV: 4 | L | 23 | 4 | HV: 4 |
| — | 22.2 | 3.2 | LmdV: 5 | Q | 24 | 5 | HV: 5 |
| — | 22.3 | 3.3 | LmdV: 6 | E | 25 | 6 | HV: 6 |
| R | 23 | 4 | LmdV: 7 | S | 26 | 7 | HV: 7 |
| — | 23.1 | 4.1 | LmdV: 8 | — | 26.1 | 7.1 | HV: 8 |
| P | 24 | 5 | LmdV: 9 | G | 27 | 8 | HV: 9 |
| — | 24.1 | 5.1 | LmdV: 10 | P | 28 | 9 | HV: 10 |
| L | 25 | 6 | LmdV: 111 | G | 29 | 10 | HV: 11 |
| S | 26 | 7 | LmdV: 12 | L | 30 | 11 | HV: 12 |
| V | 27 | 8 | LmdV: 13 | V | 31 | 12 | HV: 13 |
| A | 28 | 9 | LmdV: 14 | K | 32 | 13 | HV: 14 |
| L | 29 | 10 | LmdV: 15 | P | 33 | 14 | HV: 15 |
| G | 30 | 11 | LmdV: 16 | S | 34 | 15 | HV: 16 |
| E | 31 | 12 | LmdV: 17 | E | 35 | 16 | HV: 17 |
| T | 32 | 13 | LmdV: 18 | T | 36 | 17 | HV: 18 |
| A | 33 | 14 | LmdV: 19 | L | 37 | 18 | HV: 19 |
| R | 34 | 15 | LmdV: 20 | S | 38 | 19 | HV: 20 |
| I | 35 | 16 | LmdV: 21 | V | 39 | 20 | HV: 21 |
| S | 36 | 17 | LmdV: 22 | T | 40 | 21 | HV: 22 |
| C | 37 | 18 | LmdV: 23 | C | 41 | 22 | HV: 23 |
| G | 38 | 19 | LmdV: 24 | S | 42 | 23 | HV: 24 |
| R | 39 | 20 | LmdV: 25 | V | 43 | 24 | HV: 25 |
| Q | 40 | 21 | LmdV: 26 | S | 44 | 25 | HV: 26 |
| — | 40.1 | 21.1 | LmdV: 27 | G | 45 | 26 | HV: 27 |
| — | 40.2 | 21.2 | LmdV: 28 | — | 45.1 | 26.1 | HV: 28 |
| — | 40.3 | 21.3 | LmdV: 29 | D | 46 | 27 | HV: 29 |
| A | 41 | 22 | LmdV: 30 | S | 47 | 28 | HV: 30 |
| L | 42 | 23 | LmdV: 31 | M | 48 | 29 | HV: 31 |
| G | 43 | 24 | LmdV: 32 | N | 49 | 30 | HV: 32 |
| S | 44 | 25 | LmdV: 33 | N | 50 | 31 | HV: 33 |
| — | 44.1 | 25.1 | LmdV: 34 | — | 50.1 | 31.1 | HV: 34 |
| — | 44.2 | 25.2 | LmdV: 35 | — | 50.2 | 31.2 | HV: 35 |
| — | 44.3 | 25.3 | LmdV: 36 | — | 50.3 | 31.3 | HV: 36 |
| — | 44.4 | 25.4 | LmdV: 37 | — | 50.4 | 31.4 | HV: 37 |
| — | 44.5 | 25.5 | LmdV: 38 | — | 50.5 | 31.5 | HV: 38 |
| R | 45 | 26 | LmdV: 39 | Y | 51 | 32 | HV: 39 |
| A | 46 | 27 | LmdV: 40 | Y | 52 | 33 | HV: 40 |
| V | 47 | 28 | LmdV: 41 | W | 53 | 34 | HV: 41 |
| Q | 48 | 29 | LmdV: 42 | T | 54 | 35 | HV: 42 |
| W | 49 | 30 | LmdV: 43 | W | 55 | 36 | HV: 43 |
| Y | 50 | 31 | LmdV: 44 | I | 56 | 37 | HV: 44 |
| Q | 51 | 32 | LmdV: 45 | R | 57 | 38 | HV: 45 |
| H | 52 | 33 | LmdV: 46 | Q | 58 | 39 | HV: 46 |
| R | 53 | 34 | LmdV: 47 | S | 59 | 40 | HV: 47 |
| P | 54 | 35 | LmdV: 48 | P | 60 | 41 | HV: 48 |
| G | 55 | 36 | LmdV: 49 | G | 61 | 42 | HV: 49 |
| Q | 56 | 37 | LmdV: 50 | K | 62 | 43 | HV: 50 |
| A | 57 | 38 | LmdV: 51 | G | 63 | 44 | HV: 51 |
| P | 58 | 39 | LmdV: 52 | L | 64 | 45 | HV: 52 |
| I | 59 | 40 | LmdV: 53 | E | 65 | 46 | HV: 53 |
| L | 60 | 41 | LmdV: 54 | W | 66 | 47 | HV: 54 |

TABLE 1-continued

Residue numbering of anti-HIV antibody 10-1074 variant MS-194

| MS-194_LC | | | | MS-194_HC | | | |
|---|---|---|---|---|---|---|---|
| Residue | Linear # | Mat. Linear # | ASN # | Residue | Linear # | Mat. Linear # | ASN # |
| L | 61 | 42 | LmdV: 55 | I | 67 | 48 | HV: 55 |
| I | 62 | 43 | LmdV: 56 | G | 68 | 49 | HV: 56 |
| Y | 63 | 44 | LmdV: 57 | Y | 69 | 50 | HV: 57 |
| N | 64 | 45 | LmdV: 58 | I | 70 | 51 | HV: 58 |
| — | 64.1 | 45.1 | LmdV: 59 | S | 71 | 52 | HV: 59 |
| — | 64.2 | 45.2 | LmdV: 60 | D | 72 | 53 | HV: 60 |
| — | 64.3 | 45.3 | LmdV: 61 | — | 72.1 | 53.1 | HV: 61 |
| — | 64.4 | 45.4 | LmdV: 62 | — | 72.2 | 53.2 | HV: 62 |
| — | 64.5 | 45.5 | LmdV: 63 | — | 72.3 | 53.3 | HV: 63 |
| — | 64.6 | 45.6 | LmdV: 64 | — | 72.4 | 53.4 | HV: 64 |
| — | 64.7 | 45.7 | LmdV: 65 | R | 73 | 54 | HV: 65 |
| — | 64.8 | 45.8 | LmdV: 66 | E | 74 | 55 | HV: 66 |
| N | 65 | 46 | LmdV: 67 | S | 75 | 56 | HV: 67 |
| Q | 66 | 47 | LmdV: 68 | A | 76 | 57 | HV: 68 |
| D | 67 | 48 | LmdV: 69 | T | 77 | 58 | HV: 69 |
| R | 68 | 49 | LmdV: 70 | Y | 78 | 59 | HV: 70 |
| P | 69 | 50 | LmdV: 71 | N | 79 | 60 | HV: 71 |
| S | 70 | 51 | LmdV: 72 | P | 80 | 61 | HV: 72 |
| G | 71 | 52 | LmdV: 73 | S | 81 | 62 | HV: 73 |
| I | 72 | 53 | LmdV: 74 | L | 82 | 63 | HV: 74 |
| P | 73 | 54 | LmdV: 75 | N | 83 | 64 | HV: 75 |
| E | 74 | 55 | LmdV: 76 | S | 84 | 65 | HV: 76 |
| R | 75 | 56 | LmdV: 77 | R | 85 | 66 | HV: 77 |
| F | 76 | 57 | LmdV: 78 | V | 86 | 67 | HV: 78 |
| S | 77 | 58 | LmdV: 79 | V | 87 | 68 | HV: 79 |
| G | 78 | 59 | LmdV: 80 | I | 88 | 69 | HV: 80 |
| T | 79 | 60 | LmdV: 81 | S | 89 | 70 | HV: 81 |
| P | 80 | 61 | LmdV: 81.1 | R | 90 | 71 | HV: 82 |
| D | 81 | 62 | LmdV: 81.2 | D | 91 | 72 | HV: 83 |
| I | 82 | 63 | LmdV: 81.3 | T | 92 | 73 | HV: 84 |
| N | 83 | 64 | LmdV: 82 | S | 93 | 74 | HV: 85 |
| F | 84 | 65 | LmdV: 83 | K | 94 | 75 | HV: 86 |
| G | 85 | 66 | LmdV: 84 | N | 95 | 76 | HV: 87 |
| — | 85.1 | 66.1 | LmdV: 85 | Q | 96 | 77 | HV: 88 |
| — | 85.2 | 66.2 | LmdV: 86 | L | 97 | 78 | HV: 89 |
| T | 86 | 67 | LmdV: 87 | S | 98 | 79 | HV: 90 |
| R | 87 | 68 | LmdV: 88 | L | 99 | 80 | HV: 91 |
| A | 88 | 69 | LmdV: 89 | K | 100 | 81 | HV: 92 |
| T | 89 | 70 | LmdV: 90 | L | 101 | 82 | HV: 93 |
| L | 90 | 71 | LmdV: 91 | N | 102 | 83 | HV: 94 |
| T | 91 | 72 | LmdV: 92 | S | 103 | 84 | HV: 95 |
| I | 92 | 73 | LmdV: 93 | V | 104 | 85 | HV: 96 |
| S | 93 | 74 | LmdV: 94 | T | 105 | 86 | HV: 97 |
| G | 94 | 75 | LmdV: 95 | P | 106 | 87 | HV: 98 |
| V | 95 | 76 | LmdV: 96 | A | 107 | 88 | HV: 99 |
| E | 96 | 77 | LmdV: 97 | D | 108 | 89 | HV: 100 |
| A | 97 | 78 | LmdV: 98 | T | 109 | 90 | HV: 101 |
| G | 98 | 79 | LmdV: 99 | A | 110 | 91 | HV: 102 |
| D | 99 | 80 | LmdV: 100 | V | 111 | 92 | HV: 103 |
| E | 100 | 81 | LmdV: 101 | Y | 112 | 93 | HV: 104 |
| A | 101 | 82 | LmdV: 102 | Y | 113 | 94 | HV: 105 |
| D | 102 | 83 | LmdV: 103 | C | 114 | 95 | HV: 106 |
| Y | 103 | 84 | LmdV: 104 | A | 115 | 96 | HV: 107 |
| Y | 104 | 85 | LmdV: 105 | T | 116 | 97 | HV: 108 |
| C | 105 | 86 | LmdV: 106 | A | 117 | 98 | HV: 109 |
| H | 106 | 87 | LmdV: 107 | R | 118 | 99 | HV: 110 |
| M | 107 | 88 | LmdV: 108 | R | 119 | 100 | HV: 111 |
| W | 108 | 89 | LmdV: 109 | G | 120 | 101 | HV: 112 |
| D | 109 | 90 | LmdV: 110 | Q | 121 | 102 | HV: 113 |
| S | 110 | 91 | LmdV: 111 | R | 122 | 103 | HV: 114 |
| R | 111 | 92 | LmdV: 112 | I | 123 | 104 | HV: 115 |
| — | 111.1 | 92.1 | LmdV: 113 | Y | 124 | 105 | HV: 116 |
| — | 111.2 | 92.2 | LmdV: 114 | G | 125 | 106 | HV: 117 |
| — | 111.3 | 92.3 | LmdV: 115 | V | 126 | 107 | HV: 118 |
| — | 111.4 | 92.4 | LmdV: 116 | V | 127 | 108 | HV: 119 |
| — | 111.5 | 92.5 | LmdV: 117 | — | 127.1 | 108.1 | HV: 120 |
| — | 111.6 | 92.6 | LmdV: 118 | — | 127.2 | 108.2 | HV: 121 |
| — | 111.7 | 92.7 | LmdV: 119 | — | 127.3 | 108.3 | HV: 122 |
| — | 111.8 | 92.8 | LmdV: 120 | — | 127.4 | 108.4 | HV: 123 |
| — | 111.9 | 92.9 | LmdV: 121 | — | 127.5 | 108.5 | HV: 124 |
| — | 111.10 | 92.10 | LmdV: 122 | — | 127.6 | 108.6 | HV: 125 |
| — | 111.11 | 92.11 | LmdV: 123 | S | 128 | 109 | HV: 126 |
| — | 111.12 | 92.12 | LmdV: 124 | F | 129 | 110 | HV: 127 |

TABLE 1-continued

Residue numbering of anti-HIV antibody 10-1074 variant MS-194

| MS-194_LC | | | | MS-194_HC | | | |
|---|---|---|---|---|---|---|---|
| Residue | Linear # | Mat. Linear # | ASN # | Residue | Linear # | Mat. Linear # | ASN # |
| — | 111.13 | 92.13 | LmdV: 125 | G | 130 | 111 | HV: 128 |
| — | 111.14 | 92.14 | LmdV: 126 | E | 131 | 112 | HV: 129 |
| — | 111.15 | 92.15 | LmdV: 127 | F | 132 | 113 | HV: 130 |
| — | 111.16 | 92.16 | LmdV: 128 | F | 133 | 114 | HV: 131 |
| — | 111.17 | 92.17 | LmdV: 129 | Y | 134 | 115 | HV: 132 |
| — | 111.18 | 92.18 | LmdV: 130 | Y | 135 | 116 | HV: 133 |
| — | 111.19 | 92.19 | LmdV: 131 | Y | 136 | 117 | HV: 134 |
| — | 111.20 | 92.20 | LmdV: 132 | S | 137 | 118 | HV: 135 |
| S | 112 | 93 | LmdV: 133 | M | 138 | 119 | HV: 136 |
| G | 113 | 94 | LmdV: 134 | D | 139 | 120 | HV: 137 |
| F | 114 | 95 | LmdV: 135 | V | 140 | 121 | HV: 138 |
| S | 115 | 96 | LmdV: 136 | W | 141 | 122 | HV: 139 |
| W | 116 | 97 | LmdV: 137 | G | 142 | 123 | HV: 140 |
| S | 117 | 98 | LmdV: 138 | K | 143 | 124 | HV: 141 |
| F | 118 | 99 | LmdV: 139 | G | 144 | 125 | HV: 142 |
| G | 119 | 100 | LmdV: 140 | T | 145 | 126 | HV: 143 |
| G | 120 | 101 | LmdV: 141 | T | 146 | 127 | HV: 144 |
| A | 121 | 102 | LmdV: 142 | V | 147 | 128 | HV: 145 |
| T | 122 | 103 | LmdV: 143 | T | 148 | 129 | HV: 146 |
| R | 123 | 104 | LmdV: 144 | V | 149 | 130 | HV: 147 |
| L | 124 | 105 | LmdV: 145 | S | 150 | 131 | HV: 148 |
| T | 125 | 106 | LmdV: 146 | S | 151 | 132 | HV: 149 |
| V | 126 | 107 | LmdV: 147 | — | 151.1 | 132.1 | HCnst-Ig: 1 |
| L | 127 | 108 | LmdV: 148 | — | 151.2 | 132.2 | HCnst-Ig: 2 |
| G | 128 | 109 | LmdV: 149 | A | 152 | 133 | HCnst-Ig: 3 |
| Q | 129 | 110 | LmdCnst-Ig: 1 | S | 153 | 134 | HCnst-Ig: 4 |
| P | 130 | 111 | LmdCnst-Ig: 2 | T | 154 | 135 | HCnst-Ig: 5 |
| K | 131 | 112 | LmdCnst-Ig: 3 | K | 155 | 136 | HCnst-Ig: 6 |
| A | 132 | 113 | LmdCnst-Ig: 4 | G | 156 | 137 | HCnst-Ig: 7 |
| A | 133 | 114 | LmdCnst-Ig: 5 | P | 157 | 138 | HCnst-Ig: 8 |
| P | 134 | 115 | LmdCnst-Ig: 6 | S | 158 | 139 | HCnst-Ig: 9 |
| S | 135 | 116 | LmdCnst-Ig: 7 | V | 159 | 140 | HCnst-Ig: 10 |
| V | 136 | 117 | LmdCnst-Ig: 8 | F | 160 | 141 | HCnst-Ig: 11 |
| T | 137 | 118 | LmdCnst-Ig: 9 | P | 161 | 142 | HCnst-Ig: 12 |
| L | 138 | 119 | LmdCnst-Ig: 10 | L | 162 | 143 | HCnst-Ig: 13 |
| F | 139 | 120 | LmdCnst-Ig: 11 | A | 163 | 144 | HCnst-Ig: 14 |
| P | 140 | 121 | LmdCnst-Ig: 12 | P | 164 | 145 | HCnst-Ig: 15 |
| P | 141 | 122 | LmdCnst-Ig: 13 | — | 164.1 | 145.1 | HCnst-Ig: 16 |
| S | 142 | 123 | LmdCnst-Ig: 14 | S | 165 | 146 | HCnst-Ig: 17 |
| S | 143 | 124 | LmdCnst-Ig: 15 | — | 165.1 | 146.1 | HCnst-Ig: 18 |
| E | 144 | 125 | LmdCnst-Ig: 16 | S | 166 | 147 | HCnst-Ig: 19 |
| — | 144.1 | 125.1 | LmdCnst-Ig: 17 | K | 167 | 148 | HCnst-Ig: 20 |
| — | 144.2 | 125.2 | LmdCnst-Ig: 18 | S | 168 | 149 | HCnst-Ig: 21 |
| E | 145 | 126 | LmdCnst-Ig: 19 | T | 169 | 150 | HCnst-Ig: 22 |
| L | 146 | 127 | LmdCnst-Ig: 20 | S | 170 | 151 | HCnst-Ig: 23 |
| — | 146.1 | 127.1 | LmdCnst-Ig: 21 | G | 171 | 152 | HCnst-Ig: 24 |
| — | 146.2 | 127.2 | LmdCnst-Ig: 22 | G | 172 | 153 | HCnst-Ig: 25 |
| Q | 147 | 128 | LmdCnst-Ig: 23 | T | 173 | 154 | HCnst-Ig: 26 |
| A | 148 | 129 | LmdCnst-Ig: 24 | A | 174 | 155 | HCnst-Ig: 27 |
| N | 149 | 130 | LmdCnst-Ig: 25 | A | 175 | 156 | HCnst-Ig: 28 |
| K | 150 | 131 | LmdCnst-Ig: 26 | L | 176 | 157 | HCnst-Ig: 29 |
| A | 151 | 132 | LmdCnst-Ig: 27 | G | 177 | 158 | HCnst-Ig: 30 |
| T | 152 | 133 | LmdCnst-Ig: 28 | C | 178 | 159 | HCnst-Ig: 31 |
| L | 153 | 134 | LmdCnst-Ig: 29 | L | 179 | 160 | HCnst-Ig: 32 |
| V | 154 | 135 | LmdCnst-Ig: 30 | V | 180 | 161 | HCnst-Ig: 33 |
| C | 155 | 136 | LmdCnst-Ig: 31 | K | 181 | 162 | HCnst-Ig: 34 |
| L | 156 | 137 | LmdCnst-Ig: 32 | D | 182 | 163 | HCnst-Ig: 35 |
| I | 157 | 138 | LmdCnst-Ig: 33 | Y | 183 | 164 | HCnst-Ig: 36 |
| S | 158 | 139 | LmdCnst-Ig: 34 | F | 184 | 165 | HCnst-Ig: 37 |
| D | 159 | 140 | LmdCnst-Ig: 35 | P | 185 | 166 | HCnst-Ig: 38 |
| F | 160 | 141 | LmdCnst-Ig: 36 | — | 185.1 | 166.1 | HCnst-Ig: 39 |
| Y | 161 | 142 | LmdCnst-Ig: 37 | — | 185.2 | 166.2 | HCnst-Ig: 40 |
| P | 162 | 143 | LmdCnst-Ig: 38 | E | 186 | 167 | HCnst-Ig: 41 |
| — | 162.1 | 143.1 | LmdCnst-Ig: 39 | P | 187 | 168 | HCnst-Ig: 42 |
| — | 162.2 | 143.2 | LmdCnst-Ig: 40 | V | 188 | 169 | HCnst-Ig: 43 |
| G | 163 | 144 | LmdCnst-Ig: 41 | T | 189 | 170 | HCnst-Ig: 44 |
| A | 164 | 145 | LmdCnst-Ig: 42 | V | 190 | 171 | HCnst-Ig: 45 |
| V | 165 | 146 | LmdCnst-Ig: 43 | S | 191 | 172 | HCnst-Ig: 46 |
| T | 166 | 147 | LmdCnst-Ig: 44 | W | 192 | 173 | HCnst-Ig: 47 |
| V | 167 | 148 | LmdCnst-Ig: 45 | — | 192.1 | 173.1 | HCnst-Ig: 48 |
| A | 168 | 149 | LmdCnst-Ig: 46 | N | 193 | 174 | HCnst-Ig: 49 |
| W | 169 | 150 | LmdCnst-Ig: 47 | S | 194 | 175 | HCnst-Ig: 50 |
| — | 169.1 | 150.1 | LmdCnst-Ig: 48 | G | 195 | 176 | HCnst-Ig: 51 |

TABLE 1-continued

Residue numbering of anti-HIV antibody 10-1074 variant MS-194

| MS-194_LC | | | | MS-194_HC | | | |
|---|---|---|---|---|---|---|---|
| Residue | Linear # | Mat. Linear # | ASN # | Residue | Linear # | Mat. Linear # | ASN # |
| K | 170 | 151 | LmdCnst-Ig: 49 | A | 196 | 177 | HCnst-Ig: 52 |
| A | 171 | 152 | LmdCnst-Ig: 50 | L | 197 | 178 | HCnst-Ig: 53 |
| D | 172 | 153 | LmdCnst-Ig: 51 | T | 198 | 179 | HCnst-Ig: 54 |
| S | 173 | 154 | LmdCnst-Ig: 52 | S | 199 | 180 | HCnst-Ig: 55 |
| S | 174 | 155 | LmdCnst-Ig: 53 | G | 200 | 181 | HCnst-Ig: 56 |
| P | 175 | 156 | LmdCnst-Ig: 54 | V | 201 | 182 | HCnst-Ig: 57 |
| V | 176 | 157 | LmdCnst-Ig: 55 | H | 202 | 183 | HCnst-Ig: 58 |
| K | 177 | 158 | LmdCnst-Ig: 56 | T | 203 | 184 | HCnst-Ig: 59 |
| A | 178 | 159 | LmdCnst-Ig: 57 | — | 203.1 | 184.1 | HCnst-Ig: 60 |
| G | 179 | 160 | LmdCnst-Ig: 58 | — | 203.2 | 184.2 | HCnst-Ig: 61 |
| V | 180 | 161 | LmdCnst-Ig: 59 | F | 204 | 185 | HCnst-Ig: 62 |
| E | 181 | 162 | LmdCnst-Ig: 60 | P | 205 | 186 | HCnst-Ig: 63 |
| T | 182 | 163 | LmdCnst-Ig: 61 | A | 206 | 187 | HCnst-Ig: 64 |
| T | 183 | 164 | LmdCnst-Ig: 62 | V | 207 | 188 | HCnst-Ig: 65 |
| T | 184 | 165 | LmdCnst-Ig: 63 | L | 208 | 189 | HCnst-Ig: 66 |
| P | 185 | 166 | LmdCnst-Ig: 64 | Q | 209 | 190 | HCnst-Ig: 67 |
| S | 186 | 167 | LmdCnst-Ig: 65 | — | 209.1 | 190.1 | HCnst-Ig: 68 |
| K | 187 | 168 | LmdCnst-Ig: 66 | — | 209.2 | 190.2 | HCnst-Ig: 69 |
| Q | 188 | 169 | LmdCnst-Ig: 67 | — | 209.3 | 190.3 | HCnst-Ig: 70 |
| — | 188.1 | 169.1 | LmdCnst-Ig: 68 | — | 209.4 | 190.4 | HCnst-Ig: 71 |
| — | 188.2 | 169.2 | LmdCnst-Ig: 69 | — | 209.5 | 190.5 | HCnst-Ig: 72 |
| — | 188.3 | 169.3 | LmdCnst-Ig: 70 | S | 210 | 191 | HCnst-Ig: 73 |
| — | 188.4 | 169.4 | LmdCnst-Ig: 71 | S | 211 | 192 | HCnst-Ig: 74 |
| — | 188.5 | 169.5 | LmdCnst-Ig: 72 | G | 212 | 193 | HCnst-Ig: 75 |
| S | 189 | 170 | LmdCnst-Ig: 73 | L | 213 | 194 | HCnst-Ig: 76 |
| N | 190 | 171 | LmdCnst-Ig: 74 | Y | 214 | 195 | HCnst-Ig: 77 |
| N | 191 | 172 | LmdCnst-Ig: 75 | S | 215 | 196 | HCnst-Ig: 78 |
| K | 192 | 173 | LmdCnst-Ig: 76 | L | 216 | 197 | HCnst-Ig: 79 |
| Y | 193 | 174 | LmdCnst-Ig: 77 | S | 217 | 198 | HCnst-Ig: 80 |
| A | 194 | 175 | LmdCnst-Ig: 78 | S | 218 | 199 | HCnst-Ig: 81 |
| A | 195 | 176 | LmdCnst-Ig: 79 | V | 219 | 200 | HCnst-Ig: 82 |
| S | 196 | 177 | LmdCnst-Ig: 80 | V | 220 | 201 | HCnst-Ig: 83 |
| S | 197 | 178 | LmdCnst-Ig: 81 | T | 221 | 202 | HCnst-Ig: 84 |
| Y | 198 | 179 | LmdCnst-Ig: 82 | V | 222 | 203 | HCnst-Ig: 85 |
| L | 199 | 180 | LmdCnst-Ig: 83 | P | 223 | 204 | HCnst-Ig: 86 |
| S | 200 | 181 | LmdCnst-Ig: 84 | S | 224 | 205 | HCnst-Ig: 87 |
| L | 201 | 182 | LmdCnst-Ig: 85 | S | 225 | 206 | HCnst-Ig: 88 |
| T | 202 | 183 | LmdCnst-Ig: 86 | S | 226 | 207 | HCnst-Ig: 89 |
| P | 203 | 184 | LmdCnst-Ig: 87 | L | 227 | 208 | HCnst-Ig: 90 |
| E | 204 | 185 | LmdCnst-Ig: 88 | — | 227.1 | 208.1 | HCnst-Ig: 91 |
| Q | 205 | 186 | LmdCnst-Ig: 89 | G | 228 | 209 | HCnst-Ig: 92 |
| W | 206 | 187 | LmdCnst-Ig: 90 | T | 229 | 210 | HCnst-Ig: 93 |
| — | 206.1 | 187.1 | LmdCnst-Ig: 91 | Q | 230 | 211 | HCnst-Ig: 94 |
| K | 207 | 188 | LmdCnst-Ig: 92 | T | 231 | 212 | HCnst-Ig: 95 |
| S | 208 | 189 | LmdCnst-Ig: 93 | — | 231.1 | 212.1 | HCnst-Ig: 96 |
| H | 209 | 190 | LmdCnst-Ig: 94 | — | 231.2 | 212.2 | HCnst-Ig: 97 |
| R | 210 | 191 | LmdCnst-Ig: 95 | — | 231.3 | 212.3 | HCnst-Ig: 98 |
| S | 211 | 192 | LmdCnst-Ig: 96 | Y | 232 | 213 | HCnst-Ig: 99 |
| — | 211.1 | 192.1 | LmdCnst-Ig: 97 | I | 233 | 214 | HCnst-Ig: 100 |
| — | 211.2 | 192.2 | LmdCnst-Ig: 98 | C | 234 | 215 | HCnst-Ig: 101 |
| Y | 212 | 193 | LmdCnst-Ig: 99 | N | 235 | 216 | HCnst-Ig: 102 |
| S | 213 | 194 | LmdCnst-Ig: 100 | V | 236 | 217 | HCnst-Ig: 103 |
| C | 214 | 195 | LmdCnst-Ig: 101 | N | 237 | 218 | HCnst-Ig: 104 |
| Q | 215 | 196 | LmdCnst-Ig: 102 | H | 238 | 219 | HCnst-Ig: 105 |
| V | 216 | 197 | LmdCnst-Ig: 103 | K | 239 | 220 | HCnst-Ig: 106 |
| T | 217 | 198 | LmdCnst-Ig: 104 | P | 240 | 221 | HCnst-Ig: 107 |
| H | 218 | 199 | LmdCnst-Ig: 105 | S | 241 | 222 | HCnst-Ig: 108 |
| E | 219 | 200 | LmdCnst-Ig: 106 | N | 242 | 223 | HCnst-Ig: 109 |
| G | 220 | 201 | LmdCnst-Ig: 107 | — | 242.1 | 223.1 | HCnst-Ig: 110 |
| S | 221 | 202 | LmdCnst-Ig: 108 | — | 242.2 | 223.2 | HCnst-Ig: 111 |
| T | 222 | 203 | LmdCnst-Ig: 109 | T | 243 | 224 | HCnst-Ig: 112 |
| — | 222.1 | 203.1 | LmdCnst-Ig: 110 | K | 244 | 225 | HCnst-Ig: 113 |
| — | 222.2 | 203.2 | LmdCnst-Ig: 111 | V | 245 | 226 | HCnst-Ig: 114 |
| V | 223 | 204 | LmdCnst-Ig: 112 | D | 246 | 227 | HCnst-Ig: 115 |
| E | 224 | 205 | LmdCnst-Ig: 113 | K | 247 | 228 | HCnst-Ig: 116 |
| K | 225 | 206 | LmdCnst-Ig: 114 | — | 247.1 | 228.1 | HCnst-Ig: 117 |
| T | 226 | 207 | LmdCnst-Ig: 115 | K | 248 | 229 | HCnst-Ig: 118 |
| V | 227 | 208 | LmdCnst-Ig: 116 | V | 249 | 230 | HCnst-Ig: 119 |
| — | 227.1 | 208.1 | LmdCnst-Ig: 117 | — | 249.1 | 230.1 | HCnst-Ig: 120 |
| A | 228 | 209 | LmdCnst-Ig: 118 | — | 249.2 | 230.2 | HCnst-Ig: 121 |
| P | 229 | 210 | LmdCnst-Ig: 119 | — | 249.3 | 230.3 | HCnst-Ig: 122 |
| T | 230 | 211 | LmdCnst-Ig: 120 | — | 249.4 | 230.4 | HCnst-Ig: 123 |
| E | 231 | 212 | LmdCnst-Ig: 121 | — | 249.5 | 230.5 | Hinge: 1 |

TABLE 1-continued

Residue numbering of anti-HIV antibody 10-1074 variant MS-194

| MS-194_LC | | | | MS-194_HC | | | |
|---|---|---|---|---|---|---|---|
| Residue | Linear # | Mat. Linear # | ASN # | Residue | Linear # | Mat. Linear # | ASN # |
| C | 232 | 213 | LmdCnst-Ig: 122 | — | 249.6 | 230.6 | Hinge: 2 |
| S | 233 | 214 | LmdCnst-Ig: 123 | — | 249.7 | 230.7 | Hinge: 3 |
| | | | | — | 249.8 | 230.8 | Hinge: 4 |
| | | | | — | 249.9 | 230.9 | Hinge: 5 |
| | | | | — | 249.10 | 230.10 | Hinge: 6 |
| | | | | — | 249.11 | 230.11 | Hinge: 7 |
| | | | | — | 249.12 | 230.12 | Hinge: 8 |
| | | | | — | 249.13 | 230.13 | Hinge: 9 |
| | | | | — | 249.14 | 230.14 | Hinge: 10 |
| | | | | — | 249.15 | 230.15 | Hinge: 11 |
| | | | | — | 249.16 | 230.16 | Hinge: 12 |
| | | | | — | 249.17 | 230.17 | Hinge: 13 |
| | | | | — | 249.18 | 230.18 | Hinge: 14 |
| | | | | — | 249.19 | 230.19 | Hinge: 15 |
| | | | | — | 249.20 | 230.20 | Hinge: 16 |
| | | | | — | 249.21 | 230.21 | Hinge: 17 |
| | | | | — | 249.22 | 230.22 | Hinge: 18 |
| | | | | — | 249.23 | 230.23 | Hinge: 19 |
| | | | | — | 249.24 | 230.24 | Hinge: 20 |
| | | | | — | 249.25 | 230.25 | Hinge: 21 |
| | | | | — | 249.26 | 230.26 | Hinge: 22 |
| | | | | — | 249.27 | 230.27 | Hinge: 23 |
| | | | | — | 249.28 | 230.28 | Hinge: 24 |
| | | | | — | 249.29 | 230.29 | Hinge: 25 |
| | | | | — | 249.29 | 230.29 | Hinge: 25 |
| | | | | — | 249.30 | 230.30 | Hinge: 26 |
| | | | | — | 249.31 | 230.31 | Hinge: 27 |
| | | | | — | 249.32 | 230.32 | Hinge: 28 |
| | | | | — | 249.33 | 230.33 | Hinge: 29 |
| | | | | — | 249.34 | 230.34 | Hinge: 30 |
| | | | | — | 249.35 | 230.35 | Hinge: 31 |
| | | | | — | 249.36 | 230.36 | Hinge: 32 |
| | | | | — | 249.37 | 230.37 | Hinge: 33 |
| | | | | — | 249.38 | 230.38 | Hinge: 34 |
| | | | | — | 249.39 | 230.39 | Hinge: 35 |
| | | | | — | 249.40 | 230.40 | Hinge: 36 |
| | | | | — | 249.41 | 230.41 | Hinge: 37 |
| | | | | — | 249.42 | 230.42 | Hinge: 38 |
| | | | | — | 249.43 | 230.43 | Hinge: 39 |
| | | | | — | 249.44 | 230.44 | Hinge: 40 |
| | | | | — | 249.45 | 230.45 | Hinge: 41 |
| | | | | — | 249.46 | 230.46 | Hinge: 42 |
| | | | | — | 249.47 | 230.47 | Hinge: 43 |
| | | | | — | 249.48 | 230.48 | Hinge: 44 |
| | | | | — | 249.49 | 230.49 | Hinge: 45 |
| | | | | — | 249.50 | 230.50 | Hinge: 46 |
| | | | | — | 249.51 | 230.51 | Hinge: 47 |
| | | | | — | 249.52 | 230.52 | Hinge: 48 |
| | | | | — | 249.53 | 230.53 | Hinge: 49 |
| | | | | — | 249.54 | 230.54 | Hinge: 50 |
| | | | | — | 249.55 | 230.55 | Hinge: 51 |
| | | | | — | 249.56 | 230.56 | Hinge: 52 |
| | | | | — | 249.57 | 230.57 | Hinge: 53 |
| | | | | — | 249.58 | 230.58 | Hinge: 54 |
| | | | | — | 249.59 | 230.59 | Hinge: 55 |
| | | | | — | 249.60 | 230.60 | Hinge: 56 |
| | | | | — | 249.61 | 230.61 | Hinge: 57 |
| | | | | — | 249.62 | 230.62 | Hinge: 58 |
| | | | | — | 249.63 | 230.63 | Hinge: 59 |
| | | | | — | 249.64 | 230.64 | Hinge: 60 |
| | | | | — | 249.65 | 230.65 | Hinge: 61 |
| | | | | — | 249.66 | 230.66 | Hinge: 62 |
| | | | | — | 249.67 | 230.67 | Hinge: 63 |
| | | | | — | 249.68 | 230.68 | Hinge: 64 |
| | | | | — | 249.69 | 230.69 | Hinge: 65 |
| | | | | — | 249.70 | 230.70 | Hinge: 66 |
| | | | | — | 249.71 | 230.71 | Hinge: 67 |
| | | | | — | 249.72 | 230.72 | Hinge: 68 |
| | | | | — | 249.73 | 230.73 | Hinge: 69 |
| | | | | — | 249.74 | 230.74 | Hinge: 70 |
| | | | | — | 249.75 | 230.75 | Hinge: 71 |
| | | | | — | 249.76 | 230.76 | Hinge: 72 |
| | | | | — | 249.77 | 230.77 | Hinge: 73 |

TABLE 1-continued

| Residue numbering of anti-HIV antibody 10-1074 variant MS-194 | | | | | | | |
|---|---|---|---|---|---|---|---|
| MS-194_LC | | | | MS-194_HC | | | |
| Residue | Linear # | Mat. Linear # | ASN # | Residue | Linear # | Mat. Linear # | ASN # |
| | | | | — | 249.78 | 230.78 | Hinge: 74 |
| | | | | — | 249.79 | 230.79 | Hinge: 75 |
| | | | | — | 249.80 | 230.80 | Hinge: 76 |
| | | | | — | 249.81 | 230.81 | Hinge: 77 |
| | | | | — | 249.82 | 230.82 | Hinge: 78 |
| | | | | — | 249.83 | 230.83 | Hinge: 79 |
| | | | | — | 249.84 | 230.84 | Hinge: 80 |
| | | | | — | 249.85 | 230.85 | Hinge: 81 |
| | | | | — | 249.86 | 230.86 | Hinge: 82 |
| | | | | — | 249.87 | 230.87 | Hinge: 83 |
| | | | | — | 249.88 | 230.88 | Hinge: 84 |
| | | | | — | 249.89 | 230.89 | Hinge: 85 |
| | | | | — | 249.90 | 230.90 | Hinge: 86 |
| | | | | — | 249.91 | 230.91 | Hinge: 87 |
| | | | | — | 249.92 | 230.92 | Hinge: 88 |
| | | | | — | 249.93 | 230.93 | Hinge: 89 |
| | | | | — | 249.94 | 230.94 | Hinge: 90 |
| | | | | — | 249.95 | 230.95 | Hinge: 91 |
| | | | | — | 249.96 | 230.96 | Hinge: 92 |
| | | | | — | 249.97 | 230.97 | Hinge: 93 |
| | | | | — | 249.98 | 230.98 | Hinge: 94 |
| | | | | — | 249.99 | 230.99 | Hinge: 95 |
| | | | | E | 250 | 231 | Hinge: 96 |
| | | | | P | 251 | 232 | Hinge: 97 |
| | | | | K | 252 | 233 | Hinge: 98 |
| | | | | S | 253 | 234 | Hinge: 99 |
| | | | | — | 253.1 | 234.1 | Hinge: 100 |
| | | | | — | 253.2 | 234.2 | Hinge: 101 |
| | | | | — | 253.3 | 234.3 | Hinge: 102 |
| | | | | — | 253.4 | 234.4 | Hinge: 103 |
| | | | | — | 253.5 | 234.5 | Hinge: 104 |
| | | | | — | 253.6 | 234.6 | Hinge: 105 |
| | | | | — | 253.7 | 234.7 | Hinge: 106 |
| | | | | C | 254 | 235 | Hinge: 107 |
| | | | | D | 255 | 236 | Hinge: 108 |
| | | | | K | 256 | 237 | Hinge: 109 |
| | | | | T | 257 | 238 | Hinge: 110 |
| | | | | H | 258 | 239 | Hinge: 111 |
| | | | | T | 259 | 240 | Hinge: 112 |
| | | | | C | 260 | 241 | Hinge: 113 |
| | | | | P | 261 | 242 | Hinge: 114 |
| | | | | P | 262 | 243 | Hinge: 115 |
| | | | | C | 263 | 244 | Hinge: 116 |
| | | | | P | 264 | 245 | Hinge: 117 |
| | | | | A | 265 | 246 | Hinge: 118 |
| | | | | P | 266 | 247 | Hinge: 119 |
| | | | | E | 267 | 248 | Hinge: 120 |
| | | | | L | 268 | 249 | Hinge: 121 |
| | | | | L | 269 | 250 | Hinge: 122 |
| | | | | G | 270 | 251 | Hinge: 123 |
| | | | | — | 270.1 | 251.1 | Fc-N: 1 |
| | | | | — | 270.2 | 251.2 | Fc-N: 2 |
| | | | | — | 270.3 | 251.3 | Fc-N: 3 |
| | | | | — | 270.4 | 251.4 | Fc-N: 4 |
| | | | | G | 271 | 252 | Fc-N: 5 |
| | | | | P | 272 | 253 | Fc-N: 6 |
| | | | | S | 273 | 254 | Fc-N: 7 |
| | | | | V | 274 | 255 | Fc-N: 8 |
| | | | | F | 275 | 256 | Fc-N: 9 |
| | | | | L | 276 | 257 | Fc-N: 10 |
| | | | | F | 277 | 258 | Fc-N: 11 |
| | | | | P | 278 | 259 | Fc-N: 12 |
| | | | | P | 279 | 260 | Fc-N: 13 |
| | | | | — | 279.1 | 260.1 | Fc-N: 14 |
| | | | | K | 280 | 261 | Fc-N: 15 |
| | | | | P | 281 | 262 | Fc-N: 16 |
| | | | | K | 282 | 263 | Fc-N: 17 |
| | | | | — | 282.1 | 263.1 | Fc-N: 18 |
| | | | | D | 283 | 264 | Fc-N: 19 |
| | | | | T | 284 | 265 | Fc-N: 20 |
| | | | | L | 285 | 266 | Fc-N: 21 |
| | | | | M | 286 | 267 | Fc-N: 22 |
| | | | | I | 287 | 268 | Fc-N: 23 |

TABLE 1-continued

| Residue numbering of anti-HIV antibody 10-1074 variant MS-194 | | | | | | | |
|---|---|---|---|---|---|---|---|
| MS-194_LC | | | | MS-194_HC | | | |
| Residue | Linear # | Mat. Linear # | ASN # | Residue | Linear # | Mat. Linear # | ASN # |
| | | | | S | 288 | 269 | Fc-N: 24 |
| | | | | R | 289 | 270 | Fc-N: 25 |
| | | | | T | 290 | 271 | Fc-N: 26 |
| | | | | P | 291 | 272 | Fc-N: 27 |
| | | | | E | 292 | 273 | Fc-N: 28 |
| | | | | V | 293 | 274 | Fc-N: 29 |
| | | | | T | 294 | 275 | Fc-N: 30 |
| | | | | C | 295 | 276 | Fc-N: 31 |
| | | | | V | 296 | 277 | Fc-N: 32 |
| | | | | V | 297 | 278 | Fc-N: 33 |
| | | | | V | 298 | 279 | Fc-N: 34 |
| | | | | D | 299 | 280 | Fc-N: 35 |
| | | | | V | 300 | 281 | Fc-N: 36 |
| | | | | S | 301 | 282 | Fc-N: 37 |
| | | | | H | 302 | 283 | Fc-N: 38 |
| | | | | E | 303 | 284 | Fc-N: 39 |
| | | | | D | 304 | 285 | Fc-N: 40 |
| | | | | P | 305 | 286 | Fc-N: 41 |
| | | | | E | 306 | 287 | Fc-N: 42 |
| | | | | V | 307 | 288 | Fc-N: 43 |
| | | | | K | 308 | 289 | Fc-N: 44 |
| | | | | F | 309 | 290 | Fc-N: 45 |
| | | | | N | 310 | 291 | Fc-N: 46 |
| | | | | W | 311 | 292 | Fc-N: 47 |
| | | | | — | 311.1 | 292.1 | Fc-N: 48 |
| | | | | Y | 312 | 293 | Fc-N: 49 |
| | | | | V | 313 | 294 | Fc-N: 50 |
| | | | | D | 314 | 295 | Fc-N: 51 |
| | | | | G | 315 | 296 | Fc-N: 52 |
| | | | | V | 316 | 297 | Fc-N: 53 |
| | | | | E | 317 | 298 | Fc-N: 54 |
| | | | | — | 317.1 | 298.1 | Fc-N: 55 |
| | | | | — | 317.2 | 298.2 | Fc-N: 56 |
| | | | | V | 318 | 299 | Fc-N: 57 |
| | | | | H | 319 | 300 | Fc-N: 58 |
| | | | | N | 320 | 301 | Fc-N: 59 |
| | | | | A | 321 | 302 | Fc-N: 60 |
| | | | | K | 322 | 303 | Fc-N: 61 |
| | | | | T | 323 | 304 | Fc-N: 62 |
| | | | | K | 324 | 305 | Fc-N: 63 |
| | | | | P | 325 | 306 | Fc-N: 64 |
| | | | | R | 326 | 307 | Fc-N: 65 |
| | | | | E | 327 | 308 | Fc-N: 66 |
| | | | | E | 328 | 309 | Fc-N: 67 |
| | | | | Q | 329 | 310 | Fc-N: 68 |
| | | | | — | 329.1 | 310.1 | Fc-N: 69 |
| | | | | — | 329.2 | 310.2 | Fc-N: 70 |
| | | | | — | 329.3 | 310.3 | Fc-N: 71 |
| | | | | — | 329.4 | 310.4 | Fc-N: 72 |
| | | | | Y | 330 | 311 | Fc-N: 73 |
| | | | | N | 331 | 312 | Fc-N: 74 |
| | | | | S | 332 | 313 | Fc-N: 75 |
| | | | | T | 333 | 314 | Fc-N: 76 |
| | | | | Y | 334 | 315 | Fc-N: 77 |
| | | | | R | 335 | 316 | Fc-N: 78 |
| | | | | V | 336 | 317 | Fc-N: 79 |
| | | | | V | 337 | 318 | Fc-N: 80 |
| | | | | S | 338 | 319 | Fc-N: 81 |
| | | | | V | 339 | 320 | Fc-N: 82 |
| | | | | L | 340 | 321 | Fc-N: 83 |
| | | | | T | 341 | 322 | Fc-N: 84 |
| | | | | V | 342 | 323 | Fc-N: 85 |
| | | | | L | 343 | 324 | Fc-N: 86 |
| | | | | H | 344 | 325 | Fc-N: 87 |
| | | | | Q | 345 | 326 | Fc-N: 88 |
| | | | | D | 346 | 327 | Fc-N: 89 |
| | | | | W | 347 | 328 | Fc-N: 90 |
| | | | | — | 347.1 | 328.1 | Fc-N: 91 |
| | | | | L | 348 | 329 | Fc-N: 92 |
| | | | | N | 349 | 330 | Fc-N: 93 |
| | | | | G | 350 | 331 | Fc-N: 94 |
| | | | | K | 351 | 332 | Fc-N: 95 |
| | | | | E | 352 | 333 | Fc-N: 96 |

TABLE 1-continued

Residue numbering of anti-HIV antibody 10-1074 variant MS-194

| MS-194_LC | | | | MS-194_HC | | | |
|---|---|---|---|---|---|---|---|
| Residue | Linear # | Mat. Linear # | ASN # | Residue | Linear # | Mat. Linear # | ASN # |
| | | | | — | 352.1 | 333.1 | Fc-N: 97 |
| | | | | — | 352.2 | 333.2 | Fc-N: 98 |
| | | | | Y | 353 | 334 | Fc-N: 99 |
| | | | | K | 354 | 335 | Fc-N: 100 |
| | | | | C | 355 | 336 | Fc-N: 101 |
| | | | | K | 356 | 337 | Fc-N: 102 |
| | | | | V | 357 | 338 | Fc-N: 103 |
| | | | | S | 358 | 339 | Fc-N: 104 |
| | | | | N | 359 | 340 | Fc-N: 105 |
| | | | | K | 360 | 341 | Fc-N: 106 |
| | | | | A | 361 | 342 | Fc-N: 107 |
| | | | | L | 362 | 343 | Fc-N: 108 |
| | | | | P | 363 | 344 | Fc-N: 109 |
| | | | | — | 363.1 | 344.1 | Fc-N: 110 |
| | | | | — | 363.2 | 344.2 | Fc-N: 111 |
| | | | | A | 364 | 345 | Fc-N: 112 |
| | | | | P | 365 | 346 | Fc-N: 113 |
| | | | | I | 366 | 347 | Fc-N: 114 |
| | | | | E | 367 | 348 | Fc-N: 115 |
| | | | | K | 368 | 349 | Fc-N: 116 |
| | | | | T | 369 | 350 | Fc-N: 117 |
| | | | | I | 370 | 351 | Fc-N: 118 |
| | | | | S | 371 | 352 | Fc-N: 119 |
| | | | | K | 372 | 353 | Fc-N: 120 |
| | | | | A | 373 | 354 | Fc-N: 121 |
| | | | | K | 374 | 355 | Fc-N: 122 |
| | | | | G | 375 | 356 | Fc-N: 123 |
| | | | | — | 375.1 | 356.1 | Fc-C: 1 |
| | | | | Q | 376 | 357 | Fc-C: 2 |
| | | | | P | 377 | 358 | Fc-C: 3 |
| | | | | R | 378 | 359 | Fc-C: 4 |
| | | | | E | 379 | 360 | Fc-C: 5 |
| | | | | P | 380 | 361 | Fc-C: 6 |
| | | | | Q | 381 | 362 | Fc-C: 7 |
| | | | | V | 382 | 363 | Fc-C: 8 |
| | | | | Y | 383 | 364 | Fc-C: 9 |
| | | | | T | 384 | 365 | Fc-C: 10 |
| | | | | L | 385 | 366 | Fc-C: 11 |
| | | | | P | 386 | 367 | Fc-C: 12 |
| | | | | P | 387 | 368 | Fc-C: 13 |
| | | | | — | 387.1 | 368.1 | Fc-C: 14 |
| | | | | S | 388 | 369 | Fc-C: 15 |
| | | | | R | 389 | 370 | Fc-C: 16 |
| | | | | D | 390 | 371 | Fc-C: 17 |
| | | | | — | 390.1 | 371.1 | Fc-C: 18 |
| | | | | E | 391 | 372 | Fc-C: 19 |
| | | | | L | 392 | 373 | Fc-C: 20 |
| | | | | — | 392.1 | 373.1 | Fc-C: 21 |
| | | | | — | 392.2 | 373.2 | Fc-C: 22 |
| | | | | T | 393 | 374 | Fc-C: 23 |
| | | | | K | 394 | 375 | Fc-C: 24 |
| | | | | N | 395 | 376 | Fc-C: 25 |
| | | | | Q | 396 | 377 | Fc-C: 26 |
| | | | | V | 397 | 378 | Fc-C: 27 |
| | | | | S | 398 | 379 | Fc-C: 28 |
| | | | | L | 399 | 380 | Fc-C: 29 |
| | | | | T | 400 | 381 | Fc-C: 30 |
| | | | | C | 401 | 382 | Fc-C: 31 |
| | | | | L | 402 | 383 | Fc-C: 32 |
| | | | | V | 403 | 384 | Fc-C: 33 |
| | | | | K | 404 | 385 | Fc-C: 34 |
| | | | | G | 405 | 386 | Fc-C: 35 |
| | | | | F | 406 | 387 | Fc-C: 36 |
| | | | | Y | 407 | 388 | Fc-C: 37 |
| | | | | P | 408 | 389 | Fc-C: 38 |
| | | | | — | 408.1 | 389.1 | Fc-C: 39 |
| | | | | — | 408.2 | 389.2 | Fc-C: 40 |
| | | | | S | 409 | 390 | Fc-C: 41 |
| | | | | D | 410 | 391 | Fc-C: 42 |
| | | | | I | 411 | 392 | Fc-C: 43 |
| | | | | A | 412 | 393 | Fc-C: 44 |
| | | | | V | 413 | 394 | Fc-C: 45 |
| | | | | E | 414 | 395 | Fc-C: 46 |

TABLE 1-continued

| Residue numbering of anti-HIV antibody 10-1074 variant MS-194 | | | | | | | |
|---|---|---|---|---|---|---|---|
| MS-194_LC | | | | MS-194_HC | | | |
| Residue | Linear # | Mat. Linear # | ASN # | Residue | Linear # | Mat. Linear # | ASN # |
| | | | | W | 415 | 396 | Fc-C: 47 |
| | | | | — | 415.1 | 396.1 | Fc-C: 48 |
| | | | | E | 416 | 397 | Fc-C: 49 |
| | | | | S | 417 | 398 | Fc-C: 50 |
| | | | | N | 418 | 399 | Fc-C: 51 |
| | | | | G | 419 | 400 | Fc-C: 52 |
| | | | | Q | 420 | 401 | Fc-C: 53 |
| | | | | P | 421 | 402 | Fc-C: 54 |
| | | | | — | 421.1 | 402.1 | Fc-C: 55 |
| | | | | — | 421.2 | 402.2 | Fc-C: 56 |
| | | | | E | 422 | 403 | Fc-C: 57 |
| | | | | N | 423 | 404 | Fc-C: 58 |
| | | | | N | 424 | 405 | Fc-C: 59 |
| | | | | Y | 425 | 406 | Fc-C: 60 |
| | | | | K | 426 | 407 | Fc-C: 61 |
| | | | | T | 427 | 408 | Fc-C: 62 |
| | | | | T | 428 | 409 | Fc-C: 63 |
| | | | | P | 429 | 410 | Fc-C: 64 |
| | | | | P | 430 | 411 | Fc-C: 65 |
| | | | | V | 431 | 412 | Fc-C: 66 |
| | | | | L | 432 | 413 | Fc-C: 67 |
| | | | | D | 433 | 414 | Fc-C: 68 |
| | | | | — | 433.1 | 414.1 | Fc-C: 69 |
| | | | | — | 433.2 | 414.2 | Fc-C: 70 |
| | | | | — | 433.3 | 414.3 | Fc-C: 71 |
| | | | | — | 433.4 | 414.4 | Fc-C: 72 |
| | | | | S | 434 | 415 | Fc-C: 73 |
| | | | | D | 435 | 416 | Fc-C: 74 |
| | | | | G | 436 | 417 | Fc-C: 75 |
| | | | | S | 437 | 418 | Fc-C: 76 |
| | | | | F | 438 | 419 | Fc-C: 77 |
| | | | | F | 439 | 420 | Fc-C: 78 |
| | | | | L | 440 | 421 | Fc-C: 79 |
| | | | | Y | 441 | 422 | Fc-C: 80 |
| | | | | S | 442 | 423 | Fc-C: 81 |
| | | | | K | 443 | 424 | Fc-C: 82 |
| | | | | L | 444 | 425 | Fc-C: 83 |
| | | | | T | 445 | 426 | Fc-C: 84 |
| | | | | V | 446 | 427 | Fc-C: 85 |
| | | | | D | 447 | 428 | Fc-C: 86 |
| | | | | K | 448 | 429 | Fc-C: 87 |
| | | | | S | 449 | 430 | Fc-C: 88 |
| | | | | R | 450 | 431 | Fc-C: 89 |
| | | | | W | 451 | 432 | Fc-C: 90 |
| | | | | — | 451.1 | 432.1 | Fc-C: 91 |
| | | | | Q | 452 | 433 | Fc-C: 92 |
| | | | | Q | 453 | 434 | Fc-C: 93 |
| | | | | G | 454 | 435 | Fc-C: 94 |
| | | | | N | 455 | 436 | Fc-C: 95 |
| | | | | V | 456 | 437 | Fc-C: 96 |
| | | | | — | 456.1 | 437.1 | Fc-C: 97 |
| | | | | — | 456.2 | 437.2 | Fc-C: 98 |
| | | | | F | 457 | 438 | Fc-C: 99 |
| | | | | S | 458 | 439 | Fc-C: 100 |
| | | | | C | 459 | 440 | Fc-C: 101 |
| | | | | S | 460 | 441 | Fc-C: 102 |
| | | | | V | 461 | 442 | Fc-C: 103 |
| | | | | L | 462 | 443 | Fc-C: 104 |
| | | | | H | 463 | 444 | Fc-C: 105 |
| | | | | E | 464 | 445 | Fc-C: 106 |
| | | | | A | 465 | 446 | Fc-C: 107 |
| | | | | L | 466 | 447 | Fc-C: 108 |
| | | | | H | 467 | 448 | Fc-C: 109 |
| | | | | — | 467.1 | 448.1 | Fc-C: 110 |
| | | | | — | 467.2 | 448.2 | Fc-C: 111 |
| | | | | S | 468 | 449 | Fc-C: 112 |
| | | | | H | 469 | 450 | Fc-C: 113 |
| | | | | Y | 470 | 451 | Fc-C: 114 |
| | | | | T | 471 | 452 | Fc-C: 115 |
| | | | | — | 471.1 | 452.1 | Fc-C: 116 |
| | | | | Q | 472 | 453 | Fc-C: 117 |
| | | | | K | 473 | 454 | Fc-C: 118 |
| | | | | S | 474 | 455 | Fc-C: 119 |

TABLE 1-continued

| Residue numbering of anti-HIV antibody 10-1074 variant MS-194 | | | | | | | |
|---|---|---|---|---|---|---|---|
| MS-194_LC | | | | MS-194_HC | | | |
| Residue | Linear # | Mat. Linear # | ASN # | Residue | Linear # | Mat. Linear # | ASN # |
| | | | | L | 475 | 456 | Fc-C: 120 |
| | | | | S | 476 | 457 | Fc-C: 121 |
| | | | | L | 477 | 458 | Fc-C: 122 |
| | | | | S | 478 | 459 | Fc-C: 123 |
| | | | | P | 479 | 460 | HCnst-Po: 1 |
| | | | | G | 480 | 461 | HCnst-Po: 2 |
| | | | | K | 481 | 462 | HCnst-Po: 3 |
| | | | | — | 481.1 | 462.1 | HCnst-Po: 4 |
| | | | | — | 481.2 | 462.2 | HCnst-Po: 5 |
| | | | | — | 481.3 | 462.3 | HCnst-Po: 6 |
| | | | | — | 481.4 | 462.4 | HCnst-Po: 7 |
| | | | | — | 481.5 | 462.5 | HCnst-Po: 8 |
| | | | | — | 481.6 | 462.6 | HCnst-Po: 9 |
| | | | | — | 481.7 | 462.7 | HCnst-Po: 10 |
| | | | | — | 481.8 | 462.8 | HCnst-Po: 11 |
| | | | | — | 481.9 | 462.9 | HCnst-Po: 12 |
| | | | | — | 481.10 | 462.10 | HCnst-Po: 13 |
| | | | | — | 481.11 | 462.11 | HCnst-Po: 14 |
| | | | | — | 481.12 | 462.12 | HCnst-Po: 15 |
| | | | | — | 481.13 | 462.13 | HCnst-Po: 16 |
| | | | | — | 481.14 | 462.14 | HCnst-Po: 17 |
| | | | | — | 481.15 | 462.15 | HCnst-Po: 18 |
| | | | | — | 481.16 | 462.16 | HCnst-Po: 19 |
| | | | | — | 481.17 | 462.17 | HCnst-Po: 20 |
| | | | | — | 481.18 | 462.18 | HCnst-Po: 21 |
| | | | | — | 481.19 | 462.19 | HCnst-Po: 22 |
| | | | | — | 481.20 | 462.20 | HCnst-Po: 23 |
| | | | | — | 481.21 | 462.21 | HCnst-Po: 24 |
| | | | | — | 481.22 | 462.22 | HCnst-Po: 25 |
| | | | | — | 481.23 | 462.23 | HCnst-Po: 26 |
| | | | | — | 481.24 | 462.24 | HCnst-Po: 27 |
| | | | | — | 481.25 | 462.25 | HCnst-Po: 28 |
| | | | | — | 481.26 | 462.26 | HCnst-Po: 29 |
| | | | | — | 481.27 | 462.27 | HCnst-Po: 30 |
| | | | | — | 481.28 | 462.28 | HCnst-Po: 31 |
| | | | | — | 481.29 | 462.29 | HCnst-Po: 32 |
| | | | | — | 481.30 | 462.30 | HCnst-Po: 33 |
| | | | | — | 481.31 | 462.31 | HCnst-Po: 34 |
| | | | | — | 481.32 | 462.32 | HCnst-Po: 35 |
| | | | | — | 481.33 | 462.33 | HCnst-Po: 36 |
| | | | | — | 481.34 | 462.34 | HCnst-Po: 37 |
| | | | | — | 481.35 | 462.35 | HCnst-Po: 38 |
| | | | | — | 481.36 | 462.36 | HCnst-Po: 39 |
| | | | | — | 481.37 | 462.37 | HCnst-Po: 40 |
| | | | | — | 481.38 | 462.38 | HCnst-Po: 41 |
| | | | | — | 481.39 | 462.39 | HCnst-Po: 42 |
| | | | | — | 481.40 | 462.40 | HCnst-Po: 43 |
| | | | | — | 481.41 | 462.41 | HCnst-Po: 44 |
| | | | | — | 481.42 | 462.42 | HCnst-Po: 45 |
| | | | | — | 481.43 | 462.43 | HCnst-Po: 46 |
| | | | | — | 481.44 | 462.44 | HCnst-Po: 47 |
| | | | | — | 481.45 | 462.45 | HCnst-Po: 48 |
| | | | | — | 481.46 | 462.46 | HCnst-Po: 49 |
| | | | | — | 481.47 | 462.47 | HCnst-Po: 50 |
| | | | | — | 481.48 | 462.48 | HCnst-Po: 51 |
| | | | | — | 481.49 | 462.49 | HCnst-Po: 52 |
| | | | | — | 481.50 | 462.50 | HCnst-Po: 53 |
| | | | | — | 481.51 | 462.51 | HCnst-Po: 54 |
| | | | | — | 481.52 | 462.52 | HCnst-Po: 55 |
| | | | | — | 481.53 | 462.53 | HCnst-Po: 56 |
| | | | | — | 481.54 | 462.54 | HCnst-Po: 57 |
| | | | | — | 481.55 | 462.55 | HCnst-Po: 58 |
| | | | | — | 481.56 | 462.56 | HCnst-Po: 59 |
| | | | | — | 481.57 | 462.57 | HCnst-Po: 60 |
| | | | | — | 481.58 | 462.58 | HCnst-Po: 61 |
| | | | | — | 481.59 | 462.59 | HCnst-Po: 62 |
| | | | | — | 481.60 | 462.60 | HCnst-Po: 63 |
| | | | | — | 481.61 | 462.61 | HCnst-Po: 64 |
| | | | | — | 481.62 | 462.62 | HCnst-Po: 65 |
| | | | | — | 481.63 | 462.63 | HCnst-Po: 66 |
| | | | | — | 481.64 | 462.64 | HCnst-Po: 67 |
| | | | | — | 481.65 | 462.65 | HCnst-Po: 68 |
| | | | | — | 481.66 | 462.66 | HCnst-Po: 69 |

TABLE 1-continued

Residue numbering of anti-HIV antibody 10-1074 variant MS-194

| MS-194_LC | | | | MS-194_HC | | | |
|---|---|---|---|---|---|---|---|
| Residue | Linear # | Mat. Linear # | ASN # | Residue | Linear # | Mat. Linear # | ASN # |
| | | | | — | 481.67 | 462.67 | HCnst-Po: 70 |
| | | | | — | 481.68 | 462.68 | HCnst-Po: 71 |
| | | | | — | 481.69 | 462.69 | HCnst-Po: 72 |
| | | | | — | 481.70 | 462.70 | HCnst-Po: 73 |
| | | | | — | 481.71 | 462.71 | HCnst-Po: 74 |
| | | | | — | 481.72 | 462.72 | HCnst-Po: 75 |
| | | | | — | 481.73 | 462.73 | HCnst-Po: 76 |
| | | | | — | 481.74 | 462.74 | HCnst-Po: 77 |
| | | | | — | 481.75 | 462.75 | HCnst-Po: 78 |
| | | | | — | 481.76 | 462.76 | HCnst-Po: 79 |
| | | | | — | 481.77 | 462.77 | HCnst-Po: 80 |
| | | | | — | 481.78 | 462.78 | HCnst-Po: 81 |
| | | | | — | 481.79 | 462.79 | HCnst-Po: 82 |
| | | | | — | 481.80 | 462.80 | HCnst-Po: 83 |
| | | | | — | 481.81 | 462.81 | HCnst-Po: 84 |
| | | | | — | 481.82 | 462.82 | HCnst-Po: 85 |
| | | | | — | 481.83 | 462.83 | HCnst-Po: 86 |
| | | | | — | 481.84 | 462.84 | HCnst-Po: 87 |
| | | | | — | 481.85 | 462.85 | HCnst-Po: 88 |
| | | | | — | 481.86 | 462.86 | HCnst-Po: 89 |
| | | | | — | 481.87 | 462.87 | HCnst-Po: 90 |
| | | | | — | 481.88 | 462.88 | HCnst-Po: 91 |
| | | | | — | 481.89 | 462.89 | HCnst-Po: 92 |
| | | | | — | 481.90 | 462.90 | HCnst-Po: 93 |
| | | | | — | 481.91 | 462.91 | HCnst-Po: 94 |
| | | | | — | 481.92 | 462.92 | HCnst-Po: 95 |
| | | | | — | 481.93 | 462.93 | HCnst-Po: 96 |
| | | | | — | 481.94 | 462.94 | HCnst-Po: 97 |
| | | | | — | 481.95 | 462.95 | HCnst-Po: 98 |
| | | | | — | 481.96 | 462.96 | HCnst-Po: 99 |
| | | | | — | 481.97 | 462.97 | HCnst-Po: 100 |
| | | | | — | 481.98 | 462.98 | HCnst-Po: 101 |
| | | | | — | 481.99 | 462.99 | HCnst-Po: 102 |
| | | | | — | 481.100 | 462.100 | HCnst-Po: 103 |
| | | | | — | 481.101 | 462.101 | HCnst-Po: 104 |
| | | | | — | 481.102 | 462.102 | HCnst-Po: 105 |
| | | | | — | 481.103 | 462.103 | HCnst-Po: 106 |
| | | | | — | 481.104 | 462.104 | HCnst-Po: 107 |
| | | | | — | 481.105 | 462.105 | HCnst-Po: 108 |
| | | | | — | 481.106 | 462.106 | HCnst-Po: 109 |
| | | | | — | 481.107 | 462.107 | HCnst-Po: 110 |
| | | | | — | 481.108 | 462.108 | HCnst-Po: 111 |
| | | | | — | 481.109 | 462.109 | HCnst-Po: 112 |
| | | | | — | 481.110 | 462.110 | HCnst-Po: 113 |
| | | | | — | 481.111 | 462.111 | HCnst-Po: 114 |
| | | | | — | 481.112 | 462.112 | HCnst-Po: 115 |
| | | | | — | 481.113 | 462.113 | HCnst-Po: 116 |
| | | | | — | 481.114 | 462.114 | HCnst-Po: 117 |
| | | | | — | 481.115 | 462.115 | HCnst-Po: 118 |
| | | | | — | 481.116 | 462.116 | HCnst-Po: 119 |
| | | | | — | 481.117 | 462.117 | HCnst-Po: 120 |
| | | | | — | 481.118 | 462.118 | HCnst-Po: 121 |
| | | | | — | 481.119 | 462.119 | HCnst-Po: 122 |
| | | | | — | 481.120 | 462.120 | HCnst-Po: 123 |

TABLE 2

Amino acid sequences of light chain variable regions (hightlighted in bold) of the 10-1074 antibody variants

| SEQ ID NO. | SEQUENCE | OTHER INFORMATION |
|---|---|---|
| SEQ ID NO: 1 | MGWSCIILFLVATATGVHSS YVRPLSVALGETARISC**GRQ** **ALGSRAVQWYQHRPGQAPIL** **LIYNNQDRPSGIPERFSGTP** **DINEGTRATLTISGVEAGDE** **ADYYCHMWDSRSGFSWS**FGG | MS-193_LC |

TABLE 2-continued

Amino acid sequences of light chain variable regions (hightlighted in bold) of the 10-1074 antibody variants

| SEQ ID NO. | SEQUENCE | OTHER INFORMATION |
|---|---|---|
| | ATRLTVLGQPKAAPSVTLFP PSSEELQANKATLVCLISDF YPGAVTVAWKADSSPVKAGV ETTTPSKQSNNKYAASSYLS LTPEQWKSHRSYSCQVTHEG STVEKTVAPTECS | |

TABLE 2-continued

Amino acid sequences of light chain variable regions (hightlighted in bold) of the 10-1074 antibody variants

| SEQ ID NO. | SEQUENCE | OTHER INFORMATION |
|---|---|---|
| SEQ ID NO: 2 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINEGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-194_LC |
| SEQ ID NO: 3 | MGWSCIILFLVATATGVHSS<br>PVRPLSVALGETARISC**GRQ**<br>**ALGSRAVQWYQHRPGQAPIL**<br>**LIYNNQDRPSGIPERFSGTP**<br>**DINEGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-203_LC |
| SEQ ID NO: 4 | MGWSCIILFLVATATGVHSS<br>YVPPLSVALGETARISC**GRQ**<br>**ALGSRAVQWYQHRPGQAPIL**<br>**LIYNNQDRPSGIPERFSGTP**<br>**DINEGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-204_LC |
| SEQ ID NO: 5 | MGWSCIILFLVATATGVHSS<br>YVRSLSVALGETARISC**GRQ**<br>**ALGSRAVQWYQHRPGQAPIL**<br>**LIYNNQDRPSGIPERFSGTP**<br>**DINEGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-205_LC |
| SEQ ID NO: 6 | MGWSCIILFLVATATGVHSS<br>YVRPLSVALGQTARISC**GRQ**<br>**ALGSRAVQWYQHRPGQAPIL**<br>**LIYNNQDRPSGIPERFSGTP**<br>**DINEGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-206_LC |
| SEQ ID NO: 7 | MGWSCIILFLVATATGVHSS<br>YVRPLSVALGETARISC**GRQ**<br>**ALGSRAVQWYQQRPGQAPIL**<br>**LIYNNQDRPSGIPERFSGTP**<br>**DINEGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-207_LC |
| SEQ ID NO: 8 | MGWSCIILFLVATATGVHSS<br>YVRPLSVALGETARISC**GRQ**<br>**ALGSRAVQWYQHRPGQAPIL**<br>**LIYNNQDRPSGIPERFSGTN**<br>DINEGTRATLTISGVEAGDE<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-208_LC |
| SEQ ID NO: 9 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DSNEGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-209_LC |
| SEQ ID NO: 10 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DIGEGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-210_LC |
| SEQ ID NO: 11 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINEGTTATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-211_LC |
| SEQ ID NO: 12 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINEGTRATLTISGVEAGDE**<br>**ADYYCHMWESRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-212_LC |

TABLE 2-continued

Amino acid sequences of light chain variable regions (hightlighted in bold) of the 10-1074 antibody variants

| SEQ ID NO. | SEQUENCE | OTHER INFORMATION |
|---|---|---|
| SEQ ID NO: 13 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINEGTRATLTISGVEAGDE**<br>**ADYYCHMWDSRSGFSWS**FGG<br>GTRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-213_LC |
| SEQ ID NO: 14 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINEGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-214_LC |
| SEQ ID NO: 15 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINEGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-215_LC |
| SEQ ID NO: 16 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINEGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-216_LC |
| SEQ ID NO: 17 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINEGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-217_LC |
| SEQ ID NO: 18 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINEGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-218_LC |
| SEQ ID NO: 19 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINEGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-219_LC |
| SEQ ID NO: 20 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-220_LC |
| SEQ ID NO: 21 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-224_LC |
| SEQ ID NO: 22 | MGWSCIILFLVATATGVHSS<br>PVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-200_LC |
| SEQ ID NO: 23 | MGWSCIILFLVATATGVHSS<br>YVRPLSVALGETARISC**GRQ**<br>**ALGSRAVQWYQHRPGQAPIL**<br>**LIY**<br>**NNQDRPSGIPERFSGTPDIN**<br>**FGTRATLTISGVEAGDEADY**<br>**YCHMWDSRSGFSWS**FGGATR<br>LTVLGQPKAAPSVTLFPPSS<br>EELQANKATLVCLISDFYPG<br>AVTVAWKADSSPVKAGVETT<br>TPSKQSNNKYAASSYLSLTP<br>EQWKSHRSYSCQVTHEGSTV<br>EKTVAPTECS | MS-201_LC |
| SEQ ID NO: 24 | MGWSCIILFLVATATGVHSS<br>PVRPLSVALGETARISC**GRQ** | MS-202_LC |

TABLE 2-continued

Amino acid sequences of light chain variable regions (hightlighted in bold) of the 10-1074 antibody variants

| SEQ ID NO. | SEQUENCE | OTHER INFORMATION |
|---|---|---|
| | **ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | |
| SEQ ID NO: 25 | MGWSCIILFLVATATGVHSS<br>PVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-225_LC |
| SEQ ID NO: 26 | MGWSCIILFLVATATGVHSS<br>PVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-226_LC |
| SEQ ID NO: 27 | MGWSCIILFLVATATGVHSS<br>PVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-227_LC |
| SEQ ID NO: 28 | MGWSCIILFLVATATGVHSS<br>PVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-228_LC |
| SEQ ID NO: 29 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS | MS-229_LC |

TABLE 2-continued

Amino acid sequences of light chain variable regions (hightlighted in bold) of the 10-1074 antibody variants

| SEQ ID NO. | SEQUENCE | OTHER INFORMATION |
|---|---|---|
| | LTPEQWKSHRSYSCQVTHEG<br>STVEKTVAPTECS | |
| SEQ ID NO: 30 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-230_LC |
| SEQ ID NO: 31 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-231_LC |
| SEQ ID NO: 32 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-232_LC |
| SEQ ID NO: 33 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-233_LC |
| SEQ ID NO: 34 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-234_LC |
| SEQ ID NO: 35 | MGWSCIILFLVATATGVHSS<br>PVRPLSVALGETARISC**GRQ**<br>**ALGSRAVQWYQHRPGQAPIL**<br>**LIYNNQDRPSGIPERFSGTP**<br>**DINEGTRATLTISGVEAGDE** | MS-235_LC |

TABLE 2-continued

Amino acid sequences of light chain variable regions (hightlighted in bold) of the 10-1074 antibody variants

| SEQ ID NO. | SEQUENCE | OTHER INFORMATION |
|---|---|---|
| | **ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | |
| SEQ ID NO: 36 | MGWSCIILFLVATATGVHSS<br>PVRPLSVALGETARISC**GRQ**<br>**ALGSRAVQWYQHRPGQAPIL**<br>**LIYNNQDRPSGIPERFSGTP**<br>**DINEGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-236_LC |
| SEQ ID NO: 37 | MGWSCIILFLVATATGVHSS<br>PVRPLSVALGETARISC**GRQ**<br>**ALGSRAVQWYQHRPGQAPIL**<br>**LIYNNQDRPSGIPERFSGTP**<br>**DINEGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-237_LC |
| SEQ ID NO: 38 | MGWSCIILFLVATATGVHSS<br>PVRPLSVALGETARISC**GRQ**<br>**ALGSRAVQWYQHRPGQAPIL**<br>**LIYNNQDRPSGIPERFSGTP**<br>**DINEGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-238_LC |
| SEQ ID NO: 39 | MGWSCIILFLVATATGVHSS<br>PVRPLSVALGETARISC**GRQ**<br>**ALGSRAVQWYQHRPGQAPIL**<br>**LIYNNQDRPSGIPERFSGTP**<br>**DINEGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-239_LC |
| SEQ ID NO: 40 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-240_LC |
| SEQ ID NO: 41 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-241_LC |
| SEQ ID NO: 42 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-242_LC |
| SEQ ID NO: 43 | MGWSCIILFLVATATGVHSS<br>PVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-243_LC |
| SEQ ID NO: 44 | MGWSCIILFLVATATGVHSS<br>PVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-244_LC |
| SEQ ID NO: 45 | MGWSCIILFLVATATGVHSS<br>PVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-245_LC |
| SEQ ID NO: 46 | MGWSCIILFLVATATGVHSS<br>YVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF | MS-246_LC |

TABLE 2-continued

Amino acid sequences of light chain variable regions (hightlighted in bold) of the 10-1074 antibody variants

| SEQ ID NO. | SEQUENCE | OTHER INFORMATION |
|---|---|---|
| | YPGAVTVAWKADSSPVKAGV<br>ETTTPSKQSNNKYAASSYLS<br>LTPEQWKSHRSYSCQVTHEG<br>STVEKTVAPTECS | |
| SEQ ID NO: 47 | MGWSCIILFLVATATGVHSS<br>PVRPLSVALGETARISC**GRQ**<br>**ALGSRAVQWYQHRPGQAPIL**<br>**LIYNNQDRPSGIPERFSGTP**<br>**DINFGTRATLTISGVEAGDE**<br>**ADYYCHMWDSRSGFSWS**FGG<br>ATRLTVLGQPKAAPSVTLFP<br>PSSEELQANKATLVCLISDF<br>YPGAVTVAWKADSSPVKAGV<br>ETTTPSKQSNNKYAASSYLS<br>LTPEQWKSHRSYSCQVTHEG<br>STVEKTVAPTECS | MS-247_LC |

TABLE 3

Amino acid sequences of heavy chain variable regions (highlighted in bold) of the 10-1074 antibody variants

| SEQ ID NO. | SEQUENCE | OTHER INFORMATION |
|---|---|---|
| SEQ ID NO: 48 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISR**<br>**DTSKNQLSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVMHEA<br>LHNHYTQKSLSLSPG<br>K | MS-193_HC |
| SEQ ID NO: 49 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISR**<br>**DTSKNQLSLKLNSVT**<br>**PADTAVYYCATARRG** | MS-194_HC |

TABLE 3-continued

Amino acid sequences of heavy chain variable regions (highlighted in bold) of the 10-1074 antibody variants

| SEQ ID NO. | SEQUENCE | OTHER INFORMATION |
|---|---|---|
| | **QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | |
| SEQ ID NO: 50 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISR**<br>**DTSKNQLSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | MS-203_HC |
| SEQ ID NO: 51 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISR**<br>**DTSKNQLSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV | MS-204_HC |

TABLE 3-continued

Amino acid sequences of heavy chain variable regions (highlighted in bold) of the 10-1074 antibody variants

| SEQ ID NO. | SEQUENCE | OTHER INFORMATION |
|---|---|---|
| | KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | |
| SEQ ID NO: 52 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISR**<br>**DTSKNQLSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | MS-205_HC |
| SEQ ID NO: 53 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISR**<br>**DTSKNQLSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP | MS-206_HC |

TABLE 3-continued

Amino acid sequences of heavy chain variable regions (highlighted in bold) of the 10-1074 antibody variants

| SEQ ID NO. | SEQUENCE | OTHER INFORMATION |
|---|---|---|
| | SNTKVDKKVEPKSCD<br>KTHTCPPCAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | |
| SEQ ID NO: 54 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISR**<br>**DTSKNQLSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | MS-207_HC |
| SEQ ID NO: 55 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISR**<br>**DTSKNQLSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCAPELLG<br>GPSVFLFPPKPKDTL<br>MISRTPEVTCVVVDV | MS-208_HC |

TABLE 3-continued

Amino acid sequences of heavy chain variable regions (highlighted in bold) of the 10-1074 antibody variants

| SEQ ID NO. | SEQUENCE | OTHER INFORMATION |
|---|---|---|
| | SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | |
| SEQ ID NO: 56 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISR**<br>**DTSKNQLSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | MS-209_HC |
| SEQ ID NO: 57 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISR**<br>**DTSKNQLSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK | MS-210_HC |

TABLE 3-continued

Amino acid sequences of heavy chain variable regions (highlighted in bold) of the 10-1074 antibody variants

| SEQ ID NO. | SEQUENCE | OTHER INFORMATION |
|---|---|---|
| | ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | |
| SEQ ID NO: 58 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISR**<br>**DTSKNQLSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | MS-211_HC |
| SEQ ID NO: 59 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISR**<br>**DTSKNQLSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ | MS-212_HC |

TABLE 3-continued

Amino acid sequences of heavy chain variable regions (highlighted in bold) of the 10-1074 antibody variants

| SEQ ID NO. | SEQUENCE | OTHER INFORMATION |
|---|---|---|
| | PENNYKTTPPVLDSD<br>GSFFLYSKLTVDKSR<br>WQQGNVFSCSVLHEA<br>LHSHYTQKSLSLSPG<br>K | |
| SEQ ID NO: 60 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISR**<br>**DTSKNQLSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | MS-213_HC |
| SEQ ID NO: 61 | MGWSCIILFLVATAT<br>GVHSQVQLQESGPGL<br>VKPSETLSVTCSVSG<br>GSM**NNYYWTWIRQSP**<br>**GKGLEWIGYISDRES**<br>**ATYNPSLNSRVVISR**<br>**DTSKNQLSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ | MS-214_HC |

TABLE 3-continued

Amino acid sequences of heavy chain variable regions (highlighted in bold) of the 10-1074 antibody variants

| SEQ ID NO. | SEQUENCE | OTHER INFORMATION |
|---|---|---|
| | PENNYKTTPPVLDSD<br>GSFFLYSKLTVDKSR<br>WQQGNVFSCSVLHEA<br>LHSHYTQKSLSLSPG<br>K | |
| SEQ ID NO: 62 | MGWSCIILFLVATAT<br>GVHSQVQLQESGPGL<br>VKPSETLSVTCSVSG<br>DSM**NNYYWTWIRQPP**<br>**GKGLEWIGYISDRES**<br>**ATYNPSLNSRVVISR**<br>**DTSKNQLSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | MS-215_HC |
| SEQ ID NO: 63 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVTISR**<br>**DTSKNQLSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD | MS-216_HC |

TABLE 3-continued

Amino acid sequences of heavy chain variable regions (highlighted in bold) of the 10-1074 antibody variants

| SEQ ID NO. | SEQUENCE | OTHER INFORMATION |
|---|---|---|
| | GSFFLYSKLTVDKSR<br>WQQGNVFSCSVLHEA<br>LHSHYTQKSLSLSPG<br>K | |
| SEQ ID NO: 64 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISV**<br>**DTSKNQLSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | MS-217_HC |
| SEQ ID NO: 65 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISR**<br>**DTSKNQFSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | MS-218_HC |

TABLE 3-continued

Amino acid sequences of heavy chain variable regions (highlighted in bold) of the 10-1074 antibody variants

| SEQ ID NO. | SEQUENCE | OTHER INFORMATION |
|---|---|---|
| SEQ ID NO: 66 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISR**<br>**DTSKNQLSLKLNSVT**<br>**PADTAVYYCARARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | MS-219_HC |
| SEQ ID NO: 67 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISR**<br>**DTSKNQLSLKLNSVT**<br>**PADTAVYYCATARRG**<br>**QRIYGVVSFGEFFYY**<br>**YSMDV**WGQGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | MS-220_HC |
| SEQ ID NO: 68 | MGWSCIILFLVATAT<br>GVHSQVQLQESGPGL<br>VKPSETLSVTCSVSG | MS-224_HC |

TABLE 3-continued

Amino acid sequences of heavy chain variable regions (highlighted in bold) of the 10-1074 antibody variants

| SEQ ID NO. | SEQUENCE | OTHER INFORMATION |
|---|---|---|
| | DSM**NNYYWTWIRQSP**<br>**GKGLEWIGYISDRES**<br>**ATYNPSLQSRVVISR**<br>**DTSKNQLSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | |
| SEQ ID NO: 69 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISV**<br>**DTSKNQLSLKLNSVT**<br>**PADTAVYYCARARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | MS-200_HC |
| SEQ ID NO: 70 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVTISR**<br>**DTSKNQFSLKLNSVT** | MS-201_HC |

TABLE 3-continued

Amino acid sequences of heavy chain variable regions (highlighted in bold) of the 10-1074 antibody variants

| SEQ ID NO. | SEQUENCE | OTHER INFORMATION |
|---|---|---|
| | **PADTAVYYCARARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | |
| SEQ ID NO: 71 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVTISR**<br>**DTSKNQFSLKLNSVT**<br>**PADTAVYYCARARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | MS-202_HC |
| SEQ ID NO: 72 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVTISR**<br>**DTSKNQLSLKLNSVT**<br>**PADTAVYYCATARRG**<br>**QRIYGVVSFGEFFYY**<br>**YSMDV**WGKGTTVTVS<br>SASTKGPSVFPLAPS | MS-225_HC |

TABLE 3-continued

Amino acid sequences of heavy chain variable regions (highlighted in bold) of the 10-1074 antibody variants

| SEQ ID NO. | SEQUENCE | OTHER INFORMATION |
|---|---|---|
| | SKSTSGGTAALGCLV | |
| | KDYFPEPVTVSWNSG | |
| | ALTSGVHTFPAVLQS | |
| | SGLYSLSSVVTVPSS | |
| | SLGTQTYICNVNHKP | |
| | SNTKVDKKVEPKSCD | |
| | KTHTCPPCPAPELLG | |
| | GPSVFLFPPKPKDTL | |
| | MISRTPEVTCVVVDV | |
| | SHEDPEVKFNWYVDG | |
| | VEVHNAKTKPREEQY | |
| | NSTYRVVSVLTVLHQ | |
| | DWLNGKEYKCKVSNK | |
| | ALPAPIEKTISKAKG | |
| | QPREPQVYTLPPSRD | |
| | ELTKNQVSLTCLVKG | |
| | FYPSDIAVEWESNGQ | |
| | PENNYKTTPPVLDSD | |
| | GSFFLYSKLTVDKSR | |
| | WQQGNVFSCSVLHEA | |
| | LHSHYTQKSLSLSPG | |
| | K | |
| SEQ ID | MGWSCIILFLVATAT | MS-226_HC |
| NO: 73 | GVHSQVQLQESGPGL | |
| | VKPSETLSVTCSVSG | |
| | DSM**NNYYWTWIRQSP** | |
| | **GKGLEWIGYISDRES** | |
| | **ATYNPSLNSRVVISV** | |
| | **DTSKNQLSLKLNSVT** | |
| | **PADTAVYYCATARRG** | |
| | **QRIYGVVSFGEFFYY** | |
| | **YSMDV**WGKGTTVTVS | |
| | SASTKGPSVFPLAPS | |
| | SKSTSGGTAALGCLV | |
| | KDYFPEPVTVSWNSG | |
| | ALTSGVHTFPAVLQS | |
| | SGLYSLSSVVTVPSS | |
| | SLGTQTYICNVNHKP | |
| | SNTKVDKKVEPKSCD | |
| | KTHTCPPCPAPELLG | |
| | GPSVFLFPPKPKDTL | |
| | MISRTPEVTCVVVDV | |
| | SHEDPEVKFNWYVDG | |
| | VEVHNAKTKPREEQY | |
| | NSTYRVVSVLTVLHQ | |
| | DWLNGKEYKCKVSNK | |
| | ALPAPIEKTISKAKG | |
| | QPREPQVYTLPPSRD | |
| | ELTKNQVSLTCLVKG | |
| | FYPSDIAVEWESNGQ | |
| | PENNYKTTPPVLDSD | |
| | GSFFLYSKLTVDKSR | |
| | WQQGNVFSCSVLHEA | |
| | LHSHYTQKSLSLSPG | |
| | K | |
| SEQ ID | MGWSCIILFLVATAT | MS-227_HC |
| NO: 74 | GVHSQVQLQESGPGL | |
| | VKPSETLSVTCSVSG | |
| | DSM**NNYYWTWIRQSP** | |
| | **GKGLEWIGYISDRES** | |
| | **ATYNPSLNSRVVISR** | |
| | **DTSKNQFSLKLNSVT** | |
| | **PADTAVYYCATARRG** | |
| | **QRIYGVVSFGEFFYY** | |
| | **YSMDV**WGKGTTVTVS | |
| | SASTKGPSVFPLAPS | |
| | SKSTSGGTAALGCLV | |
| | KDYFPEPVTVSWNSG | |
| | ALTSGVHTFPAVLQS | |
| | SGLYSLSSVVTVPSS | |

TABLE 3-continued

Amino acid sequences of heavy chain variable regions (highlighted in bold) of the 10-1074 antibody variants

| SEQ ID NO. | SEQUENCE | OTHER INFORMATION |
|---|---|---|
| | SLGTQTYICNVNHKP | |
| | SNTKVDKKVEPKSCD | |
| | KTHTCPPCPAPELLG | |
| | GPSVFLFPPKPKDTL | |
| | MISRTPEVTCVVVDV | |
| | SHEDPEVKFNWYVDG | |
| | VEVHNAKTKPREEQY | |
| | NSTYRVVSVLTVLHQ | |
| | DWLNGKEYKCKVSNK | |
| | ALPAPIEKTISKAKG | |
| | QPREPQVYTLPPSRD | |
| | ELTKNQVSLTCLVKG | |
| | FYPSDIAVEWESNGQ | |
| | PENNYKTTPPVLDSD | |
| | GSFFLYSKLTVDKSR | |
| | WQQGNVFSCSVLHEA | |
| | LHSHYTQKSLSLSPG | |
| | K | |
| SEQ ID | MGWSCIILFLVATAT | MS-228_HC |
| NO: 75 | GVHSQVQLQESGPGL | |
| | VKPSETLSVTCSVSG | |
| | DSM**NNYYWTWIRQSP** | |
| | **GKGLEWIGYISDRES** | |
| | **ATYNPSLNSRVVISR** | |
| | **DTSKNQLSLKLNSVT** | |
| | **PADTAVYYCARARRG** | |
| | **QRIYGVVSFGEFFYY** | |
| | **YSMDV**WGKGTTVTVS | |
| | SASTKGPSVFPLAPS | |
| | SKSTSGGTAALGCLV | |
| | KDYFPEPVTVSWNSG | |
| | ALTSGVHTFPAVLQS | |
| | SGLYSLSSVVTVPSS | |
| | SLGTQTYICNVNHKP | |
| | SNTKVDKKVEPKSCD | |
| | KTHTCPPCPAPELLG | |
| | GPSVFLFPPKPKDTL | |
| | MISRTPEVTCVVVDV | |
| | SHEDPEVKFNWYVDG | |
| | VEVHNAKTKPREEQY | |
| | NSTYRVVSVLTVLHQ | |
| | DWLNGKEYKCKVSNK | |
| | ALPAPIEKTISKAKG | |
| | QPREPQVYTLPPSRD | |
| | ELTKNQVSLTCLVKG | |
| | FYPSDIAVEWESNGQ | |
| | PENNYKTTPPVLDSD | |
| | GSFFLYSKLTVDKSR | |
| | WQQGNVFSCSVLHEA | |
| | LHSHYTQKSLSLSPG | |
| | K | |
| SEQ ID | MGWSCIILFLVATAT | MS-229_HC |
| NO: 76 | GVHSQVQLQESGPGL | |
| | VKPSETLSVTCSVSG | |
| | DSM**NNYYWTWIRQSP** | |
| | **GKGLEWIGYISDRES** | |
| | **ATYNPSLNSRVTISV** | |
| | **DTSKNQLSLKLNSVT** | |
| | **PADTAVYYCATARRG** | |
| | **QRIYGVVSFGEFFYY** | |
| | **YSMDV**WGKGTTVTVS | |
| | SASTKGPSVFPLAPS | |
| | SKSTSGGTAALGCLV | |
| | KDYFPEPVTVSWNSG | |
| | ALTSGVHTFPAVLQS | |
| | SGLYSLSSVVTVPSS | |
| | SLGTQTYICNVNHKP | |
| | SNTKVDKKVEPKSCD | |
| | KTHTCPPCPAPELLG | |
| | GPSVFLFPPKPKDTL | |

TABLE 3-continued

Amino acid sequences of heavy chain variable regions (highlighted in bold) of the 10-1074 antibody variants

| SEQ ID NO. | SEQUENCE | OTHER INFORMATION |
| --- | --- | --- |
| | MISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK | |
| SEQ ID NO: 77 | MGWSCIILFLVATATGVHSQVQLQESGPGLVKPSETLSVTCSVSGDSM**NNYYWTWIRQSPGKGLEWIGYISDRESATYNPSLNSRVTISRDTSKNQFSLKLNSVTPADTAVYYCATARRGQRIYGVVSFGEFFYYYSMDV**WGKGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK | MS-230_HC |
| SEQ ID NO: 78 | MGWSCIILFLVATATGVHSQVQLQESGPGLVKPSETLSVTCSVSGDSM**NNYYWTWIRQSPGKGLEWIGYISDRESATYNPSLNSRVTISRDTSKNQLSLKLNSVTPADTAVYYCARARRGQRIYGVVSFGEFFYYYSMDV**WGKGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQ | MS-231_HC |

TABLE 3-continued

Amino acid sequences of heavy chain variable regions (highlighted in bold) of the 10-1074 antibody variants

| SEQ ID NO. | SEQUENCE | OTHER INFORMATION |
| --- | --- | --- |
| | DWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK | |
| SEQ ID NO: 79 | MGWSCIILFLVATATGVHSQVQLQESGPGLVKPSETLSVTCSVSGDSM**NNYYWTWIRQSPGKGLEWIGYISDRESATYNPSLNSRVVISVDTSKNQFSLKLNSVTPADTAVYYCATARRGQRIYGVVSFGEFFYYYSMDV**WGKGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK | MS-232_HC |
| SEQ ID NO: 80 | MGWSCIILFLVATATGVHSQVQLQESGPGLVKPSETLSVTCSVSGDSM**NNYYWTWIRQSPGKGLEWIGYISDRESATYNPSLNSRVVISVDTSKNQLSLKLNSVTPADTAVYYCARARRGQRIYGVVSFGEFFYYYSMDV**WGKGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKG | MS-233_HC |

TABLE 3-continued

Amino acid sequences of heavy chain variable regions (highlighted in bold) of the 10-1074 antibody variants

| SEQ ID NO. | SEQUENCE | OTHER INFORMATION |
|---|---|---|
| | FYPSDIAVEWESNGQ PENNYKTTPPVLDSD GSFFLYSKLTVDKSR WQQGNVFSCSVLHEA LHSHYTQKSLSLSPG K | |
| SEQ ID NO: 81 | MGWSCIILFLVATAT GVHSQVQLQESGPGL VKPSETLSVTCSVSG DSM**NNYYWTWIRQSP GKGLEWIGYISDRES ATYNPSLNSRVVISR DTSKNQFSLKLNSVT PADTAVYYCARARRG QRIYGVVSFGEFFYY YSMDV**WGKGTTVTVS SASTKGPSVFPLAPS SKSTSGGTAALGCLV KDYFPEPVTVSWNSG ALTSGVHTFPAVLQS SGLYSLSSVVTVPSS SLGTQTYICNVNHKP SNTKVDKKVEPKSCD KTHTCPPCPAPELLG GPSVFLFPPKPKDTL MISRTPEVTCVVVDV SHEDPEVKFNWYVDG VEVHNAKTKPREEQY NSTYRVVSVLTVLHQ DWLNGKEYKCKVSNK ALPAPIEKTISKAKG QPREPQVYTLPPSRD ELTKNQVSLTCLVKG FYPSDIAVEWESNGQ PENNYKTTPPVLDSD GSFFLYSKLTVDKSR WQQGNVFSCSVLHEA LHSHYTQKSLSLSPG K | MS-234_HC |
| SEQ ID NO: 82 | MGWSCIILFLVATAT GVHSQVQLQESGPGL VKPSETLSVTCSVSG DSM**NNYYWTWIRQSP GKGLEWIGYISDRES ATYNPSLNSRVTISV DTSKNQLSLKLNSVT PADTAVYYCATARRG QRIYGVVSFGEFFYY YSMDVWGKGTTVTVS** SASTKGPSVFPLAPS SKSTSGGTAALGCLV KDYFPEPVTVSWNSG ALTSGVHTFPAVLQS SGLYSLSSVVTVPSS SLGTQTYICNVNHKP SNTKVDKKVEPKSCD KTHTCPPCPAPELLG GPSVFLFPPKPKDTL MISRTPEVTCVVVDV SHEDPEVKFNWYVDG VEVHNAKTKPREEQY NSTYRVVSVLTVLHQ DWLNGKEYKCKVSNK ALPAPIEKTISKAKG QPREPQVYTLPPSRD ELTKNQVSLTCLVKG FYPSDIAVEWESNGQ PENNYKTTPPVLDSD GSFFLYSKLTVDKSR | MS-235_HC |

TABLE 3-continued

Amino acid sequences of heavy chain variable regions (highlighted in bold) of the 10-1074 antibody variants

| SEQ ID NO. | SEQUENCE | OTHER INFORMATION |
|---|---|---|
| | WQQGNVFSCSVLHEA LHSHYTQKSLSLSPG K | |
| SEQ ID NO: 83 | MGWSCIILFLVATAT GVHSQVQLQESGPGL VKPSETLSVTCSVSG DSM**NNYYWTWIRQSP GKGLEWIGYISDRES ATYNPSLNSRVTISR DTSKNQFSLKLNSVT PADTAVYYCATARRG QRIYGVVSFGEFFYY YSMDV**WGKGTTVTVS SASTKGPSVFPLAPS SKSTSGGTAALGCLV KDYFPEPVTVSWNSG ALTSGVHTFPAVLQS SGLYSLSSVVTVPSS SLGTQTYICNVNHKP SNTKVDKKVEPKSCD KTHTCPPCPAPELLG GPSVFLFPPKPKDTL MISRTPEVTCVVVDV SHEDPEVKFNWYVDG VEVHNAKTKPREEQY NSTYRVVSVLTVLHQ DWLNGKEYKCKVSNK ALPAPIEKTISKAKG QPREPQVYTLPPSRD ELTKNQVSLTCLVKG FYPSDIAVEWESNGQ PENNYKTTPPVLDSD GSFFLYSKLTVDKSR WQQGNVFSCSVLHEA LHSHYTQKSLSLSPG K | MS-236_HC |
| SEQ ID NO: 84 | MGWSCIILFLVATAT GVHSQVQLQESGPGL VKPSETLSVTCSVSG DSM**NNYYWTWIRQSP GKGLEWIGYISDRES ATYNPSLNSRVTISR DTSKNQLSLKLNSVT PADTAVYYCARARRG QRIYGVVSFGEFFYY YSMDV**WGKGTTVTVS SASTKGPSVFPLAPS SKSTSGGTAALGCLV KDYFPEPVTVSWNSG ALTSGVHTFPAVLQS SGLYSLSSVVTVPSS SLGTQTYICNVNHKP SNTKVDKKVEPKSCD KTHTCPPCPAPELLG GPSVFLFPPKPKDTL MISRTPEVTCVVVDV SHEDPEVKFNWYVDG VEVHNAKTKPREEQY NSTYRVVSVLTVLHQ DWLNGKEYKCKVSNK ALPAPIEKTISKAKG QPREPQVYTLPPSRD ELTKNQVSLTCLVKG FYPSDIAVEWESNGQ PENNYKTTPPVLDSD GSFFLYSKLTVDKSR WQQGNVFSCSVLHEA LHSHYTQKSLSLSPG K | MS-237_HC |

TABLE 3-continued

Amino acid sequences of heavy chain variable regions (highlighted in bold) of the 10-1074 antibody variants

| SEQ ID NO. | SEQUENCE | OTHER INFORMATION |
|---|---|---|
| SEQ ID NO: 85 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISV**<br>**DTSKNQFSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | MS-238_HC |
| SEQ ID NO: 86 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISR**<br>**DTSKNQFSLKLNSVT**<br>**PADTAVYYCARARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | MS-239_HC |
| SEQ ID NO: 87 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVTISV**<br>**DTSKNQFSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | MS-240_HC |
| SEQ ID NO: 88 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVTISV**<br>**DTSKNQLSLKLNSVT**<br>**PADTAVYYCARARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | MS-241_HC |
| SEQ ID NO: 89 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISV**<br>**DTSKNQFSLKLNSVT**<br>**PADTAVYYCARARRG** | MS-242_HC |

TABLE 3-continued

Amino acid sequences of heavy chain variable regions (highlighted in bold) of the 10-1074 antibody variants

| SEQ ID NO. | SEQUENCE | OTHER INFORMATION |
|---|---|---|
| | **QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | |
| SEQ ID NO: 90 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVTISV**<br>**DTSKNQFSLKLNSVT**<br>**PADTAVYYCATARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | MS-243_HC |
| SEQ ID NO: 91 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVTISV**<br>**DTSKNQLSLKLNSVT**<br>**PADTAVYYCARARRG**<br>**QRIYGVVSFGEFFYY**<br>**YSMDV**WGKGTTVTVS<br>SASTKGPSVFPLAPS<br>SKSTSGGTAALGCLV | MS-244_HC |

TABLE 3-continued

Amino acid sequences of heavy chain variable regions (highlighted in bold) of the 10-1074 antibody variants

| SEQ ID NO. | SEQUENCE | OTHER INFORMATION |
|---|---|---|
| | KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | |
| SEQ ID NO: 92 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVVISV**<br>**DTSKNQFSLKLNSVT**<br>**PADTAVYYCARARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP<br>SNTKVDKKVEPKSCD<br>KTHTCPPCPAPELLG<br>GPSVFLFPPKPKDTL<br>MISRTPEVTCVVVDV<br>SHEDPEVKFNWYVDG<br>VEVHNAKTKPREEQY<br>NSTYRVVSVLTVLHQ<br>DWLNGKEYKCKVSNK<br>ALPAPIEKTISKAKG<br>QPREPQVYTLPPSRD<br>ELTKNQVSLTCLVKG<br>FYPSDIAVEWESNGQ<br>PENNYKTTPPVLDSD<br>GSFFLYSKLTVDKSR<br>WQQGNVFSCSVLHEA<br>LHSHYTQKSLSLSPG<br>K | MS-245_HC |
| SEQ ID NO: 93 | MGWSCIILFLVATAT<br>GVHSQVQLQESGPGL<br>VKPSETLSVTCSVSG<br>DSM**NNYYWTWIRQSP**<br>**GKGLEWIGYISDRES**<br>**ATYNPSLNSRVTISV**<br>**DTSKNQFSLKLNSVT**<br>**PADTAVYYCARARRG**<br>**QRIYGVVSFGEFFYY**<br>**YSMDV**WGKGTTVTVS<br>SASTKGPSVFPLAPS<br>SKSTSGGTAALGCLV<br>KDYFPEPVTVSWNSG<br>ALTSGVHTFPAVLQS<br>SGLYSLSSVVTVPSS<br>SLGTQTYICNVNHKP | MS-246_HC |

TABLE 3-continued

| Amino acid sequences of heavy chain variable regions (highlighted in bold) of the 10-1074 antibody variants | | |
|---|---|---|
| SEQ ID NO. | SEQUENCE | OTHER INFORMATION |
| | SNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK | |
| SEQ ID NO: 94 | MGWSCIILFLVATATGVHSQVQLQESGPGLVKPSETLSVTCSVSGDSM**NNYYWTWIRQSPGKGLEWIGYISDRESATYNPSLNSRVTISVDTSKNQFSLKLNSVTPADTAVYYCARARRGQRIYGVVSFGEFFYYYSMDV**WGKGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK | MS-247_HC |

TABLE 4

| Amino acid sequences of CDR regions of the 10-1074 antibody variants | | |
|---|---|---|
| SEQ ID NO. | SEQUENCE | OTHER INFORMATION |
| SEQ ID NO: 95 | GRQALGSRAVQ | MS-193_LC CDR1 |
| SEQ ID NO: 96 | NNQDRPS | MS-193_LC CDR2 |
| SEQ ID NO: 97 | HMWDSRSGFSWS | MS-193_LC CDR3 |
| SEQ ID NO: 98 | NNYYWT | MS-193_HC CDR1 |
| SEQ ID NO: 99 | YISDRESATYNPSLNS | MS-193_HC CDR2 |

TABLE 4-continued

| Amino acid sequences of CDR regions of the 10-1074 antibody variants | | |
|---|---|---|
| SEQ ID NO. | SEQUENCE | OTHER INFORMATION |
| SEQ ID NO: 100 | ARRGQRIYGVVSFGEFFYYYSMDV | MS-193_HC CDR3 |
| SEQ ID NO: 101 | GRQALGSRAVQ | MS-194_LC CDR1 |
| SEQ ID NO: 102 | NNQDRPS | MS-194_LC CDR2 |
| SEQ ID NO: 103 | HMWDSRSGFSWS | MS-194_LC CDR3 |
| SEQ ID NO: 104 | NNYYWT | MS-194_HC CDR1 |
| SEQ ID NO: 105 | YISDRESATYNPSLNS | MS-194_HC CDR2 |
| SEQ ID NO: 106 | ARRGQRIYGVVSFGEFFYYYSMDV | MS-194_HC CDR3 |
| SEQ ID NO: 107 | GRQALGSRAVQ | MS-203_LC CDR1 |
| SEQ ID NO: 108 | NNQDRPS | MS-203_LC CDR2 |
| SEQ ID NO: 109 | HMWDSRSGFSWS | MS-203_LC CDR3 |
| SEQ ID NO: 110 | NNYYWT | MS-203_HC CDR1 |
| SEQ ID NO: 111 | YISDRESATYNPSLNS | MS-203_HC CDR2 |
| SEQ ID NO: 112 | ARRGQRIYGVVSFGEFFYYYSMDV | MS-203_HC CDR3 |
| SEQ ID NO: 113 | GRQALGSRAVQ | MS-204_LC CDR1 |
| SEQ ID NO: 114 | NNQDRPS | MS-204_LC CDR2 |
| SEQ ID NO: 115 | HMWDSRSGFSWS | MS-204_LC CDR3 |
| SEQ ID NO: 116 | NNYYWT | MS-204_HC CDR1 |
| SEQ ID NO: 117 | YISDRESATYNPSLNS | MS-204_HC CDR2 |
| SEQ ID NO: 118 | ARRGQRIYGVVSFGEFFYYYSMDV | MS-204_HC CDR3 |
| SEQ ID NO: 119 | GRQALGSRAVQ | MS-205_LC CDR1 |
| SEQ ID NO: 120 | NNQDRPS | MS-205_LC CDR2 |
| SEQ ID NO: 121 | HMWDSRSGFSWS | MS-205_LC CDR3 |
| SEQ ID NO: 122 | NNYYWT | MS-205_HC CDR1 |
| SEQ ID NO: 123 | YISDRESATYNPSLNS | MS-205_HC CDR2 |
| SEQ ID NO: 124 | ARRGQRIYGVVSFGEFFYYYSMDV | MS-205_HC CDR3 |
| SEQ ID NO: 125 | GRQALGSRAVQ | MS-206_LC CDR1 |
| SEQ ID NO: 126 | NNQDRPS | MS-206_LC CDR2 |
| SEQ ID NO: 127 | HMWDSRSGFSWS | MS-206_LC CDR3 |
| SEQ ID NO: 128 | NNYYWT | MS-206_HC CDR1 |
| SEQ ID NO: 129 | YISDRESATYNPSLNS | MS-206_HC CDR2 |
| SEQ ID NO: 130 | ARRGQRIYGVVSFGEFFYYYSMDV | MS-206_HC CDR3 |
| SEQ ID NO: 131 | GRQALGSRAVQ | MS-207_LC CDR1 |
| SEQ ID NO: 132 | NNQDRPS | MS-207_LC CDR2 |
| SEQ ID NO: 133 | HMWDSRSGFSWS | MS-207_LC CDR3 |

TABLE 4-continued

Amino acid sequences of CDR regions of the 10-1074 antibody variants

| SEQ ID NO. | SEQUENCE | OTHER INFORMATION |
|---|---|---|
| SEQ ID NO: 134 | NNYYWT | MS-207_HC CDR1 |
| SEQ ID NO: 135 | YISDRESATYNPSLNS | MS-207_HC CDR2 |
| SEQ ID NO: 136 | ARRGQRIYGVVSFGEF FYYYSMDV | MS-207_HC CDR3 |
| SEQ ID NO: 137 | GRQALGSRAVQ | MS-208_LC CDR1 |
| SEQ ID NO: 138 | NNQDRPS | MS-208_LC CDR2 |
| SEQ ID NO: 139 | HMWDSRSGFSWS | MS-208_LC CDR3 |
| SEQ ID NO: 140 | NNYYWT | MS-208_HC CDR1 |
| SEQ ID NO: 141 | YISDRESATYNPSLNS | MS-208_HC CDR2 |
| SEQ ID NO: 142 | ARRGQRIYGVVSFGEF FYYYSMDV | MS-208_HC CDR3 |
| SEQ ID NO: 143 | GRQALGSRAVQ | MS-209_LC CDR1 |
| SEQ ID NO: 144 | NNQDRPS | MS-209_LC CDR2 |
| SEQ ID NO: 145 | HMWDSRSGFSWS | MS-209_LC CDR3 |
| SEQ ID NO: 146 | NNYYWT | MS-209_HC CDR1 |
| SEQ ID NO: 147 | YISDRESATYNPSLNS | MS-209_HC CDR2 |
| SEQ ID NO: 148 | ARRGQRIYGVVSFGEF FYYYSMDV | MS-209_HC CDR3 |
| SEQ ID NO: 149 | GRQALGSRAVQ | MS-210_LC CDR1 |
| SEQ ID NO: 150 | NNQDRPS | MS-210_LC CDR2 |
| SEQ ID NO: 151 | HMWDSRSGFSWS | MS-210_LC CDR3 |
| SEQ ID NO: 152 | NNYYWT | MS-210_HC CDR1 |
| SEQ ID NO: 153 | YISDRESATYNPSLNS | MS-210_HC CDR2 |
| SEQ ID NO: 154 | ARRGQRIYGVVSFGEF FYYYSMDV | MS-210_HC CDR3 |
| SEQ ID NO: 155 | GRQALGSRAVQ | MS-211_LC CDR1 |
| SEQ ID NO: 156 | NNQDRPS | MS-211_LC CDR2 |
| SEQ ID NO: 157 | HMWDSRSGFSWS | MS-211_LC CDR3 |
| SEQ ID NO: 158 | NNYYWT | MS-211_HC CDR1 |
| SEQ ID NO: 159 | YISDRESATYNPSLNS | MS-211_HC CDR2 |
| SEQ ID NO: 160 | ARRGQRIYGVVSFGEF FYYYSMDV | MS-211_HC CDR3 |
| SEQ ID NO: 161 | GRQALGSRAVQ | MS-212_LC CDR1 |
| SEQ ID NO: 162 | NNQDRPS | MS-212_LC CDR2 |
| SEQ ID NO: 163 | HMWESRSGFSWS | MS-212_LC CDR3 |
| SEQ ID NO: 164 | NNYYWT | MS-212_HC CDR1 |
| SEQ ID NO: 165 | YISDRESATYNPSLNS | MS-212_HC CDR2 |
| SEQ ID NO: 166 | ARRGQRIYGVVSFGEF FYYYSMDV | MS-212_HC CDR3 |
| SEQ ID NO: 167 | GRQALGSRAVQ | MS-213_LC CDR1 |

TABLE 4-continued

Amino acid sequences of CDR regions of the 10-1074 antibody variants

| SEQ ID NO. | SEQUENCE | OTHER INFORMATION |
|---|---|---|
| SEQ ID NO: 168 | NNQDRPS | MS-213_LC CDR2 |
| SEQ ID NO: 169 | HMWDSRSGFSWS | MS-213_LC CDR3 |
| SEQ ID NO: 170 | NNYYWT | MS-213_HC CDR1 |
| SEQ ID NO: 171 | YISDRESATYNPSLNS | MS-213_HC CDR2 |
| SEQ ID NO: 172 | ARRGQRIYGVVSFGEF FYYYSMDV | MS-213_HC CDR3 |
| SEQ ID NO: 173 | GRQALGSRAVQ | MS-214_LC CDR1 |
| SEQ ID NO: 174 | NNQDRPS | MS-214_LC CDR2 |
| SEQ ID NO: 175 | HMWDSRSGFSWS | MS-214_LC CDR3 |
| SEQ ID NO: 176 | NNYYWT | MS-214_HC CDR1 |
| SEQ ID NO: 177 | YISDRESATYNPSLNS | MS-214_HC CDR2 |
| SEQ ID NO: 178 | ARRGQRIYGVVSFGEF FYYYSMDV | MS-214_HC CDR3 |
| SEQ ID NO: 179 | GRQALGSRAVQ | MS-215_LC CDR1 |
| SEQ ID NO: 180 | NNQDRPS | MS-215_LC CDR2 |
| SEQ ID NO: 181 | HMWDSRSGFSWS | MS-215_LC CDR3 |
| SEQ ID NO: 182 | NNYYWT | MS-215_HC CDR1 |
| SEQ ID NO: 183 | YISDRESATYNPSLNS | MS-215_HC CDR2 |
| SEQ ID NO: 184 | ARRGQRIYGVVSFGEF FYYYSMDV | MS-215_HC CDR3 |
| SEQ ID NO: 185 | GRQALGSRAVQ | MS-216_LC CDR1 |
| SEQ ID NO: 186 | NNQDRPS | MS-216_LC CDR2 |
| SEQ ID NO: 187 | HMWDSRSGFSWS | MS-216_LC CDR3 |
| SEQ ID NO: 188 | NNYYWT | MS-216_HC CDR1 |
| SEQ ID NO: 189 | YISDRESATYNPSLNS | MS-216_HC CDR2 |
| SEQ ID NO: 190 | ARRGQRIYGVVSFGEF FYYYSMDV | MS-216_HC CDR3 |
| SEQ ID NO: 191 | GRQALGSRAVQ | MS-217_LC CDR1 |
| SEQ ID NO: 192 | NNQDRPS | MS-217_LC CDR2 |
| SEQ ID NO: 193 | HMWDSRSGFSWS | MS-217_LC CDR3 |
| SEQ ID NO: 194 | NNYYWT | MS-217_HC CDR1 |
| SEQ ID NO: 195 | YISDRESATYNPSLNS | MS-217_HC CDR2 |
| SEQ ID NO: 196 | ARRGQRIYGVVSFGEF FYYYSMDV | MS-217_HC CDR3 |
| SEQ ID NO: 197 | GRQALGSRAVQ | MS-218_LC CDR1 |
| SEQ ID NO: 198 | NNQDRPS | MS-218_LC CDR2 |
| SEQ ID NO: 199 | HMWDSRSGFSWS | MS-218_LC CDR3 |
| SEQ ID NO: 200 | NNYYWT | MS-218_HC CDR1 |
| SEQ ID NO: 201 | YISDRESATYNPSLNS | MS-218_HC CDR2 |

TABLE 4-continued

Amino acid sequences of CDR regions of the 10-1074 antibody variants

| SEQ ID NO. | SEQUENCE | OTHER INFORMATION |
|---|---|---|
| SEQ ID NO: 202 | ARRGQRIYGVVSFGEF FYYYSMDV | MS-218_HC CDR3 |
| SEQ ID NO: 203 | GRQALGSRAVQ | MS-219_LC CDR1 |
| SEQ ID NO: 204 | NNQDRPS | MS-219_LC CDR2 |
| SEQ ID NO: 205 | HMWDSRSGFSWS | MS-219_LC CDR3 |
| SEQ ID NO: 206 | NNYYWT | MS-219_HC CDR1 |
| SEQ ID NO: 207 | YISDRESATYNPSLNS | MS-219_HC CDR2 |
| SEQ ID NO: 208 | ARRGQRIYGVVSFGEF FYYYSMDV | MS-219_HC CDR3 |
| SEQ ID NO: 209 | GRQALGSRAVQ | MS-220_LC CDR1 |
| SEQ ID NO: 210 | NNQDRPS | MS-220_LC CDR2 |
| SEQ ID NO: 211 | HMWDSRSGFSWS | MS-220_LC CDR3 |
| SEQ ID NO: 212 | NNYYWT | MS-220_HC CDR1 |
| SEQ ID NO: 213 | YISDRESATYNPSLNS | MS-220_HC CDR2 |
| SEQ ID NO: 214 | ARRGQRIYGVVSFGEF FYYYSMDV | MS-220_HC CDR3 |
| SEQ ID NO: 215 | GRQALGSRAVQ | MS-224_LC CDR1 |
| SEQ ID NO: 216 | NNQDRPS | MS-224_LC CDR2 |
| SEQ ID NO: 217 | HMWDSRSGFSWS | MS-224_LC CDR3 |
| SEQ ID NO: 218 | NNYYWT | MS-224_HC CDR1 |
| SEQ ID NO: 219 | YISDRESATYNPSLQS | MS-224_HC CDR2 |
| SEQ ID NO: 220 | ARRGQRIYGVVSFGEF FYYYSMDV | MS-224_HC CDR3 |
| SEQ ID NO: 221 | GRQALGSRAVQ | MS-200_LC CDR1 |
| SEQ ID NO: 222 | NNQDRPS | MS-200_LC CDR2 |
| SEQ ID NO: 223 | HMWDSRSGFSWS | MS-200_LC CDR3 |
| SEQ ID NO: 224 | NNYYWT | MS-200_HC CDR1 |
| SEQ ID NO: 225 | YISDRESATYNPSLNS | MS-200_HC CDR2 |
| SEQ ID NO: 226 | ARRGQRIYGVVSFGEF FYYYSMDV | MS-200_HC CDR3 |
| SEQ ID NO: 227 | GRQALGSRAVQ | MS-201_LC CDR1 |
| SEQ ID NO: 228 | NNQDRPS | MS-201_LC CDR2 |
| SEQ ID NO: 229 | HMWDSRSGFSWS | MS-201_LC CDR3 |
| SEQ ID NO: 230 | NNYYWT | MS-201_HC CDR1 |
| SEQ ID NO: 231 | YISDRESATYNPSLNS | MS-201_HC CDR2 |
| SEQ ID NO: 232 | ARRGQRIYGVVSFGEF FYYYSMDV | MS-201_HC CDR3 |
| SEQ ID NO: 233 | GRQALGSRAVQ | MS-202_LC CDR1 |
| SEQ ID NO: 234 | NNQDRPS | MS-202_LC CDR2 |
| SEQ ID NO: 235 | HMWDSRSGFSWS | MS-202_LC CDR3 |

TABLE 4-continued

Amino acid sequences of CDR regions of the 10-1074 antibody variants

| SEQ ID NO. | SEQUENCE | OTHER INFORMATION |
|---|---|---|
| SEQ ID NO: 236 | NNYYWT | MS-202_HC CDR1 |
| SEQ ID NO: 237 | YISDRESATYNPSLNS | MS-202_HC CDR2 |
| SEQ ID NO: 238 | ARRGQRIYGVVSFGEF FYYYSMDV | MS-202_HC CDR3 |
| SEQ ID NO: 239 | GRQALGSRAVQ | MS-225_LC CDR1 |
| SEQ ID NO: 240 | NNQDRPS | MS-225_LC CDR2 |
| SEQ ID NO: 241 | HMWDSRSGFSWS | MS-225_LC CDR3 |
| SEQ ID NO: 242 | NNYYWT | MS-225_HC CDR1 |
| SEQ ID NO: 243 | YISDRESATYNPSLNS | MS-225_HC CDR2 |
| SEQ ID NO: 244 | ARRGQRIYGVVSFGEF FYYYSMDV | MS-225_HC CDR3 |
| SEQ ID NO: 245 | GRQALGSRAVQ | MS-226_LC CDR1 |
| SEQ ID NO: 246 | NNQDRPS | MS-226_LC CDR2 |
| SEQ ID NO: 247 | HMWDSRSGFSWS | MS-226_LC CDR3 |
| SEQ ID NO: 248 | NNYYWT | MS-226_HC CDR1 |
| SEQ ID NO: 249 | YISDRESATYNPSLNS | MS-226_HC CDR2 |
| SEQ ID NO: 250 | ARRGQRIYGVVSFGEF FYYYSMDV | MS-226_HC CDR3 |
| SEQ ID NO: 251 | GRQALGSRAVQ | MS-227_LC CDR1 |
| SEQ ID NO: 252 | NNQDRPS | MS-227_LC CDR2 |
| SEQ ID NO: 253 | HMWDSRSGFSWS | MS-227_LC CDR3 |
| SEQ ID NO: 254 | NNYYWT | MS-227_HC CDR1 |
| SEQ ID NO: 255 | YISDRESATYNPSLNS | MS-227_HC CDR2 |
| SEQ ID NO: 256 | ARRGQRIYGVVSFGEF FYYYSMDV | MS-227_HC CDR3 |
| SEQ ID NO: 257 | GRQALGSRAVQ | MS-228_LC CDR1 |
| SEQ ID NO: 258 | NNQDRPS | MS-228_LC CDR2 |
| SEQ ID NO: 259 | HMWDSRSGFSWS | MS-228_LC CDR3 |
| SEQ ID NO: 260 | NNYYWT | MS-228_HC CDR1 |
| SEQ ID NO: 261 | YISDRESATYNPSLNS | MS-228_HC CDR2 |
| SEQ ID NO: 262 | ARRGQRIYGVVSFGEF FYYYSMDV | MS-228_HC CDR3 |
| SEQ ID NO: 263 | GRQALGSRAVQ | MS-229_LC CDR1 |
| SEQ ID NO: 264 | NNQDRPS | MS-229_LC CDR2 |
| SEQ ID NO: 265 | HMWDSRSGFSWS | MS-229_LC CDR3 |
| SEQ ID NO: 266 | NNYYWT | MS-229_HC CDR1 |
| SEQ ID NO: 267 | YISDRESATYNPSLNS | MS-229_HC CDR2 |
| SEQ ID NO: 268 | ARRGQRIYGVVSFGEF FYYYSMDV | MS-229_HC CDR3 |
| SEQ ID NO: 269 | GRQALGSRAVQ | MS-230_LC CDR1 |

TABLE 4-continued

Amino acid sequences of CDR regions of the 10-1074 antibody variants

| SEQ ID NO. | SEQUENCE | OTHER INFORMATION |
|---|---|---|
| SEQ ID NO: 270 | NNQDRPS | MS-230_LC CDR2 |
| SEQ ID NO: 271 | HMWDSRSGFSWS | MS-230_LC CDR3 |
| SEQ ID NO: 272 | NNYYWT | MS-230_HC CDR1 |
| SEQ ID NO: 273 | YISDRESATYNPSLNS | MS-230_HC CDR2 |
| SEQ ID NO: 274 | ARRGQRIYGVVSFGEF FYYYSMDV | MS-230_HC CDR3 |
| SEQ ID NO: 275 | GRQALGSRAVQ | MS-231_LC CDR1 |
| SEQ ID NO: 276 | NNQDRPS | MS-231_LC CDR2 |
| SEQ ID NO: 277 | HMWDSRSGFSWS | MS-231_LC CDR3 |
| SEQ ID NO: 278 | NNYYWT | MS-231_HC CDR1 |
| SEQ ID NO: 279 | YISDRESATYNPSLNS | MS-231_HC CDR2 |
| SEQ ID NO: 280 | ARRGQRIYGVVSFGEF FYYYSMDV | MS-231_HC CDR3 |
| SEQ ID NO: 281 | GRQALGSRAVQ | MS-232_LC CDR1 |
| SEQ ID NO: 282 | NNQDRPS | MS-232_LC CDR2 |
| SEQ ID NO: 283 | HMWDSRSGFSWS | MS-232_LC CDR3 |
| SEQ ID NO: 284 | NNYYWT | MS-232_HC CDR1 |
| SEQ ID NO: 285 | YISDRESATYNPSLNS | MS-232_HC CDR2 |
| SEQ ID NO: 286 | ARRGQRIYGVVSFGEF FYYYSMDV | MS-232_HC CDR3 |
| SEQ ID NO: 287 | GRQALGSRAVQ | MS-233_LC CDR1 |
| SEQ ID NO: 288 | NNQDRPS | MS-233_LC CDR2 |
| SEQ ID NO: 289 | HMWDSRSGFSWS | MS-233_LC CDR3 |
| SEQ ID NO: 290 | NNYYWT | MS-233_HC CDR1 |
| SEQ ID NO: 291 | YISDRESATYNPSLNS | MS-233_HC CDR2 |
| SEQ ID NO: 292 | ARRGQRIYGVVSFGEF FYYYSMDV | MS-233_HC CDR3 |
| SEQ ID NO: 293 | GRQALGSRAVQ | MS-234_LC CDR1 |
| SEQ ID NO: 294 | NNQDRPS | MS-234_LC CDR2 |
| SEQ ID NO: 295 | HMWDSRSGFSWS | MS-234_LC CDR3 |
| SEQ ID NO: 296 | NNYYWT | MS-234_HC CDR1 |
| SEQ ID NO: 297 | YISDRESATYNPSLNS | MS-234_HC CDR2 |
| SEQ ID NO: 298 | ARRGQRIYGVVSFGEF FYYYSMDV | MS-234_HC CDR3 |
| SEQ ID NO: 299 | GRQALGSRAVQ | MS-235_LC CDR1 |
| SEQ ID NO: 300 | NNQDRPS | MS-235_LC CDR2 |
| SEQ ID NO: 301 | HMWDSRSGFSWS | MS-235_LC CDR3 |
| SEQ ID NO: 302 | NNYYWT | MS-235_HC CDR1 |
| SEQ ID NO: 303 | YISDRESATYNPSLNS | MS-235_HC CDR2 |

TABLE 4-continued

Amino acid sequences of CDR regions of the 10-1074 antibody variants

| SEQ ID NO. | SEQUENCE | OTHER INFORMATION |
|---|---|---|
| SEQ ID NO: 304 | ARRGQRIYGVVSFGEF FYYYSMDV | MS-235_HC CDR3 |
| SEQ ID NO: 305 | GRQALGSRAVQ | MS-236_LC CDR1 |
| SEQ ID NO: 306 | NNQDRPS | MS-236_LC CDR2 |
| SEQ ID NO: 307 | HMWDSRSGFSWS | MS-236_LC CDR3 |
| SEQ ID NO: 308 | NNYYWT | MS-236_HC CDR1 |
| SEQ ID NO: 309 | YISDRESATYNPSLNS | MS-236_HC CDR2 |
| SEQ ID NO: 310 | ARRGQRIYGVVSFGEF FYYYSMDV | MS-236_HC CDR3 |
| SEQ ID NO: 311 | GRQALGSRAVQ | MS-237_LC CDR1 |
| SEQ ID NO: 312 | NNQDRPS | MS-237_LC CDR2 |
| SEQ ID NO: 313 | HMWDSRSGFSWS | MS-237_LC CDR3 |
| SEQ ID NO: 314 | NNYYWT | MS-237_HC CDR1 |
| SEQ ID NO: 315 | YISDRESATYNPSLNS | MS-237_HC CDR2 |
| SEQ ID NO: 316 | ARRGQRIYGVVSFGEF FYYYSMDV | MS-237_HC CDR3 |
| SEQ ID NO: 317 | GRQALGSRAVQ | MS-238_LC CDR1 |
| SEQ ID NO: 318 | NNQDRPS | MS-238_LC CDR2 |
| SEQ ID NO: 319 | HMWDSRSGFSWS | MS-238_LC CDR3 |
| SEQ ID NO: 320 | NNYYWT | MS-238_HC CDR1 |
| SEQ ID NO: 321 | YISDRESATYNPSLNS | MS-238_HC CDR2 |
| SEQ ID NO: 322 | ARRGQRIYGVVSFGEF FYYYSMDV | MS-238_HC CDR3 |
| SEQ ID NO: 323 | GRQALGSRAVQ | MS-239_LC CDR1 |
| SEQ ID NO: 324 | NNQDRPS | MS-239_LC CDR2 |
| SEQ ID NO: 325 | HMWDSRSGFSWS | MS-239_LC CDR3 |
| SEQ ID NO: 326 | NNYYWT | MS-239_HC CDR1 |
| SEQ ID NO: 327 | YISDRESATYNPSLNS | MS-239_HC CDR2 |
| SEQ ID NO: 328 | ARRGQRIYGVVSFGEF FYYYSMDV | MS-239_HC CDR3 |
| SEQ ID NO: 329 | GRQALGSRAVQ | MS-240_LC CDR1 |
| SEQ ID NO: 330 | NNQDRPS | MS-240_LC CDR2 |
| SEQ ID NO: 331 | HMWDSRSGFSWS | MS-240_LC CDR3 |
| SEQ ID NO: 332 | NNYYWT | MS-240_HC CDR1 |
| SEQ ID NO: 333 | YISDRESATYNPSLNS | MS-240_HC CDR2 |
| SEQ ID NO: 334 | ARRGQRIYGVVSFGEF FYYYSMDV | MS-240_HC CDR3 |
| SEQ ID NO: 335 | GRQALGSRAVQ | MS-241_LC CDR1 |
| SEQ ID NO: 336 | NNQDRPS | MS-241_LC CDR2 |
| SEQ ID NO: 337 | HMWDSRSGFSWS | MS-241_LC CDR3 |

TABLE 4-continued

Amino acid sequences of CDR regions of the 10-1074 antibody variants

| SEQ ID NO. | SEQUENCE | OTHER INFORMATION |
|---|---|---|
| SEQ ID NO: 338 | NNYYWT | MS-241_HC CDR1 |
| SEQ ID NO: 339 | YISDRESATYNPSLNS | MS-241_HC CDR2 |
| SEQ ID NO: 340 | ARRGQRIYGVVSFGEF FYYYSMDV | MS-241_HC CDR3 |
| SEQ ID NO: 341 | GRQALGSRAVQ | MS-242_LC CDR1 |
| SEQ ID NO: 342 | NNQDRPS | MS-242_LC CDR2 |
| SEQ ID NO: 343 | HMWDSRSGFSWS | MS-242_LC CDR3 |
| SEQ ID NO: 344 | NNYYWT | MS-242_HC CDR1 |
| SEQ ID NO: 345 | YISDRESATYNPSLNS | MS-242_HC CDR2 |
| SEQ ID NO: 346 | ARRGQRIYGVVSFGEF FYYYSMDV | MS-242_HC CDR3 |
| SEQ ID NO: 347 | GRQALGSRAVQ | MS-243_LC CDR1 |
| SEQ ID NO: 348 | NNQDRPS | MS-243_LC CDR2 |
| SEQ ID NO: 349 | HMWDSRSGFSWS | MS-243_LC CDR3 |
| SEQ ID NO: 350 | NNYYWT | MS-243_HC CDR1 |
| SEQ ID NO: 351 | YISDRESATYNPSLNS | MS-243_HC CDR2 |
| SEQ ID NO: 352 | ARRGQRIYGVVSFGEF FYYYSMDV | MS-243_HC CDR3 |
| SEQ ID NO: 353 | GRQALGSRAVQ | MS-244_LC CDR1 |
| SEQ ID NO: 354 | NNQDRPS | MS-244_LC CDR2 |
| SEQ ID NO: 355 | HMWDSRSGFSWS | MS-244_LC CDR3 |
| SEQ ID NO: 356 | NNYYWT | MS-244_HC CDR1 |
| SEQ ID NO: 357 | YISDRESATYNPSLNS | MS-244_HC CDR2 |

TABLE 4-continued

Amino acid sequences of CDR regions of the 10-1074 antibody variants

| SEQ ID NO. | SEQUENCE | OTHER INFORMATION |
|---|---|---|
| SEQ ID NO: 358 | ARRGQRIYGVVSFGEF FYYYSMDV | MS-244_HC CDR3 |
| SEQ ID NO: 359 | GRQALGSRAVQ | MS-245_LC CDR1 |
| SEQ ID NO: 360 | NNQDRPS | MS-245_LC CDR2 |
| SEQ ID NO: 361 | HMWDSRSGFSWS | MS-245_LC CDR3 |
| SEQ ID NO: 362 | NNYYWT | MS-245_HC CDR1 |
| SEQ ID NO: 363 | YISDRESATYNPSLNS | MS-245_HC CDR2 |
| SEQ ID NO: 364 | ARRGQRIYGVVSFGEF FYYYSMDV | MS-245_HC CDR3 |
| SEQ ID NO: 365 | GRQALGSRAVQ | MS-246_LC CDR1 |
| SEQ ID NO: 366 | NNQDRPS | MS-246_LC CDR2 |
| SEQ ID NO: 367 | HMWDSRSGFSWS | MS-246_LC CDR3 |
| SEQ ID NO: 368 | NNYYWT | MS-246_HC CDR1 |
| SEQ ID NO: 369 | YISDRESATYNPSLNS | MS-246_HC CDR2 |
| SEQ ID NO: 370 | ARRGQRIYGVVSFGEF FYYYSMDV | MS-246_HC CDR3 |
| SEQ ID NO: 371 | GRQALGSRAVQ | MS-247_LC CDR1 |
| SEQ ID NO: 372 | NNQDRPS | MS-247_LC CDR2 |
| SEQ ID NO: 373 | HMWDSRSGFSWS | MS-247_LC CDR3 |
| SEQ ID NO: 374 | NNYYWT | MS-247_HC CDR1 |
| SEQ ID NO: 375 | YISDRESATYNPSLNS | MS-247_HC CDR2 |
| SEQ ID NO: 376 | ARRGQRIYGVVSFGEF FYYYSMDV | MS-247_HC CDR3 |

TABLE 5

Nucleic acid sequences of light chain variable regions of the 10-1074 antibody variants

| SEQ ID NO. | SEQUENCE | OTHER INFORMATION |
|---|---|---|
| SEQ ID NO: 377 | ATGGGATGGAGCTGTATCATCCTGTTCCTCGTGGCCACAGCAACCGGTGTACATTCTTCCTAT GTGCGCCCGCTGTCAGTGGCCCTGGGGGAGACGGCCAGGATTTCCTGTGGACGACAGGCCCTT GGAAGTAGAGCTGTTCAGTGGTATCAACATAGGCCAGGCCAGGCCCCTATATTGCTCATTTAT AATAATCAAGACCGGCCCTCAGGGATCCCTGAGCGATTCTCTGGCACCCCTGATATTAATTTT GGGACCAGGGCCACCCTGACCATCAGCGGGGTCGAAGCCGGGGATGAAGCCGACTATTACTGT CACATGTGGGATAGTAGAAGTGGCTTCAGTTGGTCTTTCGGCGGGGCGACCAGGCTGACCGTC CTAGGTCAGCCCAAGGCTGCCCCCTCGGTCACTCTGTTCCCGCCCTCCTCTGAGGAGCTTCAA GCCAACAAGGCCACACTGGTGTGTCTCATAAGTGACTTCTACCCGGGAGCCGTGACAGTGGCC TGGAAGGCAGATAGCAGCCCCGTCAAGGCGGGAGTGGAGACCACCACACCCTCCAAACAAAGC AACAACAAGTACGCGGCCAGCAGCTATCTGAGCCTGACGCCTGAGCAGTGGAAGTCCCACAGA AGCTACAGCTGCCAGGTCACGCATGAAGGGAGCACCGTGGAGAAGACAGTGGCCCCTACAGAA TGTTCA | MS-193_LC |
| SEQ ID NO: 378 | ATGGGATGGAGCTGTATCATCCTGTTCCTCGTGGCCACAGCAACCGGTGTACATTCTTCCTAT GTGCGCCCGCTGTCAGTGGCCCTGGGGGAGACGGCCAGGATTTCCTGTGGACGACAGGCCCTT GGAAGTAGAGCTGTTCAGTGGTATCAACATAGGCCAGGCCAGGCCCCTATATTGCTCATTTAT AATAATCAAGACCGGCCCTCAGGGATCCCTGAGCGATTCTCTGGCACCCCTGATATTAATTTT GGGACCAGGGCCACCCTGACCATCAGCGGGGTCGAAGCCGGGGATGAAGCCGACTATTACTGT CACATGTGGGATAGTAGAAGTGGCTTCAGTTGGTCTTTCGGCGGGGCGACCAGGCTGACCGTC CTAGGTCAGCCCAAGGCTGCCCCCTCGGTCACTCTGTTCCCGCCCTCCTCTGAGGAGCTTCAA | MS-194_LC |

TABLE 5-continued

Nucleic acid sequences of light chain variable regions of the 10-1074 antibody variants

| SEQ ID NO. | SEQUENCE | OTHER INFORMATION |
|---|---|---|
| | GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | |
| SEQ ID NO: 379 | ATGGGATGGAGCTGTATCATCCTGTTCCTCGTGGCCACAGCAACCGGTGTACATTCTTCCCCT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-203_LC |
| SEQ ID NO: 380 | ATGGGATGGAGCTGTATCATCCTGTTCCTCGTGGCCACAGCAACCGGTGTACATTCTTCCTAT<br>GTGCCACCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-204_LC |
| SEQ ID NO: 381 | ATGGGATGGAGCTGTATCATCCTGTTCCTCGTGGCCACAGCAACCGGTGTACATTCTTCCTAT<br>GTGCGCAGCCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-205_LC |
| SEQ ID NO: 382 | ATGGGATGGAGCTGTATCATCCTGTTCCTCGTGGCCACAGCAACCGGTGTACATTCTTCCTAT<br>GTGCGCCCGCTGTCAGTGGCCCTGGGGCAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-206_LC |
| SEQ ID NO: 383 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACAGAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-207_LC |
| SEQ ID NO: 384 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT | MS-208_LC |

TABLE 5-continued

Nucleic acid sequences of light chain variable regions of the 10-1074 antibody variants

| SEQ ID NO. | SEQUENCE | OTHER INFORMATION |
| --- | --- | --- |
| | AATAATCAAGACCGGCCCTCAGGGATCCCTGAGCGATTCTCTGGCACCAATGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | |
| SEQ ID NO: 385 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATTCCAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-209_LC |
| SEQ ID NO: 386 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTGGCTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-210_LC |
| SEQ ID NO: 387 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCACCGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-211_LC |
| SEQ ID NO: 388 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGAGAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-212_LC |
| SEQ ID NO: 389 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGGAACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-213_LC |

TABLE 5-continued

| Nucleic acid sequences of light chain variable regions of the 10-1074 antibody variants | | |
|---|---|---|
| SEQ ID NO. | SEQUENCE | OTHER INFORMATION |
| SEQ ID NO: 390 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-214_LC |
| SEQ ID NO: 391 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-215_LC |
| SEQ ID NO: 392 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-216_LC |
| SEQ ID NO: 393 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-217_LC |
| SEQ ID NO: 394 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-218_LC |
| SEQ ID NO: 395 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC | MS-219_LC |

TABLE 5-continued

Nucleic acid sequences of light chain variable regions of the 10-1074 antibody variants

| SEQ ID NO. | SEQUENCE | OTHER INFORMATION |
|---|---|---|
| | TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCC<br>CCTACAGAATGTTCA | |
| SEQ ID NO: 396 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-220_LC |
| SEQ ID NO: 397 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCC<br>CCTACAGAATGTTCA | MS-224_LC |
| SEQ ID NO: 398 | ATGGGATGGAGCTGTATCATCCTGTTCCTCGTGGCCACAGCAACCGGTGTACATTCTTCCCCT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCC<br>CCTACAGAATGTTCA | MS-200_LC |
| SEQ ID NO: 399 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-201_LC |
| SEQ ID NO: 400 | ATGGGATGGAGCTGTATCATCCTGTTCCTCGTGGCCACAGCAACCGGTGTACATTCTTCCCCT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-202_LC |
| SEQ ID NO: 401 | ATGGGATGGAGCTGTATCATCCTGTTCCTCGTGGCCACAGCAACCGGTGTACATTCTTCCCCT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT | MS-225_LC |

TABLE 5-continued

Nucleic acid sequences of light chain variable regions of the 10-1074 antibody variants

| SEQ ID NO. | SEQUENCE | OTHER INFORMATION |
|---|---|---|
| | GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCC<br>CCTACAGAATGTTCA | |
| SEQ ID NO: 402 | ATGGGATGGAGCTGTATCATCCTGTTCCTCGTGGCCACAGCAACCGGTGTACATTCTTCCCCT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-226_LC |
| SEQ ID NO: 403 | ATGGGATGGAGCTGTATCATCCTGTTCCTCGTGGCCACAGCAACCGGTGTACATTCTTCCCCT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-227_LC |
| SEQ ID NO: 404 | ATGGGATGGAGCTGTATCATCCTGTTCCTCGTGGCCACAGCAACCGGTGTACATTCTTCCCCT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-228_LC |
| SEQ ID NO: 405 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-229_LC |
| SEQ ID NO: 406 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-230_LC |

TABLE 5-continued

Nucleic acid sequences of light chain variable regions of the 10-1074 antibody variants

| SEQ ID NO. | SEQUENCE | OTHER INFORMATION |
|---|---|---|
| SEQ ID NO: 407 | ATGGGATGGAGCTGTATCATCCTGTTCCTCGTGGCCACAGCAACCGGTGTACATTCTTCCTAT GTGCGCCCGCTGTCAGTGGCCCTGGGGGAGACGGCCAGGATTTCCTGTGGACGACAGGCCCTT GGAAGTAGAGCTGTTCAGTGGTATCAACATAGGCCAGGCCAGGCCCCTATATTGCTCATTTAT AATAATCAAGACCGGCCCTCAGGGATCCCTGAGCGATTCTCTGGCACCCCTGATATTAATTTT GGGACCAGGGCCACCCTGACCATCAGCGGGGTCGAAGCCGGGGATGAAGCCGACTATTACTGT CACATGTGGGATAGTAGAAGTGGCTTCAGTTGGTCTTTCGGCGGGGCGACCAGGCTGACCGTC CTAGGTCAGCCCAAGGCTGCCCCCTCGGTCACTCTGTTCCCGCCCTCCTCTGAGGAGCTTCAA GCCAACAAGGCCACACTGGTGTGTCTCATAAGTGACTTCTACCCGGGAGCCGTGACAGTGGCC TGGAAGGCAGATAGCAGCCCCGTCAAGGCGGGAGTGGAGACCACCACACCCTCCAAACAAAGC AACAACAAGTACGCGGCCAGCAGCTATCTGAGCCTGACGCCTGAGCAGTGGAAGTCCCACAGA AGCTACAGCTGCCAGGTCACGCATGAAGGGAGCACCGTGGAGAAGACAGTGGCCCCTACAGAA TGTTCA | MS-231_LC |
| SEQ ID NO: 408 | ATGGGATGGAGCTGTATCATCCTGTTCCTCGTGGCCACAGCAACCGGTGTACATTCTTCCTAT GTGCGCCCGCTGTCAGTGGCCCTGGGGGAGACGGCCAGGATTTCCTGTGGACGACAGGCCCTT GGAAGTAGAGCTGTTCAGTGGTATCAACATAGGCCAGGCCAGGCCCCTATATTGCTCATTTAT AATAATCAAGACCGGCCCTCAGGGATCCCTGAGCGATTCTCTGGCACCCCTGATATTAATTTT GGGACCAGGGCCACCCTGACCATCAGCGGGGTCGAAGCCGGGGATGAAGCCGACTATTACTGT CACATGTGGGATAGTAGAAGTGGCTTCAGTTGGTCTTTCGGCGGGGCGACCAGGCTGACCGTC CTAGGTCAGCCCAAGGCTGCCCCCTCGGTCACTCTGTTCCCGCCCTCCTCTGAGGAGCTTCAA GCCAACAAGGCCACACTGGTGTGTCTCATAAGTGACTTCTACCCGGGAGCCGTGACAGTGGCC TGGAAGGCAGATAGCAGCCCCGTCAAGGCGGGAGTGGAGACCACCACACCCTCCAAACAAAGC AACAACAAGTACGCGGCCAGCAGCTATCTGAGCCTGACGCCTGAGCAGTGGAAGTCCCACAGA AGCTACAGCTGCCAGGTCACGCATGAAGGGAGCACCGTGGAGAAGACAGTGGCC CCTACAGAATGTTCA | MS-232_LC |
| SEQ ID NO: 409 | ATGGGATGGAGCTGTATCATCCTGTTCCTCGTGGCCACAGCAACCGGTGTACATTCTTCCTAT GTGCGCCCGCTGTCAGTGGCCCTGGGGGAGACGGCCAGGATTTCCTGTGGACGACAGGCCCTT GGAAGTAGAGCTGTTCAGTGGTATCAACATAGGCCAGGCCAGGCCCCTATATTGCTCATTTAT AATAATCAAGACCGGCCCTCAGGGATCCCTGAGCGATTCTCTGGCACCCCTGATATTAATTTT GGGACCAGGGCCACCCTGACCATCAGCGGGGTCGAAGCCGGGGATGAAGCCGACTATTACTGT CACATGTGGGATAGTAGAAGTGGCTTCAGTTGGTCTTTCGGCGGGGCGACCAGGCTGACCGTC CTAGGTCAGCCCAAGGCTGCCCCCTCGGTCACTCTGTTCCCGCCCTCCTCTGAGGAGCTTCAA GCCAACAAGGCCACACTGGTGTGTCTCATAAGTGACTTCTACCCGGGAGCCGTGACAGTGGCC TGGAAGGCAGATAGCAGCCCCGTCAAGGCGGGAGTGGAGACCACCACACCCTCCAAACAAAGC AACAACAAGTACGCGGCCAGCAGCTATCTGAGCCTGACGCCTGAGCAGTGGAAGTCCCACAGA AGCTACAGCTGCCAGGTCACGCATGAAGGGAGCACCGTGGAGAAGACAGTGGCCCCTACAGAA TGTTCA | MS-233_LC |
| SEQ ID NO: 410 | ATGGGATGGAGCTGTATCATCCTGTTCCTCGTGGCCACAGCAACCGGTGTACATTCTTCCTAT GTGCGCCCGCTGTCAGTGGCCCTGGGGGAGACGGCCAGGATTTCCTGTGGACGACAGGCCCTT GGAAGTAGAGCTGTTCAGTGGTATCAACATAGGCCAGGCCAGGCCCCTATATTGCTCATTTAT AATAATCAAGACCGGCCCTCAGGGATCCCTGAGCGATTCTCTGGCACCCCTGATATTAATTTT GGGACCAGGGCCACCCTGACCATCAGCGGGGTCGAAGCCGGGGATGAAGCCGACTATTACTGT CACATGTGGGATAGTAGAAGTGGCTTCAGTTGGTCTTTCGGCGGGGCGACCAGGCTGACCGTC CTAGGTCAGCCCAAGGCTGCCCCCTCGGTCACTCTGTTCCCGCCCTCCTCTGAGGAGCTTCAA GCCAACAAGGCCACACTGGTGTGTCTCATAAGTGACTTCTACCCGGGAGCCGTGACAGTGGCC TGGAAGGCAGATAGCAGCCCCGTCAAGGCGGGAGTGGAGACCACCACACCCTCCAAACAAAGC AACAACAAGTACGCGGCCAGCAGCTATCTGAGCCTGACGCCTGAGCAGTGGAAGTCCCACAGA AGCTACAGCTGCCAGGTCACGCATGAAGGGAGCACCGTGGAGAAGACAGTGGCCCCTACAGAA TGTTCA | MS-234_LC |
| SEQ ID NO: 411 | ATGGGATGGAGCTGTATCATCCTGTTCCTCGTGGCCACAGCAACCGGTGTACATTCTTCCCCT GTGCGCCCGCTGTCAGTGGCCCTGGGGGAGACGGCCAGGATTTCCTGTGGACGACAGGCCCTT GGAAGTAGAGCTGTTCAGTGGTATCAACATAGGCCAGGCCAGGCCCCTATATTGCTCATTTAT AATAATCAAGACCGGCCCTCAGGGATCCCTGAGCGATTCTCTGGCACCCCTGATATTAATTTT GGGACCAGGGCCACCCTGACCATCAGCGGGGTCGAAGCCGGGGATGAAGCCGACTATTACTGT CACATGTGGGATAGTAGAAGTGGCTTCAGTTGGTCTTTCGGCGGGGCGACCAGGCTGACCGTC CTAGGTCAGCCCAAGGCTGCCCCCTCGGTCACTCTGTTCCCGCCCTCCTCTGAGGAGCTTCAA GCCAACAAGGCCACACTGGTGTGTCTCATAAGTGACTTCTACCCGGGAGCCGTGACAGTGGCC TGGAAGGCAGATAGCAGCCCCGTCAAGGCGGGAGTGGAGACCACCACACCCTCCAAACAAAGC AACAACAAGTACGCGGCCAGCAGCTATCTGAGCCTGACGCCTGAGCAGTGGAAGTCCCACAGA AGCTACAGCTGCCAGGTCACGCATGAAGGGAGCACCGTGGAGAAGACAGTGGCCCCTACAGAA TGTTCA | MS-235_LC |
| SEQ ID NO: 412 | ATGGGATGGAGCTGTATCATCCTGTTCCTCGTGGCCACAGCAACCGGTGTACATTCTTCCCCT GTGCGCCCGCTGTCAGTGGCCCTGGGGGAGACGGCCAGGATTTCCTGTGGACGACAGGCCCTT GGAAGTAGAGCTGTTCAGTGGTATCAACATAGGCCAGGCCAGGCCCCTATATTGCTCATTTAT AATAATCAAGACCGGCCCTCAGGGATCCCTGAGCGATTCTCTGGCACCCCTGATATTAATTTT GGGACCAGGGCCACCCTGACCATCAGCGGGGTCGAAGCCGGGGATGAAGCCGACTATTACTGT CACATGTGGGATAGTAGAAGTGGCTTCAGTTGGTCTTTCGGCGGGGCGACCAGGCTGACCGTC CTAGGTCAGCCCAAGGCTGCCCCCTCGGTCACTCTGTTCCCGCCCTCCTCTGAGGAGCTTCAA GCCAACAAGGCCACACTGGTGTGTCTCATAAGTGACTTCTACCCGGGAGCCGTGACAGTGGCC TGGAAGGCAGATAGCAGCCCCGTCAAGGCGGGAGTGGAGACCACCACACCCTCCAAACAAAGC | MS-236_LC |

TABLE 5-continued

Nucleic acid sequences of light chain variable regions of the 10-1074 antibody variants

| SEQ ID NO. | SEQUENCE | OTHER INFORMATION |
|---|---|---|
| | AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | |
| SEQ ID NO: 413 | ATGGGATGGAGCTGTATCATCCTGTTCCTCGTGGCCACAGCAACCGGTGTACATTCTTCCCCT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-237_LC |
| SEQ ID NO: 414 | ATGGGATGGAGCTGTATCATCCTGTTCCTCGTGGCCACAGCAACCGGTGTACATTCTTCCCCT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-238_LC |
| SEQ ID NO: 415 | ATGGGATGGAGCTGTATCATCCTGTTCCTCGTGGCCACAGCAACCGGTGTACATTCTTCCCCT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-239_LC |
| SEQ ID NO: 416 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-240_LC |
| SEQ ID NO: 417 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-241_LC |
| SEQ ID NO: 418 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT | MS-242_LC |

TABLE 5-continued

Nucleic acid sequences of light chain variable regions of the 10-1074 antibody variants

| SEQ ID NO. | SEQUENCE | OTHER INFORMATION |
|---|---|---|
| | CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | |
| SEQ ID NO: 419 | ATGGGATGGAGCTGTATCATCCTGTTCCTCGTGGCCACAGCAACCGGTGTACATTCTTCCCCT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-243_LC |
| SEQ ID NO: 420 | ATGGGATGGAGCTGTATCATCCTGTTCCTCGTGGCCACAGCAACCGGTGTACATTCTTCCCCT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-244_LC |
| SEQ ID NO: 421 | ATGGGATGGAGCTGTATCATCCTGTTCCTCGTGGCCACAGCAACCGGTGTACATTCTTCCCCT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-245_LC |
| SEQ ID NO: 422 | ATGGGATGGAGCTGTATCATCCTGTTCCTCGTGGCCACAGCAACCGGTGTACATTCTTCCTAT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-246_LC |
| SEQ ID NO: 423 | ATGGGATGGAGCTGTATCATCCTGTTCCTCGTGGCCACAGCAACCGGTGTACATTCTTCCCCT<br>GTGCGCCCGCTGTCAGTGGCCCTGGGGGAGACGGCCAGGATTTCCTGTGGACGACAGGCCCTT<br>GGAAGTAGAGCTGTTCAGTGGTATCAACATAGGCCAGGCCAGGCCCCTATATTGCTCATTTAT<br>AATAATCAAGACCGGCCCTCAGGGATCCCTGAGCGATTCTCTGGCACCCCTGATATTAATTTT<br>GGGACCAGGGCCACCCTGACCATCAGCGGGGTCGAAGCCGGGGATGAAGCCGACTATTACTGT<br>CACATGTGGGATAGTAGAAGTGGCTTCAGTTGGTCTTTCGGCGGGGCGACCAGGCTGACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA | MS-247_LC |

TABLE 6

Nucleic acid sequences of heavy chain variable regions of the 10-1074 antibody variants

| SEQ ID NO. | SEQUENCE | OTHER INFORMATION |
|---|---|---|
| SEQ ID NO: 424 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCACGAGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGAT<br>GCATGAGGCTCTGCACAACCACTACACGCAGAAGAGCCTCTCCCTGTCTCCGGGTAAA | MS-193_HC |
| SEQ ID NO: 425 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCACGAGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-194_HC |
| SEQ ID NO: 426 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCACGAGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-203_HC |
| SEQ ID NO: 427 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC | MS-204_HC |

TABLE 6-continued

Nucleic acid sequences of heavy chain variable regions of the 10-1074 antibody variants

| SEQ ID NO. | SEQUENCE | OTHER INFORMATION |
|---|---|---|
| | TGGAGTGGATAGGCTATATCTCTGACAGAGAATCAGCGACTTACAACCCCTCCCTCAATAGTC<br>GAGTCGTCATATCACGAGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | |
| SEQ ID NO: 428 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCACGAGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-205_HC |
| SEQ ID NO: 429 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCACGAGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-206_HC |
| SEQ ID NO: 430 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCACGAGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG | MS-207_HC |

TABLE 6-continued

Nucleic acid sequences of heavy chain variable regions of the 10-1074 antibody variants

| SEQ ID NO. | SEQUENCE | OTHER INFORMATION |
|---|---|---|
| | TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | |
| SEQ ID NO: 431 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCACGAGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-208_HC |
| SEQ ID NO: 432 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCACGAGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-209_HC |
| SEQ ID NO: 433 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCACGAGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG | MS-210_HC |

TABLE 6-continued

Nucleic acid sequences of heavy chain variable regions of the 10-1074 antibody variants

| SEQ ID NO. | SEQUENCE | OTHER INFORMATION |
|---|---|---|
| | TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | |
| SEQ ID NO: 434 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCACGAGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-211_HC |
| SEQ ID NO: 435 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCACGAGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-212_HC |
| SEQ ID NO: 436 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCACGAGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC | MS-213_HC |

TABLE 6-continued

Nucleic acid sequences of heavy chain variable regions of the 10-1074 antibody variants

| SEQ ID NO. | SEQUENCE | OTHER INFORMATION |
|---|---|---|
| | TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | |
| SEQ ID NO: 437 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGGTTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCACGAGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-214_HC |
| SEQ ID NO: 438 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGCCACCCGGAAAGGGAC<br>TGGAGTGGATAGGCTATATCTCTGACAGAGAATCAGCGACTTACAACCCCTCCCTCAATAGTC<br>GAGTCGTCATATCACGAGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-215_HC |
| SEQ ID NO: 439 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCACCATATCACGAGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT | MS-216_HC |

TABLE 6-continued

| Nucleic acid sequences of heavy chain variable regions of the 10-1074 antibody variants | | |
|---|---|---|
| SEQ ID NO. | SEQUENCE | OTHER INFORMATION |
| | GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | |
| SEQ ID NO: 440 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCAGTTGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-217_HC |
| SEQ ID NO: 441 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCACGAGACACGTCGAAAAACCAATTTTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-218_HC |
| SEQ ID NO: 442 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCACGAGACACGTCGAAAAACCAATTGTCCCTAAAATTAAACTCCGTCACCC<br>CTGCGGACACGGCCGTCTATTACTGTGCGCGCGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA | MS-219_HC |

TABLE 6-continued

Nucleic acid sequences of heavy chain variable regions of the 10-1074 antibody variants

| SEQ ID NO. | SEQUENCE | OTHER INFORMATION |
|---|---|---|
| | GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | |
| SEQ ID NO: 443 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCACGAGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCCAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-220_HC |
| SEQ ID NO: 444 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCCAAAGTC<br>GAGTCGTCATATCACGAGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-224_HC |
| SEQ ID NO: 445 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCAGTTGACACGTCGAAAAACCAATTGTCCCTAAAATTAAACTCCGTCACCC<br>CTGCGGACACGGCCGTCTATTACTGTGCGCGCGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC | MS-200_HC |

TABLE 6-continued

Nucleic acid sequences of heavy chain variable regions of the 10-1074 antibody variants

| SEQ ID NO. | SEQUENCE | OTHER INFORMATION |
|---|---|---|
| | AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | |
| SEQ ID NO: 446 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCACCATATCACGAGACACGTCGAAAAACCAATTTTCCCTAAAATTAAACTCCGTCACCC<br>CTGCGGACACGGCCGTCTATTACTGTGCGCGCGCGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-201_HC |
| SEQ ID NO: 447 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCACCATATCACGAGACACGTCGAAAAACCAATTTTCCCTAAAATTAAACTCCGTCACCC<br>CTGCGGACACGGCCGTCTATTACTGTGCGCGCGCGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-202_HC |
| SEQ ID NO: 448 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCACCATATCACGAGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-225_HC |

TABLE 6-continued

Nucleic acid sequences of heavy chain variable regions of the 10-1074 antibody variants

| SEQ ID NO. | SEQUENCE | OTHER INFORMATION |
|---|---|---|
| SEQ ID NO: 449 | ATGGGATGGTCATGTATCATCCTTTTTCTAGTAGCAACTGCAACCGGTGTACACTCGCAGGTGC AGCTGCAGGAGTCGGGCCCAGGACTGGTGAAACCTTCGGAGACCCTGTCCGTCACCTGCAGTG TCTCTGGAGATTCCATGAATAATTACTACTGGACTTGGATCCGGCAGTCCCCCGGAAAGGGAC TGGAGTGGATAGGCTATATCTCTGACAGAGAATCAGCGACTTACAACCCCTCCCTCAATAGTC GAGTCGTCATATCAGTTGACACGTCGAAAAACCAATTGTCCCTAAAATTAAACTCCGTCACCC CTGCGGACACGGCCGTCTATTACTGTGCGACAGCGCGCCGAGGACAGAGGATTTATGGAGTGG TTTCCTTTGGAGAGTTCTTCTACTACTACTCCATGGACGTCTGGGGCAAGGGGACCACGGTCAC CGTCTCCTCAGCTAGCACCAAGGGCCCATCGGTCTTCCCCCTGGCACCCTCCTCCAAGAGCACC TCTGGGGGCACAGCGGCCCTGGGCTGCCTGGTCAAGGACTACTTCCCCGAGCCGGTGACGGTG TCGTGGAACTCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACCCAGACCTAC ATCTGCAACGTGAATCACAAGCCCAGCAACACCAAGGTGGACAAGAAAGTTGAGCCCAAATC TTGTGACAAAACTCACACATGCCCACCGTGCCCAGCACCTGAACTCCTGGGGGGACCGTCAGT CTTCCTCTTCCCCCCAAAACCCAAGGACACCCTCATGATCTCCCGGACCCCTGAGGTCACATGC GTGGTGGTGGACGTGAGCCACGAAGACCCTGAGGTCAAGTTCAACTGGTACGTGGACGGCGT GGAGGTGCATAATGCCAAGACAAAGCCGCGGGAGGAGCAGTACAACAGCACGTACCGTGTGG TCAGCGTCCTCACCGTCCTGCACCAGGACTGGCTGAATGGCAAGGAGTACAAGTGCAAGGTCT CCAACAAAGCCCTCCCAGCCCCCATCGAGAAAACCATCTCCAAAGCCAAAGGGCAGCCCCGA GAACCACAGGTGTACACCCTGCCCCCATCCCGGGATGAGCTGACCAAGAACCAGGTCAGCCTG ACCTGCCTGGTCAAAGGCTTCTATCCCAGCGACATCGCCGTGGAGTGGGAGAGCAATGGGCAG CCGGAGAACAACTACAAGACCACGCCTCCCGTGCTGGACTCCGACGGCTCCTTCTTCCTCTAC AGCAAGCTCACCGTGGACAAGAGCAGGTGGCAGCAGGGGAACGTCTTCTCATGCTCCGTGCTG CATGAGGCTCTGCACTCCCACTACACGCAGAAGAGCCTCTCCCTGTCTCCGGGTAAA | MS-226_HC |
| SEQ ID NO: 450 | ATGGGATGGTCATGTATCATCCTTTTTCTAGTAGCAACTGCAACCGGTGTACACTCGCAGGTGC AGCTGCAGGAGTCGGGCCCAGGACTGGTGAAACCTTCGGAGACCCTGTCCGTCACCTGCAGTG TCTCTGGAGATTCCATGAATAATTACTACTGGACTTGGATCCGGCAGTCCCCCGGAAAGGGAC TGGAGTGGATAGGCTATATCTCTGACAGAGAATCAGCGACTTACAACCCCTCCCTCAATAGTC GAGTCGTCATATCACGAGACACGTCGAAAAACCAATTTTCCCTAAAATTAAACTCCGTCACCC CTGCGGACACGGCCGTCTATTACTGTGCGACAGCGCGCCGAGGACAGAGGATTTATGGAGTGG TTTCCTTTGGAGAGTTCTTCTACTACTACTCCATGGACGTCTGGGGCAAGGGGACCACGGTCAC CGTCTCCTCAGCTAGCACCAAGGGCCCATCGGTCTTCCCCCTGGCACCCTCCTCCAAGAGCACC TCTGGGGGCACAGCGGCCCTGGGCTGCCTGGTCAAGGACTACTTCCCCGAGCCGGTGACGGTG TCGTGGAACTCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACCCAGACCTAC ATCTGCAACGTGAATCACAAGCCCAGCAACACCAAGGTGGACAAGAAAGTTGAGCCCAAATC TTGTGACAAAACTCACACATGCCCACCGTGCCCAGCACCTGAACTCCTGGGGGGACCGTCAGT CTTCCTCTTCCCCCCAAAACCCAAGGACACCCTCATGATCTCCCGGACCCCTGAGGTCACATGC GTGGTGGTGGACGTGAGCCACGAAGACCCTGAGGTCAAGTTCAACTGGTACGTGGACGGCGT GGAGGTGCATAATGCCAAGACAAAGCCGCGGGAGGAGCAGTACAACAGCACGTACCGTGTGG TCAGCGTCCTCACCGTCCTGCACCAGGACTGGCTGAATGGCAAGGAGTACAAGTGCAAGGTCT CCAACAAAGCCCTCCCAGCCCCCATCGAGAAAACCATCTCCAAAGCCAAAGGGCAGCCCCGA GAACCACAGGTGTACACCCTGCCCCCATCCCGGGATGAGCTGACCAAGAACCAGGTCAGCCTG ACCTGCCTGGTCAAAGGCTTCTATCCCAGCGACATCGCCGTGGAGTGGGAGAGCAATGGGCAG CCGGAGAACAACTACAAGACCACGCCTCCCGTGCTGGACTCCGACGGCTCCTTCTTCCTCTAC AGCAAGCTCACCGTGGACAAGAGCAGGTGGCAGCAGGGGAACGTCTTCTCATGCTCCGTGCTG CATGAGGCTCTGCACTCCCACTACACGCAGAAGAGCCTCTCCCTGTCTCCGGGTAAA | MS-227_HC |
| SEQ ID NO: 451 | ATGGGATGGTCATGTATCATCCTTTTTCTAGTAGCAACTGCAACCGGTGTACACTCGCAGGTGC AGCTGCAGGAGTCGGGCCCAGGACTGGTGAAACCTTCGGAGACCCTGTCCGTCACCTGCAGTG TCTCTGGAGATTCCATGAATAATTACTACTGGACTTGGATCCGGCAGTCCCCCGGAAAGGGAC TGGAGTGGATAGGCTATATCTCTGACAGAGAATCAGCGACTTACAACCCCTCCCTCAATAGTC GAGTCGTCATATCACGAGACACGTCGAAAAACCAATTGTCCCTAAAATTAAACTCCGTCACCC CTGCGGACACGGCCGTCTATTACTGTGCGCGCGCGCGCCGAGGACAGAGGATTTATGGAGTGG TTTCCTTTGGAGAGTTCTTCTACTACTACTCCATGGACGTCTGGGGCAAGGGGACCACGGTCAC CGTCTCCTCAGCTAGCACCAAGGGCCCATCGGTCTTCCCCCTGGCACCCTCCTCCAAGAGCACC TCTGGGGGCACAGCGGCCCTGGGCTGCCTGGTCAAGGACTACTTCCCCGAGCCGGTGACGGTG TCGTGGAACTCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACCCAGACCTAC ATCTGCAACGTGAATCACAAGCCCAGCAACACCAAGGTGGACAAGAAAGTTGAGCCCAAATC TTGTGACAAAACTCACACATGCCCACCGTGCCCAGCACCTGAACTCCTGGGGGGACCGTCAGT CTTCCTCTTCCCCCCAAAACCCAAGGACACCCTCATGATCTCCCGGACCCCTGAGGTCACATGC GTGGTGGTGGACGTGAGCCACGAAGACCCTGAGGTCAAGTTCAACTGGTACGTGGACGGCGT GGAGGTGCATAATGCCAAGACAAAGCCGCGGGAGGAGCAGTACAACAGCACGTACCGTGTGG TCAGCGTCCTCACCGTCCTGCACCAGGACTGGCTGAATGGCAAGGAGTACAAGTGCAAGGTCT CCAACAAAGCCCTCCCAGCCCCCATCGAGAAAACCATCTCCAAAGCCAAAGGGCAGCCCCGA GAACCACAGGTGTACACCCTGCCCCCATCCCGGGATGAGCTGACCAAGAACCAGGTCAGCCTG ACCTGCCTGGTCAAAGGCTTCTATCCCAGCGACATCGCCGTGGAGTGGGAGAGCAATGGGCAG CCGGAGAACAACTACAAGACCACGCCTCCCGTGCTGGACTCCGACGGCTCCTTCTTCCTCTAC AGCAAGCTCACCGTGGACAAGAGCAGGTGGCAGCAGGGGAACGTCTTCTCATGCTCCGTGCTG CATGAGGCTCTGCACTCCCACTACACGCAGAAGAGCCTCTCCCTGTCTCCGGGTAAA | MS-228_HC |
| SEQ ID NO: 452 | ATGGGATGGTCATGTATCATCCTTTTTCTAGTAGCAACTGCAACCGGTGTACACTCGCAGGTGC AGCTGCAGGAGTCGGGCCCAGGACTGGTGAAACCTTCGGAGACCCTGTCCGTCACCTGCAGTG TCTCTGGAGATTCCATGAATAATTACTACTGGACTTGGATCCGGCAGTCCCCCGGAAAGGGAC | MS-229_HC |

TABLE 6-continued

| Nucleic acid sequences of heavy chain variable regions of the 10-1074 antibody variants | | |
|---|---|---|
| SEQ ID NO. | SEQUENCE | OTHER INFORMATION |
| | TGGAGTGGATAGGCTATATCTCTGACAGAGAATCAGCGACTTACAACCCCTCCCTCAATAGTC<br>GAGTCACCATATCAGTTGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | |
| SEQ ID NO: 453 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCACCATATCACGAGACACGTCGAAAAACCAATTTTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-230_HC |
| SEQ ID NO: 454 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCACCATATCACGAGACACGTCGAAAAACCAATTGTCCCTAAAATTAAACTCCGTCACCC<br>CTGCGGACACGGCCGTCTATTACTGTGCGCGCGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-231_HC |
| SEQ ID NO: 455 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCAGTTGACACGTCGAAAAACCAATTTTCCCTAAAATTAAACTCCGTCACCC<br>CTGCGGACACGGCCGTCTATTACTGTGCGACAGCGCGCCGAGGACAGAGGATTTATGGAGTGG | MS-232_HC |

TABLE 6-continued

Nucleic acid sequences of heavy chain variable regions of the 10-1074 antibody variants

| SEQ ID NO. | SEQUENCE | OTHER INFORMATION |
|---|---|---|
| | TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | |
| SEQ ID NO: 456 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCAGTTGACACGTCGAAAAACCAATTGTCCCTAAAATTAAACTCCGTCACCC<br>CTGCGGACACGGCCGTCTATTACTGTGCGCGCGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-233_HC |
| SEQ ID NO: 457 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCACGAGACACGTCGAAAAACCAATTTTCCCTAAAATTAAACTCCGTCACCC<br>CTGCGGACACGGCCGTCTATTACTGTGCGCGCGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-234_HC |
| SEQ ID NO: 458 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCACCATATCAGTTGACACGTCGAAAAACCAATTGTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG | MS-235_HC |

TABLE 6-continued

Nucleic acid sequences of heavy chain variable regions of the 10-1074 antibody variants

| SEQ ID NO. | SEQUENCE | OTHER INFORMATION |
|---|---|---|
| | TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | |
| SEQ ID NO: 459 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCACCATATCACGAGACACGTCGAAAAACCAATTTTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-236_HC |
| SEQ ID NO: 460 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCACCATATCACGAGACACGTCGAAAAACCAATTGTCCCTAAAATTAAACTCCGTCACCC<br>CTGCGGACACGGCCGTCTATTACTGTGCGCGCGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-237_HC |
| SEQ ID NO: 461 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCAGTTGACACGTCGAAAAACCAATTTTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC | MS-238_HC |

TABLE 6-continued

Nucleic acid sequences of heavy chain variable regions of the 10-1074 antibody variants

| SEQ ID NO. | SEQUENCE | OTHER INFORMATION |
|---|---|---|
| | TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | |
| SEQ ID NO: 462 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCACGAGACACGTCGAAAAACCAATTTTCCCTAAAATTAAACTCCGTCACCC<br>CTGCGGACACGGCCGTCTATTACTGTGCGCGCGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-239_HC |
| SEQ ID NO: 463 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCACCATATCAGTTGACACGTCGAAAAACCAATTTTCCCTAAAATTAAACTCCGTCACCC<br>CTGCGGACACGGCCGTCTATTACTGTGCGACAGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-240_HC |
| SEQ ID NO: 464 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCACCATATCAGTTGACACGTCGAAAAACCAATTGTCCCTAAAATTAAACTCCGTCACCC<br>CTGCGGACACGGCCGTCTATTACTGTGCGCGCGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT | MS-241_HC |

TABLE 6-continued

Nucleic acid sequences of heavy chain variable regions of the 10-1074 antibody variants

| SEQ ID NO. | SEQUENCE | OTHER INFORMATION |
|---|---|---|
| | GGAGGTGCATAATGCCAAGACAAAGCCGCGGGAGGAGCAGTACAACAGCACGTACCGTGTGG TCAGCGTCCTCACCGTCCTGCACCAGGACTGGCTGAATGGCAAGGAGTACAAGTGCAAGGTCT CCAACAAAGCCCTCCCAGCCCCCATCGAGAAAACCATCTCCAAAGCCAAAGGGCAGCCCCGA GAACCACAGGTGTACACCCTGCCCCCATCCCGGGATGAGCTGACCAAGAACCAGGTCAGCCTG ACCTGCCTGGTCAAAGGCTTCTATCCCAGCGACATCGCCGTGGAGTGGGAGAGCAATGGGCAG CCGGAGAACAACTACAAGACCACGCCTCCCGTGCTGGACTCCGACGGCTCCTTCTTCCTCTAC AGCAAGCTCACCGTGGACAAGAGCAGGTGGCAGCAGGGGAACGTCTTCTCATGCTCCGTGCTG CATGAGGCTCTGCACTCCCACTACACGCAGAAGAGCCTCTCCCTGTCTCCGGGTAAA | |
| SEQ ID NO: 465 | ATGGGATGGTCATGTATCATCCTTTTTCTAGTAGCAACTGCAACCGGTGTACACTCGCAGGTGC AGCTGCAGGAGTCGGGCCCAGGACTGGTGAAACCTTCGGAGACCCTGTCCGTCACCTGCAGTG TCTCTGGAGATTCCATGAATAATTACTACTGGACTTGGATCCGGCAGTCCCCCGGAAAGGGAC TGGAGTGGATAGGCTATATCTCTGACAGAGAATCAGCGACTTACAACCCCTCCCTCAATAGTC GAGTCGTCATATCAGTTGACACGTCGAAAAACCAATTTTCCCTAAAATTAAACTCCGTCACCC CTGCGGACACGGCCGTCTATTACTGTGCGCGCGCGCGCGCCGAGGACAGAGGATTTATGGAGTGG TTTCCTTTGGAGAGTTCTTCTACTACTACTCCATGGACGTCTGGGGCAAGGGGACCACGGTCAC CGTCTCCTCAGCTAGCACCAAGGGCCCATCGGTCTTCCCCCTGGCACCCTCCTCCAAGAGCACC TCTGGGGGCACAGCGGCCCTGGGCTGCCTGGTCAAGGACTACTTCCCCGAGCCGGTGACGGTG TCGTGGAACTCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACCCAGACCTAC ATCTGCAACGTGAATCACAAGCCCAGCAACACCAAGGTGGACAAGAAAGTTGAGCCCAAATC TTGTGACAAAACTCACACATGCCCACCGTGCCCAGCACCTGAACTCCTGGGGGGACCGTCAGT CTTCCTCTTCCCCCCAAAACCCAAGGACACCCTCATGATCTCCCGGACCCCTGAGGTCACATGC GTGGTGGTGGACGTGAGCCACGAAGACCCTGAGGTCAAGTTCAACTGGTACGTGGACGGCGT GGAGGTGCATAATGCCAAGACAAAGCCGCGGGAGGAGCAGTACAACAGCACGTACCGTGTGG TCAGCGTCCTCACCGTCCTGCACCAGGACTGGCTGAATGGCAAGGAGTACAAGTGCAAGGTCT CCAACAAAGCCCTCCCAGCCCCCATCGAGAAAACCATCTCCAAAGCCAAAGGGCAGCCCCGA GAACCACAGGTGTACACCCTGCCCCCATCCCGGGATGAGCTGACCAAGAACCAGGTCAGCCTG ACCTGCCTGGTCAAAGGCTTCTATCCCAGCGACATCGCCGTGGAGTGGGAGAGCAATGGGCAG CCGGAGAACAACTACAAGACCACGCCTCCCGTGCTGGACTCCGACGGCTCCTTCTTCCTCTAC AGCAAGCTCACCGTGGACAAGAGCAGGTGGCAGCAGGGGAACGTCTTCTCATGCTCCGTGCTG CATGAGGCTCTGCACTCCCACTACACGCAGAAGAGCCTCTCCCTGTCTCCGGGTAAA | MS-242_HC |
| SEQ ID NO: 466 | ATGGGATGGTCATGTATCATCCTTTTTCTAGTAGCAACTGCAACCGGTGTACACTCGCAGGTGC AGCTGCAGGAGTCGGGCCCAGGACTGGTGAAACCTTCGGAGACCCTGTCCGTCACCTGCAGTG TCTCTGGAGATTCCATGAATAATTACTACTGGACTTGGATCCGGCAGTCCCCCGGAAAGGGAC TGGAGTGGATAGGCTATATCTCTGACAGAGAATCAGCGACTTACAACCCCTCCCTCAATAGTC GAGTCACCATATCAGTTGACACGTCGAAAAACCAATTTTCCCTAAAATTAAACTCCGTCACCC CTGCGGACACGGCCGTCTATTACTGTGCGACAGCGCGCCGAGGACAGAGGATTTATGGAGTGG TTTCCTTTGGAGAGTTCTTCTACTACTACTCCATGGACGTCTGGGGCAAGGGGACCACGGTCAC CGTCTCCTCAGCTAGCACCAAGGGCCCATCGGTCTTCCCCCTGGCACCCTCCTCCAAGAGCACC TCTGGGGGCACAGCGGCCCTGGGCTGCCTGGTCAAGGACTACTTCCCCGAGCCGGTGACGGTG TCGTGGAACTCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACCCAGACCTAC ATCTGCAACGTGAATCACAAGCCCAGCAACACCAAGGTGGACAAGAAAGTTGAGCCCAAATC TTGTGACAAAACTCACACATGCCCACCGTGCCCAGCACCTGAACTCCTGGGGGGACCGTCAGT CTTCCTCTTCCCCCCAAAACCCAAGGACACCCTCATGATCTCCCGGACCCCTGAGGTCACATGC GTGGTGGTGGACGTGAGCCACGAAGACCCTGAGGTCAAGTTCAACTGGTACGTGGACGGCGT GGAGGTGCATAATGCCAAGACAAAGCCGCGGGAGGAGCAGTACAACAGCACGTACCGTGTGG TCAGCGTCCTCACCGTCCTGCACCAGGACTGGCTGAATGGCAAGGAGTACAAGTGCAAGGTCT CCAACAAAGCCCTCCCAGCCCCCATCGAGAAAACCATCTCCAAAGCCAAAGGGCAGCCCCGA GAACCACAGGTGTACACCCTGCCCCCATCCCGGGATGAGCTGACCAAGAACCAGGTCAGCCTG ACCTGCCTGGTCAAAGGCTTCTATCCCAGCGACATCGCCGTGGAGTGGGAGAGCAATGGGCAG CCGGAGAACAACTACAAGACCACGCCTCCCGTGCTGGACTCCGACGGCTCCTTCTTCCTCTAC AGCAAGCTCACCGTGGACAAGAGCAGGTGGCAGCAGGGGAACGTCTTCTCATGCTCCGTGCTG CATGAGGCTCTGCACTCCCACTACACGCAGAAGAGCCTCTCCCTGTCTCCGGGTAAA | MS-243_HC |
| SEQ ID NO: 467 | ATGGGATGGTCATGTATCATCCTTTTTCTAGTAGCAACTGCAACCGGTGTACACTCGCAGGTGC AGCTGCAGGAGTCGGGCCCAGGACTGGTGAAACCTTCGGAGACCCTGTCCGTCACCTGCAGTG TCTCTGGAGATTCCATGAATAATTACTACTGGACTTGGATCCGGCAGTCCCCCGGAAAGGGAC TGGAGTGGATAGGCTATATCTCTGACAGAGAATCAGCGACTTACAACCCCTCCCTCAATAGTC GAGTCACCATATCAGTTGACACGTCGAAAAACCAATTGTCCCTAAAATTAAACTCCGTCACCC CTGCGGACACGGCCGTCTATTACTGTGCGCGCGCGCGCGCCGAGGACAGAGGATTTATGGAGTGG TTTCCTTTGGAGAGTTCTTCTACTACTACTCCATGGACGTCTGGGGCAAGGGGACCACGGTCAC CGTCTCCTCAGCTAGCACCAAGGGCCCATCGGTCTTCCCCCTGGCACCCTCCTCCAAGAGCACC TCTGGGGGCACAGCGGCCCTGGGCTGCCTGGTCAAGGACTACTTCCCCGAGCCGGTGACGGTG TCGTGGAACTCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACCCAGACCTAC ATCTGCAACGTGAATCACAAGCCCAGCAACACCAAGGTGGACAAGAAAGTTGAGCCCAAATC TTGTGACAAAACTCACACATGCCCACCGTGCCCAGCACCTGAACTCCTGGGGGGACCGTCAGT CTTCCTCTTCCCCCCAAAACCCAAGGACACCCTCATGATCTCCCGGACCCCTGAGGTCACATGC GTGGTGGTGGACGTGAGCCACGAAGACCCTGAGGTCAAGTTCAACTGGTACGTGGACGGCGT GGAGGTGCATAATGCCAAGACAAAGCCGCGGGAGGAGCAGTACAACAGCACGTACCGTGTGG TCAGCGTCCTCACCGTCCTGCACCAGGACTGGCTGAATGGCAAGGAGTACAAGTGCAAGGTCT CCAACAAAGCCCTCCCAGCCCCCATCGAGAAAACCATCTCCAAAGCCAAAGGGCAGCCCCGA | MS-244_HC |

TABLE 6-continued

Nucleic acid sequences of heavy chain variable regions of the 10-1074 antibody variants

| SEQ ID NO. | SEQUENCE | OTHER INFORMATION |
|---|---|---|
| | GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | |
| SEQ ID NO: 468 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCGTCATATCAGTTGACACGTCGAAAAACCAATTTTCCCTAAAATTAAACTCCGTCACCC<br>CTGCGGACACGGCCGTCTATTACTGTGCGCGCGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-245_HC |
| SEQ ID NO: 469 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCACCATATCAGTTGACACGTCGAAAAACCAATTTTCCCTAAAATTAAACTCCGTCACCC<br>CTGCGGACACGGCCGTCTATTACTGTGCGCGCGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTCATGCTCCGTGCTG<br>CATGAGGCTCTGCACTCCCACTACACGCAGAAGAGCCTCTCCCTGTCTCCGGGTAAA | MS-246_HC |
| SEQ ID NO: 470 | ATGGGATGGTCATGTATCATCCTTTTTCTAGTAGCAACTGCAACCGGTGTACACTCGCAGGTGC<br>AGCTGCAGGAGTCGGGCCCAGGACTGGTGAAACCTTCGGAGACCCTGTCCGTCACCTGCAGTG<br>TCTCTGGAGATTCCATGAATAATTACTACTGGACTTGGATCCGGCAGTCCCCCGGAAAGGGAC<br>TGGAGTGGATAGGCTATATCTCTGACAGAGAATCAGCGACTTACAACCCCTCCCTCAATAGTC<br>GAGTCACCATATCAGTTGACACGTCGAAAAACCAATTTTCCCTAAAATTAAACTCCGTCACCC<br>CTGCGGACACGGCCGTCTATTACTGTGCGCGCGCGCGCCGAGGACAGAGGATTTATGGAGTGG<br>TTTCCTTTGGAGAGTTCTTCTACTACTACTCCATGGACGTCTGGGGCAAGGGGACCACGGTCAC<br>CGTCTCCTCAGCTAGCACCAAGGGCCCATCGGTCTTCCCCCTGGCACCCTCCTCCAAGAGCACC<br>TCTGGGGGCACAGCGGCCCTGGGCTGCCTGGTCAAGGACTACTTCCCCGAGCCGGTGACGGTG<br>TCGTGGAACTCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGCCCAAATC<br>TTGTGACAAAACTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGACGGCGT<br>GGAGGTGCATAATGCCAAGACAAAGCCGCGGGAGGAGCAGTACAACAGCACGTACCGTGTGG<br>TCAGCGTCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGCCCCGA<br>GAACCACAGGTGTACACCCTGCCCCCATCCCGGGATGAGCTGACCAAGAACCAGGTCAGCCTG<br>ACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTAC | MS-247_HC |

TABLE 6-continued

Nucleic acid sequences of heavy chain variable regions of the 10-1074 antibody variants

| SEQ ID NO. | SEQUENCE | OTHER INFORMATION |
|---|---|---|
| | AGCAAGCTCACCGTGGACAAGAGCAGGTGGCAGCAGGGGAACGTCTTCTCATGCTCCGTGCTG CATGAGGCTCTGCACTCCCACTACACGCAGAAGAGCCTCTCCCTGTCTCCGGGTAAA | |

TABLE 7

Nucleic acid sequences of CDR regions of the 10-1074 antibody variants

| SEQ ID NO. | SEQUENCE | OTHER INFORMATION |
|---|---|---|
| SEQ ID NO: 471 | ATGGGATGGAGCTGTATCATCCTGTTCCTCGTGGCCACAGCAACCGGTGTACATTCTTCCTATGTGCGCCCGCTGTCAGTGGCCCTGGGGGAGACGGCCAGGATTTCCTGTGGACGACAGGCCCTTGGAAGTAGAGCTGTTCAGTGGTATCAACATAGGCCAGGCCAGGCCCCTATATTGCTCATTTATAATAATCAAGACCGGCCCTCAGGGATCCCTGAGCGATTCTCTGGCACCCCTGATATTAATTTTGGGACCAGGGCCACCCTGACCATCAGCGGGGTCGAAGCCGGGGATGAAGCCGACTATTACTGTCACATGTGGGATAGTAGAAGTGGCTTCAGTTGGTCTTTCGGCGGGGCGACCAGGCTGACCGTCCTAGGTCAGCCCAAGGCTGCCCCCTCGGTCACTCTGTTCCCGCCCTCCTCTGAGGAGCTTCAAGCCAACAAGGCCACACTGGTGTGTCTCATAAGTGACTTCTACCCGGGAGCCGTGACAGTGGCCTGGAAGGCAGATAGCAGCCCCGTCAAGGCGGGAGTGGAGACCACCACACCCTCCAAACAAAGCAACAACAAGTACGCGGCCAGCAGCTATCTGAGCCTGACGCCTGAGCAGTGGAAGTCCCACAGAAGCTACAGCTGCCAGGTCACGCATGAAGGGAGCACCGTGGAGAAGACAGTGGCCCCTACAGAATGTTCA | MS-193_LC |
| SEQ ID NO: 472 | GGACGACAGGCCCTTGGAAGTAGAGCTGTTCAG | MS-193_LC CDR1 |
| SEQ ID NO: 473 | AATAATCAAGACCGGCCCTCA | MS-193_LC CDR2 |
| SEQ ID NO: 474 | CACATGTGGGATAGTAGAAGTGGCTTCAGTTGGTCT | MS-193_LC CDR3 |
| SEQ ID NO: 475 | AATAATTACTACTGGACT | MS-193_HC CDR1 |
| SEQ ID NO: 476 | TATATCTCTGACAGAGAATCAGCGACTTACAACCCCTCCCTCAATAGT | MS-193_HC CDR2 |
| SEQ ID NO: 477 | GCGCGCCGAGGACAGAGGATTTATGGAGTGGTTTCCTTTGGAGAGTTCTTCTACTACTACTCCATGGACGTC | MS-193_HC CDR3 |
| SEQ ID NO: 478 | GGACGACAGGCCCTTGGAAGTAGAGCTGTTCAG | MS-194_LC CDR1 |
| SEQ ID NO: 479 | AATAATCAAGACCGGCCCTCA | MS-194_LC CDR2 |
| SEQ ID NO: 480 | CACATGTGGGATAGTAGAAGTGGCTTCAGTTGGTCT | MS-194_LC CDR3 |
| SEQ ID NO: 481 | AATAATTACTACTGGACT | MS-194_HC CDR1 |
| SEQ ID NO: 482 | TATATCTCTGACAGAGAATCAGCGACTTACAACCCCTCCCTCAATAGT | MS-194_HC CDR2 |
| SEQ ID NO: 483 | GCGCGCCGAGGACAGAGGATTTATGGAGTGGTTTCCTTTGGAGAGTTCTTCTACTACTACTCCATGGACGTC | MS-194_HC CDR3 |
| SEQ ID NO: 484 | GGACGACAGGCCCTTGGAAGTAGAGCTGTTCAG | MS-203_LC CDR1 |
| SEQ ID NO: 485 | AATAATCAAGACCGGCCCTCA | MS-203_LC CDR2 |
| SEQ ID NO: 486 | CACATGTGGGATAGTAGAAGTGGCTTCAGTTGGTCT | MS-203_LC CDR3 |
| SEQ ID NO: 487 | AATAATTACTACTGGACT | MS-203_HC CDR1 |

TABLE 7-continued

Nucleic acid sequences of CDR regions of the 10-1074 antibody variants

| SEQ ID NO. | SEQUENCE | OTHER INFORMATION |
|---|---|---|
| SEQ ID NO: 488 | TATATCTCTGACAGA GAATCAGCGACTTAC AACC CCTCCCTCAATAGT | MS-203_HC CDR2 |
| SEQ ID NO: 489 | GCGCGCCGAGGACAG AGGATTTATGGAGTG GTTT CCTTTGGAGAGTTCT TCTACTACTACTCCA TGGAC GTC | MS-203_HC CDR3 |
| SEQ ID NO: 490 | GGACGACAGGCCCTT GGAAGTAGAGCTGTT CAG | MS-204_LC CDR1 |
| SEQ ID NO: 491 | AATAATCAAGACCGG CCCTCA | MS-204_LC CDR2 |
| SEQ ID NO: 492 | CACATGTGGGATAGT AGAAGTGGCTTCAGT TGGT CT | MS-204_LC CDR3 |
| SEQ ID NO: 493 | AATAATTACTACTGG ACT | MS-204_HC CDR1 |
| SEQ ID NO: 494 | TATATCTCTGACAGA GAATCAGCGACTTAC AACC CCTCCCTCAATAGT | MS-204_HC CDR2 |
| SEQ ID NO: 495 | GCGCGCCGAGGACAG AGGATTTATGGAGTG GTTT CCTTTGGAGAGTTCT TCTACTACTACTCCA TGGAC GTC | MS-204_HC CDR3 |
| SEQ ID NO: 496 | GGACGACAGGCCCTT GGAAGTAGAGCTGTT CAG | MS-205_LC CDR1 |
| SEQ ID NO: 497 | AATAATCAAGACCGG CCCTCA | MS-205_LC CDR2 |
| SEQ ID NO: 498 | CACATGTGGGATAGT AGAAGTGGCTTCAGT TGGT CT | MS-205_LC CDR3 |
| SEQ ID NO: 499 | AATAATTACTACTGG ACT | MS-205_HC CDR1 |
| SEQ ID NO: 500 | TATATCTCTGACAGA GAATCAGCGACTTAC AACC CCTCCCTCAATAGT | MS-205_HC CDR2 |
| SEQ ID NO: 501 | GCGCGCCGAGGACAG AGGATTTATGGAGTG GTTT CCTTTGGAGAGTTCT TCTACTACTACTCCA TGGAC GTC | MS-205_HC CDR3 |
| SEQ ID NO: 502 | GGACGACAGGCCCTT GGAAGTAGAGCTGTT CAG | MS-206_LC CDR1 |

TABLE 7-continued

Nucleic acid sequences of CDR regions of the 10-1074 antibody variants

| SEQ ID NO. | SEQUENCE | OTHER INFORMATION |
|---|---|---|
| SEQ ID NO: 503 | AATAATCAAGACCGG CCCTCA | MS-206_LC CDR2 |
| SEQ ID NO: 504 | CACATGTGGGATAGT AGAAGTGGCTTCAGT TGGT CT | MS-206_LC CDR3 |
| SEQ ID NO: 505 | AATAATTACTACTGG ACT | MS-206_HC CDR1 |
| SEQ ID NO: 506 | TATATCTCTGACAGA GAATCAGCGACTTAC AACC CCTCCCTCAATAGT | MS-206_HC CDR2 |
| SEQ ID NO: 507 | GCGCGCCGAGGACAG AGGATTTATGGAGTG GTTT CCTTTGGAGAGTTCT TCTACTACTACTCCA TGGAC GTC | MS-206_HC CDR3 |
| SEQ ID NO: 508 | GGACGACAGGCCCTT GGAAGTAGAGCTGTT CAG | MS-207_LC CDR1 |
| SEQ ID NO: 509 | AATAATCAAGACCGG CCCTCA | MS-207_LC CDR2 |
| SEQ ID NO: 510 | CACATGTGGGATAGT AGAAGTGGCTTCAGT TGGT CT | MS-207_LC CDR3 |
| SEQ ID NO: 511 | AATAATTACTACTGG ACT | MS-207_HC CDR1 |
| SEQ ID NO: 512 | TATATCTCTGACAGA GAATCAGCGACTTAC AACC CCTCCCTCAATAGT | MS-207_HC CDR2 |
| SEQ ID NO: 513 | GCGCGCCGAGGACAG AGGATTTATGGAGTG GTTT CCTTTGGAGAGTTCT TCTACTACTACTCCA TGGAC GTC | MS-207_HC CDR3 |
| SEQ ID NO: 514 | GGACGACAGGCCCTT GGAAGTAGAGCTGTT CAG | MS-208_LC CDR1 |
| SEQ ID NO: 515 | AATAATCAAGACCGG CCCTCA | MS-208_LC CDR2 |
| SEQ ID NO: 516 | CACATGTGGGATAGT AGAAGTGGCTTCAGT TGGT CT | MS-208_LC CDR3 |
| SEQ ID NO: 517 | AATAATTACTACTGG ACT | MS-208_HC CDR1 |
| SEQ ID NO: 518 | TATATCTCTGACAGA GAATCAGCGACTTAC AACC CCTCCCTCAATAGT | MS-208_HC CDR2 |

TABLE 7-continued

Nucleic acid sequences of CDR regions of the 10-1074 antibody variants

| SEQ ID NO. | SEQUENCE | OTHER INFORMATION |
|---|---|---|
| SEQ ID NO: 519 | GCGCGCCGAGGACAG AGGATTTATGGAGTG GTTT CCTTTGGAGAGTTCT TCTACTACTACTCCA TGGAC GTC | MS-208_HC CDR3 |
| SEQ ID NO: 520 | GGACGACAGGCCCTT GGAAGTAGAGCTGTT CAG | MS-209_LC CDR1 |
| SEQ ID NO: 521 | AATAATCAAGACCGG CCCTCA | MS-209_LC CDR2 |
| SEQ ID NO: 522 | CACATGTGGGATAGT AGAAGTGGCTTCAGT TGGT CT | MS-209_LC CDR3 |
| SEQ ID NO: 523 | AATAATTACTACTGG ACT | MS-209_HC CDR1 |
| SEQ ID NO: 524 | TATATCTCTGACAGA GAATCAGCGACTTAC AACC CCTCCCTCAATAGT | MS-209_HC CDR2 |
| SEQ ID NO: 525 | GCGCGCCGAGGACAG AGGATTTATGGAGTG GTTT CCTTTGGAGAGTTCT TCTACTACTACTCCA TGGAC GTC | MS-209_HC CDR3 |
| SEQ ID NO: 526 | GGACGACAGGCCCTT GGAAGTAGAGCTGTT CAG | MS-210_LC CDR1 |
| SEQ ID NO: 527 | AATAATCAAGACCGG CCCTCA | MS-210_LC CDR2 |
| SEQ ID NO: 528 | CACATGTGGGATAGT AGAAGTGGCTTCAGT TGGT CT | MS-210_LC CDR3 |
| SEQ ID NO: 529 | AATAATTACTACTGG ACT | MS-210_HC CDR1 |
| SEQ ID NO: 530 | TATATCTCTGACAGA GAATCAGCGACTTAC AACC CCTCCCTCAATAGT | MS-210_HC CDR2 |
| SEQ ID NO: 531 | GCGCGCCGAGGACAG AGGATTTATGGAGTG GTTT CCTTTGGAGAGTTCT TCTACTACTACTCCA TGGAC GTC | MS-210_HC CDR3 |
| SEQ ID NO: 532 | GGACGACAGGCCCTT GGAAGTAGAGCTGTT CAG | MS-211_LC CDR1 |
| SEQ ID NO: 533 | AATAATCAAGACCGG CCCTCA | MS-211_LC CDR2 |

TABLE 7-continued

Nucleic acid sequences of CDR regions of the 10-1074 antibody variants

| SEQ ID NO. | SEQUENCE | OTHER INFORMATION |
|---|---|---|
| SEQ ID NO: 534 | CACATGTGGGATAGT AGAAGTGGCTTCAGT TGGT CT | MS-211_LC CDR3 |
| SEQ ID NO: 535 | AATAATTACTACTGG ACT | MS-211_HC CDR1 |
| SEQ ID NO: 536 | TATATCTCTGACAGA GAATCAGCGACTTAC AACC CCTCCCTCAATAGT | MS-211_HC CDR2 |
| SEQ ID NO: 537 | GCGCGCCGAGGACAG AGGATTTATGGAGTG GTTT CCTTTGGAGAGTTCT TCTACTACTACTCCA TGGAC GTC | MS-211_HC CDR3 |
| SEQ ID NO: 538 | GGACGACAGGCCCTT GGAAGTAGAGCTGTT CAG | MS-212_LC CDR1 |
| SEQ ID NO: 539 | AATAATCAAGACCGG CCCTCA | MS-212_LC CDR2 |
| SEQ ID NO: 540 | CACATGTGGGAGAGT AGAAGTGGCTTCAGT TGGT CT | MS-212_LC CDR3 |
| SEQ ID NO: 541 | AATAATTACTACTGG ACT | MS-212_HC CDR1 |
| SEQ ID NO: 542 | TATATCTCTGACAGA GAATCAGCGACTTAC AACC CCTCCCTCAATAGT | MS-212_HC CDR2 |
| SEQ ID NO: 543 | GCGCGCCGAGGACAG AGGATTTATGGAGTG GTTT CCTTTGGAGAGTTCT TCTACTACTACTCCA TGGAC GTC | MS-212_HC CDR3 |
| SEQ ID NO: 544 | GGACGACAGGCCCTT GGAAGTAGAGCTGTT CAG | MS-213_LC CDR1 |
| SEQ ID NO: 545 | AATAATCAAGACCGG CCCTCA | MS-213_LC CDR2 |
| SEQ ID NO: 546 | CACATGTGGGATAGT AGAAGTGGCTTCAGT TGGT CT | MS-213_LC CDR3 |
| SEQ ID NO: 547 | AATAATTACTACTGG ACT | MS-213_HC CDR1 |
| SEQ ID NO: 548 | TATATCTCTGACAGA GAATCAGCGACTTAC AACC CCTCCCTCAATAGT | MS-213_HC CDR2 |

TABLE 7-continued

Nucleic acid sequences of CDR regions of the 10-1074 antibody variants

| SEQ ID NO. | SEQUENCE | OTHER INFORMATION |
|---|---|---|
| SEQ ID NO: 549 | GCGCGCCGAGGACAG AGGATTTATGGAGTG GTTT CCTTTGGAGAGTTCT TCTACTACTACTCCA TGGAC GTC | MS-213_HC CDR3 |
| SEQ ID NO: 550 | GGACGACAGGCCCTT GGAAGTAGAGCTGTT CAG | MS-214_LC CDR1 |
| SEQ ID NO: 551 | AATAATCAAGACCGG CCCTCA | MS-214_LC CDR2 |
| SEQ ID NO: 552 | CACATGTGGGATAGT AGAAGTGGCTTCAGT TGGT CT | MS-214_LC CDR3 |
| SEQ ID NO: 553 | AATAATTACTACTGG ACT | MS-214_HC CDR1 |
| SEQ ID NO: 554 | TATATCTCTGACAGA GAATCAGCGACTTAC AACC CCTCCCTCAATAGT | MS-214_HC CDR2 |
| SEQ ID NO: 555 | GCGCGCCGAGGACAG AGGATTTATGGAGTG GTTT CCTTTGGAGAGTTCT TCTACTACTACTCCA TGGAC GTC | MS-214_HC CDR3 |
| SEQ ID NO: 556 | GGACGACAGGCCCTT GGAAGTAGAGCTGTT CAG | MS-215_LC CDR1 |
| SEQ ID NO: 557 | AATAATCAAGACCGG CCCTCA | MS-215_LC CDR2 |
| SEQ ID NO: 558 | CACATGTGGGATAGT AGAAGTGGCTTCAGT TGGT CT | MS-215_LC CDR3 |
| SEQ ID NO: 559 | AATAATTACTACTGG ACT | MS-215_HC CDR1 |
| SEQ ID NO: 560 | TATATCTCTGACAGA GAATCAGCGACTTAC AACC CCTCCCTCAATAGT | MS-215_HC CDR2 |
| SEQ ID NO: 561 | GCGCGCCGAGGACAG AGGATTTATGGAGTG GTTT CCTTTGGAGAGTTCT TCTACTACTACTCCA TGGAC GTC | MS-215_HC CDR3 |
| SEQ ID NO: 562 | GGACGACAGGCCCTT GGAAGTAGAGCTGTT CAG | MS-216_LC CDR1 |
| SEQ ID NO: 563 | AATAATCAAGACCGG CCCTCA | MS-216_LC CDR2 |

TABLE 7-continued

Nucleic acid sequences of CDR regions of the 10-1074 antibody variants

| SEQ ID NO. | SEQUENCE | OTHER INFORMATION |
|---|---|---|
| SEQ ID NO: 564 | CACATGTGGGATAGT AGAAGTGGCTTCAGT TGGT CT | MS-216_LC CDR3 |
| SEQ ID NO: 565 | AATAATTACTACTGG ACT | MS-216_HC CDR1 |
| SEQ ID NO: 566 | TATATCTCTGACAGA GAATCAGCGACTTAC AACC CCTCCCTCAATAGT | MS-216_HC CDR2 |
| SEQ ID NO: 567 | GCGCGCCGAGGACAG AGGATTTATGGAGTG GTTT CCTTTGGAGAGTTCT TCTACTACTACTCCA TGGAC GTC | MS-216_HC CDR3 |
| SEQ ID NO: 568 | GGACGACAGGCCCTT GGAAGTAGAGCTGTT CAG | MS-217_LC CDR1 |
| SEQ ID NO: 569 | AATAATCAAGACCGG CCCTCA | MS-217_LC CDR2 |
| SEQ ID NO: 570 | CACATGTGGGATAGT AGAAGTGGCTTCAGT TGGT CT | MS-217_LC CDR3 |
| SEQ ID NO: 571 | AATAATTACTACTGG ACT | MS-217_HC CDR1 |
| SEQ ID NO: 572 | TATATCTCTGACAGA GAATCAGCGACTTAC AACC CCTCCCTCAATAGT | MS-217_HC CDR2 |
| SEQ ID NO: 573 | GCGCGCCGAGGACAG AGGATTTATGGAGTG GTTT CCTTTGGAGAGTTCT TCTACTACTACTCCA TGGAC GTC | MS-217_HC CDR3 |
| SEQ ID NO: 574 | GGACGACAGGCCCTT GGAAGTAGAGCTGTT CAG | MS-218_LC CDR1 |
| SEQ ID NO: 575 | AATAATCAAGACCGG CCCTCA | MS-218_LC CDR2 |
| SEQ ID NO: 576 | CACATGTGGGATAGT AGAAGTGGCTTCAGT TGGT CT | MS-218_LC CDR3 |
| SEQ ID NO: 577 | AATAATTACTACTGG ACT | MS-218_HC CDR1 |
| SEQ ID NO: 578 | TATATCTCTGACAGA GAATCAGCGACTTAC AACC CCTCCCTCAATAGT | MS-218_HC CDR2 |

TABLE 7-continued

Nucleic acid sequences of CDR regions of the 10-1074 antibody variants

| SEQ ID NO. | SEQUENCE | OTHER INFORMATION |
|---|---|---|
| SEQ ID NO: 579 | GCGCGCCGAGGACAG AGGATTTATGGAGTG GTTT CCTTTGGAGAGTTCT TCTACTACTACTCCA TGGAC GTC | MS-218_HC CDR3 |
| SEQ ID NO: 580 | GGACGACAGGCCCTT GGAAGTAGAGCTGTT CAG | MS-219_LC CDR1 |
| SEQ ID NO: 581 | AATAATCAAGACCGG CCCTCA | MS-219_LC CDR2 |
| SEQ ID NO: 582 | CACATGTGGGATAGT AGAAGTGGCTTCAGT TGGT CT | MS-219_LC CDR3 |
| SEQ ID NO: 583 | AATAATTACTACTGG ACT | MS-219_HC CDR1 |
| SEQ ID NO: 584 | TATATCTCTGACAGA GAATCAGCGACTTAC AACC CCTCCCTCAATAGT | MS-219_HC CDR2 |
| SEQ ID NO: 585 | GCGCGCCGAGGACAG AGGATTTATGGAGTG GTTT CCTTTGGAGAGTTCT TCTACTACTACTCCA TGGAC GTC | MS-219_HC CDR3 |
| SEQ ID NO: 586 | GGACGACAGGCCCTT GGAAGTAGAGCTGTT CAG | MS-220_LC CDR1 |
| SEQ ID NO: 587 | AATAATCAAGACCGG CCCTCA | MS-220_LC CDR2 |
| SEQ ID NO: 588 | CACATGTGGGATAGT AGAAGTGGCTTCAGT TGGT CT | MS-220_LC CDR3 |
| SEQ ID NO: 589 | AATAATTACTACTGG ACT | MS-220_HC CDR1 |
| SEQ ID NO: 590 | TATATCTCTGACAGA GAATCAGCGACTTAC AACC CCTCCCTCAATAGT | MS-220_HC CDR2 |
| SEQ ID NO: 591 | GCGCGCCGAGGACAG AGGATTTATGGAGTG GTTT CCTTTGGAGAGTTCT TCTACTACTACTCCA TGGAC GTC | MS-220_HC CDR3 |
| SEQ ID NO: 592 | GGACGACAGGCCCTT GGAAGTAGAGCTGTT CAG | MS-224_LC CDR1 |
| SEQ ID NO: 593 | AATAATCAAGACCGG CCCTCA | MS-224_LC CDR2 |

TABLE 7-continued

Nucleic acid sequences of CDR regions of the 10-1074 antibody variants

| SEQ ID NO. | SEQUENCE | OTHER INFORMATION |
|---|---|---|
| SEQ ID NO: 594 | CACATGTGGGATAGT AGAAGTGGCTTCAGT TGGT CT | MS-224_LC CDR3 |
| SEQ ID NO: 595 | AATAATTACTACTGG ACT | MS-224_HC CDR1 |
| SEQ ID NO: 596 | TATATCTCTGACAGA GAATCAGCGACTTAC AACC CCTCCCTCCAAAGT | MS-224_HC CDR2 |
| SEQ ID NO: 597 | GCGCGCCGAGGACAG AGGATTTATGGAGTG GTTT CCTTTGGAGAGTTCT TCTACTACTACTCCA TGGAC GTC | MS-224_HC CDR3 |
| SEQ ID NO: 598 | GGACGACAGGCCCTT GGAAGTAGAGCTGTT CAG | MS-200_LC CDR1 |
| SEQ ID NO: 599 | AATAATCAAGACCGG CCCTCA | MS-200_LC CDR2 |
| SEQ ID NO: 600 | CACATGTGGGATAGT AGAAGTGGCTTCAGT TGGT CT | MS-200_LC CDR3 |
| SEQ ID NO: 601 | AATAATTACTACTGG ACT | MS-200_HC CDR1 |
| SEQ ID NO: 602 | TATATCTCTGACAGA GAATCAGCGACTTAC AACC CCTCCCTCAATAGT | MS-200_HC CDR2 |
| SEQ ID NO: 603 | GCGCGCCGAGGACAG AGGATTTATGGAGTG GTTT CCTTTGGAGAGTTCT TCTACTACTACTCCA TGGAC GTC | MS-200_HC CDR3 |
| SEQ ID NO: 604 | GGACGACAGGCCCTT GGAAGTAGAGCTGTT CAG | MS-201_LC CDR1 |
| SEQ ID NO: 605 | AATAATCAAGACCGG CCCTCA | MS-201_LC CDR2 |
| SEQ ID NO: 606 | CACATGTGGGATAGT AGAAGTGGCTTCAGT TGGT CT | MS-201_LC CDR3 |
| SEQ ID NO: 607 | AATAATTACTACTGG ACT | MS-201_HC CDR1 |
| SEQ ID NO: 608 | TATATCTCTGACAGA GAATCAGCGACTTAC AACC CCTCCCTCAATAGT | MS-201_HC CDR2 |

TABLE 7-continued

Nucleic acid sequences of CDR regions of the 10-1074 antibody variants

| SEQ ID NO. | SEQUENCE | OTHER INFORMATION |
|---|---|---|
| SEQ ID NO: 609 | GCGCGCCGAGGACAG AGGATTTATGGAGTG GTTT CCTTTGGAGAGTTCT TCTACTACTACTCCA TGGAC GTC | MS-201_HC CDR3 |
| SEQ ID NO: 610 | GGACGACAGGCCCTT GGAAGTAGAGCTGTT CAG | MS-202_LC CDR1 |
| SEQ ID NO: 611 | AATAATCAAGACCGG CCCTCA | MS-202_LC CDR2 |
| SEQ ID NO: 612 | CACATGTGGGATAGT AGAAGTGGCTTCAGT TGGT CT | MS-202_LC CDR3 |
| SEQ ID NO: 613 | AATAATTACTACTGG ACT | MS-202_HC CDR1 |
| SEQ ID NO: 614 | TATATCTCTGACAGA GAATCAGCGACTTAC AACC CCTCCCTCAATAGT | MS-202_HC CDR2 |
| SEQ ID NO: 615 | GCGCGCCGAGGACAG AGGATTTATGGAGTG GTTT CCTTTGGAGAGTTCT TCTACTACTACTCCA TGGAC GTC | MS-202_HC CDR3 |
| SEQ ID NO: 616 | GGACGACAGGCCCTT GGAAGTAGAGCTGTT CAG | MS-225_LC CDR1 |
| SEQ ID NO: 617 | AATAATCAAGACCGG CCCTCA | MS-225_LC CDR2 |
| SEQ ID NO: 618 | CACATGTGGGATAGT AGAAGTGGCTTCAGT TGGT CT | MS-225_LC CDR3 |
| SEQ ID NO: 619 | AATAATTACTACTGG ACT | MS-225_HC CDR1 |
| SEQ ID NO: 620 | TATATCTCTGACAGA GAATCAGCGACTTAC AACC CCTCCCTCAATAGT | MS-225_HC CDR2 |
| SEQ ID NO: 621 | GCGCGCCGAGGACAG AGGATTTATGGAGTG GTTT CCTTTGGAGAGTTCT TCTACTACTACTCCA TGGAC GTC | MS-225_HC CDR3 |
| SEQ ID NO: 622 | GGACGACAGGCCCTT GGAAGTAGAGCTGTT CAG | MS-226_LC CDR1 |
| SEQ ID NO: 623 | AATAATCAAGACCGG CCCTCA | MS-226_LC CDR2 |
| SEQ ID NO: 624 | CACATGTGGGATAGT AGAAGTGGCTTCAGT TGGT CT | MS-226_LC CDR3 |
| SEQ ID NO: 625 | AATAATTACTACTGG ACT | MS-226_HC CDR1 |
| SEQ ID NO: 626 | TATATCTCTGACAGA GAATCAGCGACTTAC AACC CCTCCCTCAATAGT | MS-226_HC CDR2 |
| SEQ ID NO: 627 | GCGCGCCGAGGACAG AGGATTTATGGAGTG GTTT CCTTTGGAGAGTTCT TCTACTACTACTCCA TGGAC GTC | MS-226_HC CDR3 |
| SEQ ID NO: 628 | GGACGACAGGCCCTT GGAAGTAGAGCTGTT CAG | MS-227_LC CDR1 |
| SEQ ID NO: 629 | AATAATCAAGACCGG CCCTCA | MS-227_LC CDR2 |
| SEQ ID NO: 630 | CACATGTGGGATAGT AGAAGTGGCTTCAGT TGGT CT | MS-227_LC CDR3 |
| SEQ ID NO: 631 | AATAATTACTACTGG ACT | MS-227_HC CDR1 |
| SEQ ID NO: 632 | TATATCTCTGACAGA GAATCAGCGACTTAC AACC CCTCCCTCAATAGT | MS-227_HC CDR2 |
| SEQ ID NO: 633 | GCGCGCCGAGGACAG AGGATTTATGGAGTG GTTT CCTTTGGAGAGTTCT TCTACTACTACTCCA TGGAC GTC | MS-227_HC CDR3 |
| SEQ ID NO: 634 | GGACGACAGGCCCTT GGAAGTAGAGCTGTT CAG | MS-228_LC CDR1 |
| SEQ ID NO: 635 | AATAATCAAGACCGG CCCTCA | MS-228_LC CDR2 |
| SEQ ID NO: 636 | CACATGTGGGATAGT AGAAGTGGCTTCAGT TGGT CT | MS-228_LC CDR3 |
| SEQ ID NO: 637 | AATAATTACTACTGG ACT | MS-228_HC CDR1 |
| SEQ ID NO: 638 | TATATCTCTGACAGA GAATCAGCGACTTAC AACC CCTCCCTCAATAGT | MS-228_HC CDR2 |

TABLE 7-continued

Nucleic acid sequences of CDR regions of the 10-1074 antibody variants

| SEQ ID NO. | SEQUENCE | OTHER INFORMATION |
|---|---|---|
| SEQ ID NO: 639 | GCGCGCCGAGGACAG AGGATTTATGGAGTG GTTT CCTTTGGAGAGTTCT TCTACTACTACTCCA TGGAC GTC | MS-228_HC CDR3 |
| SEQ ID NO: 640 | GGACGACAGGCCCTT GGAAGTAGAGCTGTT CAG | MS-229_LC CDR1 |
| SEQ ID NO: 641 | AATAATCAAGACCGG CCCTCA | MS-229_LC CDR2 |
| SEQ ID NO: 642 | CACATGTGGGATAGT AGAAGTGGCTTCAGT TGGT CT | MS-229_LC CDR3 |
| SEQ ID NO: 643 | AATAATTACTACTGG ACT | MS-229_HC CDR1 |
| SEQ ID NO: 644 | TATATCTCTGACAGA GAATCAGCGACTTAC AACC CCTCCCTCAATAGT | MS-229_HC CDR2 |
| SEQ ID NO: 645 | GCGCGCCGAGGACAG AGGATTTATGGAGTG GTTT CCTTTGGAGAGTTCT TCTACTACTACTCCA TGGAC GTC | MS-229_HC CDR3 |
| SEQ ID NO: 646 | GGACGACAGGCCCTT GGAAGTAGAGCTGTT CAG | MS-230_LC CDR1 |
| SEQ ID NO: 647 | AATAATCAAGACCGG CCCTCA | MS-230_LC CDR2 |
| SEQ ID NO: 648 | CACATGTGGGATAGT AGAAGTGGCTTCAGT TGGT CT | MS-230_LC CDR3 |
| SEQ ID NO: 649 | AATAATTACTACTGG ACT | MS-230_HC CDR1 |
| SEQ ID NO: 650 | TATATCTCTGACAGA GAATCAGCGACTTAC AACC CCTCCCTCAATAGT | MS-230_HC CDR2 |
| SEQ ID NO: 651 | GCGCGCCGAGGACAG AGGATTTATGGAGTG GTTT CCTTTGGAGAGTTCT TCTACTACTACTCCA TGGAC GTC | MS-230_HC CDR3 |
| SEQ ID NO: 652 | GGACGACAGGCCCTT GGAAGTAGAGCTGTT CAG | MS-231_LC CDR1 |
| SEQ ID NO: 653 | AATAATCAAGACCGG CCCTCA | MS-231_LC CDR2 |

TABLE 7-continued

Nucleic acid sequences of CDR regions of the 10-1074 antibody variants

| SEQ ID NO. | SEQUENCE | OTHER INFORMATION |
|---|---|---|
| SEQ ID NO: 654 | CACATGTGGGATAGT AGAAGTGGCTTCAGT TGGT CT | MS-231_LC CDR3 |
| SEQ ID NO: 655 | AATAATTACTACTGG ACT | MS-231_HC CDR1 |
| SEQ ID NO: 656 | TATATCTCTGACAGA GAATCAGCGACTTAC AACC CCTCCCTCAATAGT | MS-231_HC CDR2 |
| SEQ ID NO: 657 | GCGCGCCGAGGACAG AGGATTTATGGAGTG GTTT CCTTTGGAGAGTTCT TCTACTACTACTCCA TGGAC GTC | MS-231_HC CDR3 |
| SEQ ID NO: 658 | GGACGACAGGCCCTT GGAAGTAGAGCTGTT CAG | MS-232_LC CDR1 |
| SEQ ID NO: 659 | AATAATCAAGACCGG CCCTCA | MS-232_LC CDR2 |
| SEQ ID NO: 660 | CACATGTGGGATAGT AGAAGTGGCTTCAGT TGGT CT | MS-232_LC CDR3 |
| SEQ ID NO: 661 | AATAATTACTACTGG ACT | MS-232_HC CDR1 |
| SEQ ID NO: 662 | TATATCTCTGACAGA GAATCAGCGACTTAC AACC CCTCCCTCAATAGT | MS-232_HC CDR2 |
| SEQ ID NO: 663 | GCGCGCCGAGGACAG AGGATTTATGGAGTG GTTT CCTTTGGAGAGTTCT TCTACTACTACTCCA TGGAC GTC | MS-232_HC CDR3 |
| SEQ ID NO: 664 | GGACGACAGGCCCTT GGAAGTAGAGCTGTT CAG | MS-233_LC CDR1 |
| SEQ ID NO: 665 | AATAATCAAGACCGG CCCTCA | MS-233_LC CDR2 |
| SEQ ID NO: 666 | CACATGTGGGATAGT AGAAGTGGCTTCAGT TGGT CT | MS-233_LC CDR3 |
| SEQ ID NO: 667 | AATAATTACTACTGG ACT | MS-233_HC CDR1 |
| SEQ ID NO: 668 | TATATCTCTGACAGA GAATCAGCGACTTAC AACC CCTCCCTCAATAGT | MS-233_HC CDR2 |

TABLE 7-continued

Nucleic acid sequences of CDR regions of the 10-1074 antibody variants

| SEQ ID NO. | SEQUENCE | OTHER INFORMATION |
|---|---|---|
| SEQ ID NO: 669 | GCGCGCCGAGGACAG AGGATTTATGGAGTG GTTT CCTTTGGAGAGTTCT TCTACTACTACTCCA TGGAC GTC | MS-233_HC CDR3 |
| SEQ ID NO: 670 | GGACGACAGGCCCTT GGAAGTAGAGCTGTT CAG | MS-234_LC CDR1 |
| SEQ ID NO: 671 | AATAATCAAGACCGG CCCTCA | MS-234_LC CDR2 |
| SEQ ID NO: 672 | CACATGTGGGATAGT AGAAGTGGCTTCAGT TGGT CT | MS-234_LC CDR3 |
| SEQ ID NO: 673 | AATAATTACTACTGG ACT | MS-234_HC CDR1 |
| SEQ ID NO: 674 | TATATCTCTGACAGA GAATCAGCGACTTAC AACC CCTCCCTCAATAGT | MS-234_HC CDR2 |
| SEQ ID NO: 675 | GCGCGCCGAGGACAG AGGATTTATGGAGTG GTTT CCTTTGGAGAGTTCT TCTACTACTACTCCA TGGAC GTC | MS-234_HC CDR3 |
| SEQ ID NO: 676 | GGACGACAGGCCCTT GGAAGTAGAGCTGTT CAG | MS-235_LC CDR1 |
| SEQ ID NO: 677 | AATAATCAAGACCGG CCCTCA | MS-235_LC CDR2 |
| SEQ ID NO: 678 | CACATGTGGGATAGT AGAAGTGGCTTCAGT TGGT CT | MS-235_LC CDR3 |
| SEQ ID NO: 679 | AATAATTACTACTGG ACT | MS-235_HC CDR1 |
| SEQ ID NO: 680 | TATATCTCTGACAGA GAATCAGCGACTTAC AACC CCTCCCTCAATAGT | MS-235_HC CDR2 |
| SEQ ID NO: 681 | GCGCGCCGAGGACAG AGGATTTATGGAGTG GTTT CCTTTGGAGAGTTCT TCTACTACTACTCCA TGGAC GTC | MS-235_HC CDR3 |
| SEQ ID NO: 682 | GGACGACAGGCCCTT GGAAGTAGAGCTGTT CAG | MS-236_LC CDR1 |
| SEQ ID NO: 683 | AATAATCAAGACCGG CCCTCA | MS-236_LC CDR2 |

TABLE 7-continued

Nucleic acid sequences of CDR regions of the 10-1074 antibody variants

| SEQ ID NO. | SEQUENCE | OTHER INFORMATION |
|---|---|---|
| SEQ ID NO: 684 | CACATGTGGGATAGT AGAAGTGGCTTCAGT TGGT CT | MS-236_LC CDR3 |
| SEQ ID NO: 685 | AATAATTACTACTGG ACT | MS-236_HC CDR1 |
| SEQ ID NO: 686 | TATATCTCTGACAGA GAATCAGCGACTTAC AACC CCTCCCTCAATAGT | MS-236_HC CDR2 |
| SEQ ID NO: 687 | GCGCGCCGAGGACAG AGGATTTATGGAGTG GTTT CCTTTGGAGAGTTCT TCTACTACTACTCCA TGGAC GTC | MS-236_HC CDR3 |
| SEQ ID NO: 688 | GGACGACAGGCCCTT GGAAGTAGAGCTGTT CAG | MS-237_LC CDR1 |
| SEQ ID NO: 689 | AATAATCAAGACCGG CCCTCA | MS-237_LC CDR2 |
| SEQ ID NO: 690 | CACATGTGGGATAGT AGAAGTGGCTTCAGT TGGT CT | MS-237_LC CDR3 |
| SEQ ID NO: 691 | AATAATTACTACTGG ACT | MS-237_HC CDR1 |
| SEQ ID NO: 692 | TATATCTCTGACAGA GAATCAGCGACTTAC AACC CCTCCCTCAATAGT | MS-237_HC CDR2 |
| SEQ ID NO: 693 | GCGCGCCGAGGACAG AGGATTTATGGAGTG GTTT CCTTTGGAGAGTTCT TCTACTACTACTCCA TGGAC GTC | MS-237_HC CDR3 |
| SEQ ID NO: 694 | GGACGACAGGCCCTT GGAAGTAGAGCTGTT CAG | MS-238_LC CDR1 |
| SEQ ID NO: 695 | AATAATCAAGACCGG CCCTCA | MS-238_LC CDR2 |
| SEQ ID NO: 696 | CACATGTGGGATAGT AGAAGTGGCTTCAGT TGGT CT | MS-238_LC CDR3 |
| SEQ ID NO: 697 | AATAATTACTACTGG ACT | MS-238_HC CDR1 |
| SEQ ID NO: 698 | TATATCTCTGACAGA GAATCAGCGACTTAC AACC CCTCCCTCAATAGT | MS-238_HC CDR2 |

TABLE 7-continued

Nucleic acid sequences of CDR regions of the 10-1074 antibody variants

| SEQ ID NO. | SEQUENCE | OTHER INFORMATION |
|---|---|---|
| SEQ ID NO: 699 | GCGCGCCGAGGACAG AGGATTTATGGAGTG GTTT CCTTTGGAGAGTTCT TCTACTACTACTCCA TGGAC GTC | MS-238_HC CDR3 |
| SEQ ID NO: 700 | GGACGACAGGCCCTT GGAAGTAGAGCTGTT CAG | MS-239_LC CDR1 |
| SEQ ID NO: 701 | AATAATCAAGACCGG CCCTCA | MS-239_LC CDR2 |
| SEQ ID NO: 702 | CACATGTGGGATAGT AGAAGTGGCTTCAGT TGGT CT | MS-239_LC CDR3 |
| SEQ ID NO: 703 | AATAATTACTACTGG ACT | MS-239_HC CDR1 |
| SEQ ID NO: 704 | TATATCTCTGACAGA GAATCAGCGACTTAC AACC CCTCCCTCAATAGT | MS-239_HC CDR2 |
| SEQ ID NO: 705 | GCGCGCCGAGGACAG AGGATTTATGGAGTG GTTT CCTTTGGAGAGTTCT TCTACTACTACTCCA TGGAC GTC | MS-239_HC CDR3 |
| SEQ ID NO: 706 | GGACGACAGGCCCTT GGAAGTAGAGCTGTT CAG | MS-240_LC CDR1 |
| SEQ ID NO: 707 | AATAATCAAGACCGG CCCTCA | MS-240_LC CDR2 |
| SEQ ID NO: 708 | CACATGTGGGATAGT AGAAGTGGCTTCAGT TGGT CT | MS-240_LC CDR3 |
| SEQ ID NO: 709 | AATAATTACTACTGG ACT | MS-240_HC CDR1 |
| SEQ ID NO: 710 | TATATCTCTGACAGA GAATCAGCGACTTAC AACC CCTCCCTCAATAGT | MS-240_HC CDR2 |
| SEQ ID NO: 711 | GCGCGCCGAGGACAG AGGATTTATGGAGTG GTTT CCTTTGGAGAGTTCT TCTACTACTACTCCA TGGAC GTC | MS-240_HC CDR3 |
| SEQ ID NO: 712 | GGACGACAGGCCCTT GGAAGTAGAGCTGTT CAG | MS-241_LC CDR1 |
| SEQ ID NO: 713 | AATAATCAAGACCGG CCCTCA | MS-241_LC CDR2 |

TABLE 7-continued

Nucleic acid sequences of CDR regions of the 10-1074 antibody variants

| SEQ ID NO. | SEQUENCE | OTHER INFORMATION |
|---|---|---|
| SEQ ID NO: 714 | CACATGTGGGATAGT AGAAGTGGCTTCAGT TGGT CT | MS-241_LC CDR3 |
| SEQ ID NO: 715 | AATAATTACTACTGG ACT | MS-241_HC CDR1 |
| SEQ ID NO: 716 | TATATCTCTGACAGA GAATCAGCGACTTAC AACC CCTCCCTCAATAGT | MS-241_HC CDR2 |
| SEQ ID NO: 717 | GCGCGCCGAGGACAG AGGATTTATGGAGTG GTTT CCTTTGGAGAGTTCT TCTACTACTACTCCA TGGAC GTC | MS-241_HC CDR3 |
| SEQ ID NO: 718 | GGACGACAGGCCCTT GGAAGTAGAGCTGTT CAG | MS-242_LC CDR1 |
| SEQ ID NO: 719 | AATAATCAAGACCGG CCCTCA | MS-242_LC CDR2 |
| SEQ ID NO: 720 | CACATGTGGGATAGT AGAAGTGGCTTCAGT TGGT CT | MS-242_LC CDR3 |
| SEQ ID NO: 721 | AATAATTACTACTGG ACT | MS-242_HC CDR1 |
| SEQ ID NO: 722 | TATATCTCTGACAGA GAATCAGCGACTTAC AACC CCTCCCTCAATAGT | MS-242_HC CDR2 |
| SEQ ID NO: 723 | GCGCGCCGAGGACAG AGGATTTATGGAGTG GTTT CCTTTGGAGAGTTCT TCTACTACTACTCCA TGGAC GTC | MS-242_HC CDR3 |
| SEQ ID NO: 724 | GGACGACAGGCCCTT GGAAGTAGAGCTGTT CAG | MS-243_LC CDR1 |
| SEQ ID NO: 725 | AATAATCAAGACCGG CCCTCA | MS-243_LC CDR2 |
| SEQ ID NO: 726 | CACATGTGGGATAGT AGAAGTGGCTTCAGT TGGT CT | MS-243_LC CDR3 |
| SEQ ID NO: 727 | AATAATTACTACTGG ACT | MS-243_HC CDR1 |
| SEQ ID NO: 728 | TATATCTCTGACAGA GAATCAGCGACTTAC AACC CCTCCCTCAATAGT | MS-243_HC CDR2 |

TABLE 7-continued

Nucleic acid sequences of CDR regions of the 10-1074 antibody variants

| SEQ ID NO. | SEQUENCE | OTHER INFORMATION |
|---|---|---|
| SEQ ID NO: 729 | GCGCGCCGAGGACAG AGGATTTATGGAGTG GTTT CCTTTGGAGAGTTCT TCTACTACTACTCCA TGGAC GTC | MS-243_HC CDR3 |
| SEQ ID NO: 730 | GGACGACAGGCCCTT GGAAGTAGAGCTGTT CAG | MS-244_LC CDR1 |
| SEQ ID NO: 731 | AATAATCAAGACCGG CCCTCA | MS-244_LC CDR2 |
| SEQ ID NO: 732 | CACATGTGGGATAGT AGAAGTGGCTTCAGT TGGT CT | MS-244_LC CDR3 |
| SEQ ID NO: 733 | AATAATTACTACTGG ACT | MS-244_HC CDR1 |
| SEQ ID NO: 734 | TATATCTCTGACAGA GAATCAGCGACTTAC AACC CCTCCCTCAATAGT | MS-244_HC CDR2 |
| SEQ ID NO: 735 | GCGCGCCGAGGACAG AGGATTTATGGAGTG GTTT CCTTTGGAGAGTTCT TCTACTACTACTCCA TGGAC GTC | MS-244_HC CDR3 |
| SEQ ID NO: 736 | GGACGACAGGCCCTT GGAAGTAGAGCTGTT CAG | MS-245_LC CDR1 |
| SEQ ID NO: 737 | AATAATCAAGACCGG CCCTCA | MS-245_LC CDR2 |
| SEQ ID NO: 738 | CACATGTGGGATAGT AGAAGTGGCTTCAGT TGGT CT | MS-245_LC CDR3 |
| SEQ ID NO: 739 | AATAATTACTACTGG ACT | MS-245_HC CDR1 |
| SEQ ID NO: 740 | TATATCTCTGACAGA GAATCAGCGACTTAC AACC CCTCCCTCAATAGT | MS-245_HC CDR2 |
| SEQ ID NO: 741 | GCGCGCCGAGGACAG AGGATTTATGGAGTG GTTT CCTTTGGAGAGTTCT TCTACTACTACTCCA TGGAC GTC | MS-245_HC CDR3 |
| SEQ ID NO: 742 | GGACGACAGGCCCTT GGAAGTAGAGCTGTT CAG | MS-246_LC CDR1 |
| SEQ ID NO: 743 | AATAATCAAGACCGG CCCTCA | MS-246_LC CDR2 |

TABLE 7-continued

Nucleic acid sequences of CDR regions of the 10-1074 antibody variants

| SEQ ID NO. | SEQUENCE | OTHER INFORMATION |
|---|---|---|
| SEQ ID NO: 744 | CACATGTGGGATAGT AGAAGTGGCTTCAGT TGGT CT | MS-246_LC CDR3 |
| SEQ ID NO: 745 | AATAATTACTACTGG ACT | MS-246_HC CDR1 |
| SEQ ID NO: 746 | TATATCTCTGACAGA GAATCAGCGACTTAC AACC CCTCCCTCAATAGT | MS-246_HC CDR2 |
| SEQ ID NO: 747 | GCGCGCCGAGGACAG AGGATTTATGGAGTG GTTT CCTTTGGAGAGTTCT TCTACTACTACTCCA TGGAC GTC | MS-246_HC CDR3 |
| SEQ ID NO: 748 | GGACGACAGGCCCTT GGAAGTAGAGCTGTT CAG | MS-247_LC CDR1 |
| SEQ ID NO: 749 | AATAATCAAGACCGG CCCTCA | MS-247_LC CDR2 |
| SEQ ID NO: 750 | CACATGTGGGATAGT AGAAGTGGCTTCAGT TGGT CT | MS-247_LC CDR3 |
| SEQ ID NO: 751 | AATAATTACTACTGG ACT | MS-247_HC CDR1 |
| SEQ ID NO: 752 | TATATCTCTGACAGA GAATCAGCGACTTAC AACC CCTCCCTCAATAGT | MS-247_HC CDR2 |
| SEQ ID NO: 753 | GCGCGCCGAGGACAG AGGATTTATGGAGTG GTTT CCTTTGGAGAGTTCT TCTACTACTACTCCA TGGAC GTC | MS-247_HC CDR3 |

TABLE 8

| Methods for characterizing anti-HIV antibody 10-1074 variants | | |
|---|---|---|
| Method Name | Discard limits | Priority molecules |
| Titer (with caveat that transient titer is not correlative with stable titer) | Discard molecules with significant reduction in titer | Variants with significant increase in titer over parental |
| Purification Yield | Discard molecules with a significant decrease in yield as compared to the titer | Variants with yield close to 100% based on the titer |
| Neutralization | Discard molecules with greater than 3-fold reduction in neutralization potency for any given virus | Variants with no decrease in potency |
| Size Exclusion Chromatography (SEC) | Dimer and higher order aggregates less than 10%. Priority for molecules with lower values. | Molecules with less than 5% dimer and higher order aggregates |
| Differential Scanning Fluorimetry (DSF) | Discard molecules with loss of Tm2 | Molecules with increased or additional Tm |
| Chemical Unfolding by Guanidine-HCl | Discard molecules with inflection point of unfolding less than parental molecule | Molecules with inflection point of unfolding greater than parental molecule |
| Relative Solubility Analysis (RSA) | Discard molecules with decreased solubility | Molecules with increased relative solubility given priority |
| Low pH Stability | Discard molecules with greater than 5% increase in aggregation following low pH incubation | No change in aggregation level following low pH incubation |

TABLE 9

| Molecule sets and biophysical analysis of 10-1074 antibody variants (Round 1) | | | | | | | | | |
|---|---|---|---|---|---|---|---|---|---|
| Molecule Set | LC | IgG1 HC | Amount Purified (mg) | SEC (% Monomer) | SEC (% HMW) | DSF Tm1, ° C. (rep 1) | DSF Tm2, ° C. (rep 1) | DSF Tm1, ° C. (rep 2) | DSF Tm2, ° C. (rep 2) |
| MS-194 | | | 1.20 | 91.52 | 8.48 | 69.8 | | 70.0 | |
| MS-203 | LmdV: Y2P | | 0.60 | 95.24 | 4.76 | 69.3 | 81.6 | 69.3 | 81.1 |
| MS-204 | LmdV: R7P | | 0.87 | 65.98 | 34.02 | 69.9 | | 70.1 | |
| MS-205 | LmdV: P9S | | 1.25 | 71.66 | 28.34 | 70.1 | | 70.2 | |
| MS-206 | LmdV: E17Q | | 1.25 | 91.35 | 8.65 | 70.0 | | 70.0 | |
| MS-207 | LmdV: H46Q | | 0.87 | 65.30 | 34.70 | 69.8 | 80.8 | 69.9 | |
| MS-208 | LmdV: P81.1N | | 0.24 | 88.68 | 11.32 | 68.8 | 81.3 | 69.0 | |
| MS-209 | LmdV: I81.3S | | 1.27 | 60.79 | 39.21 | 70.0 | 81.3 | 70.1 | 80.1 |
| MS-210 | LmdV: N82G | | 0.28 | 88.24 | 11.76 | 70.1 | 81.7 | 70.3 | 81.3 |
| MS-211 | LmdV: R88T | | 0.22 | 83.11 | 16.89 | 66.9 | | 67.1 | |
| MS-212 | LmdV: D110E | | 0.25 | 82.78 | 17.22 | 68.5 | | 68.6 | |
| MS-213 | LmdV: A142G | | 0.44 | 90.48 | 9.52 | 68.1 | | 68.2 | |
| MS-214 | | HV: D29G | 2.01 | 94.00 | 6.00 | 69.9 | | 69.9 | |
| MS-215 | | HV: S47P | 2.68 | 92.88 | 7.12 | 70.0 | | 70.1 | |
| MS-216 | | HV: V79T | 1.48 | 94.67 | 5.33 | 69.8 | 81.8 | 69.9 | 80.1 |
| MS-217 | | HV: R82V | 1.31 | 94.21 | 5.79 | 69.8 | 80.9 | 69.9 | 80.1 |
| MS-218 | | HV: L89F | 0.68 | 96.33 | 3.67 | 70.0 | 80.9 | 70.1 | 81.3 |
| MS-219 | | HV: T108R | 2.24 | 91.93 | 8.07 | 70.3 | 75.4 | 70.3 | 76.0 |
| MS-220 | | HV: K141Q | 2.87 | 94.56 | 5.44 | 69.9 | | 69.9 | |
| MS-224 | | HV: N75Q | 0.05 | | | 70.2 | | 69.9 | 80.8 |

TABLE 10

Molecule sets and neutralization analysis against 10-1074 sensitive virus panel in TZM.bl cells (Round 1)

| Molecule | Du156.12 | | WITO4160.33 | | CNE17 | | CNE30 | | CAAN5342.A2 | | Du172.17 | |
|---|---|---|---|---|---|---|---|---|---|---|---|---|
| Set | IC50 | IC80 | IC50 | IC80 | IC50 | IC80 | IC50 | IC80 | IC50 | IC80 | IC50 | IC80 |
| Control | 0.010 | 0.030 | 0.168 | 1.173 | 1.201 | 6.067 | 0.164 | 0.605 | 0.009 | 0.029 | 0.110 | 0.391 |
| MS-203 | 0.008 | 0.025 | 0.205 | 0.979 | 1.291 | 4.519 | 0.193 | 0.546 | 0.009 | 0.024 | 0.084 | 0.295 |
| MS-204 | 0.014 | 0.040 | 0.236 | 1.664 | 1.211 | 5.895 | 0.270 | 0.902 | 0.017 | 0.048 | 0.092 | 0.334 |
| MS-205 | 0.012 | 0.035 | 0.162 | 0.922 | 1.237 | 4.411 | 0.249 | 0.824 | 0.011 | 0.029 | 0.098 | 0.329 |
| MS-206 | 0.010 | 0.035 | 0.161 | 1.142 | 0.986 | 3.484 | 0.225 | 0.614 | 0.009 | 0.024 | 0.095 | 0.272 |
| MS-207 | 0.010 | 0.036 | 0.252 | 0.840 | 1.285 | 5.873 | 0.240 | 0.836 | 0.026 | 0.115 | 0.211 | 0.875 |
| MS-208 | 0.007 | 0.036 | 0.699 | 5.174 | 3.569 | 17.98 | 0.206 | 1.018 | 0.016 | 0.047 | 0.231 | 0.816 |
| MS-209 | 0.007 | 0.025 | 0.276 | 1.833 | 1.155 | 5.751 | 0.174 | 0.618 | 0.009 | 0.029 | 0.088 | 0.303 |
| MS-210 | 0.005 | 0.013 | 0.091 | 0.594 | 0.598 | 2.834 | 0.097 | 0.340 | 0.003 | 0.013 | 0.044 | 0.156 |
| MS-211 | 0.008 | 0.028 | 0.237 | 1.514 | 1.151 | 4.240 | 0.205 | 0.744 | 0.010 | 0.025 | 0.092 | 0.309 |
| MS-212 | 0.009 | 0.041 | 0.304 | 1.938 | 1.395 | 6.928 | 0.242 | 1.130 | 0.007 | 0.031 | 0.113 | 0.399 |
| MS-213 | 0.007 | 0.028 | 0.183 | 1.271 | 0.955 | 5.049 | 0.141 | 0.689 | 0.011 | 0.033 | 0.119 | 0.315 |
| MS-214 | 0.005 | 0.018 | 0.221 | 1.553 | 0.987 | 4.567 | 0.185 | 0.630 | 0.009 | 0.024 | 0.090 | 0.238 |
| MS-215 | 0.007 | 0.023 | 0.157 | 1.118 | 1.174 | 5.438 | 0.224 | 0.760 | 0.011 | 0.031 | 0.095 | 0.305 |
| MS-216 | 0.007 | 0.020 | 0.132 | 0.887 | 1.116 | 4.999 | 0.194 | 0.517 | 0.009 | 0.032 | 0.084 | 0.277 |
| MS-217 | 0.010 | 0.037 | 0.260 | 1.678 | 1.159 | 5.397 | 0.216 | 0.743 | 0.010 | 0.038 | 0.075 | 0.275 |
| MS-218 | 0.005 | 0.018 | 0.142 | 1.016 | 0.815 | 4.195 | 0.156 | 0.557 | 0.010 | 0.027 | 0.091 | 0.312 |
| MS-219 | 0.006 | 0.020 | 0.308 | 1.349 | 0.966 | 3.559 | 0.176 | 0.609 | 0.007 | 0.022 | 0.104 | 0.278 |
| MS-220 | 0.009 | 0.027 | 0.215 | 1.023 | 1.242 | 4.415 | 0.193 | 0.528 | 0.009 | 0.027 | 0.099 | 0.335 |
| MS-224 | 0.005 | 0.022 | 0.269 | 1.219 | 1.147 | 4.026 | 0.162 | 0.564 | 0.009 | 0.032 | 0.096 | 0.329 |

TABLE 11

Reasons for including or excluding variants based on neutralization activity and biophysical analysis (Round1)

| Molecule Set | Reason for inclusion/exclusion in Round 2 |
|---|---|
| MS-203 | Include: presence of Tm2 by DSF, HMW <10% |
| MS-204 | Exclude: Lack of Tm2 |
| MS-205 | Exclude: Lack of Tm2 |
| MS-206 | Exclude: Lack of Tm2 |
| MS-207 | Exclude: Lack of Tm2 |
| MS-208 | Exclude: Lack of Tm2; Reduced neutralization activity |
| MS-209 | Exclude: SEC shows HMW of 39.2% |
| MS-210 | Exclude: Low production titer |
| MS-211 | Exclude: Lack of Tm2 |
| MS-212 | Exclude: Lack of Tm2 |
| MS-213 | Exclude: Lack of Tm2 |
| MS-214 | Exclude: Lack of Tm2 |
| MS-215 | Exclude: Lack of Tm2 |
| MS-216 | Include: presence of Tm2 by DSF, HMW <10% |
| MS-217 | Include: presence of Tm2 by DSF, HMW <10% |
| MS-218 | Include: presence of Tm2 by DSF, HMW <10% |
| MS-219 | Include: presence of Tm2 by DSF, HMW <10% |
| MS-220 | Exclude: Lack of Tm2 |
| MS-224 | Exclude: Low production titer |

TABLE 12

Molecule sets of anti-HIV antibody 10-1074 variants (Round 2)

| Molecule Set | LC | IgG1 HC |
|---|---|---|
| MS-194 | | |
| MS-225 | LmdV: Y2P | HV: V79T |
| MS-226 | LmdV: Y2P | HV: R82V |
| MS-227 | LmdV: Y2P | HV: L89F |
| MS-228 | LmdV: Y2P | HV: T108R |
| MS-229 | | HV: V79T, HV: R82V |
| MS-230 | | HV: V79T, HV: L89F |
| MS-231 | | HV: V79T, HV: T108R |
| MS-232 | | HV: R82V, HV: L89F |
| MS-233 | | HV: R82V, HV: T108R |
| MS-234 | | HV: L89F, HV: T108R |
| MS-235 | LmdV: Y2P | HV: V79T, HV: R82V |
| MS-236 | LmdV: Y2P | HV: V79T, HV: L89F |
| MS-237 | LmdV: Y2P | HV: V79T, HV: T108R |
| MS-238 | LmdV: Y2P | HV: R82V, HV: L89F |
| MS-200 | LmdV: Y2P | HV: R82V, HV: T108R |
| MS-239 | LmdV: Y2P | HV: L89F, HV: T108R |
| MS-240 | | HV: V79T, HV: R82V, HV: L89F |
| MS-241 | | HV: V79T, HV: R82V, HV: T108R |
| MS-201 | | HV: V79T, HV: L89F, HV: T108R |
| MS-242 | | HV: R82V, HV: L89F, HV: T108R |
| MS-243 | LmdV: Y2P | HV: V79T, HV: R82V, HV: L89F |
| MS-244 | LmdV: Y2P | HV: V79T, HV: R82V, HV: T108R |
| MS-202 | LmdV: Y7P | HV: V79T, HV: L89F, HV: T108R |
| MS-245 | LmdV: Y2P | HV: R82V, HV: L89F, HV: T108R |
| MS-246 | | HV: V79T, HV: R82V, HV: L89F, HV: T108R |
| MS-247 | LmdV: Y2P | HV: V79T, HV: R82V, HV: L89F, HV: T108R |

TABLE 13

Molecule sets and biophysical analysis of 10-1074 antibody variants (Round 2)

| Molecule Set | SEC (% monomer) | SEC (% dimer) | SEC (% Oligomer) | DSF Tm1 ° C. (Avg. n = 2) | DSF Tm1 (Std Dev) | DSF Tm2 ° C. (Avg. n = 2) | DSF Tm2 (Std Dev) |
|---|---|---|---|---|---|---|---|
| MS-194 | 92.40 | 3.72 | 3.89 | 70.00 | 0.01 | | |
| MS-225 | 89.07 | 3.12 | 7.81 | 69.44 | 0.05 | | |
| MS-226 | 93.49 | 3.51 | 3.00 | 69.52 | 0.03 | | |
| MS-227 | 90.18 | 3.10 | 6.72 | 69.76 | 0.07 | | |

TABLE 13-continued

Molecule sets and biophysical analysis of 10-1074 antibody variants (Round 2)

| Molecule Set | SEC (% monomer) | SEC (% dimer) | SEC (% Oligomer) | DSF Tm1 ° C. (Avg. n = 2) | DSF Tm1 (Std Dev) | DSF Tm2 ° C. (Avg. n = 2) | DSF Tm2 (Std Dev) |
|---|---|---|---|---|---|---|---|
| MS-228 | 95.37 | 3.59 | 1.04 | 70.48 | 0.02 | 74.50 | 0.00 |
| MS-229 | 93.39 | 4.03 | 2.58 | 70.04 | 0.05 | | |
| MS-230 | 94.00 | 3.42 | 2.58 | 70.25 | 0.05 | | |
| MS-231 | 95.35 | 3.87 | 0.79 | 70.41 | 0.02 | 74.50 | 0.03 |
| MS-232 | 94.62 | 3.52 | 1.86 | 70.07 | 0.03 | | |
| MS-233 | 95.45 | 3.94 | 0.61 | 70.30 | 0.00 | 76.69 | 0.15 |
| MS-234 | 96.70 | 2.94 | 0.36 | 70.40 | 0.06 | 76.85 | 0.11 |
| MS-235 | 92.77 | 3.46 | 3.77 | 69.74 | 0.05 | | |
| MS-236 | 93.06 | 3.78 | 3.16 | 69.92 | 0.10 | | |
| MS-237 | 94.61 | 4.03 | 1.36 | 70.47 | 0.02 | 74.50 | 0.00 |
| MS-238 | 91.73 | 3.94 | 4.33 | 69.36 | 0.01 | | |
| MS-200 | 94.64 | 4.56 | 0.80 | 70.15 | 0.01 | 74.62 | 0.33 |
| MS-239 | 95.99 | 3.35 | 0.66 | 70.28 | 0.01 | 75.42 | 0.09 |
| MS-240 | 94.87 | 3.61 | 1.52 | 69.99 | 0.01 | | |
| MS-241 | 94.36 | 4.93 | 0.71 | 70.11 | 0.02 | 76.41 | 0.04 |
| MS-201 | 94.58 | 4.68 | 0.73 | 70.28 | 0.04 | 76.69 | 0.01 |
| MS-242 | 94.82 | 4.52 | 0.66 | 70.25 | 0.02 | 77.30 | 0.03 |
| MS-243 | 91.81 | 4.51 | 3.67 | 69.57 | 0.06 | | |
| MS-244 | 93.97 | 5.04 | 0.99 | 70.17 | 0.02 | 74.70 | 0.18 |
| MS-202 | 93.88 | 5.04 | 1.08 | 70.42 | 0.00 | 75.43 | 0.15 |
| MS-245 | 93.40 | 5.61 | 0.99 | 70.36 | 0.02 | 76.15 | 0.04 |
| MS-246 | 94.88 | 4.59 | 0.53 | 70.19 | 0.05 | 77.13 | 0.09 |
| MS-247 | 94.37 | 4.88 | 0.75 | 69.44 | 0.05 | | |

TABLE 14

Additional biophysical characterization for the combination variants (Round 2)

| Molecule Set | Shoulder Score (Avg. n = 2) | (Std Dev) | Inflection Pt of Unfolding (Avg n = 3) | Std Dev | pH 3.3 HMW % (Avg n = 2) | Std Dev | PEG solubility (avg. n = 2) | Std Dev |
|---|---|---|---|---|---|---|---|---|
| MS-194 | 7.65 | 0.17 | 2.44 | 0.01 | 39.76 | 0.19 | 0.14 | 0.02 |
| MS-225 | 7.22 | 0.97 | 2.37 | 0.03 | 40.43 | 14.01 | 0.18 | 0.02 |
| MS-226 | 7.72 | 0.16 | 2.49 | 0.04 | 14.33 | 6.02 | 0.19 | 0.01 |
| MS-227 | 8.12 | 0.61 | 2.53 | 0.03 | 28.13 | 14.86 | 0.18 | 0.02 |
| MS-228 | 16.25 | 0.55 | 2.64 | 0.02 | 9.10 | 6.29 | 0.17 | 0.02 |
| MS-229 | 9.03 | 0.98 | 2.60 | 0.01 | 9.77 | 2.43 | 0.19 | 0.02 |
| MS-230 | 10.03 | 0.39 | 2.62 | 0.05 | 12.14 | 2.04 | 0.18 | 0.02 |
| MS-231 | 20.80 | 0.22 | 2.63 | 0.02 | 3.35 | 0.16 | 0.14 | 0.02 |
| MS-232 | 9.70 | 0.25 | 2.65 | 0.06 | 8.67 | 1.77 | 0.19 | 0.01 |
| MS-233 | 20.00 | 0.23 | 2.98 | 0.03 | 2.48 | 0.03 | 0.17 | 0.02 |
| MS-234 | 28.36 | 2.18 | 2.97 | 0.19 | 2.61 | 0.51 | 0.15 | 0.02 |
| MS-235 | 7.79 | 0.22 | 2.60 | 0.03 | 13.92 | 1.48 | 0.19 | 0.01 |
| MS-236 | 8.32 | 0.07 | 2.53 | 0.00 | 22.13 | 6.12 | 0.19 | 0.02 |
| MS-237 | 16.01 | 0.05 | 2.65 | 0.05 | 4.58 | 0.49 | 0.15 | 0.03 |
| MS-238 | 8.21 | 0.56 | 2.57 | 0.01 | 31.37 | 25.30 | 0.20 | 0.01 |
| MS-200 | 16.12 | 0.42 | 2.93 | 0.04 | 2.93 | 0.01 | 0.19 | 0.02 |
| MS-239 | 22.28 | 0.72 | 2.98 | 0.04 | 3.19 | 0.49 | 0.18 | 0.02 |
| MS-240 | 9.98 | 0.18 | 2.71 | 0.03 | 9.63 | 4.33 | 0.19 | 0.02 |
| MS-241 | 21.39 | 0.09 | 2.98 | 0.06 | 3.12 | 0.06 | 0.17 | 0.03 |
| MS-201 | 29.39 | 0.45 | 3.15 | 0.03 | 2.21 | 0.06 | 0.17 | 0.02 |
| MS-242 | 23.85 | 0.29 | 2.89 | 0.14 | 2.49 | 0.06 | 0.19 | 0.02 |
| MS-243 | 7.62 | 0.22 | 2.57 | 0.03 | 9.86 | 1.38 | 0.18 | 0.01 |
| MS-244 | 16.12 | 0.51 | 2.90 | 0.08 | 3.25 | 0.16 | 0.18 | 0.02 |
| MS-202 | 22.49 | 1.53 | 3.08 | 0.09 | 3.64 | 0.09 | 0.17 | 0.02 |
| MS-245 | 18.77 | 0.55 | 3.06 | 0.07 | 3.29 | 0.30 | 0.18 | 0.02 |
| MS-246 | 22.39 | 0.97 | 3.29 | 0.03 | 2.32 | 0.23 | 0.17 | 0.03 |
| MS-247 | 7.22 | 0.97 | 2.91 | 0.07 | 3.14 | 0.24 | 0.19 | 0.02 |

TABLE 15

Neutralization analysis of selected variants in Round 2 in TZM.bl cells. Loss of potency are values >3-fold of control value

| Molecule | SC422661.8 | | WITO4160.33 | | CAAN5342.A2 | | DU156.12 | | DU172.17 | | CNE17 | |
|---|---|---|---|---|---|---|---|---|---|---|---|---|
| Set | IC50 | IC80 | IC50 | IC80 | IC50 | IC80 | IC50 | IC80 | IC50 | IC80 | IC50 | IC80 |
| Control | 0.045 | 0.157 | 0.205 | 1.439 | 0.005 | 0.019 | 0.008 | 0.034 | 0.055 | 0.156 | 1.34 | 4.574 |
| MS-228 | 0.03 | 0.114 | 0.097 | 0.71 | 0.002 | 0.01 | 0.003 | 0.017 | 0.036 | 0.134 | 0.928 | 3.21 |
| MS-231 | 0.032 | 0.092 | 0.092 | 0.646 | 0.001 | 0.012 | 0.003 | 0.017 | 0.034 | 0.125 | 0.796 | 2.719 |
| MS-233 | 0.037 | 0.128 | 0.172 | 0.789 | 0.005 | 0.015 | 0.004 | 0.02 | 0.033 | 0.124 | 0.625 | 3.085 |
| MS-234 | 0.04 | 0.136 | 0.22 | 0.932 | 0.003 | 0.011 | 0.004 | 0.017 | 0.058 | 0.232 | 0.734 | 2.646 |
| MS-237 | 0.028 | 0.126 | 0.113 | 0.744 | 0.004 | 0.016 | 0.004 | 0.019 | 0.037 | 0.117 | 0.792 | 3.673 |
| MS-200 | 0.036 | 0.156 | 0.13 | 0.794 | 0.005 | 0.02 | 0.007 | 0.028 | 0.037 | 0.152 | 0.922 | 3.21 |
| MS-239 | 0.033 | 0.114 | 0.199 | 0.951 | 0.003 | 0.012 | 0.005 | 0.017 | 0.03 | 0.125 | 0.63 | 2.887 |
| MS-241 | 0.034 | 0.106 | 0.229 | 0.999 | 0.004 | 0.014 | 0.008 | 0.02 | 0.038 | 0.137 | 0.81 | 2.939 |
| MS-201 | 0.027 | 0.104 | 0.177 | 1.153 | 0.002 | 0.011 | 0.005 | 0.016 | 0.028 | 0.102 | 0.782 | 2.62 |
| MS-242 | 0.04 | 0.116 | 0.145 | 0.889 | 0.003 | 0.012 | 0.006 | 0.021 | 0.034 | 0.161 | 0.762 | 3.331 |
| MS-244 | 0.041 | 0.123 | 0.172 | 1.169 | 0.005 | 0.017 | 0.003 | 0.017 | 0.045 | 0.167 | 0.694 | 3.637 |
| MS-202 | 0.028 | 0.135 | 0.185 | 0.708 | 0.003 | 0.011 | 0.004 | 0.021 | 0.028 | 0.104 | 0.825 | 2.903 |
| MS-245 | 0.029 | 0.102 | 0.132 | 0.774 | 0.002 | 0.012 | 0.006 | 0.022 | 0.038 | 0.139 | 0.991 | 4.443 |
| MS-246 | 0.037 | 0.128 | 0.145 | 0.82 | 0.004 | 0.017 | 0.006 | 0.025 | 0.039 | 0.146 | 0.907 | 3.175 |
| MS-247 | 0.034 | 0.151 | 0.107 | 0.611 | 0.003 | 0.014 | 0.009 | 0.032 | 0.03 | 0.149 | 0.642 | 3.141 |

| Molecule | CNE30 | | CNE53 | | 235-47 | | X1193_c1 | | X1254_c3 | | 3301.v1.c24 | |
|---|---|---|---|---|---|---|---|---|---|---|---|---|
| Set | IC50 | IC80 | IC50 | IC80 | IC50 | IC80 | IC50 | IC80 | IC50 | IC80 | IC50 | IC80 |
| Control | 0.258 | 0.709 | 0.017 | 0.049 | 0.029 | 0.116 | 0.04 | 0.139 | 0.055 | 0.154 | 0.008 | 0.021 |
| MS-228 | 0.215 | 0.595 | 0.007 | 0.028 | 0.019 | 0.086 | 0.03 | 0.13 | 0.039 | 0.117 | 0.003 | 0.013 |
| MS-231 | 0.184 | 0.517 | 0.007 | 0.025 | 0.016 | 0.078 | 0.028 | 0.12 | 0.035 | 0.116 | 0.002 | 0.012 |
| MS-233 | 0.186 | 0.649 | 0.006 | 0.023 | 0.03 | 0.113 | 0.03 | 0.133 | 0.041 | 0.129 | 0.003 | 0.016 |
| MS-234 | 0.184 | 0.5 | 0.008 | 0.037 | 0.019 | 0.077 | 0.031 | 0.142 | 0.03 | 0.122 | 0.003 | 0.014 |
| MS-237 | 0.17 | 0.46 | 0.005 | 0.027 | 0.022 | 0.086 | 0.042 | 0.146 | 0.035 | 0.101 | 0.002 | 0.014 |
| MS-200 | 0.17 | 0.583 | 0.007 | 0.027 | 0.022 | 0.085 | 0.059 | 0.177 | 0.047 | 0.133 | 0.005 | 0.019 |
| MS-239 | 0.175 | 0.588 | 0.004 | 0.02 | 0.023 | 0.088 | 0.03 | 0.182 | 0.036 | 0.102 | 0.002 | 0.011 |
| MS-241 | 0.181 | 0.498 | 0.006 | 0.023 | 0.028 | 0.08 | 0.042 | 0.155 | 0.034 | 0.119 | 0.003 | 0.01 |
| MS-201 | 0.173 | 0.471 | 0.003 | 0.025 | 0.011 | 0.067 | 0.033 | 0.154 | 0.037 | 0.1 | 0.003 | 0.008 |
| MS-242 | 0.197 | 0.535 | 0.004 | 0.023 | 0.028 | 0.092 | 0.042 | 0.185 | 0.031 | 0.107 | 0.003 | 0.009 |
| MS-244 | 0.18 | 0.639 | 0.001 | 0.014 | 0.032 | 0.113 | 0.041 | 0.184 | 0.027 | 0.108 | 0.001 | 0.005 |
| MS-202 | 0.16 | 0.568 | 0.005 | 0.021 | 0.022 | 0.084 | 0.037 | 0.139 | 0.028 | 0.117 | 0.005 | 0.018 |
| MS-245 | 0.156 | 0.553 | 0.004 | 0.019 | 0.028 | 0.1 | 0.049 | 0.172 | 0.04 | 0.137 | 0.006 | 0.019 |
| MS-246 | 0.204 | 0.557 | 0.002 | 0.021 | 0.037 | 0.128 | 0.046 | 0.199 | 0.047 | 0.164 | 0.007 | 0.021 |
| MS-247 | 0.197 | 0.554 | 0.005 | 0.027 | 0.036 | 0.126 | 0.043 | 0.203 | 0.029 | 0.113 | 0.008 | 0.023 |

TABLE 16

Reasons for excluding combinatorial variants based on biophysical analysis (Round 2)

| Molecule Set | Reasons for exclusion of molecules from further in-depth analysis |
|---|---|
| MS-225 | Excluded: Lack of Tm2, Aggregation at 65° C., Lower chemical unfolding stability, aggregation at pH 3.3 >5% |
| MS-226 | Excluded: Lack of Tm2, Aggregation at 65° C., Lower chemical unfolding stability, aggregation at pH 3.3 >5% |
| MS-227 | Excluded: Lack of Tm2, Aggregation at 65° C., Lower chemical unfolding stability, aggregation at pH 3.3 >5% |
| MS-228 | Excluded: Lower chemical unfolding stability, aggregation at pH 3.3 >5% |
| MS-229 | Excluded: Lack of Tm2, Aggregation at 65° C., Lower chemical unfolding stability, aggregation at pH 3.3 >5% |
| MS-230 | Excluded: Lack of Tm2, Aggregation at 65° C., Lower chemical unfolding stability, aggregation at pH 3.3 >5% |
| MS-231 | Excluded: Aggregation at 65° C., Lower chemical unfolding stability |
| MS-232 | Excluded: Lack of Tm2, Aggregation at 65° C., Lower chemical unfolding stability, aggregation at pH 3.3 >5% |
| MS-233 | Excluded: Aggregation at 65° C. |
| MS-234 | Excluded: Low titer |
| MS-235 | Excluded: Lack of Tm2, Aggregation at 65° C., Lower chemical unfolding stability, aggregation at pH 3.3 >5% |
| MS-236 | Excluded: Lack of Tm2, Aggregation at 65° C., Lower chemical unfolding stability, aggregation at pH 3.3 >5% |

TABLE 16-continued

Reasons for excluding combinatorial variants based on biophysical analysis (Round 2)

| Molecule Set | Reasons for exclusion of molecules from further in-depth analysis |
|---|---|
| MS-237 | Excluded: Lower chemical unfolding stability |
| MS-238 | Excluded: Lack of Tm2, Aggregation at 65° C., Lower chemical unfolding stability, aggregation at pH 3.3 >5% |
| MS-200 | Include |
| MS-239 | Excluded: Low Titer |
| MS-240 | Excluded: Lack of Tm2, Aggregation at 65° C., Lower chemical unfolding stability, aggregation at pH 3.3 >5% |
| MS-241 | Excluded: Similar to 19, but slightly less stability to chemical unfolding |
| MS-201 | Include |
| MS-242 | Exclude: Decreased chemical unfolding stability compared to 19 |
| MS-243 | Excluded: Lack of Tm2, Aggregation at 65° C., Lower chemical unfolding stability, aggregation at pH 3.3 >5% |
| MS-244 | Excluded: Aggregation at 65° C. |
| MS-202 | Include |
| MS-245 | Exclude: No improvement over variants 15, 19, or 23 |
| MS-246 | Excluded: Low titer (less than parental) |
| MS-247 | Excluded: Low titer (less than parental) |

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

What is claimed is:

1. An isolated anti-HIV antibody, or antigen-binding portion thereof, comprising a light chain variable region having a light chain amino acid sequence that is at least 95% identical to SEQ ID NO: 24, wherein the light chain complementarity determining regions (CDRL1, CDRL2, and CDRL3) of the antibody or antigen-binding portion thereof comprise the CDRL1 of SEQ ID NO: 233 (GRQALGSRAVQ), the CDRL2 of SEQ ID NO: 234 (NNQDRPS), and the CDRL3 of SEQ ID NO: 235 (HMWDSRSGFSWS), and a heavy chain variable region having a heavy chain amino acid sequence that is at least 95% identical to SEQ ID NO: 71, wherein the heavy chain complementarity determining regions (CDRH1, CDRH2, and CDRH3) of the antibody or antigen-binding portion thereof comprises the CDRH1 of SEQ ID NO: 236 (NNYYWT), the CDRH2 of SEQ ID NO: 237 (YISDRESATYNPSLNS) and the CDRH3 of SEQ ID NO: 238 (ARRGQRIYGVVSFGEFFYYYSMDV), wherein (i) the light chain amino acid sequence comprises a residue at position 21 with respect to SEQ ID NO: 24 that is not Tyr or (ii) the heavy chain amino acid sequence comprises a residue at position 87 with respect to SEQ ID NO: 71 that is not Val, a residue at position 97 with respect to SEQ ID NO: 71 that is not Leu, and a residue at position 116 with respect to SEQ ID NO: 71 that is not Thr, and wherein the anti-HIV antibody, or antigen-binding portion thereof retains its ability to bind to HIV.

2. The isolated anti-HIV antibody, or antigen-binding portion thereof, of claim 1, wherein the residue at position 21 with respect to SEQ ID NO: 24 is Pro.

3. The isolated anti-HIV antibody, or antigen-binding portion thereof, of claim 1, wherein the residue at position 21 with respect to SEQ ID NO: 24 is Pro, the residue at position 87 with respect to SEQ ID NO: 71 is Thr, the residue at position 97 with respect to SEQ ID NO: 71 is Phe, and the residue at position 116 with respect to SEQ ID NO: 71 is Arg.

4. The isolated anti-HIV antibody, or antigen-binding portion thereof, of claim 1, wherein the light chain amino acid sequence is at least 95% identical to the light chain variable region of SEQ ID NO: 3 and the residue at position 87 with respect to SEQ ID NO: 71 is Thr.

5. A pharmaceutical composition comprising the isolated anti-HIV antibody, or antigen-binding portion thereof, of claim 1, and a pharmaceutically acceptable carrier or excipient.

6. The pharmaceutical composition of claim 5 further comprising a second therapeutic agent.

7. A method of treating an HIV infection or an HIV-related disease comprising the steps of:

a. identifying a patient in need of such treatment, and b. administering to said patient a first therapeutic agent comprising a therapeutically effective amount of at least one anti-HIV antibody of claim 1, or antigen-binding portion thereof.

8. The method of claim 7, further comprising administering a second therapeutic agent.

9. The method of claim 8, wherein the second therapeutic agent is administered before, concurrently with or after the administration of the anti-HIV antibody or antigen-binding portion thereof.

10. The pharmaceutical composition of claim 6, wherein the second therapeutic agent is an anti-HIV-1 broadly neutralizing antibody (bNAb).

11. The method of claim 8, wherein the second therapeutic agent is 3BNC117.

12. A kit comprising a pharmaceutically acceptable dose unit of a pharmaceutically effective amount of at least one isolated anti-HIV antibody according to claim 1, or antigen-binding portion thereof.

13. The kit of claim 12 further comprising a pharmaceutically acceptable dose unit of a pharmaceutically effective amount of an anti-HIV agent, wherein the two pharmaceutically acceptable dose units can optionally take the form of a single pharmaceutically acceptable dose unit.

14. The kit of claim 13, wherein the anti-HIV agent is one selected from the group consisting of a non-nucleoside reverse transcriptase inhibitor, a protease inhibitor, an entry or fusion inhibitor, and an integrase inhibitor.

15. The kit of claim 13, wherein the anti-HIV agent is an anti-HIV broadly neutralizing antibody.

16. The kit of claim 15, wherein the anti-HIV broadly neutralizing antibody is 3BNC117.

* * * * *